United States Patent
Jiang et al.

(10) Patent No.: US 10,174,011 B2
(45) Date of Patent: Jan. 8, 2019

(54) HETEROCYCLIC COMPOUNDS, PROCESS FOR PREPARATION OF THE SAME AND USE THEREOF

(71) Applicants: SHANGHAI INSTITUTE OF MATERIA MEDICA, CHINESE ACADEMY OF SCIENCES, Shanghai (CN); SUZHOU VIGONVITA LIFE SCIENCES CO., LTD., Jiangsu (CN); TOPHARMAN SHANDONG CO., LTD., Shandong (CN)

(72) Inventors: Hualiang Jiang, Shanghai (CN); Zhen Wang, Shanghai (CN); Jianfeng Li, Shanghai (CN); Rongxia Zhang, Shanghai (CN); Yang He, Shanghai (CN); Yongjian Liu, Shandong (CN); Minghao Bi, Shandong (CN); Zheng Liu, Shandong (CN); Guanghui Tian, Jiangsu (CN); Weiming Chen, Shandong (CN); Feipu Yang, Shanghai (CN); Chunhui Wu, Shanghai (CN); Yu Wang, Shanghai (CN); Xiangrui Jiang, Shanghai (CN); Jingjing Yin, Shandong (CN); Guan Wang, Shanghai (CN); Jingshan Shen, Shanghai (CN)

(73) Assignees: SHANGHAI INSTITUTE OF MATERIA MEDICA, CHINESE ACADEMY OF SCIENCES, Shanghai (CN); SUZHOU VIGONVITA LIFE SCIENCES CO., LTD., Jiangsu (CN); TOPHARMAN SHANDONG CO., LTD., Shandong (CN)

(*) Notice: Subject to any disclaimer, the term of this patent is extended or adjusted under 35 U.S.C. 154(b) by 0 days.

(21) Appl. No.: 15/124,264

(22) PCT Filed: Mar. 9, 2015

(86) PCT No.: PCT/CN2015/073854
§ 371 (c)(1),
(2) Date: Sep. 7, 2016

(87) PCT Pub. No.: WO2015/131856
PCT Pub. Date: Sep. 11, 2015

(65) Prior Publication Data
US 2017/0158680 A1    Jun. 8, 2017

(30) Foreign Application Priority Data

Mar. 7, 2014   (CN) .......................... 2014 1 0083602
Dec. 31, 2014   (CN) .......................... 2014 1 0853950

(51) Int. Cl.
*C07D 409/12*   (2006.01)
*C07D 409/14*   (2006.01)
(Continued)

(52) U.S. Cl.
CPC ......... *C07D 409/12* (2013.01); *C07D 409/14* (2013.01); *C07D 413/12* (2013.01); *C07D 417/12* (2013.01); *C07D 471/04* (2013.01); *C07D 495/04* (2013.01); *C07D 519/00* (2013.01)

(58) Field of Classification Search
CPC combination set(s) only.
See application file for complete search history.

(56) References Cited

U.S. PATENT DOCUMENTS

| 4,771,053 A | 9/1988 | Cott et al. |
| 5,137,894 A | 8/1992 | New et al. |

(Continued)

FOREIGN PATENT DOCUMENTS

| CN | 101155804 A | 4/2008 |
| CN | 101754964 A | 6/2010 |

(Continued)

OTHER PUBLICATIONS

New et al. "The thieno[3,2-c]pyridine and furo[3,2-c]pyridine rings: new pharmacophores with potential antipsychotic activity" J. Med. Chem. 1989, 32, 1147-1156.*

(Continued)

*Primary Examiner* — Amanda L Aguirre
(74) *Attorney, Agent, or Firm* — Carter, DeLuca, Farrell & Schmidt, LLP

(57) ABSTRACT

The present invention provides a heterocyclic compound represented by the formula (I), its stereoisomers, or a pharmaceutically acceptable salt thereof, pharmaceutical compositions thereof, and their use in preparing a medicament for the prevention and/or treatment of central nervous system disease.

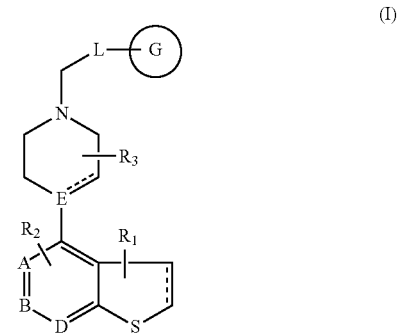

17 Claims, No Drawings

(51) Int. Cl.
  C07D 413/12    (2006.01)
  C07D 417/12    (2006.01)
  C07D 471/04    (2006.01)
  C07D 495/04    (2006.01)
  C07D 519/00    (2006.01)
  A61K 31/496    (2006.01)
  A61K 31/519    (2006.01)
  A61K 31/4709   (2006.01)
  A61K 31/517    (2006.01)
  A61K 31/538    (2006.01)
  A61K 31/5415   (2006.01)
  A61K 31/55     (2006.01)

(56) References Cited

U.S. PATENT DOCUMENTS

| | | | |
|---|---|---|---|
| 5,824,680 A | 10/1998 | Turner et al. | |
| 2010/0063047 A1 | 3/2010 | Borchardt et al. | |
| 2011/0065690 A1* | 3/2011 | Grembecka | A61K 31/519 514/218 |

FOREIGN PATENT DOCUMENTS

| | | | | |
|---|---|---|---|---|
| CN | 102186479 A | 9/2011 | | |
| CN | 102984941 A | 3/2013 | | |
| JP | 2006-513167 A | 4/2006 | | |
| JP | 2006-316052 A | 11/2006 | | |
| JP | 2008-37850 A | 2/2008 | | |
| JP | 2008-115172 A | 5/2008 | | |
| JP | 2008-115175 A | 5/2008 | | |
| JP | 2014-162781 A | 9/2014 | | |
| JP | 2014162781 A | * | 9/2014 | A61K 31/496 |
| WO | 200016777 A1 | 3/2000 | | |
| WO | 0250067 A2 | 6/2002 | | |
| WO | 2004046124 A1 | 6/2004 | | |
| WO | 2006112464 A1 | 10/2006 | | |
| WO | 2008047883 A1 | 4/2008 | | |
| WO | 2009094279 A1 | 7/2009 | | |
| WO | 2010030757 A2 | 3/2010 | | |
| WO | 2011029054 A1 | 3/2011 | | |
| WO | 2011111875 A1 | 9/2011 | | |
| WO | 2013024291 A2 | 2/2013 | | |
| WO | WO-2016003296 A1 | * | 1/2016 | C07D 401/14 |

OTHER PUBLICATIONS

Yamashita et al. "Heterocyclic Compound" JP 2014162781A (Sep. 8, 2014), English machine translation, obtained [online] from Espacenet Database. Retrieved on Jan. 20, 2018. <https://worldwide.espacenet.com/> (Year: 2014).*

Chemical Abstract Service STN Registry Database RN 1021415-93-9 [Entered STN: May 16, 2008]. (Year: 2008).*

International Search Report for corresponding International Application No. PCT/CN2015/073854 dated Jun. 18, 2015.

CAS Registry No. 1331035-38-1; STN Entry Date Sep. 11, 2011; 6,7,8,9-tetrahydro-3-[(4-thieno[2,3-d]pyrimidin-4-yl-1-piperazinyl)methyl]-5H-1,2,4-Triazolo[4,3-a]azepine.

Grembecka, J. et al., "Menin-MLL inhibitors reverse oncogenic activity of MLL fusion proteins in leukemia", Nature Chemical Biology, vol. 8, Jan. 2012, pp. 277-284.

European Search Report for corresponding European Application No. 15757771.9 dated Mar. 28, 2017.

Database Registry [Online] Chemical Abstracts Service, Columbus, Ohio, US; Aug. 28, 2011, XP002765685, retrieved from STN; Database accession No. 1324587-94-1.

Database Registry [Online] Chemical Abstracts Service, Columbus, Ohio, US; Aug. 31, 2011, XP002765686, retrieved from STN; Database accession No. 1326276-13-4.

Database Registry [Online] Chemical Abstracts Service, Columbus, Ohio, US; Sep. 11, 2011, XP002765687, retrieved from STN; Database accession No. 1331079-26-5.

Database Registry [Online] Chemical Abstracts Service, Columbus, Ohio, US; Sep. 18, 2012, XP002765688, retrieved from STN; Database accession No. 1394718-37-6.

Database Registry [Online] Chemical Abstracts Service, Columbus, Ohio, US; Feb. 7, 2012, XP002765689, retrieved from STN; Database accession No. 1355745-62-8.

Database Registry [Online] Chemical Abstracts Service, Columbus, Ohio, US; Jul. 7, 2011, XP002765690, retrieved from STN; Database accession No. 1311964-47-2.

Database Registry [Online] Chemical Abstracts Service, Columbus, Ohio, US; May 15, 2011, XP002765691, retrieved from STN; Database accession No. 1294647-95-2.

Database Registry [Online] Chemical Abstracts Service, Columbus, Ohio, US; Sep. 16, 2010, XP002765692, retrieved from STN; Database accession No. 1241659-07-3.

Database Registry [Online] Chemical Abstracts Service, Columbus, Ohio, US; May 20, 2009, XP002765693, retrieved from STN; Database accession No. 1147758-38-0.

Database Registry [Online] Chemical Abstracts Service, Columbus, Ohio, US; Apr. 9, 2007, XP002768251, retrieved from STN, Database accession No. 929445-63-6.

Database Registry [Online] Chemical Abstracts Service, Columbus, Ohio, US; Mar. 20, 2007, XP002768252, retrieved from STN; Database accession No. 927576-45-2.

Database Registry [Online] Chemical Abstracts Service, Columbus, Ohio, US; Dec. 28, 2008, XP002768253, retrieved from STN; Database accession No. 1090704-58-7.

Database Registry [Online] Chemical Abstracts Service, Columbus, Ohio, US; Apr. 2, 2010, XP002768254, retrieved from STN; Database accession No. 1215526-35-4.

Database Registry [Online] Chemical Abstracts Service, Columbus, Ohio, US; Apr. 4, 2010, XP002768255, retrieved from STN; Database accession No. 1216599-30-2.

Database Registry [Online] Chemical Abstracts Service, Columbus, Ohio, US; May 19, 2011, XP002768256, retrieved from STN; Database accession No. 1297398-96-9.

Examination Report for corresponding Australian Application No. 2015226578 dated Jan. 19, 2017.

Examination Report for corresponding Australian Application No. 2015226578 dated Jul. 31, 2017.

Office Action for corresponding Japanese Application No. 2016-556278 dated Aug. 29, 2017.

Office Action for corresponding Chinese Application No. 201410853950.9 dated Jun. 15, 2017.

CAS Registry No. 1311748-02-3; STN Entry Date Jul. 7, 2011; 4-[3-methyl-4-[(1-methyl-1H-imidazol-2-yl)methyl]-1-piperazinyl]-Thieno[2,3-d]pyrimidine.

CAS Registry No. 1301595-14-1; STN Entry Date May 27, 2011; 2-[[4-(6-ethylthieno[2,3-d]pyrimidin-4-yl)-1-piperazinyl]methyl]-4-Quinazolinamine.

CAS Registry No. 1269222-01-6; STN Entry Date Mar. 21, 2011; 5-[[4-(5-ethyl-6-methylthieno[2,3-d]pyrimidin-4-yl)-1-piperazinyl]methyl]-2-Furanmethanol.

CAS Registry No. 930055-49-5; STN Entry Date Apr. 13, 2007; 2-[[4-[2-[(diethylamino)methyl]-5,6-dimethylthieno[2,3-d]pyrimidin-4 yl]-1-piperazinyl]methyl]-4(3H)-Quinazolinone.

CAS Registry No. 1330518-02-9; STN Entry Date Sep. 9, 2011; 5,6-dimethyl-4-[4-(3-thienylmethyl)-1-piperazinyl]-Thieno[2,3-d]pyrimidine.

CAS Registry No. 434916-97-9; STN Entry Date Jun. 28, 2002; 4-[4-(1,3-benzodioxol-5-ylmethyl)-1-piperazinyl]-2,6-dimethyl-Thieno[2,3-d]pyrimidine.

CAS Registry No. 1323856-54-7; STN Entry Date Aug. 26, 2011; 4-[4-[(2,3-dihydro-1,4-benzodioxin-6-yl)methyl]-1-piperazinyl]-Thieno[2,3-d]pyrimidine.

CAS Registry No. 920727-99-7; STN Entry Date Feb. 13, 2007; 5,6-dimethyl-2 [(4-thieno[2,3-d]pyrimidin-4-yl-1-piperazinyl)methyl]-Thieno[2,3-d]pyrimidin-4(1H)-one.

* cited by examiner

HETEROCYCLIC COMPOUNDS, PROCESS FOR PREPARATION OF THE SAME AND USE THEREOF

CROSS REFERENCE TO RELATED APPLICATIONS

This application is a national stage application of International Application No. PCT/CN2015/073854, filed Mar. 9, 2015, which claims the benefit of and priority to Chinese Patent Application Nos. 201410083602.8 and 201410853950.9, filed Mar. 7, 2014 and Dec. 31, 2014, respectively, the entire contents of each of which are hereby incorporated by reference herein in their entireties.

TECHNICAL FIELD

The present invention belongs to the field of medicinal chemistry. More specifically, the present invention provide a heterocyclic compound represented by general formula (I), stereoisomer or pharmaceutically acceptable salt thereof, the producing processes thereof, pharmaceutical compositions and their use in the manufacture of drugs for the treatment of central nervous system diseases.

BACKGROUND ART

Mental illness is a group of neurological disease mainly manifested in behavior and mental activity disorder, clinically manifested in abnormal mental activity, specifically manifested in disorders in varying degrees in perception, thinking, attention, memory, emotion, behavior, intelligence and consciousness.

Due to the complexity of the central nervous system, conventional antipsychotics still have their limitations. For example, the clinical drugs for the treatment of major depressive disorder (MDD) and anxiety have slow onset of action and poor efficacy; existing antipsychotic drugs are mostly ineffective in improving the negative symptoms and cognitive impairment in schizophrenia, and they are usually associated with side effects such as extrapyramidal reactions (EPS) and metabolic disorder. Therefore, there is a need to find new antipsychotics with high efficacy, low side effect, and broad treatment spectrum.

Dopamine system is involved in the regulation of many physiological functions such as movement, emotion, reward and cognition. Serotonin (5-HT) is also involved in the regulation of many physiological functions, such as body temperature regulation, emotional activities, pain, sleep-awakening. Therefore, the therapeutic effects of existing drugs for the treatment of central nervous system disease correlate closely to the regulation of neurotransmitters such as dopamine and 5-HT in the brain.

$D_2$ receptor antagonists are developed as typical antipsychotics and they are also used in the treatment of insomnia; 5-$HT_{2A}$ receptor antagonism can reduce EPS, improve negative symptoms, cognitive impairment, depression, anxiety and insomnia (European Journal of Pharmacology, 2000, 407: 39-46). However, pure $D_2$ antagonists or $D_2$/5-$HT_{2A}$ antagonists still have side effects of varying degrees.

5-$HT_{1A}$ receptor agonists have showed good prospect for the clinical treatment of severe depression, anxiety, depression and improvement of negative symptoms and cognitive function in patients with schizophrenia (CNS Drugs, 2013 September, 27: 703-16). For example, 5-$HT_{1A}$ receptor agonist BAY-3702 showed neuroprotective, anxiolytic and antidepressant effects in animal models (European Journal of Pharmacology, 1998, 357: 1-8); gepirone can be used to alleviate specific primary depressive disorder (U.S. Pat. No. 4,771,053), such as severe depression, endogenous depression and atypical depression; buspirone can be used to treat various symptoms associated with attention deficit and hyperactivity disorder (ADHD). $D_2$ receptor agonist in combination with 5-$HT_{1A}$ receptor agonist can be effective in the treatment of ADHD and Parkinson's disease (WO200016777A); ixabepilone can be effective in the treatment of cognitive impairment associated with Alzheimer's disease or Parkinson's disease by improving memory (U.S. Pat. No. 5,824,680).

Dopamine receptor partial agonists can improve the positive symptoms, negative symptoms, depression, anxiety and cognitive deficits associated with schizophrenia while rarely cause increased serum prolactin level as $D_2$ receptor antagonists, rarely cause weight gain and metabolic disorders as $D_2$/5-$HT_{2A}$ receptor antagonists. Generally, they are safety and well tolerated.

Thus, a drug has multiple pharmacological effects on DA/5-HT receptors is conducive to better regulation of DA/5-HT system in the brain so as to treat central nervous system diseases. The present invention provides a novel class of compounds endowed with $D_2$/5-$HT_{1A}$/5-$HT_{2A}$ multireceptor activities that are effective for the treatment of central nervous system disorders, particularly depression, manic-depression, schizophrenia, anxiety, phobias, autism, Alzheimer's disease, bipolar disorder, hysteria, obsessive-compulsive disorder, hyperkinetic syndrome and the like.

DISCLOSURE OF THE INVENTION

Object of the Invention

It is an object of the present invention to provide a novel class of compounds have serotonin 2A (5-$HT_{2A}$) receptor antagonism activity and/or good activity on dopamine $D_2$ receptor and/or good activity on serotonin 1A (5-$HT_{1A}$) receptor. An object of the present invention is to provide a heterocyclic compound represented by the general formula (I), a stereoisomer thereof or a pharmaceutically acceptable salt thereof.

Another object of the present invention is to provide a process for preparing a heterocyclic compound represented by the general formula (I), a stereoisomer thereof or a pharmaceutically acceptable salt thereof. A further object of the present invention is to provide a heterocyclic compound of the general formula (I), a stereoisomer thereof or a pharmaceutically acceptable salt thereof in the manufacture of drugs for the prevention and/or treatment of central nervous system disease.

A further object of the present invention is to provide pharmaceutical compositions containing a therapeutically effective amount of the compound of the general formula (I) of the present invention, a stereoisomer thereof or a pharmaceutically acceptable salt thereof.

SUMMARY OF THE INVENTION

The present invention provides a heterocyclic compound represented by formula (I), a stereoisomer, or a pharmaceutically acceptable salt thereof:

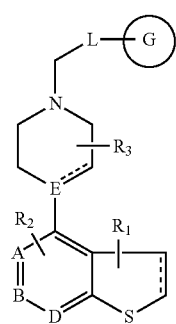

(I)

wherein:

A, B and D are each independently C or N, and when A is N, D is N simultaneously;

=== represents a single or double bond;

E is CH, N or C; when E is CH or N, the bond === connected to E represents a single bond; when E is C, the bond === connected to E represents a double bond;

$R_1$ is hydrogen or 1 to 4 substituents each independently selected from the group consisting of halogen, hydroxy, mercapto, oxo(=O), thioxo(=S), C1~C6 alkoxy, halogenated C1~C6 alkoxy, C1~C6 alkylthio, C1~C6 alkyl, halogenated C1~C6 alkyl, nitro, amino, C1~C6 alkyl-substituted amino, cyano, carboxy, aldehyde group, amino C1~C6 alkyl, hydroxyl C1~C6 alkyl, cyano C1~C6 alkyl, C1~C6 alkanoyl, halogenated C1~C6 alkanoyl, sulfonic group (—SO$_2$OH), aminosulfonyl(—SO$_2$NH$_2$), carbamoyl(—CONH$_2$), C1~C6 alkyl-substituted carbamoyl, carboxyl C1~C6 alkyl, C1~C6 alkylsulfonyl, halogenated C1~C6 alkylsulfonyl, C1~C6 alkyl-substituted amino C1~C6 alkyl, carbamoyl C1~C6 alkyl and C1~C6 alkyl-substituted carbamoyl C1~C6 alkyl group;

preferably, $R_1$ is hydrogen or 1 to 4 substituents each independently selected from the group consisting of halogen, hydroxy, mercapto, oxo(=O), thioxo(=S), C1~C4 alkoxy, halogenated C1~C4 alkoxy, C1~C4 alkylthio, C1~C4 alkyl, halogenated C1~C4 alkyl, nitro, amino, C1~C4 alkyl-substituted amino, cyano, carboxy, aldehyde group, amino C1~C4 alkyl, hydroxyl C1~C4 alkyl, cyano C1~C4 alkyl, C1~C4 alkanoyl, halogenated C1~C4 alkanoyl, sulfonic group(—SO$_2$OH), aminosulfonyl(—SO$_2$NH$_2$), carbamoyl (—CONH$_2$), C1~C4 alkyl-substituted carbamoyl, carboxyl C1~C4 alkyl, C1~C4 alkylsulfonyl, halogenated C1~C4 alkylsulfonyl, C1~C4 alkyl-substituted amino C1~C4 alkyl, carbamoyl C1~C4 alkyl and C1~C4 alkyl-substituted carbamoyl C1~C4 alkyl group;

more Preferably, $R_1$ is hydrogen or 1 to 4 substituents each independently selected from the group consisting of fluorine, chlorine, bromine, hydroxy, mercapto, oxo(=O), thioxo(=S), methoxy, ethoxy, trifluoromethoxy, —SCH$_3$, —SCH$_2$CH$_3$, methyl, ethyl, propyl, isopropyl, t-butyl, trifluoromethyl, bromomethyl, chloromethyl, nitro, amino, N-methylamino, N-ethylamino, N, N-dimethylamino, N,N-diethylamino, cyano, carboxyl, aldehyde group, —CH$_2$NH$_2$, —CH$_2$CH$_2$NH$_2$, —CH$_2$OH, —CH$_2$CH$_2$OH, —CH$_2$CN, —CH$_2$CH$_2$CN, formyl, acetyl, propionyl, trifluoroacetyl, sulfonic group(—SO$_2$OH), aminosulfonyl (—SO$_2$NH$_2$), carbamoyl, N-methylcarbamoyl, N,N-dimethylcarbamoyl, N-ethylcarbamoyl, N,N-diethylcarbamoyl, —CH$_2$CO$_2$H, —CH$_2$CH$_2$CO$_2$H, —SO$_2$CH$_3$, —SO$_2$CF$_3$, —CH$_2$NHMe, —CH$_2$NMe$_2$, —CH$_2$CONH$_2$, —CH$_2$CONHMe and —CH$_2$CONMe$_2$;

$R_2$ does not exist, or is 1 to 3 substituents each independently selected from the group consisting of halogen, hydroxy, mercapto, C1~C6 alkoxy, halogenated C1~C6 alkoxy, C1~C6 alkylthio, C1~C6 alkyl, halogenated C1~C6 alkyl, nitro, amino, C1~C6 alkyl-substituted amino, cyano, carboxyl, aldehyde group, amino C1~C6 alkyl, hydroxyl C1~C6 alkyl, cyano C1~C6 alkyl, C1~C6 alkanoyl, halogenated C1~C6 alkanoyl, sulfonic group (—SO$_2$OH), aminosulfonyl (—SO$_2$NH$_2$), carbamoyl (—CONH$_2$), C1~C6 alkyl-substituted carbamoyl, carboxy C1~C6 alkyl, C1~C6 alkylsulfonyl, halogenated C1~C6 alkylsulfonyl, C1~C6 alkyl-substituted amino C1~C6 alkyl, carbamoyl C1~C6 alkyl and C1~C6 alkyl-substituted carbamoyl C1~C6 alkyl group;

preferably, $R_2$ does not exist, or is 1 to 3 substituents each independently selected from the group consisting of halogen, hydroxy, mercapto, C1~C4 alkoxy, halogenated C1~C4 alkoxy, C1~C4 alkylthio, C1~C4 alkyl group, halogenated C1~C4 alkyl, nitro, amino, C1~C4 alkyl-substituted amino, cyano, carboxyl, aldehyde group, amino C1~C4 alkyl, hydroxyl C1~C4 alkyl, cyano C1~C4 alkyl, C1~C4 alkanoyl, halogenated C1~C4 alkanoyl, sulfonic group(—SO$_2$OH), aminosulfonyl(—SO$_2$NH$_2$), carbamoyl(—CONH$_2$), C1~C4 alkyl-substituted carbamoyl, carboxy C1~C4 alkyl, C1~C4 alkylsulfonyl, halogenated C1~C4 alkylsulfonyl, C1~C4 alkyl-substituted amino C1~C4 alkyl, carbamoyl C1~C4 alkyl and C1~C4 alkyl-substituted carbamoyl C1~C4 alkyl group;

more Preferably, $R_2$ does not exist, or is 1 to 3 substituents each independently selected from the group consisting of fluorine, chlorine, bromine, hydroxy, mercapto, methoxy, ethoxy, trifluoromethoxy, —SCH$_3$, —SCH$_2$CH$_3$, methyl, ethyl, propyl, isopropyl, t-butyl, trifluoromethyl, bromomethyl, chloromethyl, nitro, amino, N-methylamino, N-ethylamino, N, N-dimethylamino, N,N-diethylamino, cyano, carboxyl, aldehyde group, —CH$_2$OH, —CH$_2$CH$_2$OH, —CH$_2$CN, —CH$_2$CH$_2$CN, formyl, acetyl, propionyl, trifluoroacetyl, sulfonic acid group (—SO$_2$OH), aminosulfonyl (—SO$_2$NH$_2$), carbamoyl, N-methylcarbamoyl, N, N-dimethylcarbamoyl, N-ethylcarbamoyl, N,N-diethyl carbamoyl, —CH$_2$CO$_2$H, —CH$_2$CH$_2$CO$_2$H, —SO$_2$CH$_3$, —SO$_2$CF$_3$, —CH$_2$NH$_2$, —CH$_2$CH$_2$NH$_2$, —CH$_2$NHMe, —CH$_2$NMe$_2$, —CH$_2$CONH$_2$, —CH$_2$CONHMe and —CH$_2$CONMe$_2$;

$R_3$ is hydrogen or 1 to 4 substituents each independently selected from the group consisting of hydroxyl and C1~C6 alkyl group; preferably $R_3$ is hydrogen or 1 to 4 substituents each independently selected from the group consisting of hydroxyl and C1~C4 alkyl group; more preferably $R_3$ is hydrogen or 1 to 4 substituents each independently selected from the group consisting of hydroxyl, methyl and ethyl group;

L does not exist or is C1~C5 alkylene group(e.g., C1 alkylene, C2 alkylene, C3 alkylene, C4 alkylene, C5 alkylene group), and when L is C1~C5 alkylene group, the alkylene group is optionally substituted with one or more substituents selected from the group consisting of hydroxy, C1~C6 alkoxy and oxo(O=) group; Preferably, L does not exist or is C1~C4 alkylene group, and when L is C1~C4 alkylene group, the alkylene group is optionally substituted with one or more substituents selected from the group consisting of hydroxy, C1~C6 alkoxy and oxo(O=) group;

ring G is a heteromonocyclic or heterobicyclic group, said heterobicyclic group is a phenyl-fused heteromonocyclic group, a cyclohydrocarbyl-fused heteromonocyclic group or a heteromonocycle-fused heteromonocyclic group, wherein said heteromonocyclic group contains at least one heteroatom selected from the group consisting of N, S and O;

preferably ring G is a 3 to 10-membered heteromonocyclic group, a phenyl-fused 3 to 10-membered heteromonocyclic group, a C3~C10 cyclohydrocarbyl-fused 3 to 10-membered heteromonocyclic group or 3 to 10-membered heteromonocycle-fused 3 to 10-membered heteromonocyclic group;

more preferably, ring G is a 5 to 7-membered heteromonocyclic group, a phenyl-fused 5 to 7-membered heteromonocyclic group, a C5~C7 cyclohydrocarbyl-fused 5 to 7-membered heteromonocyclic group or a 5 to 7-membered heteromonocycle-fused 5 to 7-membered heteromonocyclic group;

more preferably, ring G is a heterocyclic group selected from the group consisting of furyl, dihydrofuranyl, tetrahydrofuranyl, thienyl, dihydrothienyl, tetrahydrothienyl, pyrrolyl, dihydro-pyrrolyl, pyrrolidinyl, pyrazolyl, dihydropyrazolyl, pyrazolidinyl, triazolyl, dihydro-triazole, triazolidinyl, thiazolyl, dihydro-thiazolyl, thiazolidinyl, isothiazolyl, dihydro-isothiazolyl, isothiazolidinyl, oxazolyl, dihydro-oxazolyl, oxazolidinyl, isoxazolyl, dihydro-isoxazolyl, isoxazolidinyl, pyranyl, dihydropyranyl, tetrahydropyranyl, pyrazinyl, dihydropyrazinyl, tetrahydro-pyrazinyl, piperazinyl, pyridazinyl, dihydropyridazinyl, tetrahydropyridazinyl,

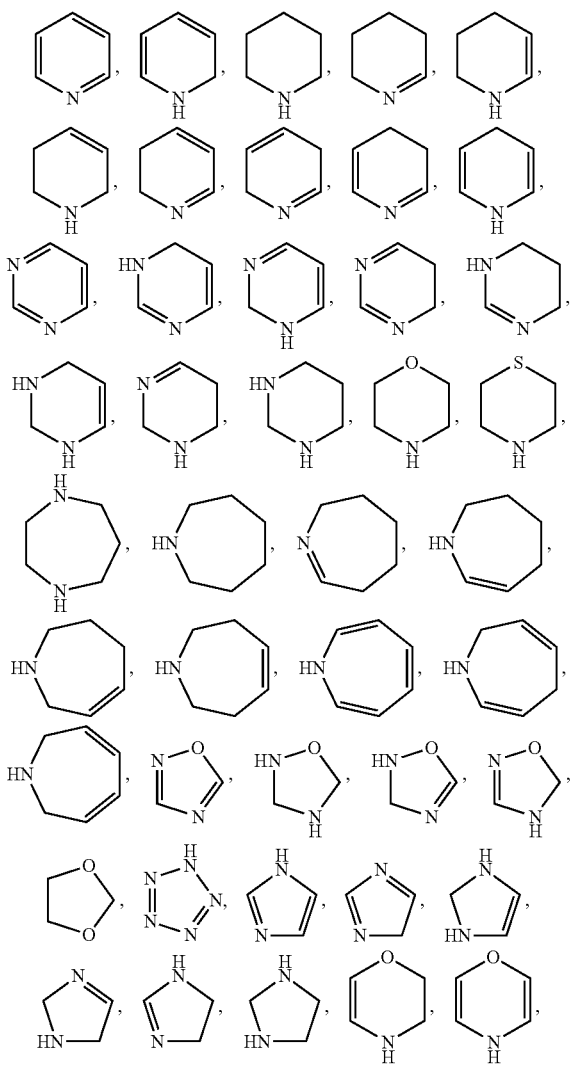

-continued

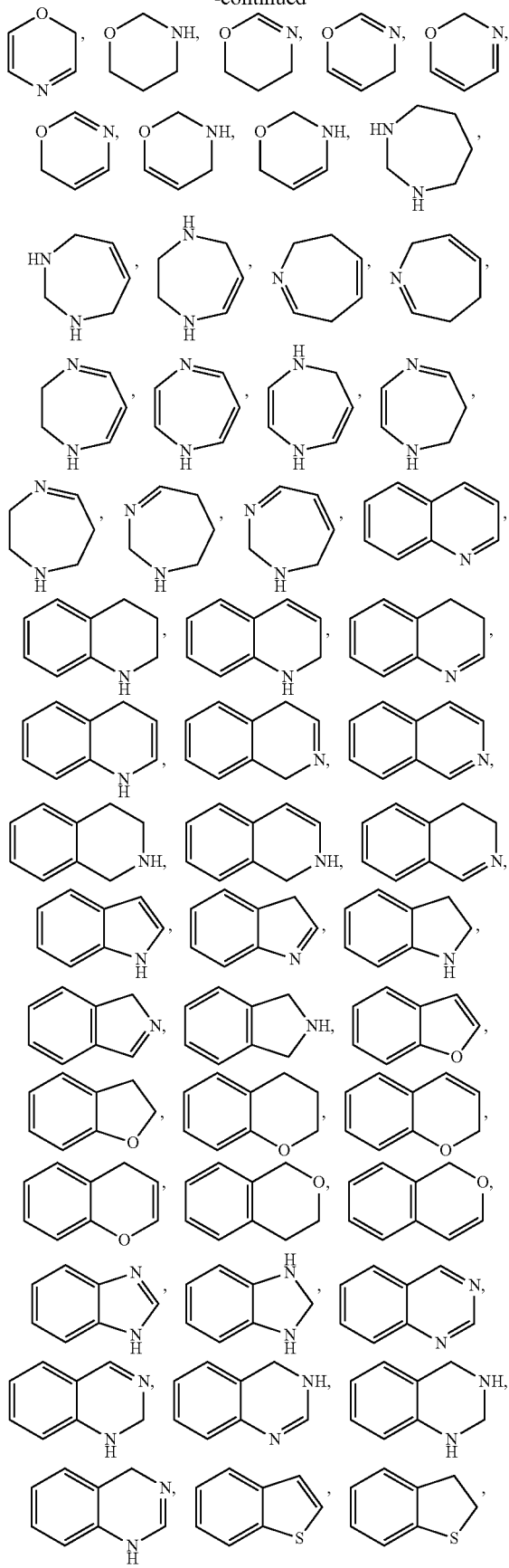

7
-continued
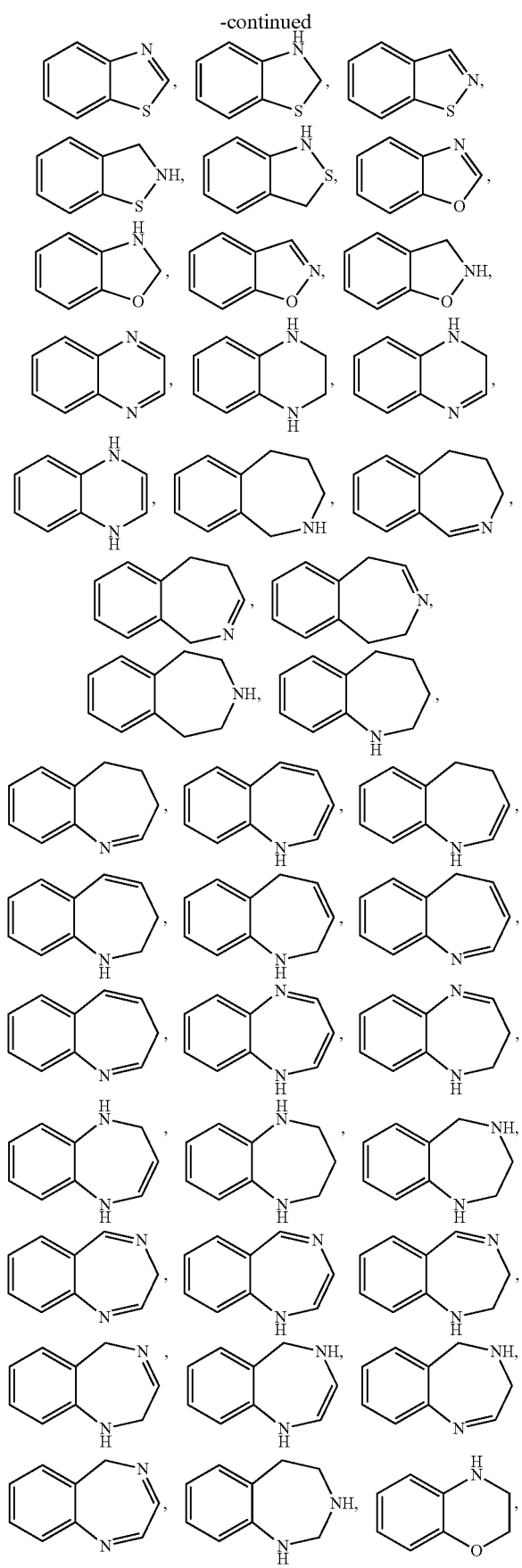
8
-continued
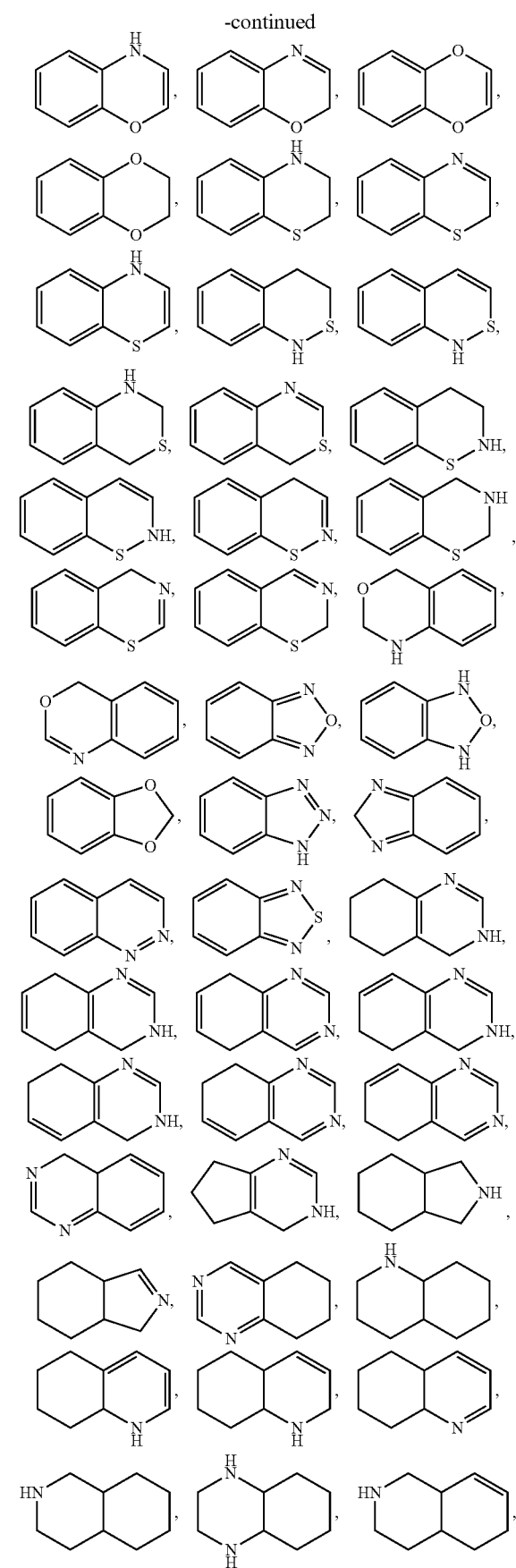

-continued
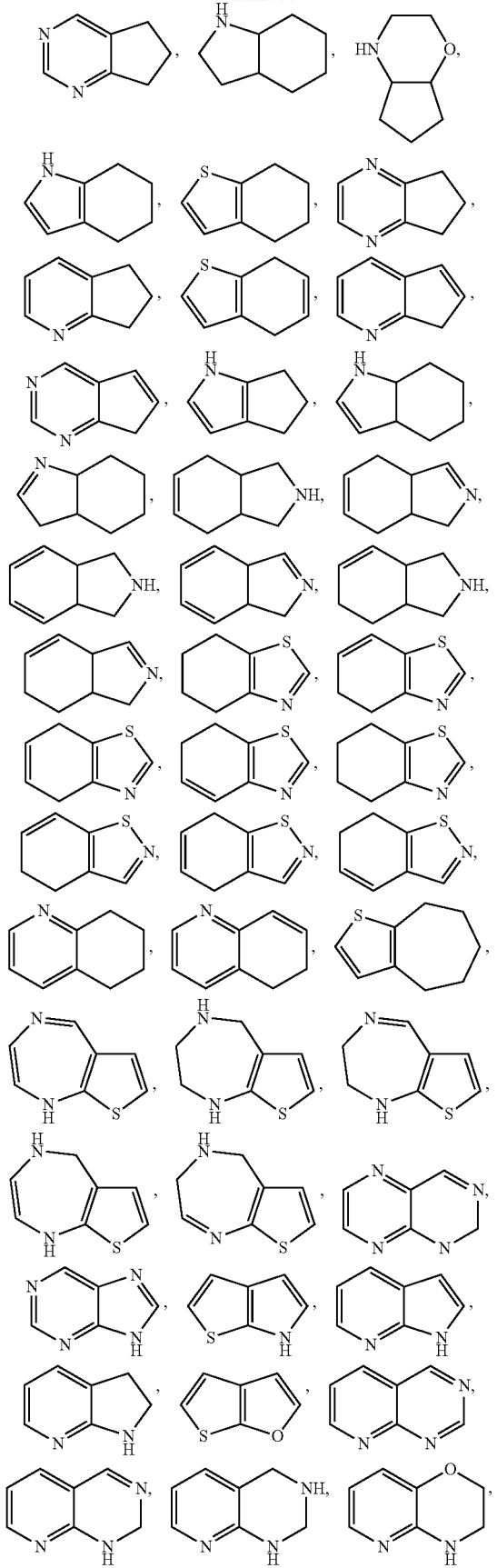
-continued
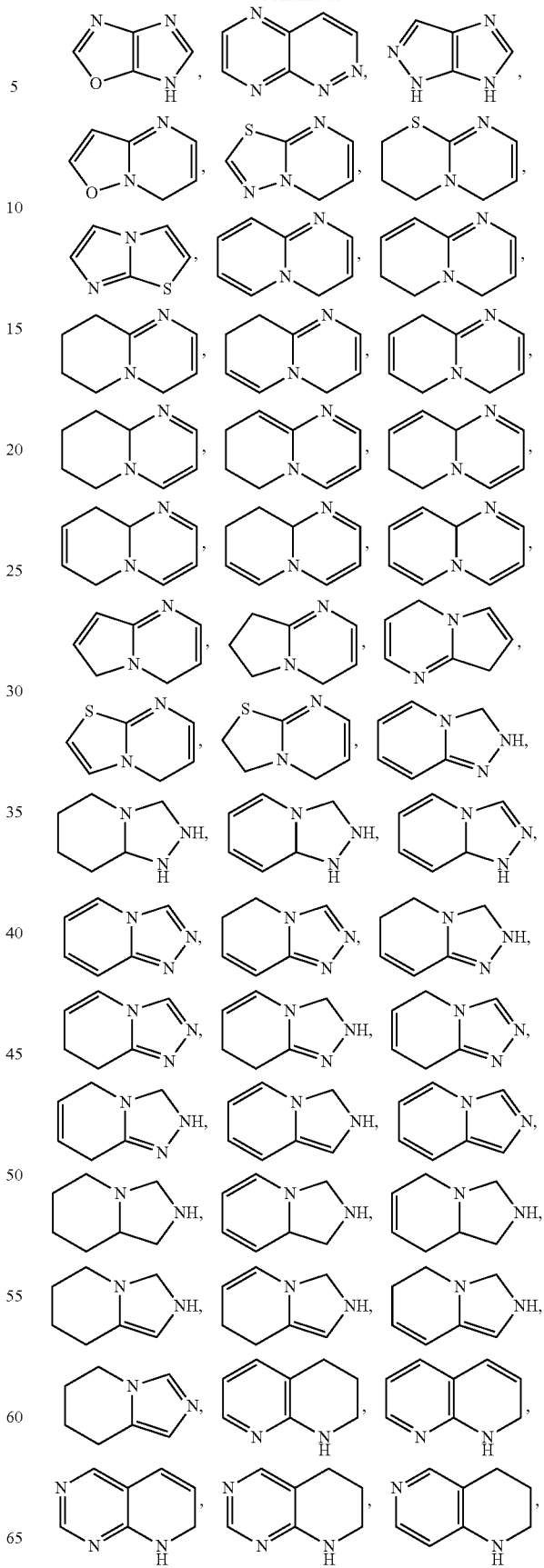

-continued

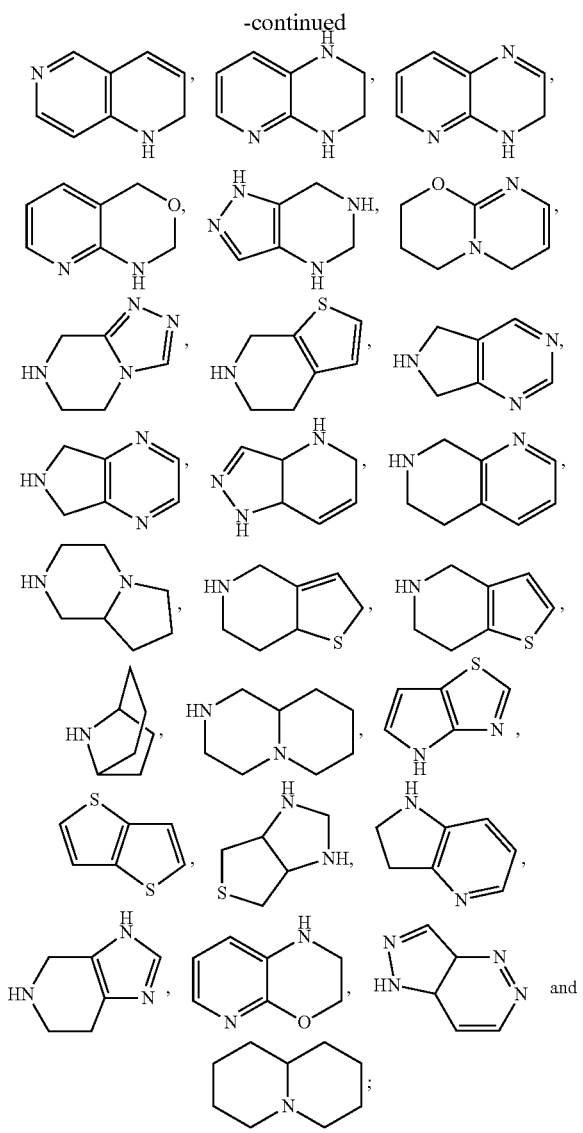

and

Ring G is connected to L through a carbon atom on G ring rather than other atoms; and ring G is optionally substituted with one or more substituents which are identical or different;

the substituent on the ring G is selected from the group consisting of halogen, C1~C6 alkyl, halogenated C1~C6 alkyl, C1~C6 alkoxy, halogenated C1~C6 alkoxy, nitro, cyano, hydroxy, mercapto, amino, C1~C6 alkyl-substituted amino, azido, C1~C6 alkanoyl, halogenated C1~C6 alkanoyl, C2~C6 alkenyl, C2~C6 alkynyl, carboxy C1~C6 alkyl, cyano C1~C6 alkyl, C2~C6 alkenyloxy, carboxy C1~C6 alkyl, cyano C1~C6 alkyl, C2~C6 alkenyloxy, C2~C6 alkynyloxy, carbamoyl(—CONH$_2$), C1~C6 alkyl-substituted carbamoyl, carboxyl, hydroxyl C1~C6 alkyl, oxo(=O), thioxo(=S), sulfonamido, C1~C6 alkylthio, C1~C6 alkylsulfonyl, halogenated C1~C6 alkylsulfonyl, sulfonic group(—SO$_2$OH), aldehyde group, amino C1~C6 alkyl, C1~C6 alkyl-substituted amino C1~C6 alkyl, carbamoyl C1~C6 alkyl, C1~C6 alkyl-substituted carbamoyl C1~C6 alkyl, C3~C10 cyclohydrocarbyl, C3~C10 cyclohydrocarbyl C1~C6 alkyl, C3~C10 cyclohydrocarbylformamido, furyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C10 cyclohydrocarbyl C1~C6 alkoxy, furyl C1~C6 alkyl, furanyl C1~C6 alkoxy, thienyl C1~C6 alkyl, thienyl C1~C6 alkoxy, pyrrolyl C1~C6 alkyl, pyrrolyl C1~C6 alkoxy, pyrrolidinyl C1~C6 alkyl, pyrrolidinyl C1~C6 alkoxy, pyrazolyl C1~C6 alkyl, pyrazolyl C1~C6 alkoxy, triazolyl C1~C6 alkyl, triazolyl C1~C6 alkoxy, thiazolyl C1~C6 alkyl, thiazolyl C1~C6 alkoxy, isothiazolyl C1~C6 alkyl, isothiazolyl C1~C6 alkoxy, oxazolyl C1~C6 alkyl, oxazolyl C1~C6 alkoxy, isoxazolyl C1~C6 alkyl, isoxazolyl C1~C6 alkoxy, pyrazinyl C1~C6 alkyl, pyrazinyl C1~C6 alkoxy, pyridazinyl C1~C6 alkyl, pyridazinyl C1~C6 alkoxy, pyridyl C1~C6 alkyl, pyridyl C1~C6 alkoxy, pyrimidinyl C1~C6 alkyl, pyrimidinyl C1~C6 alkoxy, phenyl, phenoxy, phenylsulfonyl, phenyl C1~C6 alkyl, phenyl C1~C6 alkoxy, phenyl C1~C6 alkanoyl and phenyl C1~C6 alkanoyloxy group;

said C3~C10 cyclohydrocarbyl, C3~C10 cyclohydrocarbyl C1~C6 alkyl group, furyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C10 cyclohydrocarbyl C1~C6 alkoxy, furyl C1~C6 alkyl, furanyl C1~C6 alkoxy, thienyl C1~C6 alkyl, thienyl C1~C6 alkoxy, pyrrolyl C1~C6 alkyl, pyrrolyl C1~C6 alkoxy, pyrrolidinyl C1~C6 alkyl, pyrrolidinyl C1~C6 alkoxy, pyrazolyl C1~C6 alkyl, pyrazolyl C1~C6 alkoxy, triazolyl C1~C6 alkyl, triazolyl C1~C6 alkoxy, thiazolyl C1~C6 alkyl, thiazolyl C1~C6 alkoxy, isothiazolyl C1~C6 alkyl, isothiazolyl C1~C6 alkoxy, oxazolyl C1~C6 alkyl, oxazolyl C1~C6 alkoxy, isoxazolyl C1~C6 alkyl, isoxazolyl C1~C6 alkoxy, pyrazinyl C1~C6 alkyl, pyrazinyl C1~C6 alkoxy, pyridazinyl C1~C6 alkyl, pyridazinyl C1~C6 alkoxy, pyridyl C1~C6 alkyl, pyridyl C1~C6 alkoxy, pyrimidinyl C1~C6 alkyl, pyrimidinyl C1~C6 alkoxy, phenyl, phenoxy, phenylsulfonyl, phenyl C1~C6 alkyl, phenyl C1~C6 alkoxy, phenyl C1~C6 alkanoyl or phenyl C1~C6 alkanoyloxy group is optionally substituted with one or more substituents selected from the group consisting of halogen, C1~C6 alkyl, halogenated C1~C6 alkyl, C1~C6 alkoxy, C1~C6 alkoxycarbonyl, halogenated C1~C6 alkoxy, nitro, cyano, hydroxy, amino, C1~C6 alkanoyl, halogenated C1~C6 alkanoyl, carbamoyl and carboxyl group;

preferably, the substituent on the ring G is selected from the group consisting of halogen, C1~C4 alkyl, halogenated C1~C4 alkyl, C1~C4 alkoxy, halogenated C1~C4 alkoxy, nitro, cyano, hydroxy, mercapto, amino, C1~C4 alkyl-substituted amino, azido, C1~C4 alkanoyl, halogenated C1~C4 alkanoyl, C2~C4 alkenyl, C2<C4 alkynyl, carboxy C1~C4 alkyl, cyano C1~C4 alkyl, C2~C4 alkenyloxy, C2'C4 alkynyloxy, carbamoyl(—CONH$_2$), C1~C4 alkyl-substituted carbamoyl, carboxyl, hydroxyl C1~C4 alkyl group, oxo (=O), thioxo(=S), sulfonamido, C1~C4 alkylthio, C1~C4 alkylsulfonyl, halogenated C1~C4 alkylsulfonyl, sulfonic group (—SO$_2$OH), aldehyde group, amino C1~C4 alkyl, C1~C4 alkyl-substituted amino C1~C4 alkyl, carbamoyl C1~C4 alkyl, C1~C4 alkyl-substituted carbamoyl C1~C4 alkyl, C3~C7 cyclohydrocarbyl, C3~C7 cyclohydrocarbyl C1~C4 alkyl, C3~C7 cyclohydrocarbyl formamido, furyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C7 cyclohydrocarbyl C1~C4 alkoxy, furyl C1~C4 alkyl, furanyl C1~C4 alkoxy, thienyl C1~C4 alkyl, thienyl C1~C4 alkoxy, pyrrolyl C1~C4 alkyl, pyrrolyl C1~C4 alkoxy, pyrrolidinyl C1~C4 alkyl, pyrrolidinyl C1~C4 alkoxy, pyrazolyl C1~C4 alkyl, pyrazolyl C1~C4 alkoxy, triazolyl C1~C6 alkyl, triazolyl C1~C4 alkoxy, thiazolyl C1~C4 alkyl, thiazolyl C1~C4 alkoxy, isothiazolyl C1~C6 alkyl, isothiazolyl C1~C4 alkoxy, oxazolyl C1~C4 alkyl, oxazolyl C1~C4 alkoxy, isoxazolyl C1~C4 alkyl, isoxazolyl C1~C4 alkoxy, pyrazinyl C1~C4 alkyl, pyrazinyl C1~C4 alkoxy, pyridazinyl C1~C4 alkyl, pyridazinyl C1~C4 alkoxy, pyridyl C1~C4 alkyl, pyridyl C1~C4 alkoxy, pyrimidinyl C1~C4 alkyl, pyrimidinyl C1~C4 alkoxy, phenyl, phenoxy, phenylsulfonyl, phenyl C1~C4 alkyl, phenyl C1~C4 alkoxy, phenyl C1~C4 alkanoyl and phenyl C1~C4 alkanoyloxy group;

said C3~C7 cyclohydrocarbyl, C3~C7 cyclohydrocarbyl C1~C4 alkyl, furyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C7 cyclohydrocarbyl C1~C4 alkoxy group, furyl C1~C4 alkyl, furanyl C1~C4 alkoxy, thienyl C1~C4 alkyl, thienyl C1~C4 alkoxy, pyrrolyl C1~C4 alkyl, pyrrolyl C1~C4 alkoxy, pyrrolidinyl C1~C4 alkyl, pyrrolidinyl C1~C4 alkoxy, pyrazolyl C1~C4 alkyl, pyrazolyl C1~C4 alkoxy, triazolyl C1~C4 alkyl, triazolyl C1~C4 alkoxy, thiazolyl C1~C4 alkyl, thiazolyl C1~C4 alkoxy, isothiazolyl C1~C4 alkyl, isothiazolyl C1~C4, oxazolyl C1~C4 alkyl, oxazolyl C1~C4 alkoxy, isoxazolyl C1~C4 alkyl, isoxazolyl C1~C4 alkoxy, pyrazinyl C1~C4 alkyl, pyrazinyl C1~C4 alkoxy, pyridazinyl C1~C4 alkyl, pyridazinyl C1~C4 alkoxy, pyridyl C1~C4 alkyl, pyridyl C1~C4 alkoxy, pyrimidinyl C1~C4 alkyl, pyrimidinyl C1~C4 alkoxy, phenyl, phenoxy, phenylsulfonyl, phenyl C1~C4 alkyl, phenyl C1~C4 alkoxy, phenyl C1~C4 alkanoyl or phenyl C1~C4 alkanoyloxy group is optionally substituted with one or more substituents selected from the group consisting of halogen, C1~C4 alkyl, halogenated C1~C4 alkyl, C1~C4 alkoxy, C1~C4 alkoxycarbonyl, halogenated C1~C4 alkoxy, nitro, cyano, hydroxy, amino, C1~C4 alkanoyl, halogenated C1~C4 alkanoyl, carbamoyl and carboxyl group;

more preferably, the substituent on the ring G is selected from the group consisting of fluorine, chlorine, bromine, methyl, ethyl, propyl, isopropyl, t-butyl, trifluoromethyl, methoxy, ethoxy, trifluoromethoxy, nitro, cyano, hydroxy, mercapto, amino, N-methylamino, N-ethylamino, N,N-dimethylamino, N,N-diethylamino, azido, formyl, acetyl, propionyl, trifluoroacetyl, —CH$_2$CO$_2$H, —CH$_2$CH$_2$CO$_2$H, —CH$_2$CN, —CH$_2$CH$_2$CN, carbamoyl, N-methylcarbamoyl, N,N-dimethylcarbamoyl, N-ethylcarbamoyl, N,N-diethylcarbamoyl, carboxyl, —CH$_2$OH, —CH$_2$CH$_2$OH, oxo(=O), thio(=S), aminosulfonyl group(—SO$_2$NH$_2$), —SCH$_3$, —SCH$_2$CH$_3$, —SO$_2$CH$_3$, —SO$_2$CF$_3$, sulfonic acid group (—SO$_2$OH), aldehyde group, —CH$_2$NH$_2$, —CH$_2$CH$_2$NH$_2$, —CH$_2$NHMe, —CH$_2$NMe$_2$, —CH$_2$NHEt, —CH$_2$NEt$_2$, —CH$_2$CH$_2$NHMe, —CH$_2$CH$_2$NHEt, —CH$_2$CH$_2$NMe$_2$, —CH$_2$CH$_2$NEt$_2$, —CH$_2$CONH$_2$, —CH$_2$CONHMe, —CH$_2$CONMe$_2$, —CH$_2$CONHEt, —CH$_2$CONEt$_2$, —CH$_2$CH$_2$CONH$_2$, —CH$_2$CH$_2$CONHMe, —CH$_2$CH$_2$CONMe$_2$, —CH$_2$CH$_2$CONHEt, —CH$_2$CH$_2$CONEt$_2$, phenyl, phenoxy, phenylsulfonyl, —CH$_2$Ph, —CH$_2$CH$_2$Ph, —OCH$_2$Ph, —OCH$_2$CH$_2$Ph, —COPh, —COCH$_2$Ph and —CH$_2$Ph(OMe)$_2$;

provided that the following compounds are excluded:
1) 1-(2-(4-(2-cyano-7-fluorobenzo[b]thiophen-4-yl)-2-methylpiperazin-1-yl)ethyl)isochroman-6-carboxamide;
2) 1-(2-(4-(7-fluorobenzo[b]thiophen-4-yl)-2-methylpiperazin-1-yl)ethyl)isochroman-6-carboxamide;
3) 6-ethyl-4-(4-(2-(thiophen-2-yl)ethyl)piperazin-1-yl)thieno[2,3-d]pyrimidine;
4) 6-(2-(4-(5-methylthieno[2,3-d]pyrimidin-4-yl)piperazin-1-yl)ethyl)-2H-benzo[b][1,4]oxazin-3(4H)-one;
5) 5-(3-(4-(6-ethylthieno[2,3-d]pyrimidin-4-yl)piperazin-1-yl)propyl)-3-(thiophen-2-yl)-1,2,4-oxadiazole;
6) 5-(3-(4-(5,6-dimethylthieno[2,3-d]pyrimidin-4-yl)piperazin-1-yl)propyl)-3-(p-tolyl)-1,2,4-oxadiazole.

In a preferred embodiment,

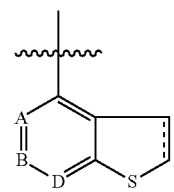

in the heterocyclic compound of the formula (I) of the present invention is selected from the group consisting of

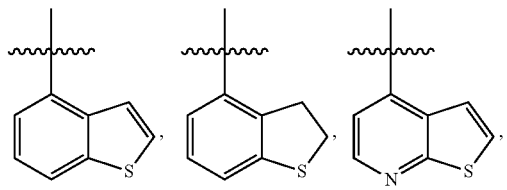

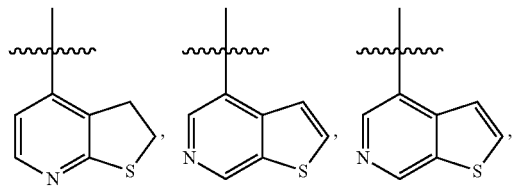

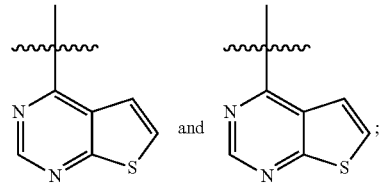

Preferably,

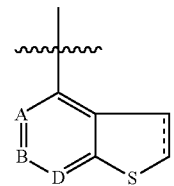

represents
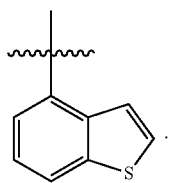.
In a preferred embodiment the heterocyclic compound of the formula (I) of the present invention is represented by the compounds selected from the following:
(I-a)
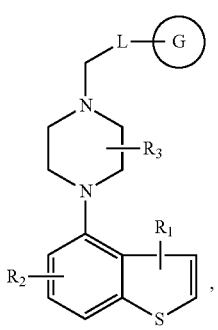,
(I-b)
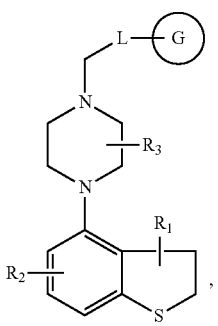,
(I-c)
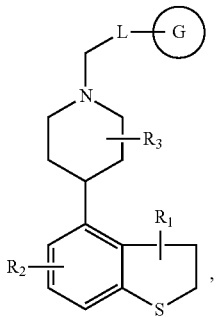,
(I-d)
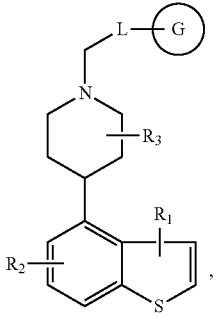,
(I-e)
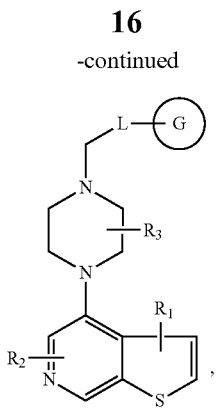,
(I-f)
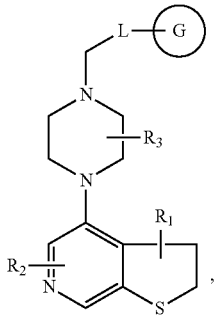,
(I-g)
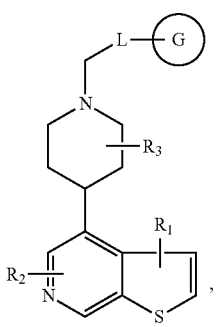,
(I-h)
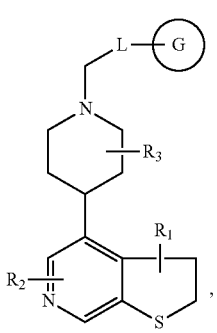,
(I-i)
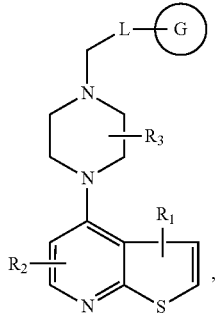,

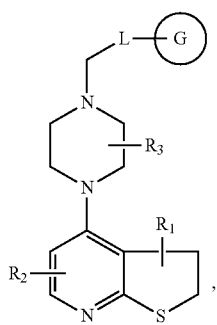
(I-j)
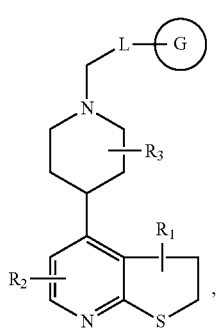
(I-k)
(I-l)
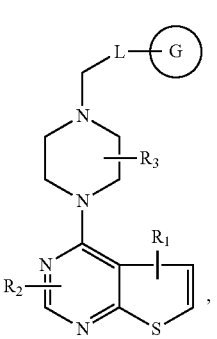
(I-m)
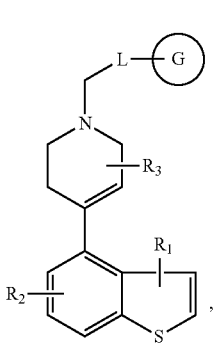
,
(I-n)
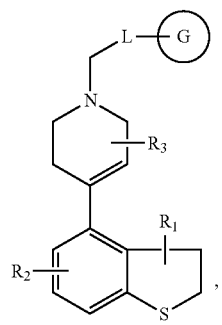
(I-o)
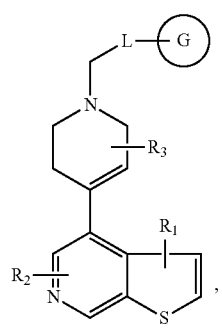
(I-p)
(I-q)
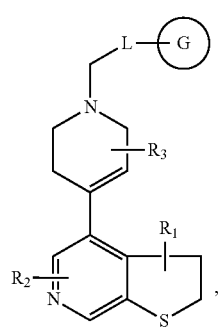
,
(I-r)
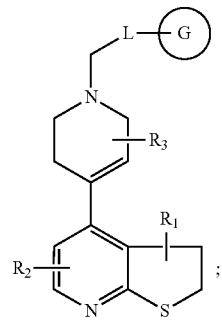
and
(I-s)

more preferably, the heterocyclic compound of the formula (I) of the present invention is represented by a compound selected from the following:

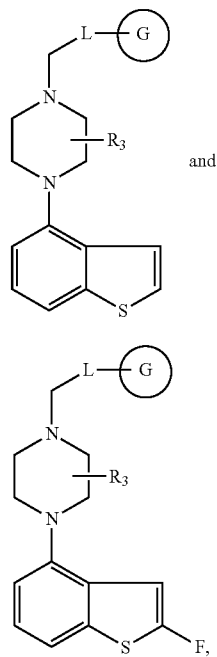

wherein, $R_1$, $R_2$, $R_3$, L and ring G are defined and preferred as hereinbefore.

Among the heterocyclic compound of general formula (I), stereoisomers or pharmaceutically acceptable salt thereof, most preferable compounds include a compound or a pharmaceutically acceptable salt thereof selected from:

(1) 6-chloro-5-(2-(4-(2,3-dihydrobenzo[b]thiophen-4-yl)piperazin-1-yl)ethyl)indolin-2-one;
(2) 3-(2-(4-(2,3-dihydrobenzo[b]thiophen-4-yl)piperazin-1-yl)ethyl)-9-hydroxy-2-methyl-6,7,8,9-tetrahydro-4H-pyrido[1,2-a]pyrimidin-4-one;
(3) 3-(2-(4-(benzo[b]thiophen-4-yl)piperazin-1-yl)ethyl)-2-methyl-6,7,8,9-tetrahydro-4H-pyrido[1,2-a]pyrimidin-4-one;
(4) 3-(2-(4-(benzo[b]thiophen-4-yl)piperazin-1-yl)ethyl)-9-hydroxy-2-methyl-6,7,8,9-tetrahydro-4H-pyrido[1,2-a]pyrimidin-4-one;
(4a) (+)-3-(2-(4-(benzo[b]thiophen-4-yl)piperazin-1-yl)ethyl)-9-hydroxy-2-methyl-6,7,8,9-tetrahydro-4H-pyrido[1,2-a]pyrimidin-4-one;
(4b) (−)-3-(2-(4-(benzo[b]thiophen-4-yl)piperazin-1-yl)ethyl)-9-hydroxy-2-methyl-6,7,8,9-tetrahydro-4H-pyrido[1,2-a]pyrimidin-4-one;
(5) 3-(2-(4-(benzo[b]thiophen-4-yl)piperazin-1-yl)ethyl)-2-methyl-7,8-dihydro-4H-pyrido[1,2-a]pyrimidine-4,9(6H)-dione;
(6) 3-(2-(4-(benzo[b]thiophen-4-yl)piperazin-1-yl)ethyl)-9-hydroxy-2,9-dimethyl-6,7,8,9-tetrahydro-4H-pyrido[1,2-a]pyrimidin-4-one;
(7) 3-(2-(4-(benzo[b]thiophen-4-yl)piperazin-1-yl)ethyl)-9-fluoro-2-methyl-6,7,8,9-tetrahydro-4H-pyrido[1,2-a]pyrimidin-4-one;
(8) 5-(2-(4-(benzo[b]thiophen-4-yl)piperazin-1-yl)ethyl)indolin-2-one;
(9) 7-(2-(4-(benzo[b]thiophen-4-yl)piperazin-1-yl)ethyl)quinolin-2(1H)-one;
(10) 7-(5-(4-(benzo[b]thiophen-4-yl)piperazin-1-yl)pentyl)-3,4-dihydroquinolin-2(1H)-one;
(11) 7-(5-(4-(benzo[b]thiophen-4-yl)piperazin-1-yl)pentyl)quinolin-2(1H)-one;
(12) 7-(5-(4-(2-chlorobenzo[b]thiophen-4-yl)piperazin-1-yl)pentyl)quinolin-2(1H)-one;
(13) 7-(5-(4-(2-fluorobenzo[b]thiophen-4-yl)piperazin-1-yl)pentyl)quinolin-2(1H)-one;
(14) 7-(5-(4-(benzo[b]thiophen-4-yl)-5,6-dihydropyridin-1(2H)-yl)pentyl)quinolin-2(1H)-one;
(15) 5-(2-(4-(benzo[b]thiophen-4-yl)piperazin-1-yl)ethyl)-6-chloroindolin-2-one;
(16) 3-(2-(4-(benzo[b]thiophen-4-yl)piperazin-1-yl)ethyl)-2-methyl-6,7-dihydro-4H-pyrido[1,2-a]pyrimidin-4-one;
(17) 3-(2-(4-(benzo[b]thiophen-4-yl)piperazin-1-yl)ethyl)-9-(benzyloxy)-2-methyl-4H-pyrido[1,2-a]pyrimidin-4-one;
(18) 3-(2-(4-(benzo[b]thiophen-4-yl)piperazin-1-yl)ethyl)-9-hydroxy-2-methyl-4H-pyrido[1,2-a]pyrimidin-4-one;
(19) 7-(2-(4-(benzo[b]thiophen-4-yl)piperazin-1-yl)ethyl)-3,4-dihydroquinolin-2(1H)-one;
(20) 9-hydroxy-2-methyl-3-(2-(4-(thieno[2,3-d]pyrimidin-4-yl)piperazin-1-yl)ethyl)-6,7,8,9-tetrahydro-4H-pyrido[1,2-a]pyrimidin-4-one;
(21) 2-methyl-3-(2-(4-(thieno[2,3-d]pyrimidin-4-yl)piperazin-1-yl)ethyl)-6,7,8,9-tetrahydro-4H-pyrido[1,2-a]pyrimidin-4-one;
(22) 7-(4-(4-(benzo[b]thiophen-4-yl)piperazin-1-yl)butyl)-3,4-dihydroquinolin-2(1H)-one;
(23) 7-(2-(4-(benzo[b]thiophen-4-yl)piperazin-1-yl)ethyl)-6-chloro-3,4-dihydroquinolin-2(1H)-one;
(24) 6-(5-(4-(benzo[b]thiophen-4-yl)piperazin-1-yl)pentyl)-2-methylquinazolin-4(3H)-one;
(25) 7-(2-(4-(2,3-dihydrobenzo[b]thiophen-4-yl)piperazin-1-yl)ethyl)quinolin-2(1H)-one;
(26) 5-(2-(4-(benzo[b]thiophen-4-yl)piperazin-1-yl)ethyl)-4-methylthiazole;
(27) 5-(2-(4-(benzo[b]thiophen-4-yl)piperazin-1-yl)ethyl)-1H-benzo[d]imidazol-2(3H)-one;
(28) 3-(2-(4-(benzo[b]thiophen-4-yl)piperazin-1-yl)ethyl)-9,9-difluoro-2-methyl-6,7, 8,9-tetrahydro-4H-pyrido[1,2-a]pyrimidin-4-one;
(29) 6-(2-(4-(benzo[b]thiophen-4-yl)piperazin-1-yl)ethyl)benzo[d]thiazol-2(3H)-one;
(30) 6-(2-(4-(benzo[b]thiophen-4-yl)piperazin-1-yl)ethyl)-2H-benzo[b][1,4]oxazin-3(4H)-one;
(31) 6-(2-(4-(benzo[b]thiophen-4-yl)piperazin-1-yl)ethyl)-2H-benzo[b][1,4]thiazin-3(4H)-one;
(32) 7-(2-(4-(thieno[2,3-d]pyrimidin-4-yl)piperazin-1-yl)ethyl)quinolin-2(1H)-one;
(33) 7-(4-(4-(benzo[b]thiophen-4-yl)piperazin-1-yl)butyl)quinolin-2(1H)-one;
(34) 6-(5-(4-(benzo[b]thiophen-4-yl)piperazin-1-yl)pentyl)quinazolin-4(3H)-one;
(35) 2-(2-(4-(benzo[b]thiophen-4-yl)piperazin-1-yl)ethyl)quinazolin-4(3H)-one;
(36) 3-(2-(4-(benzo[b]thiophen-4-yl)piperidin-1-yl)ethyl)-9-hydroxy-2-methyl-6,7,8,9-tetrahydro-4H-pyrido[1,2-a]pyrimidin-4-one;
(37) 5-(2-(4-(benzo[b]thiophen-4-yl)piperidin-1-yl)ethyl)-6-chloroindolin-2-one;
(38) 4-(2-(4-(benzo[b]thiophen-4-yl)piperazin-1-yl)ethyl)indolin-2-one;
(39) 6-(2-(4-(benzo[b]thiophen-4-yl)piperazin-1-yl)ethyl)indolin-2-one;

(40) 7-(2-(4-(benzo[b]thiophen-4-yl)piperazin-1-yl)ethyl)-6-chloroquinolin-2(1H)-one;
(41) 9-hydroxy-2-methyl-3-(2-(4-(thieno[2,3-c]pyridin-4-yl)piperazin-1-yl)ethyl)-6,7,8,9-tetrahydro-4H-pyrido[1,2-a]pyrimidin-4-one;
(42) 6-chloro-5-(2-(4-(thieno[2,3-c]pyridin-4-yl)piperazin-1-yl)ethyl)indolin-2-one;
(43) 7-(2-(4-(thieno[2,3-c]pyridin-4-yl)piperazin-1-yl)ethyl)quinolin-2(1H)-one;
(44) 7-(3-(4-(benzo[b]thiophen-4-yl)piperazin-1-yl)propyl)quinolin-2(1H)-one;
(45) 7-(3-(4-(benzo[b]thiophen-4-yl)piperazin-1-yl)propyl)-3,4-dihydroquinolin-2(1H)-one;
(46) 3-(2-(4-(benzo[b]thiophen-4-yl)piperazin-1-yl)ethyl)-1H-indole;
(47) 6-(2-(4-(benzo[b]thiophen-4-yl)piperazin-1-yl)ethyl)-3,4-dihydroquinolin-2(1H)-one;
(48) 5-(3-(4-(benzo[b]thiophen-4-yl)piperazin-1-yl)propyl)indolin-2-one;
(49) 7-(2-(4-(benzo[b]thiophen-4-yl)piperazin-1-yl)ethyl)-4,5-dihydro-1H-benzo[b]azepin-2(3H)-one;
(50) 3-(2-(4-(benzo[b]thiophen-4-yl)piperazin-1-yl)ethyl)-2-methyl-4H-pyrido[1,2-a]pyrimidin-4-one;
(51) 6-(2-(4-(benzo[b]thiophen-4-yl)piperazin-1-yl)ethyl)-3-methyl-3,4-dihydroquinazolin-2(1H)-one;
(52) 3-(2-(4-(benzo[b]thiophen-4-yl)piperazin-1-yl)ethyl)-9-chloro-2-methyl-6,7,8,9-tetrahydro-4H-pyrido[1,2-a]pyrimidin-4-one;
(53) 5-(2-(4-(benzo[b]thiophen-4-yl)piperazin-1-yl)ethyl)indoline-2-thione;
(54) 7-(2-(4-(benzo[b]thiophen-4-yl)piperazin-1-yl)ethyl)quinoline-2(1H)-thione;
(55) 2-(2-(4-(benzo[b]thiophen-4-yl)piperazin-1-yl)ethyl)-5,6-diethylpyrimidin-4(3H)-one;
(56) 2-(2-(4-(benzo[b]thiophen-4-yl)piperazin-1-yl)ethyl)pyrimidin-4(3H)-one;
(57) 7-(2-(4-(2-fluorobenzo[b]thiophen-4-yl)piperazin-1-yl)ethyl)quinolin-2(1H)-one;
(58) 2-((4-(benzo[b]thiophen-4-yl)piperazin-1-yl)methyl)-1H-benzo[d]imidazole;
(59) 6-(2-(4-(benzo[b]thiophen-4-yl)piperazin-1-yl)ethyl)benzo[d]thiazole;
(60) 7-(2-(4-(2-fluorobenzo[b]thiophen-4-yl)piperazin-1-yl)ethyl)benzo[d]thiazol-2-amine;
(61) N-(7-(2-(4-(2-fluorobenzo[b]thiophen-4-yl)piperazin-1-yl)ethyl)benzo[d]thiazol-2-yl)acetamide;
(62) 5-(2-(4-(2-fluorobenzo[b]thiophen-4-yl)piperazin-1-yl)ethyl)benzo[d]thiazol-2-amine;
(63) N-(5-(2-(4-(2-fluorobenzo[b]thiophen-4-yl)piperazin-1-yl)ethyl)benzo[d]thiazol-2-yl)acetamide;
(64) 7-(2-(4-(2-fluorobenzo[b]thiophen-4-yl)piperazin-1-yl)ethyl)-3,4-dihydroquinolin-2(1H)-one;
(65) 6-(2-(4-(2-fluorobenzo[b]thiophen-4-yl)piperazin-1-yl)ethyl)-3,4-dihydroquinolin-2(1H)-one;
(66) 6-(2-(4-(benzo[b]thiophen-4-yl)piperazin-1-yl)ethyl)-7-fluoro-2H-benzo[b][1,4]oxazin-3(4H)-one;
(67) 7-(2-(4-(3-methylbenzo[b]thiophen-4-yl)piperazin-1-yl)ethyl)-3,4-dihydroquinolin-2(1H)-one;
(68) 6-(2-(4-(benzo[b]thiophen-4-yl)piperazin-1-yl)ethyl)benzo[d]oxazol-2(3H)-one;
(69) 4-((4-(benzo[b]thiophen-4-yl)piperazin-1-yl)methyl)quinolin-2(1H)-one;
(70) 3-(4-(4-(benzo[b]thiophen-4-yl)piperazin-1-yl)butyl)-1H-indole-5-carbonitrile;
(71) 7-(5-(4-(6-fluorobenzo[b]thiophen-4-yl)piperazin-1-yl)pentyl)quinolin-2(1H)-one;
(72) 6-(4-(4-(benzo[b]thiophen-4-yl)piperazin-1-yl)butyl)-8-fluoro-2H-benzo[b][1,4]oxazin-3(4H)-one;
(73) 1-(benzo[b]thiophen-4-yl)-4-((2,3-dihydrobenzo[b][1,4]dioxin-2-yl)methyl)piperazine;
(74) 6-(4-(4-(2-fluorobenzo[b]thiophen-4-yl)piperazin-1-yl)butyl)-3,4-dihydroquinolin-2(1H)-one;
(75) 2-(2-(4-(benzo[b]thiophen-4-yl)piperazin-1-yl)ethyl)-1H-benzo[d]imidazole;
(76) N-(6-(2-(4-(2-fluorobenzo[b]thiophen-4-yl)piperazin-1-yl)ethyl)benzo[d]thiazol-2-yl)acetamide;
(77) 5-(2-(4-(2-fluorobenzo[b]thiophen-4-yl)piperazin-1-yl)ethyl)-1H-benzo[d]imidazol-2(3H)-one;
(78) 6-(2-(4-(6-fluorobenzo[b]thiophen-4-yl)piperazin-1-yl)ethyl)-2H-benzo[b][1,4]oxazin-3(4H)-one;
(79) 5-(2-(4-(2-fluorobenzo[b]thiophen-4-yl)piperazin-1-yl)ethyl)indolin-2-one;
(80) 6-(2-(4-(benzo[b]thiophen-4-yl)piperazin-1-yl)ethyl)-2-methylquinazolin-4(3H)-one;
(81) 7-(2-(4-(benzo[b]thiophen-4-yl)piperazin-1-yl)ethyl)-1,1-dioxide-3,4-dihydro-2H-benzo[e][1,2]thiazine;
(82) 5-(2-(4-(benzo[b]thiophen-4-yl)piperidin-1-yl)ethyl)indolin-2-one;
(83) 7-(2-(4-(benzo[b]thiophen-4-yl)piperidin-1-yl)ethyl)-3,4-dihydroquinolin-2(1H)-one;
(84) 5-(2-(4-(6-fluorobenzo[b]thiophen-4-yl)piperazin-1-yl)ethyl)indolin-2-one;
(85) 7-(2-(4-(6-fluorobenzo[b]thiophen-4-yl)piperazin-1-yl)ethyl)-3,4-dihydroquinolin-2(1H)-one;
(86) 6-(2-(4-(benzo[b]thiophen-4-yl)piperazin-1-yl)ethyl)-1-methyl-1H-benzo[d]imidazol-2(3H)-one;
(87) 5-(2-(4-(benzo[b]thiophen-4-yl)piperazin-1-yl)ethyl)-1,3-dimethyl-1H-benzo[d]imidazol-2(3H)-one;
(88) 5-(2-(4-(benzo[b]thiophen-4-yl)piperazin-1-yl)ethyl)-1-methyl-1H-benzo[d]imidazol-2(3H)-one;
(89) 6-(2-(4-(2-methoxybenzo[b]thiophen-4-yl)piperazin-1-yl)ethyl)-3,4-dihydroquinolin-2(1H)-one;
(90) 3-(2-(4-(6-fluorobenzo[b]thiophen-4-yl)piperazin-1-yl)ethyl)-2-methyl-6,7,8,9-tetrahydro-4H-pyrido[1,2-a]pyrimidin-4-one;
(91) 7-(2-(4-(2-oxo-2,3-dihydrobenzo[b]thiophen-4-yl)piperazin-1-yl)ethyl)-3,4-dihydroquinolin-2(1H)-one;
(92) 6-(2-(4-(2-fluorobenzo[b]thiophen-4-yl)piperazin-1-yl)ethyl)-2H-benzo[b][1,4]oxazin-3(4H)-one;
(93) 5-(2-(4-(2-fluorobenzo[b]thiophen-4-yl)piperazin-1-yl)ethyl)-1,3-dimethyl-1H-benzo[d]imidazol-2(3H)-one;
(94) 6-fluoro-5-(2-(4-(2-fluorobenzo[b]thiophen-4-yl)piperazin-1-yl)ethyl)indolin-2-one;
(95) 5-(2-(4-(benzo[b]thiophen-4-yl)piperazin-1-yl)ethyl)-6-fluoroindolin-2-one;
(96) 7-(2-(4-(benzo[b]thiophen-4-yl)piperazin-1-yl)ethyl)-1-benzyl-3-methylquinazoline-2,4(1H,3H)-dione;
(97) 6-(2-(4-(benzo[b]thiophen-4-yl)piperidin-1-yl)ethyl)-2H-benzo[b][1,4]oxazin-3(4H)-one;
(98) 6-(2-(4-(benzo[b]thiophen-4-yl)piperidin-1-yl)ethyl)-3,4-dihydroquinolin-2(1H)-one;
(99) 3-(2-(4-(benzo[b]thiophen-4-yl)piperidin-1-yl)ethyl)-2-methyl-6,7,8,9-tetrahydro-4H-pyrido[1,2-a]pyrimidin-4-one;
(100) 6-(2-(4-(2-fluorobenzo[b]thiophen-4-yl)piperazin-1-yl)ethyl)quinolin-2(1H)-one;
(101) 5-(4-(4-(2-fluorobenzo[b]thiophen-4-yl)piperazin-1-yl)butyl)indolin-2-one;
(102) 7-(2-(4-(6-fluorobenzo[b]thiophen-4-yl)piperazin-1-yl)ethyl)quinolin-2(1H)-one;
(103) 3-(4-(4-(benzo[b]thiophen-4-yl)piperazin-1-yl)butyl)-6,7-dimethoxy-4H-chromen-4-one;

(104) 6-(4-(4-(benzo[b]thiophen-4-yl)piperidin-1-yl)butyl)-3,4-dihydroquinolin-2(1H)-one;
(105) 3-(2-(4-(benzo[b]thiophen-4-yl)piperazin-1-yl)ethyl)-5-methoxy-1H-indole;
(106) 3-(3-(4-(benzo[b]thiophen-4-yl)piperazin-1-yl)propyl)-5-methoxy-H-indole;
(107) 3-(4-(4-(benzo[b]thiophen-4-yl)piperazin-1-yl)butyl)-5-methoxy-1H-indole;
(108) 3-(3-(4-(benzo[b]thiophen-4-yl)piperazin-1-yl)propyl)-1H-indole-5-carbonitrile;
(109) 3-(2-(4-(benzo[b]thiophen-4-yl)piperazin-1-yl)ethyl)-1H-indole-5-carbonitrile;
(110) 1-acetyl-3-(4-(4-(benzo[b]thiophen-4-yl)piperazin-1-yl)butyl)-1H-indole-5-carbonitrile;
(111) 6-(4-(4-(benzo[b]thiophen-4-yl)piperazin-1-yl)butyl)-3,4-dihydroquinolin-2(1H)-one;
(112) 5-(4-(4-(benzo[b]thiophen-4-yl)piperazin-1-yl)butyl)indolin-2-one;
(113) 6-chloro-5-(2-(4-(2-fluorobenzo[b]thiophen-4-yl)piperazin-1-yl)ethyl)indolin-2-one;
(114) 6-(2-(4-(benzo[b]thiophen-4-yl)piperazin-1-yl)ethyl)-4-methyl-2H-benzo[b][1,4]oxazin-3(4H)-one;
(115) 7-(2-(4-(benzo[b]thiophen-4-yl)piperazin-1-yl)ethyl)-1-methyl-3,4-dihydroquinolin-2(1H)-one;
(116) 5-(2-(4-(benzo[b]thiophen-4-yl)piperazin-1-yl)ethyl)benzo[d]thiazol-2-amine;
(117) 7-(2-(4-(benzo[b]thiophen-4-yl)piperazin-1-yl)ethyl)benzo[d]thiazol-2-amine;
(118) N-(5-(2-(4-(benzo[b]thiophen-4-yl)piperazin-1-yl)ethyl)benzo[d]thiazol-2-yl)acetamide;
(119) N-(7-(2-(4-(benzo[b]thiophen-4-yl)piperazin-1-yl)ethyl)benzo[d]thiazol-2-yl)acetamide;
(120) 4-(2-(4-(benzo[b]thiophen-4-yl)piperazin-1-yl)ethyl)benzo[d]thiazol-2-amine;
(121) N-(4-(2-(4-(benzo[b]thiophen-4-yl)piperazin-1-yl)ethyl)benzo[d]thiazol-2-yl)acetamide;
(122) 7-(2-(4-(2-methylbenzo[b]thiophen-4-yl)piperazin-1-yl)ethyl)-3,4-dihydroquinolin-2(1H)-one;
(123) 3-((4-(benzo[b]thiophen-4-yl)piperazin-1-yl)methyl)-1-methyl-1H-indole;
(124) 1-(3-(2-(4-(benzo[b]thiophen-4-yl)piperazin-1-yl)ethyl)indolin-1-yl)ethanone;
(125) 3-(2-(4-(benzo[b]thiophen-4-yl)piperazin-1-yl)ethyl)-1-tosyl-1H-indole-5-carbonitrile;
(126) 3-(3-(4-(benzo[b]thiophen-4-yl)piperazin-1-yl)propyl)-1-tosyl-1H-indole-5-carbonitrile;
(127) 3-(4-(4-(benzo[b]thiophen-4-yl)piperazin-1-yl)butyl)-5-methoxy-1-tosyl-1H-indole;
(128) 3-(3-(4-(benzo[b]thiophen-4-yl)piperazin-1-yl)propyl)-5-methoxy-1-tosyl-1H-indole;
(129) 3-(2-(4-(benzo[b]thiophen-4-yl)piperazin-1-yl)ethyl)-5-methoxy-1-tosyl-1H-indole;
(130) 6-(2-(4-(2-oxo-2,3-dihydrobenzo[b]thiophen-4-yl)piperazin-1-yl)ethyl)-3,4-dihydroquinolin-2(1H)-one;
(131) 3-(2-(4-(2-fluorobenzo[b]thiophen-4-yl)piperazin-1-yl)ethyl)-9-hydroxy-2-methyl-6,7,8,9-tetrahydro-4H-pyrido[1,2-a]pyrimidin-4-one;
(132) 2-(2-(4-(benzo[b]thiophen-4-yl)piperazin-1-yl)ethyl)-2H-benzo[b][1,4]oxazin-3(4H)-one;
(133) 7-(2-(4-(benzo[b]thiophen-4-yl)piperazin-1-yl)ethyl)-3,4-dihydroquinoline-2(1H)-thione;
(134) (3aR,4R,6aS)-4-(5-(4-(benzo[b]thiophen-4-yl)piperazin-1-yl)pentyl)tetrahydro-1H-thieno[3,4-d]imidazol-2(3H)-one;
(135) pentyl(6-(2-(4-(benzo[b]thiophen-4-yl)piperazin-1-yl)ethyl)benzo[d]thiazol-2-yl)carbamate;
(136) 3-(2-(4-(benzo[b]thiophen-4-yl)piperazin-1-yl)ethyl)-2-methyl-4-oxo-6,7,8,9-tetrahydro-4H-pyrido[1,2-a]pyrimidin-9-yl benzoate;
(137) 6-(4-(4-(benzo[b]thiophen-4-yl)piperazin-1-yl)butyl)-2H-benzo[b][1,4]oxazin-3(4H)-one;
(138) 1-(benzo[b]thiophen-4-yl)-4-(4-(1-cyclohexyl-1H-tetrazol-5-yl)butyl)piperazine;
(139) 6-(2-(4-(benzo[b]thiophen-4-yl)piperazin-1-yl)ethyl)-8-fluoro-2H-benzo[b][1,4]oxazin-3(4H)-one;
(140) 7-(2-(4-(benzo[b]thiophen-4-yl)piperazin-1-yl)-1-hydroxyethyl)quinolin-2(1H)-one;
(141) 6-(2-(4-(benzo[b]thiophen-4-yl)piperazin-1-yl)-1-hydroxyethyl)-2H-benzo[b][1,4]oxazin-3(4H)-one;
(142) 6-(2-(4-(benzo[b]thiophen-4-yl)piperazin-1-yl)-1-hydroxyethyl)-2H-benzo[b][1,4]thiazin-3(4H)-one;
(143) 5-(2-(4-(benzo[b]thiophen-4-yl)piperazin-1-yl)acetyl)indolin-2-one;
(144) 8-(2-(4-(benzo[b]thiophen-4-yl)piperazin-1-yl)-1-methoxyethyl)-2H-benzo[b][1,4]oxazin-3(4H)-one;
(145) 5-(2-(4-(benzo[b]thiophen-4-yl)piperazin-1-yl)-1-hydroxyethyl)indolin-2-one;
(146) 6-(2-(4-(benzo[b]thiophen-4-yl)piperazin-1-yl)acetyl)benzo[d]thiazol-2(3H)-one;
(147) 5-(2-(4-(benzo[b]thiophen-4-yl)piperazin-1-yl)acetyl)-1H-benzo[d]imidazol-2(3H)-one;
(148) 7-(2-(4-(benzo[b]thiophen-4-yl)piperazin-1-yl)acetyl)-3,4-dihydroquinolin-2(1H)-one;
(149) 7-(5-(4-(benzo[b]thiophen-4-yl)piperazin-1-yl)pentanoyl)quinolin-2(1H)-one;
(150) 7-(5-(4-(benzo[b]thiophen-4-yl)piperazin-1-yl)-1-hydroxypentyl)-3,4-dihydroquinolin-2(1H)-one;
(151) 7-(5-(4-(benzo[b]thiophen-4-yl)piperazin-1-yl)pentanoyl)-3,4-dihydroquinolin-2(1H)-one;
(152) N-(6-(2-(4-(benzo[b]thiophen-4-yl)piperazin-1-yl)ethyl)benzo[d]thiazol-2-yl)cyclopentanecarboxamide;
(153) N-(6-(2-(4-(benzo[b]thiophen-4-yl)piperazin-1-yl)ethyl)benzo[d]thiazol-2-yl)acetamide;
(154) 6-(2-(4-(benzo[b]thiophen-4-yl)piperazin-1-yl)ethyl)benzo[d]thiazol-2-amine.

The present invention provides a process for producing a heterocyclic compound represented by formula (I) as shown in methods 1 to 5.

Method 1: The method comprises the step to obtain the compound of formula (I) or a salt thereof by the N-alkylation reaction of the compound of formula (II) or a salt thereof with the compound of formula (III) or a salt thereof, as shown in Reaction Formula 1:

Reaction Formula 1

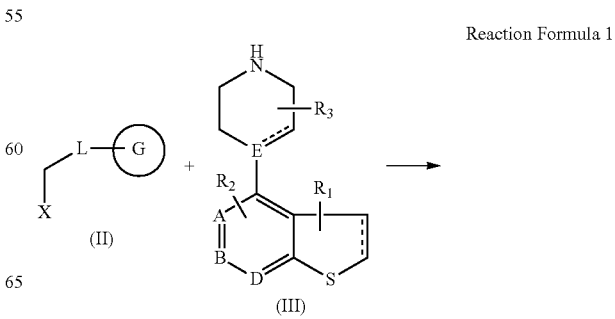

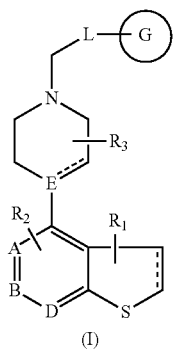

(I)

wherein, ring G, L, A, B, D, E, $R_1$, $R_2$ and $R_3$ are defined and preferred as hereinbefore;

X represents a leaving group such as halogen, C1~C6 alkylsulfonyloxy, phenylsulfonyloxy, naphthylsulfonyloxy, said C1~C6 alkylsulfonyloxy, phenylsulfonyloxy or naphthylsulfonyloxy is optionally substituted with one or more substituents selected from the group consisting of halogen, C1~C6 alkyl, C1~C6 alkoxy, nitro, hydroxy, amino and C1~C6 alkanoyl group; preferably X represents halogen, C1~C4 alkylsulfonyloxy, phenylsulfonyloxy and naphthylsulfonyloxy group, said C1~C4 alkylsulfonyloxy, phenylsulfonyloxy or naphthylsulfonyloxy group is optionally substituted with one or more substituents selected from the group consisting of halogen, C1~C4 alkyl, C1~C4 alkoxy, nitro, hydroxy, amino and C1~C4 alkanoyl; most preferably, X represents chlorine, bromine, methylsulfonyloxy, trifluoromethylsulfonyloxy, phenylsulfonyloxy, naphthylsulfonyloxy, methyl-phenylsulfonyloxy, nitro-phenylsulfonyloxy, amino-phenylsulfonyloxy, chloro-phenylsulfonyloxy, bromo-phenylsulfonyloxy or methoxy-phenylsulfonyloxy group.

Said N-alkylation reaction between the compound of formula (II) or a salt thereof and the compound of formula (III) or a salt thereof was conducted in solvents in the presence or absence of a base, or it may be conducted without solvents. Said solvents include water; ethers such as dioxane, tetrahydrofuran, diethyl ether, methyl t-butyl ether, diisopropyl ether, diglyme, ethylene glycol dimethyl ether; aromatic hydrocarbons such as benzene, toluene, xylene, nitrobenzene, chlorobenzene; alcohols such as methanol, ethanol, isopropanol, butanol, tert-butanol, ethylene glycol; ketones such as acetone, methyl ethyl ketone, 4-methyl-2-pentanone; amides such as N,N-dimethylformamide, N,N-dimethylacetamide, 1-methyl-2-pyrrolidinone; halogenated hydrocarbons such as chloroform, dichloromethane, dichloroethane, carbon tetrachloride; esters such as ethyl acetate, ethyl formate, methyl acetate, isopropyl acetate; others such as dimethyl sulfoxide, acetonitrile. These solvents may be used singly or in combination with two or more.

Said base may be inorganic or organic base, the inorganic base is selected from the group consisting of alkali metal hydroxides (e.g., sodium hydroxide, potassium hydroxide, cesium hydroxide, lithium hydroxide); alkali metal carbonates (e.g., sodium carbonate, potassium carbonate, cesium carbonate, lithium carbonate); alkali metal bicarbonates such as sodium hydrogencarbonate, potassium hydrogencarbonate, lithium hydrogencarbonate; alkali metal such as potassium, sodium; others such as sodium amide, potassium amide, sodium hydride, potassium hydride; the organic base is selected from the group consisting of sodium methoxide, sodium ethoxide, potassium methoxide, potassium ethoxide, sodium acetate, triethylamine, pyridine, diisopropylamine, diisopropylethylamine, tripropylamine, diethylamine, pyrimidine, quinoline, piperidine, piperazine, imidazole, dimethylaminopyridine, trimethylamine, N-ethyldiisopropylamine, N-methylmorpholine, dimethylaniline, 1,8-diazabicyclo[5.4.0]undec-7-ene (DBU), 1,5-diazabicyclo[4.3.0]non-5-ene (DBN), 1,4-diazabicyclo[2.2.2] octane (DABCO). These bases may be used singly or in combination with two or more.

The above reaction may be conducted in the presence of an iodide of alkali metal such as potassium iodide and sodium iodide as a catalyst if necessary.

The reaction temperature is room temperature to 200° C., preferably from room temperature to 150° C. The reaction time is 1 hour to 30 hours, preferably 5 hours to 20 hours.

Method 2: The method comprises the step to obtain the compound of formula (Ia) or a salt thereof by the coupling reaction of the compound of formula (IV) or a salt thereof with the compound of formula (V) or a salt thereof, as shown in Reaction Formula 2:

Reaction Formula 2

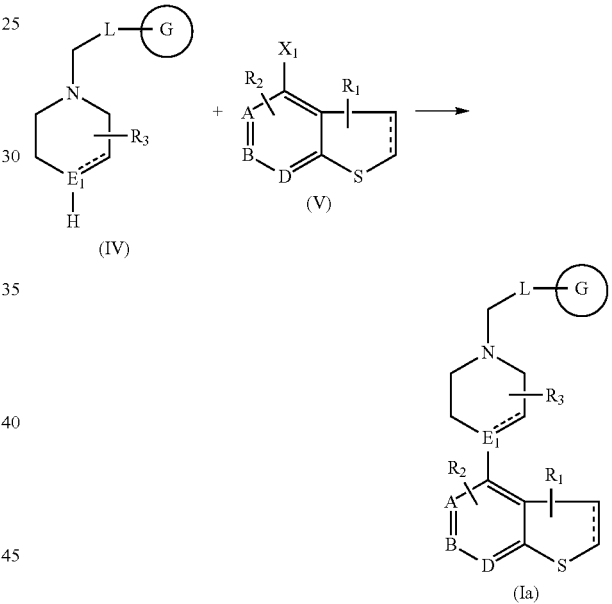

wherein, ring G, L, A, B, D, $R_1$, $R_2$ and $R_3$ are defined and preferred as hereinbefore, $E_1$ represents a nitrogen atom; $X_1$ represents halogen or trifluoromethylsulfonyloxy, preferably, $X_1$ is selected from the group consisting of bromine, iodine, chlorine and trifluoromethylsulfonyloxy group;

the coupling reaction is carried out in the presence of a base and a palladium catalyst and the compounds of formula (Ia) is a special case of the compound of formula (I).

Said palladium catalyst is selected from the group consisting of palladium acetate (Pd (OAc)$_2$), bis(triphenylphosphine)palladium(II) chloride(($Ph_3P)_2PdCl_2$), bis(benzonitrile) palladium(II) chloride (($PhCN)_2PdCl_2$), Tetrakis (triphenylphosphine)palladium (Pd(PPh$_3$)$_4$), bis (triphenylphosphine)palladium acetate (($Ph_3P)_2Pd(OAc)_2$), [1,2-Bis(diphenylphosphino)ethane]dichloropalladium(II) (PdCl$_2$(dppe)), bis (1,2-bis (diphenylphosphino) ethane) palladium (Pd(dppe)$_2$), bis(dibenzylideneacetone)palladium (Pd(dba)$_2$), tris(dibenzylideneacetone) dipalladium (Pd$_2$(dba)$_3$), [1,3-bis(diphenylphosphino)propane]palladium dichloride (PdCl$_2$(dippp)), and [1,1'-bis(diphenylphosphino) ferrocene] dichloropalladium (Pd(dppf)Cl$_2$); said base is one or more selected from the group consisting of sodium bis (trimethylsilyl) amide, potassium tert-butoxide, sodium tert-butoxide, potassium phosphate, sodium phosphate, sodium methoxide, sodium ethoxide, potassium hydroxide, sodium hydroxide, potassium fluoride, sodium fluoride, tetrabutylammonium fluoride (TBAF), sodium acetate, potassium acetate, cesium carbonate, potassium carbonate or sodium carbonate. The reaction solvent is not particularly limited and include water; ethers such a dioxane, tetrahydrofuran; aromatic hydrocarbons such as toluene, xylene; alcohols such as t-butanol; ketones such as acetone; amides such as N,N-dimethylformamide; others such as dimethylsulfoxide, acetonitrile; or a mixture of the above solvents; a suitable ligand can be added thereto as a reaction accelerator if necessary. Examples of said suitable ligands are 2,2'-Bis(diphenylphosphino)-1,1'-binaphthalene(BINAP), Tri-t-butyl phosphine(P(t-Bu)$_3$), 1,1'-bis(diphenylphosphino)ferrocene (dppf), 2-Dicyclohexylphosphino-2',4',6'-triisopropylbiphenyl (x-phos), 4,5-bis(diphenylphosphino)-9,9-dimethyl xanthene(Xantphos), tri-tert-butylphosphine tetrafluoroborate and Tri(o-tolyl) phosphine (P (o-tolyl)$_3$).

Method 3: The method comprises the step to obtain the compound of formula (VII) or a salt thereof by the amidation reaction of the compound of formula (VI) or a salt thereof with the compound of formula (III) compound or a salt thereof, followed by the reduction step to give a compound of formula (I), as shown in Reaction Formula 3:

Reaction Formula 3

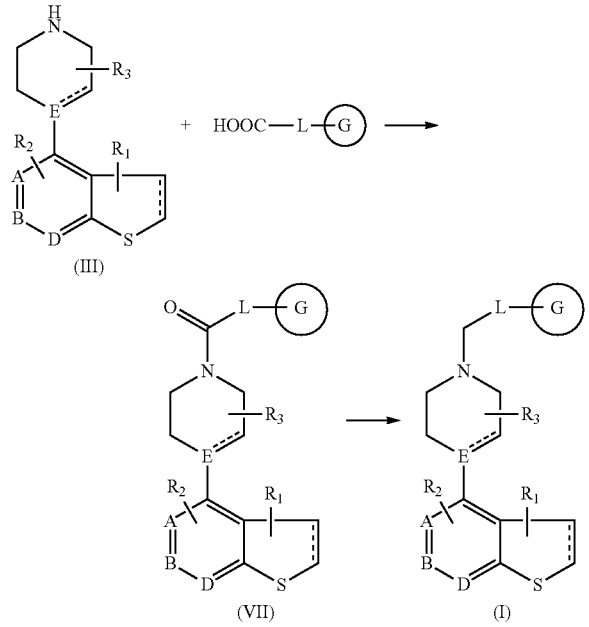

wherein, ring G, L, A, B, D, E, R$_1$, R$_2$ and R$_3$ are defined and preferred as hereinbefore.

The amidation reaction can be performed in two ways.

The first amidation method is conducted in the presence or absence of a catalyst, by activating the carboxyl group of the compound of formula (VI) followed by the ammonolysis reaction with the compound of formula (III). The activator may be one or more selected from the group consisting of thionyl chloride, oxalyl chloride, thionyl bromide, phosphorus oxychloride, phosphorus pentachloride, pivaloyl chloride, ethyl chloroformate, isobutyl chloroformate, carbonyl diimidazole (CDI), methanesulfonyl chloride, p-toluenesulfonyl chloride, p-nitrobenzenesulfonyl chloride and the like. The catalyst may be one or more selected from the group consisting of N,N-dimethylformamide (DMF), diethylaniline, dimethylaniline, N-methylmorpholine and the like. The solvent for the carboxyl group activation reaction is not particularly limited, for example, may be one or more selected from the group consisting of dichloromethane, dichloroethane, dimethylsulfoxide, tetrahydrofuran, benzene, toluene, chloroform, carbon tetrachloride, xylene, N,N-dimethylformamide, N,N-dimethylacetamide and the like. The aminolysis reaction is conducted in the presence of a base in an appropriate solvent. Said base may be one or more selected from the group consisting of pyridine, piperidine, pyrrolidine, morpholine, N-methylmorpholine, quinoline, 4-dimethylaminopyridine (DMAP), triethylamine, diethylamine, tri-n-butyl amine, tripropylamine, diisopropylamine, diisopropylethylamine, sodium methoxide, sodium ethoxide, potassium t-butoxide, butyl lithium, 1,8-diazabicyclo[5,4,0]undec-7-ene (DBU), sodium hydride, sodium hydroxide, potassium hydroxide, lithium hydroxide, sodium hydrogencarbonate, potassium hydrogencarbonate, sodium carbonate and potassium carbonate. The ammonolysis reaction solvent is one or more selected from the group consisting of aromatic hydrocarbon solvents, ether solvents, halogenated hydrocarbon solvents and other solvents. Wherein said aromatic hydrocarbon solvents may be one or more selected from the group consisting of benzene, toluene, xylene and the like; said ether solvents may be one or more selected from the group consisting of tetrahydrofuran (THF), diethyl ether, methyl t-butyl ether, ethylene glycol dimethyl ether, diethylene glycol dimethyl ether, ethylene glycol monomethyl ether, 1,4-dioxane and the like; said halogenated hydrocarbon solvents may be one or more selected from the group consisting of dichloromethane, chloroform, carbon tetrachloride, dichloroethane, and the like; said other solvents may be one or more selected from the group consisting of methanol, ethanol, ethylene glycol, hexane, cyclohexane, N,N-dimethylformamide (DMF), N, N-dimethylacetamide, dimethylsulfoxide (DMSO), N-methyl pyrrolidone, acetone, acetonitrile, ethyl acetate, and the like; but the present invention is not limited to the above solvents. The temperature for the ammonolysis reaction is not particularly limited, but preferably is −30° C.~150° C., more preferably is −10° C.~120° C. The reaction time for the ammonolysis reaction is not particularly limited, but preferably is 10 minutes to 24 hours.

The second amidation method is conducted in the presence of a condensing agent, with or without a catalyst, with or without a base. Said condensing agent can be one or more selected from the group consisting of N,N'-dicyclohexyl carbodiimide (DCC), 1-ethyl-3-(3-dimethylaminopropyl) carbodiimide (EDCI), N,N'-diisopropyl carbodiimide (DIC), O-(Benzotriazol-1-yl)-N,N,N',N'-tetramethyluronium tetrafluoroborate (TBTU), o-(7-Azabenzotriazol-1-yl)-N,N,N', N'-te-tramethyluronium hexafluorophosphate (HATU), o-Benzotriazol-1-yl-N,N,N',N'-tetramethyluronium hexafluorophosphate (HBTU), (Benzotriazol-1-yloxy)tris (dimethylamino)phosphonium hexafluorophosphate (BOP) and Benzotriazole-1-yl-oxytripyrrolidinophosphonium hexafluorophosphate (PyBOP). Said catalyst may be one or more selected from the group consisting of 1-hydroxybenzotriazole (HOBt) and 4-dimethylaminopyridine (DMAP). Said base may be one or more selected from the group consisting of triethylamine, diethylamine, n-butylamine, tripropylamine, diisopropylamine, diisopropylethylamine, trimethylamine, pyridine, 2,6-dimethyl pyridine, 4-dimethylaminopyridine, piperidine, pyrrolidine, quinoline, morpholine, N-methyl morpholine, N-ethyl morpholine, 1,8-diazabicyclo[5,4,0]undecene-7(DBU) or 1,5-diazabicyclo[4.3.0]non-5-ene (DBN) and the like. The solvent of the second amidation method may be selected from the group consisting of hydrocarbons, such as benzene, xylene, toluene, dichloromethane or chloroform; ethers such as tetrahydrofuran, diethyl ether, dipropyl ether, or 1,4-dioxane; amides such as N,N-dimethylformamide, N,N-diethylformamide or N,N-dimethylacetamide; nitriles such as acetonitrile; others such as dimethyl sulfoxide; these solvents may be used singly or in combination with two or more. Preferably, the reaction solvent is selected from the group consisting of tetrahydrofuran, acetonitrile, dichloromethane, N,N-dimethylformamide, N,N-dimethylacetamide or dimethylsulfoxide. The reaction temperature of the second amidation method is not particularly limited, but preferably is −20° C.~80° C., more preferably is 0° C.~50° C.

Said reducing agent is one or more selected from the group consisting of borane, hydrogen/palladium on carbon, lithium aluminum tetrahydride, triacetoxy sodium borohydride, diisobutyl aluminum hydride, boron trifluoride, boron tribromide, sodium borohydride and potassium borohydride.

Method 4: The compound of Formula (I) was obtained by the reductive amination reaction of the compound of Formula (VIII) or a salt thereof and the compound of formula (III) or a salt thereof, as shown in Reaction Formula 4:

Reaction Formula 4

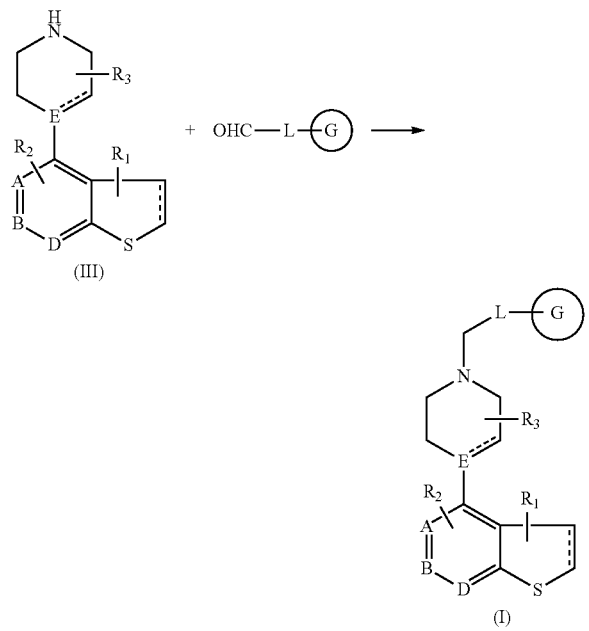

wherein, ring G, L, A, B, D, E, $R_1$, $R_2$ and $R_3$ are defined and preferred as hereinbefore. The reductive amination reaction is carried out in the presence of a reductant, the reductant included but not limited to: sodium borohydride, potassium borohydride, sodium triacetoxy borohydride (NaBH(OAc)$_3$), Tetramethylammonium Triacetoxyborohydride and sodium cyanoborohydride.

Said reaction solvent is selected from the group consisting of water; ethers such as dioxane, tetrahydrofuran, diethyl ether, methyl t-butyl ether, diisopropyl ether, diglyme, ethylene glycol dimethyl ether; aromatic hydrocarbons such as benzene, toluene, xylene, nitrobenzene, chlorobenzene; alcohols such as methanol, ethanol, isopropanol, butanol, tert-butanol, ethylene glycol; ketones such as acetone, methyl ethyl ketone, 4-methyl-2-pentanone; amides such as N,N-dimethylformamide, N,N-dimethylacetamide, 1-methyl-2-pyrrolidinone; halogenated hydrocarbons such as chloroform, dichloromethane, dichloroethane, carbon tetrachloride; esters such as ethyl acetate, ethyl formate, methyl acetate, isopropyl acetate; nitriles such as acetonitrile; others such as dimethyl sulfoxide. These solvents may be used singly or in combination with two or more. The reaction temperature is generally 10° C. to 100° C., preferably from 20° C. to 50° C. The reaction time is generally 1 hour to 30 hours.

Method 5: The compound of Formula (I) was obtained through the functional group conversion from the product obtained by method 1-4. e.g., by the oxidation reaction, the Grignard reaction, the hydrolysis reaction, the fluorination reaction, the chlorination reaction or the thiosulfate reaction.

Said oxidation reaction is carried out in the presence of an oxidant, the oxidant included but not limited to: Dess-Martin reagent, Jones reagent, Swern reagents (DMSO and oxalyl chloride) or 2,3-Dichloro-5,6-dicyano-1,4-benzoquinone (DDQ) and the like.

Said Grignard reaction is carried out in the presence of a Grignard reagent, the Grignard reagent included but are not limited to: Methylmagnesium chloride, Methylmagnesium bromide, Methylmagnesium iodide or Ethylmagnesium bromide and the like.

Said hydrolysis reaction may be carried out in the presence of an acid or a base, the acid or base included but are not limited to: hydrochloric acid, sulfuric acid, sodium hydroxide or potassium hydroxide and the like.

Said fluorination reaction is carried out in the presence of a fluorinated agent, the fluorinated agents included but are not limited to: diethylamino sulfur trifluoride (DAST), sulfur tetrafluoride or iodine pentafluoride and the like.

Said chlorination reaction is carried out in the presence of a chlorinated agents, the chlorinated agents included but are not limited to: thionyl chloride, phosphorus pentachloride or N-chlorosuccinimide (NCS) and the like.

Said thiosulfate reaction is carried out in the presence of a thiosulfate reagent, the thiosulfate agents included but are not limited to: phosphorus pentasulfide or Lawesson reagent and the like.

The compounds of Formula (II), formula (III), formula (IV), Formula (V), formula (VI), and formula (VIII) are commercially available or are prepared according to the reported methods or are prepared according to the reported methods of their analogs.

The starting compounds used in the above reaction may be in the form of suitable salts, the suitable salts include alkali metal salts and alkaline earth metal salts such as sodium, potassium, calcium, magnesium salt and the like; organic base salts such as pyridine salt, triethylamine salt and the like; inorganic acid salts such as hydrochloride, hydrobromide, hydroiodide, sulfate, nitrate, phosphate and the like; organic acid salts such as formate, acetate, propionate, glycolate, oxalate, malonate, succinate, fumarate, maleate, lactate, malate, citrate, tartrate, picrate, glutamate, methanesulfonate and benzene sulfonate;

Further, the starting compound used in the above reactions may be in the form of solvates, e.g. hydrates, alcoholates and the like.

The heterocyclic compounds represented by the general formula (I) and stereoisomers thereof in the present invention also include compounds in the form of solvate, such as hydrates, alcoholates, and the solvates are included within the scope of the present invention.

The Pharmaceutically acceptable salt of the heterocyclic compound represented by formula (I) or its stereoisomer refers to converting the heterocyclic compound represented by formula (I) or its stereoisomer to non-toxic addition salt forms with therapeutic activity with suitable acid. Specific examples of said salts include hydrochloride, hydrobromide, hydroiodide, sulfate, bisulfate, nitrate, phosphate, acid phosphate, perchlorate, formate, acetate, trifluoroacetate, propionate, pyruvate, glycolate, oxalate, malonate, succinate, glutarate, maleate, fumarate, lactate, malate, citrate, tartrate, picrate, glutamate, benzoate, methanesulfonate, ethanesulfonate, benzenesulfonate, p-toluenesulfonate, salicylate, ascorbate, camphor acid salt or camphorsulfonic acid salt. Conversely, the acid addition salt can also be converted to the free base form with a base.

The term "pharmaceutically acceptable salts" used above also includes solvates thereof, and the solvates are included within the scope of the present invention. Examples of solvates include the hydrates, alcoholates and the like.

The objective compounds prepared by the above reaction formula may be isolated and purified from the reaction mixture by the following methods: the reaction mixture was cooled and filtered or extracted or concentrated to give a crude, then the crude was purified by chromatography, recrystallization or slurrying process.

The present invention also provides a use of the heterocyclic compounds of the general formula (I) in the present invention, stereoisomers or a pharmaceutically acceptable salt thereof in the manufacture of medicament for the prevention and/or treatment of central nervous system disease.

The present invention also provides a method for the treatment or prevention of the central nervous system disease. Such method comprises administering to a human or animal the heterocyclic compound represented by formula (I), stereoisomer or a pharmaceutically acceptable salt thereof. The present invention also provides a pharmaceutical composition comprising a therapeutically effective amount of the heterocyclic compound represented by formula (I), stereoisomer or a pharmaceutically acceptable salt thereof and one or more pharmaceutically acceptable carrier. The pharmaceutical composition is very useful in the treatment or prevention of central nervous system disease.

The present invention further provides a process for preparing a pharmaceutical composition comprising mixing the heterocyclic compound represented by formula (I), stereoisomer or a pharmaceutically acceptable salt thereof with one or more pharmaceutically acceptable carrier.

In the pharmaceutical compositions of the present invention, various forms of pharmaceutical preparations can be selected according to the treatment purpose, generally include: tablets, pills, capsules, granules, suspensions, solutions, creams, ointments, powders, suppositories, aerosols and injections.

Said central nervous system disease is selected from the group consisting of schizophrenia; refractory, intractable or chronic schizophrenia; emotional disturbance; psychotic disorder; mood disorder; bipolar I type disorder; bipolar II type disorder; depression; endogenous depression; major depression; refractory depression; dysthymic disorder; cyclothymic disorder; panic attack; panic disorder; social phobia; obsessive-compulsive disorder; impulse disorder; post-traumatic stress disorder; anxiety disorder; acute stress disorder; hysteria; anorexia nervosa; sleep disorder; adjustment disorder; cognitive disorder; autism; neuropathic headache; mania; Parkinson's disease; Huntington's disease; Alzheimer's disease; dementia; memory disorder; hyperkinetic syndrome; attention deficit/hyperactivity disorder, tic disorder and the like.

The groups in the general formula (I) are defined as follows:

The term halogen generally refers to fluorine, chlorine, bromine and iodine; preferably fluorine, chlorine or bromine; more preferably fluorine or chlorine;

C1~C6 alkyl group refers to a linear or branched alkyl group having 1 to 6 carbon atoms, for example, methyl, ethyl, n-propyl, isopropyl, n-butyl, isobutyl, tert-butyl, sec-butyl, n-pentyl, 1-ethylpropyl, isopentyl, neopentyl, isohexyl, 3-methylpentyl or n-hexyl group and the like, preferably methyl, ethyl, n-propyl, isopropyl, butyl, isobutyl or tert-butyl group;

Halogenated C1~C6 alkyl group refers to a linear or branched alkyl group having 1 to 6 carbon atoms that was substituted with one or more identical or different halogen atoms, for example, trifluoromethyl, fluoromethyl, difluoromethyl, chloromethyl, bromomethyl, dichlorofluoromethyl, chloroethyl, bromopropyl, 2-chloro-butyl or pentafluoroethyl group;

C1~C6 alkoxy group refers to a linear or branched alkoxy group having 1 to 6 carbon atoms, for example, methoxy, ethoxy, n-propoxy, isopropoxy, n-butoxy, isobutoxy, tert-butoxy, sec-butoxy, n-pentyloxy, isopentyloxy, neopentyloxy, isohexyloxy, 3-methylpentyloxy or n-hexyloxy group and the like, preferably methoxy, ethoxy, n-propoxy, isopropoxy, n-butoxy, isobutoxy or tert-butoxy group;

Halogenated C1~C6 alkoxy refers to a linear or branched alkoxy group having 1 to 6 carbon atoms that was substituted with one or more identical or different halogen atoms, for example, $-OCF_3$, $-OCH_2CH_2Cl$, $-OCHBrCH_2Cl$ or $-OCF_2CF_3$ and the like;

C1~C6 alkylthio group refers to a linear or branched alkylthio group having 1 to 6 carbon atoms, for example, methylthio, ethylthio, n-propylthio, isopropylthio, n-butylthio, isobutylthio, tert-butylthio, sec-butylthio, n-pentylthio, isopentylthio, neopentylthio or n-hexylthio and the like, preferably methylthio, ethylthio, n-propylthio, isopropylthio, n-butylthio, iso-butylthio or tert-butylthio group;

C2~C6 alkenyl refers to an unsaturated linear or branched alkyl group having 1 to 3 double bonds and 2 to 6 carbon atoms, including both cis and trans configuration, for example, vinyl, 1-propenyl, 2-propenyl, 1-methyl-1-propenyl, 2-methyl-1-propenyl, 2-methyl-2-propenyl, 1-butenyl, 2-butenyl, 3-butenyl, 1-pentenyl, 2-pentenyl, 3-pentenyl, 4-pentenyl, 1,3-butadienyl, 1,3-pentadienyl, 1-hexenyl, 2-hexenyl, 3-hexenyl, 4-hexenyl, 5-hexenyl, 3,3-dimethyl-1-propenyl or 2-ethyl-1-propenyl group and the like;

C2~C6 alkynyl refers to a linear or branched alkynyl group having 2 to 6 carbon atoms, for example, ethynyl, 2-propynyl, 2-butynyl, 3-butynyl, 1-methyl-2-propynyl, 2-pentynyl or 2-hexynyl group and the like;

Phenyl C1~C6 alkyl refers to a saturated linear or branched hydrocarbon group having 1 to 6 carbon atoms was linked with phenyl group through carbon atoms, for example, benzyl, phenylethyl or phenylpropyl group and the like; Phenyl-C1~C6 alkoxy refers to a linear or branched alkoxy group having 1 to 6 carbon atoms was linked with phenyl group through carbon atoms, for example, benzyloxy, —OCH(CH₃)Ph, phenylethoxy or phenylpropoxy group and the like;

Phenyl C1~C6 alkanoyl group refers to a linear or branched alkanoyl group having 1 to 6 carbon atoms was linked with phenyl group through carbon atoms, for example, benzoyl, phenylacetyl or phenylpropionyl and the like;

C2~C6 alkenyloxy group refers to a linear or branched alkenyloxy group containing 1 to 3 double bonds and 2 to 6 carbon atoms, such as vinyloxy, 1-propenyloxy, 1-methyl-1-propenyloxy, 2-methyl-1-propenyloxy, 1-pentenyloxy, 1,3-pentadienyloxy or 2-pentenyloxy group and the like;

C2~C6 alkynyl group refers to a linear or branched alkynyl group having 2 to 6 carbon atoms, for example, ethynyloxy, 2-propynyloxy, 2-butynyloxy, 3-butynyloxy, 1-methyl-2-propynyloxy, 2-pentynyloxy or 2-hexynyloxy group and the like;

C1~C6 alkanoyl group refers to a linear or branched alkoxy group having 1 to 6 carbon atoms, for example, formyl, acetyl, propionyl, butyryl, isobutyryl, pentanoyl, t-butyryl or hexanoyl group and the like;

Halogenated C1~C6 alkanoyl group refers to a linear or branched alkanoyl group having 1 to 6 carbon atoms that was substituted with one or more identical or different halogen atoms, for example, trifluoroacetyl group and the like;

C1~C6 alkyl-substituted carbamoyl group refers to an carbamoyl group substituted with one or two identical or different C1~C6 alkyl group, for example, —CONHMe, —CON(Me)Et, —CONEt₂ or —CONMe₂ and the like;

Hydroxy C1~C6 alkyl group refers to a linear or branched alkyl group having 1 to 6 carbon atoms was linked with a hydroxyl group through a carbon atom, for example, —CH₂OH, —CH₂CH₂OH, —CH(OH)CH₃, —CH₂CH₂CH₂OH, —CH₂CH₂CH₂CH₂OH or —CH₂CH(CH₃)CH₂OH and the like;

Amino C1~C6 alkyl refers to a linear or branched alkyl group having 1 to 6 carbon atoms was linked with an amino group through a carbon atom, for example, —CH₂NH₂, —CH₂CH₂NH₂, —CH(NH₂)CH₃, —CH₂CH₂CH₂NH₂ or —CH₂CH₂CH₂CH₂NH₂ and the like;

C1~C6 alkyl-substituted amino C1~C6 alkyl group refers to an amino C1~C6 alkyl group whose hydrogen atom on the amino part is replaced by one or two identical or different C1~C6 alkyl group, for example, —CH₂NHMe or —CH₂CH₂NEt₂ and the like.

Carbamoyl C1~C6 alkyl refers to a linear or branched alkyl group having 1 to 6 carbon atoms was linked with a carbamoyl group through a carbonyl carbon atom, for example, —CH₂CONH₂, —CH₂CH₂CONH₂, —CH(CONH₂)CH₃ or —CH₂CH₂CH₂CONH₂ and the like;

C1~C6 alkyl-substituted carbamoyl C1~C6 alkyl group refers to an carbamoyl C1~C6 alkyl group whose hydrogen atoms on the carbamoyl part is replaced by one or two identical or different C1~C6 alkyl group, for example, —CH₂CONHMe, —CH₂CH₂CONHEt, —CH₂CH₂CONMe₂ or —CH₂CONEt₂ and the like;

Cyano C1~C6 alkyl refers to a linear or branched alkyl group having 1 to 6 carbon atoms was linked with a cyano group through a carbon atom, for example, cyanomethyl, 2-cyanoethyl, 1-cyanoethyl, 3-cyanopropyl, 4-cyanobutyl or 5-cyano-pentyl group and the like;

Carboxy C1~C6 alkyl group refers to a linear or branched alkyl group having 1 to 6 carbon atoms was linked with a carboxyl group through a carbon atom, for example, carboxymethyl, 2-carboxyethyl, 1-carboxyethyl, 3-carboxypropyl, 4-carboxybutyl or 5-carboxy-pentyl group and the like;

C1~C6 alkylsulfonyl group refers to a linear or branched alkylsulfonyl group having 1 to 6 carbon atoms, for example, methylsulfonyl, ethylsulfonyl or propylsulfonyl and the like;

Halogenated C1~C6 alkylsulfonyl group refers to a linear or branched alkylsulfonyl group having 1 to 6 carbon atoms that was substituted with one or more identical or different halogen atoms, for example, trifluoromethylsulfonyl group;

C1~C6 alkyl-substituted amino group refers to an amino group substituted with one or two identical or different C1~C6 alkyl group, for example, —NHMe or —NEt₂ and the like;

C3~C10 cyclohydrocarbyl refers to a saturated or unsaturated cycloalkyl group having 3-10 carbon atoms, such as cyclopropyl, cyclobutyl, cyclopentyl, cyclohexyl, cycloheptyl, cyclooctyl, cyclobutenyl, cyclohexenyl, cyclohexadienyl, cyclopentenyl, or cyclopentadienyl group and the like;

3-10 membered heteromonocyclic group refers to a 3-10 membered monocyclic group containing at least one hetero atom selected from N, S and O, such as oxiranyl, azetidinyl, furanyl, dihydrofuranyl, tetrahydrofuranyl, thienyl, dihydrothienyl, tetrahydrothienyl, pyrrolyl, dihydro-pyrrolyl, pyrrolidinyl, pyrazolyl, dihydro-pyrazolyl, pyrazolidinyl, triazolyl, dihydro-triazole, triazolidinyl, thiazolyl, dihydrothiazolyl, thiazolidinyl, isothiazolyl, dihydro-isothiazolyl, isothiazolidinyl, oxazolyl, dihydro-oxazolyl, oxazolidinyl, isoxazolyl, dihydro-isoxazolyl, isoxazolidinyl, pyranyl, dihydro-pyranyl, tetrahydropyranyl, pyrazinyl, dihydro-pyrazinyl, tetrahydro-pyrazinyl, piperazinyl, pyridazinyl, dihydro-pyridazinyl, tetrahydro-pyridazinyl,

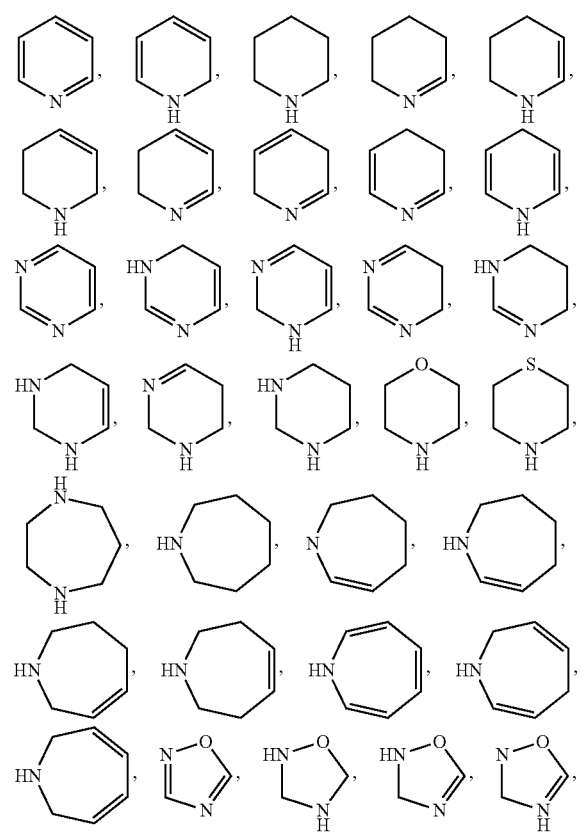

-continued

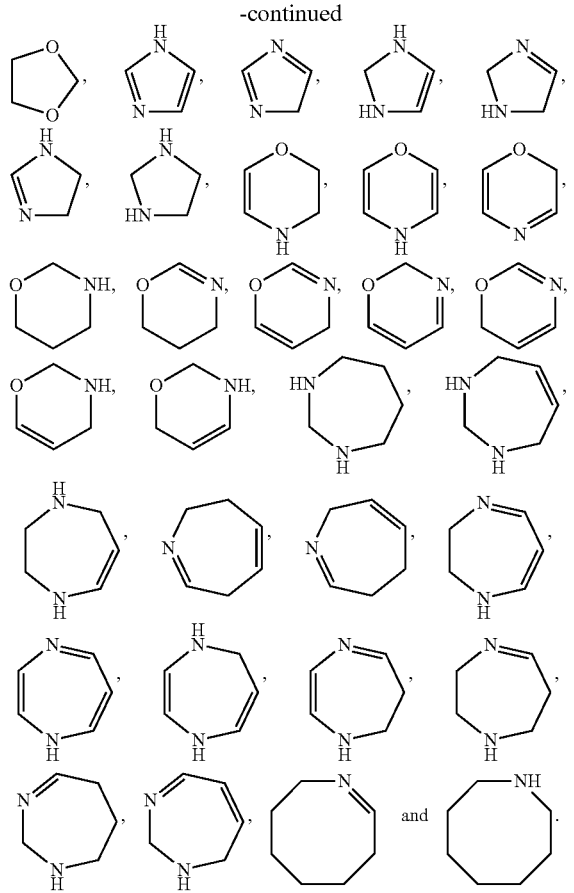

The compounds of this invention have the following advantages:

1) The compounds of the present invention show good activities for the serotonin 1A (5-HT$_{1A}$) receptor and/or dopamine D$_2$ receptor and/or serotonin 2A (5-HT$_{2A}$) receptor, especially for 5-HT$_{1A}$ receptor, the EC$_{50}$ value of some compounds even reach 1~0.1 nM level.

2) The compounds of the present invention have multi-target effect and simultaneously act on multiple subtypes of dopamine/serotonin receptors, specifically, they have high activity on dopamine D$_2$ receptor, 5-HT$_{1A}$ receptor and 5-HT$_{2A}$ receptor. As seen from the results of pharmacological experiments, most of the compounds have D$_2$ receptor antagonism/5-HT$_{1A}$ receptor agonism/5-HT$_{2A}$ receptor antagonism activities or D$_2$ receptor partial agonism/5-HT$_{1A}$ receptor agonism/5-HT$_{2A}$ receptor antagonism activities. In particular, some compounds have extremely potent D$_2$ receptor antagonism/5-HT$_{1A}$ receptor agonism/5-HT$_{2A}$ receptor antagonism activities and the IC$_{50}$/EC$_{50}$ values reached $10^{-9}$~$10^{-10}$M level. The multi-target effect characteristic is helpful to maintain receptor-balance in the brain, especially the balance of 5-HT and DA system, so as to treat central nervous system disease effectively.

3) Since the compounds of the present invention are multi-target modulators for the central nervous system receptors, they are devoid of side effects associated with D$_2$ receptor antagonists or D$_2$/5-HT$_{2A}$ receptor antagonists, such as extrapyramidal symptom (EPS) and metabolic disorders.

4) The compounds of the present invention are highly potent, orally active, and endowed with low effective dose and low toxicity. They are extremely effective for the treatment of central nervous system disorders, especially for major depressive disorder (MDD), anxiety disorder, negative symptoms in schizophrenia, cognitive impairment, Parkinson's disease, ADHD and the like.

In summary, the compounds of the present invention have advantages of multi-target effect, lower effective dose, fewer side effects, better safety and tolerability compared with conventional antipsychotics and show good clinical prospect.

EXAMPLE

Hereinbelow, the present invention will be further made clear with reference to Reference Examples, Examples and Pharmacological Experimental Examples. It should be understood, the following examples are only used for illustration of the present invention without intended to limit the scope of the invention.

Reference Example 1

Preparation of 1-(benzo[b]thiophen-4-yl)piperazine hydrochloride

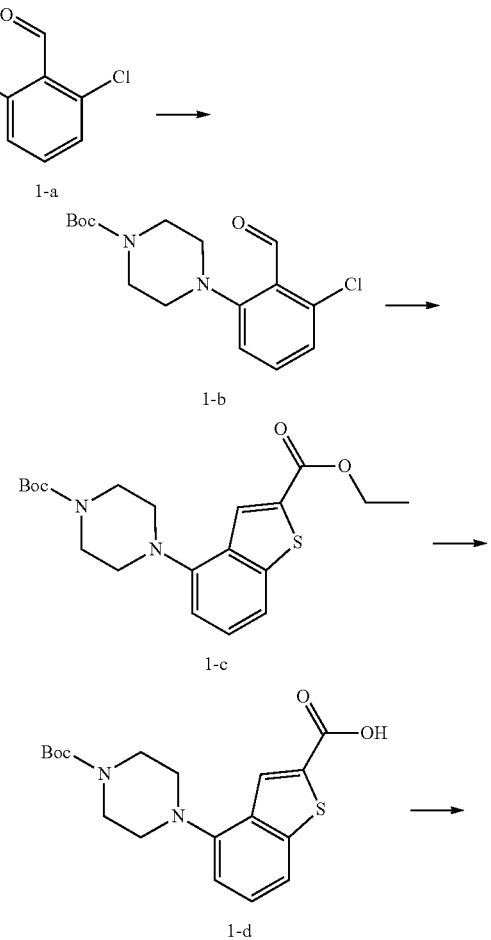

37

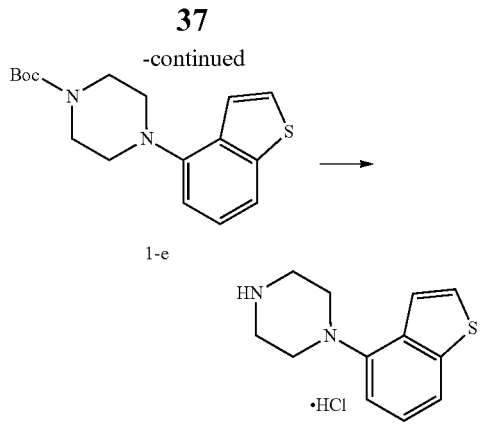

1-e

•HCl

Step 1:

2-chloro-6-fluorobenzaldehyde 1-a (500 mg, 3.15 mmol) and 1-boc-piperazine (646 mg, 3.47 mmol) were dissolved in N,N-dimethylformamide (5 ml), potassium carbonate (2.18 g, 15.77 mmol) was added thereto at room temperature under a nitrogen atmosphere. The mixture was stirred at 80° C. for 4 hours, cooled and filtered. The mixture was extracted with ethyl acetate (5 ml×3) and water (20 ml), washed with 1N hydrochloric acid (3 ml) and saturated sodium bicarbonate solution, dried over anhydrous sodium sulfate and concentrated. The residue was slurried in petroleum ether (50 ml) for 1 hour, filtered to give compound 1-b as a pale yellow solid (1.0 g, yield: 90%). $^1$H-NMR (300 Hz, DMSO-$d_6$): δ ppm 10.19(s, 1H), 7.52(t, 1H), 7.18(d, 2H), 3.46(t, 4H), 2.94(t, 4H), 1.39(s, 9H).

Step 2:

Compound 1-b (5 g, 15.3 mmol), ethyl thioglycolate (1.8 g, 15.3 mmol), potassium carbonate (6.2 g, 44.9 mmol) were added to N,N-dimethylformamide (50 ml) at room temperature under a nitrogen atmosphere. The mixture was stirred at 80° C. for 5 hours, cooled, filtered after ethyl acetate (50 ml) was added. The filtrate was extracted with ethyl acetate and water (200 ml). The organic phase was dried and concentrated to give a red-brown oil, which was slurried in petroleum ether, filtered to give compound 1-c (5.9 g, yield: 98%). ESI-MS (m/z): 391.4 [M+H]$^+$. $^1$H-NMR (300 Hz, CDCl3): δ ppm 8.10(s, 1H), 7.52(d, 1H), 7.37(t, 1H), 6.88(d, 1H), 4.40(q, 2H), 3.68(t, 4H), 3.10(t, 4H), 1.49(s, 9H), 1.41(t, 3H).

Step 3:

Compound 1-c (1.0 g, 2.5 mmol) was dissolved in 1,4-dioxane (5 ml), 4N aqueous sodium hydroxide (1.8 ml, 7.2 mmol) was added and the mixture was stirred at 80° C. for 3 hours. The reaction mixture was cooled to room temperature and extracted with ethyl acetate (10 ml) and water (5 ml). The pH value of the aqueous phase was adjusted with 1N hydrochloric acid to 4.0, the resulting solid was filtered, dried to give compound 1-d as a pale yellow solid (0.83 g, yield: 90%). $^1$H-NMR (300 Hz, DMSO-$d_6$): δ ppm 13.51 (brs, 1H), 7.96(s, 1H), 7.65(d, 1H), 7.40(t, 1H), 6.95(d, 1H), 3.55(s, 4H), 3.00(s, 4H), 1.41(s, 9H).

Step 4:

Compound 1-d (20 g, 54 mmol) and cuprous oxide (1 g) were dissolved in quinoline (50 ml). The mixture was stirred at 140° C. overnight and filtered after cooling. The mixture was extracted with ethyl acetate and water, washed with 1N hydrochloric acid and saturated sodium bicarbonate solution sequentially, dried over anhydrous sodium sulfate, filtered, concentrated and purified by column chromatography to give a crude. The crude was slurried in petroleum ether and then filtered to give compound 1-e as a white solid (10 g).

38

ESI-MS (m/z): 319.2 [M+H]$^+$. $^1$H-NMR (300 Hz, CDCl$_3$): δ ppm 7.57(d, 1H), 7.41(s, 2H), 7.27(t, 1H), 6.88(d, 1H), 3.66(t, 4H), 3.09(t, 4H), 1.50(s, 9H).

Step 5:

Compound 1-e (1 g, 3.14 mmol) was added into hydrochloric acid-methanol solution (5 ml) and the mixture was stirred at 50° C. for half an hour. The reaction mixture was concentrated to dryness, slurried in acetonitrile and filtered to give an off-white solid (800 mg, yield: 100%). ESI-MS (m/z): 219.2 [M+H]+.

Reference Example 2

Preparation of 5-(2-oxo-1,2,3,4-tetrahydroquinolin-7-yl)pentyl methanesulfonate

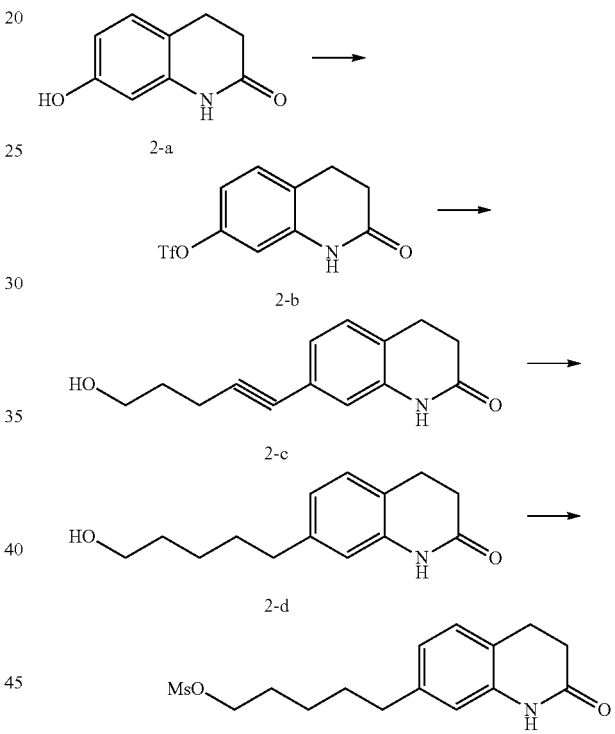

Step 1:

The reaction flask was charged with 7-hydroxy-3,4-dihydro-quinolin-2(1H)-one 2-a (10 g, 61.3 mmol), chloroform (100 ml) and pyridine (10.6 g, 134 mmol) were added thereto. The mixture was stirred at room temperature for 10 minutes and then cooled to 0° C. Trifluoromethanesulfonic anhydride (17.2 g, 60.99 mmol) was slowly added dropwise under ice bath followed by stirring for 30 minutes. The reaction was stirred at room temperature for 1 hour, filtered, the filtrate was washed with aqueous potassium bisulfate (1M) and water twice, dried over anhydrous sodium sulfate, concentrated, subjected to column chromatography to give 2-b as a pale yellow solid (12 g, yield: 67%).

Step 2:

Compound 2-b (18 g, 61.0 mmol), bis(triphenylphosphine) palladium dichloride (3.6 g, 5.12 mmol) and cuprous iodide (3.96 g, 20.8 mmol) were added into the reaction flask under a nitrogen atmosphere. 4-pentyn-1-ol (5 g, 59.5 mmol), triethylamine (26 g, 25.7 mmol) and N,N-dimethylformamide (100 ml) were injected and the mixture was stirred at 80° C. overnight. The reaction was cooled to room temperature, ethyl acetate (300 ml) was added. The insoluble solid was filtered off, the filtrate was washed twice with 1N hydrochloric acid and water, dried over anhydrous sodium sulfate, concentrated and the residue was purified by column chromatography to give compound 2-c as a white solid (5.5 g, yield: 39%).

Step 3:

A single-necked flask was charged with compound 2-c (5.5 g, 24.0 mmol), methanol (55 ml) and 10% Pd/C (150 mg) were added and the mixture was stirred at 55° C. under a hydrogen atmosphere for 15 hours. The mixture was cooled, filtered, concentrated and subjected to column chromatography to give 2-d as a white solid (3.3 g, yield: 60%).

Step 4:

Compound 2-d (0.5 g, 2.14 mmol) was dissolved in dichloromethane (5 ml) and triethylamine (0.6 ml, 4.28 mmol) was added. Methanesulfonyl chloride (0.2 ml, 2.56 mmol) was slowly injected into the above solution under ice bath condition in 15 minutes. Then the mixture was stirred at room temperature for 2 hours. The reaction mixture was extracted with dichloromethane and water. The organic phase was washed with brine, dried over anhydrous sodium sulfate and concentrated to give the target compound as a white solid (0.6 g, yield: 90%). ESI-MS (m/z): 312.1 [M+H]+.

Reference Example 3

Preparation of 5-(2-oxo-1,2-dihydroquinolin-7-yl)pentyl methanesulfonate

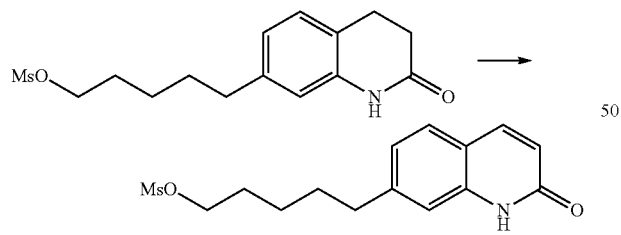

1,4-dioxane (5 ml) and 2,3-dichloro-5,6-dicyano-1,4-benzoquinone (0.875 mg, 3.85 mmol) were added into the product of Reference Example 2(0.8 g, 2.57 mmol) and the mixture was stirred at 95° C. for 3 hours. The reaction mixture was cooled, filtered, the filtrate was extracted with dichloromethane, washed with saturated sodium bicarbonate solution, saturated sodium thiosulfate solution, and brine sequentially, then dried over anhydrous sodium sulfate, concentrated and the residue was subjected to column chromatography to give a white solid (0.6 g, yield: 75%). ESI-MS (m/z): 310.1 [M+H]+.

Reference Example 4

Preparation of 4-(2-oxo-1,2,3,4-tetrahydroquinolin-7-yl)buyl methanesulfonate

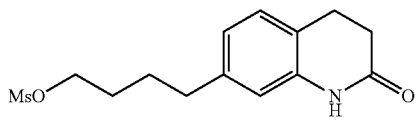 [SMILES: CS(=O)(=O)OCCCCc1ccc2c(c1)NC(=O)CC2]

By a similar method as in Reference example 2, 4-(2-oxo-1,2,3,4-tetrahydroquinolin-7-yl)butyl methanesulfonate was prepared from 3-butyn-1-ol as pale yellow oil, yield 34%. ESI-MS (m/z): 298.1 [M+H]+. $^1$H-NMR (300 Hz, CDCl$_3$): δ ppm 8.43(s, 1H), 7.07(d, 1H), 6.79(d, 1H), 6.60(s, 1H), 4.23(t, 2H), 3.00(s, 3H), 2.93(t, 2H), 2.62(m, 4H), 1.75(m, 4H).

Reference Example 5

Preparation of 4-(2-oxo-1,2-dihydroquinolin-7-yl)butyl methanesulfonate

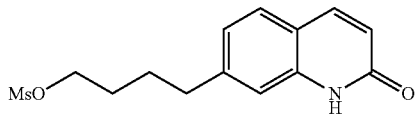 [SMILES: CS(=O)(=O)OCCCCc1ccc2ccc(=O)[nH]c2c1]

By a similar method as in Reference example 3, 4-(2-oxo-1,2-dihydroquinolin-7-yl)butyl methanesulfonate was prepared from the product of Reference example 4 as grey solid, yield 61%. ESI-MS (m/z): 296.1 [M+H]+. $^1$H-NMR (300 Hz, CDCl$_3$): δ ppm 12.37(s, 1H), 7.85(d, 1H), 7.52(d, 1H), 7.26(s, 1H), 7.09(d, 1H), 6.72(d, 1H), 4.25(t, 2H), 3.00(s, 3H), 2.78(t, 2H), 1.79(m, 4H).

Reference Example 6

Preparation of 2-(2-oxo-1,2,3,4-tetrahydroquinolin-7-yl)ethyl methanesulfonate

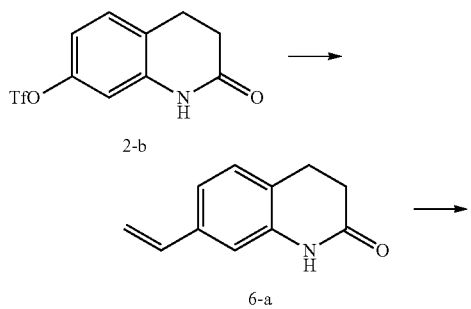

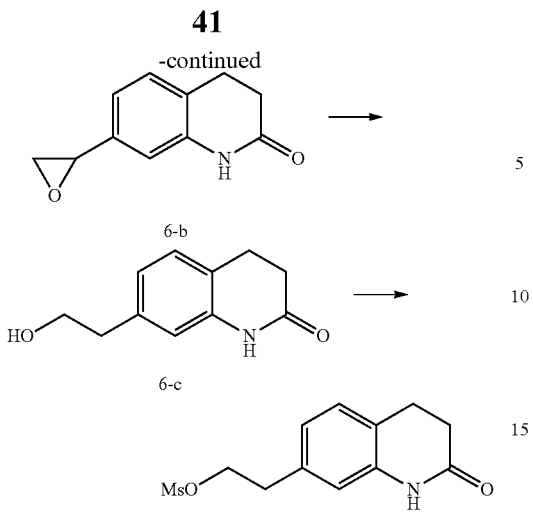

Step 1:

Lithium chloride (8.7 g, 203.1 mmol), bis(triphenylphosphine)palladium dichloride (5.7 g, 8.12 mmol) and N,N-dimethyl formamide (200 ml) were added into compound 2-b (20 g, 67.7 mmol). Tributylvinyltin (21 ml, 74.4 mmol) was injected thereto under a nitrogen atmosphere followed by stirring at 100° C. overnight. The mixture was filtered, extracted with dichloromethane and water, the organic phase was washed with brine, dried, concentrated, and subjected to column chromatography to give compound 6-a (8.0 g, yield: 68%).

Step 2:

Potassium peroxomonosulfate (Oxone, 43.6 g, 69.3 mmol), sodium bicarbonate (29.2 g) and acetone-water (400 ml: 400 ml) solution were added into compound 6-a (8 g, 46.2 mmol) and the mixture was stirred at room temperature for 2 hours. The mixture was filtered, extracted with dichloromethane and water. The organic phase was washed with brine, dried, concentrated, and subjected to column chromatography to obtain the target 6-b (5.7 g, yield: 65%). ESI-MS (m/z): 190.1 [M+H]$^+$. $^1$H-NMR (300 Hz, CDCl$_3$): δ ppm 8.42(brs, 1H), 7.16(d, 1H), 6.94(dd, 1H), 6.71(d, 1H), 3.85(dd, 1H), 3.15(dd, 1H), 2.98(t, 2H), 2.78(dd, 1H), 2.66(t, 2H).

Step 3:

A mixture of compound 6-b (3.6 g, 19.0 mmol), ammonium formate (3.0 g, 47.6 mmol), ethyl acetate (100 ml), methanol (100 ml) and 10% Pd/C (460 mg) was stirred at reflux under a nitrogen atmosphere overnight. The mixture was filtered, concentrated, subjected to column chromatography to obtain the compound 6-c (1.5 g, yield: 41%). ESI-MS (m/z): 192.0 [M+H]$^+$. $^1$H-NMR (300 Hz, CDCl$_3$): δ ppm 8.87(brs, 1H), 7.07(d, 1H), 6.84(d, 1H), 6.69(s, 1H), 3.84(t, 2H), 3.78(s, 1H), 2.90(t, 2H), 2.80(t, 2H), 2.59(t, 2H).

Step 4:

Compound 6-c (1.5 g, 7.85 mmol) was dissolved in dichloromethane (60 ml) and triethylamine (3 ml, 23.55 mmol) was added. Methanesulfonyl chloride (0.92 ml, 11.77 mmol) was added dropwise under ice bath followed by stirring at room temperature for 3 hours. The mixture was extracted with dichloromethane and water, the organic phase was dried, concentrated, subjected to column chromatography to obtain a white solid (1.3 g, yield: 61%). $^1$H-NMR (300 Hz, CDCl$_3$): δ ppm 8.97(brs, 1H), 7.11(d, 1H), 6.86(dd, 1H), 6.69(d, 1H), 4.39(t, 2H), 3.00(t, 2H), 2.94(t, 2H), 2.93(s, 3H), 2.63(t, 2H).

Reference Example 7

Preparation of 2-(2-oxo-1,2-dihydroquinolin-7-yl)ethyl methanesulfonate

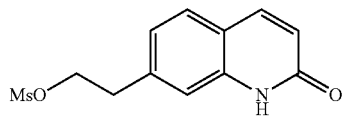 [SMILES: CS(=O)(=O)OCCc1ccc2ccc(=O)[nH]c2c1]

By a similar method as in Reference example 3, 2-(2-oxo-1,2-dihydroquinolin-7-yl)ethyl methanesulfonate was prepared from the product of Reference example 6 as a white solid, yield 75%. ESI-MS (m/z): 268.1 [M+H]$^+$. $^1$H-NMR (300 Hz, DMSO-d$_6$): δ ppm 11.74(brs, 1H), 7.87(d, 1H), 7.61(d, 1H), 7.18(s, 1H), 7.12(d, 1H), 6.45(d, 1H), 4.44(t, 2H), 3.13(s, 3H), 3.07(t, 2H).

Reference Example 8

Preparation of 1-(2-fluorobenzo[b]thiophen-4-yl) piperazine

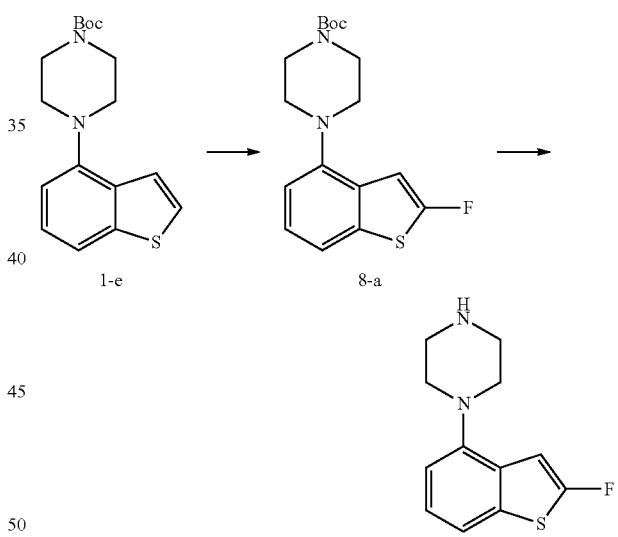

Step 1:

Compound 1-e (1 g, 3.14 mmol) was dissolved in dry tetrahydrofuran, stirred at −78° C. under a nitrogen atmosphere for 30 minutes. 2.5M n-butyllithium in n-hexane (1.65 ml, 4.08 mmol) was added dropwise and the mixture was stirred at the same temperature for 3 hours. N-Fluorobenzenesulfonimide (1.5 g, 4.71 mmol) dissolved in tetrahydrofuran (5 ml) was added dropwise into the system. The mixture was maintained at −78° C. for one hour and then stirred at room temperature overnight. The reaction was quenched with saturated ammonium chloride solution. The mixture was extracted with dichloromethane and water. The organic phase was washed with brine, dried over anhydrous sodium sulfate, concentrated, subjected to column chromatography to obtain 8-a as an oil (600 mg, yield: 57%).

Step 2:

Compound 8-a (600 mg) was dissolved in dichloromethane (1 ml) and trifluoroacetic acid (1 ml), the mixture was stirred at room temperature for 1 hour. The reaction mixture was concentrated and saturated sodium bicarbonate solution (5 ml) was added. The precipitated solid was filtered, dried to obtain a pale yellow solid (400 mg, 95% yield). ESI-MS (m/z): 237.1 [M+H]$^+$.

Reference Example 9

Preparation of 1-(2-chlorobenzo[b]thiophen-4-yl)piperazine

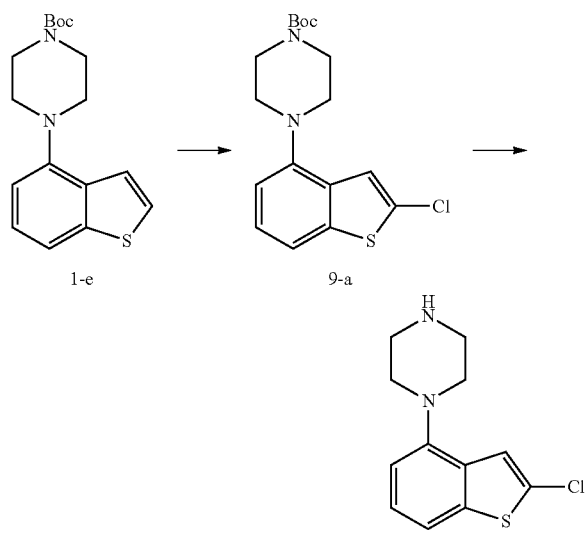

Step 1:

Compound 1-e (900 mg, 2.83 mmol) was dissolved in tetrahydrofuran (3 ml) in a three-necked flask under a nitrogen atmosphere. The mixture was cooled to −78° C., 2.5M n-butyllithium in n-hexane (1.47 ml, 3.67 mmol) was injected and the mixture was stirred at −78° C. for 3 hours. N-chlorosuccinimide (677 mg, 5.09 mmol) dissolved in tetrahydrofuran (3 ml) was slowly injected into the reaction system in 0.5 h. Then the mixture was stirred at room temperature overnight and quenched with saturated ammonium chloride solution. The mixture was extracted with dichloromethane and water. The organic phase was washed with brine, dried over anhydrous sodium sulfate, concentrated, subjected to column chromatography to obtain 9-a as an oil (540 mg, yield: 54%).

Step 2:

Compound 9-a (540 mg, 1.53 mmol) was dissolved in dichloromethane (1 ml) and trifluoroacetic acid (1 ml), the mixture was stirred at room temperature for 3 hours. The reaction mixture was concentrated and saturated sodium bicarbonate solution was added (3 ml). The precipitated solid was filtered, slurried in acetonitrile to give a white solid (210 mg, yield: 54%). ESI-MS (m/z): 253.2 [M+H]$^+$.
$^1$HNMR (300 MHz, DMSO-d$_6$): δ ppm 8.19(brs, 1H), 7.46-7.68(m, 2H), 7.32(t, 1H), 6.98(d, 1H), 3.25(s, 4H), 3.16(s, 4H).

Reference Example 10

Preparation of 3-(2-chloroethyl)-2-methyl-6,7-dihydro-4H-pyrido[1,2-a]pyrimidin-4-one

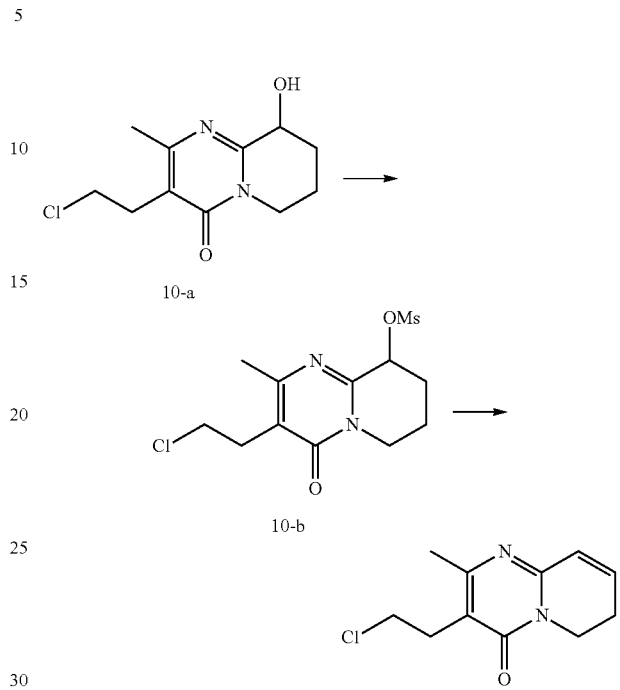

Step 1:

Triethylamine (0.85 ml, 6.19 mmol) and dichloromethane (10 ml) were added into compound 10-a (1 g, 4.13 mmol), then methanesulfonyl chloride (0.38 ml, 4.95 mmol) was added dropwise under ice bath condition. The mixture was stirred at room temperature for 30 minutes and extracted with dichloromethane and water. The organic phase was washed with brine, dried, and concentrated to give 10-b as an oil (1.23 g, yield: 93%).

Step 2:

Lithium bromide (418 mg, 4.86 mmol), lithium carbonate (358 mg, 4.86 mmol) and N,N-dimethylformamide (5 ml) were added into compound 10-b (520 mg, 1.62 mmol), the mixture was stirred at 115° C. for 2 hours and extracted with dichloromethane and water. The organic phase was washed with brine, dried and concentrated to give a yellow solid (400 mg, yield: 100%). ESI-MS (m/z): 225.1 [M+H]$^+$.
$^1$H-NMR (300 Hz, CDCl$_3$): δ ppm 2.35(s, 3H), 2.54(m, 2H), 3.01(t, 2H), 3.76(t, 2H), 4.14(t, 2H), 6.35(dt, 1H), 6.64(m, 1H).

Reference Example 11

Preparation of 6-(5-chloropentyl)-2-methylquinazolin-4(3H)-one

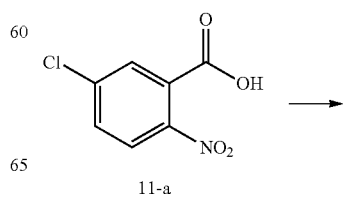

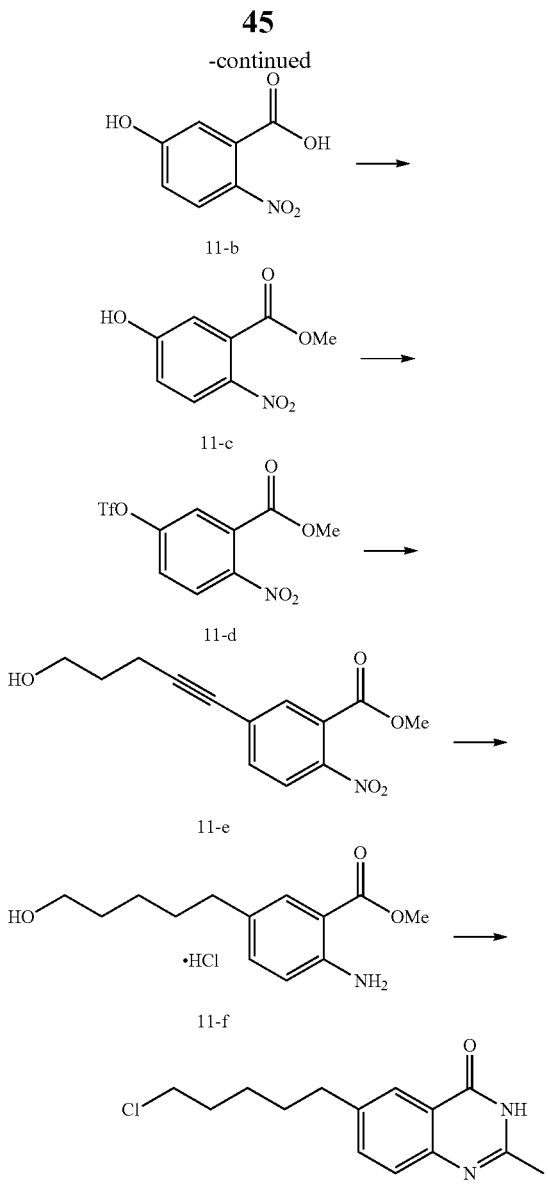

Step 1:

Potassium hydroxide aqueous solution (13.8 g, 248 mmol, 40 ml) was added into 5-chloro-2-nitrobenzoic acid 11-a (5 g, 24.8 mmol) and the mixture was stirred at reflux for 24 hours. The pH value of the reaction mixture was adjusted to 2 with concentrated hydrochloric acid under ice-cooling, the precipitated solid was filtered and dried to give 11-b as a white solid (4.1 g, yield: 90%).

Step 2:

Thionyl chloride (26.8 mmol) and methanol (10 ml) were added into compound 11-b (4.1 g, 22.4 mmol) and the mixture was stirred at reflux for 5 hours. The reaction solution was concentrated, extracted with ethyl acetate and water, washed with brine, dried, and concentrated to give the target 11-c (3.19 g, yield: 72%).

Step 3:

Pyridine (67.5 mmol) and dichloromethane (10 ml) were added into compound 11-c (2.66 g, 13.5 mmol). Trifluoromethanesulfonic anhydride (20.2 mmol) was slowly added dropwise thereto under ice-cooling followed by stirring at room temperature for 6 hours. The mixture was diluted with dichloromethane (100 ml), washed with 1N hydrochloric acid (70 ml) and brine, the organic phase was dried over anhydrous sodium sulfate and concentrated to give 11-d as a tan solid (3.86 g, yield: 87%).

Step 4:

A mixture of compound 11-d (2.83 g, 8.6 mmol), 4-pentyn-1-ol (789 mg, 9.4 mmol), bis (triphenylphosphine) palladium dichloride (603 mg, 0.86 mmol), cuprous iodide (245 mg, 1.29 mmol), triethylamine (5.9 ml, 43 mmol) and N,N-dimethylformamide (10 ml) was stirred at room temperature overnight. The reaction mixture was diluted with dichloromethane, washed twice with dilute hydrochloric acid, the organic phase was dried, concentrated, subjected to column chromatography to obtain 11-e as an oil (2.2 g, yield: 97%). $^1$H-NMR (300 Hz, CDCl$_3$): δ ppm 7.88(d, 1H), 7.67(d, 1H), 7.57(dd, 1H), 3.92(s, 3H), 3.80(q, 2H), 2.58(t, 2H), 1.87(m, 2H), 1.49(t, 1H).

Step 5:

Ethanol (5 ml) and Pd/C (150 mg) were added into compound 11-e (1.04 g, 3.95 mmol) and the reaction mixture was stirred at 50° C. under a hydrogen atmosphere for 24 hours. The mixture was filtered and the filtrate was concentrated. Hydrogen chloride-ethanol solution was added, the resulting hydrochloride salt was slurried in acetone/methyl tert-butyl ether system, filtered, and dried to give 11-f as a yellow solid (840 mg, yield: 89%). ESI-MS (m/z): 238.1 [M+H]$^+$.

Step 6:

Compound 11-f (455 mg, 1.91 mmol) was dissolved in acetonitrile (3 ml) and hydrogen chloride/1,4-dioxane solution (3 ml) in a sealed tube and the mixture was stirred at 70° C. overnight. The reaction mixture was concentrated, the pH value thereof was adjusted to be around 7 with saturated sodium bicarbonate solution. The mixture was extracted with ethyl acetate, the organic phase was dried, concentrated and subjected to silica gel column chromatography to give the title compound (280 mg, yield: 55%). ESI-MS (m/z): 265.1 [M+H]$^+$. $^1$H-NMR (300 Hz, DMSO-d$_6$): δ ppm 12.11 (brs, 1H), 7.86(d, 1H), 7.60(dd, 1H), 7.48(d, 1H), 3.61(t, 2H), 2.69(t, 2H), 2.32(s, 3H), 1.73(m, 2H), 1.62(m, 2H), 1.39(m, 2H).

Reference Example 12

Preparation of 1-(2,3-dihydrobenzo[b]thiophen-4-yl) piperazine hydrochloride

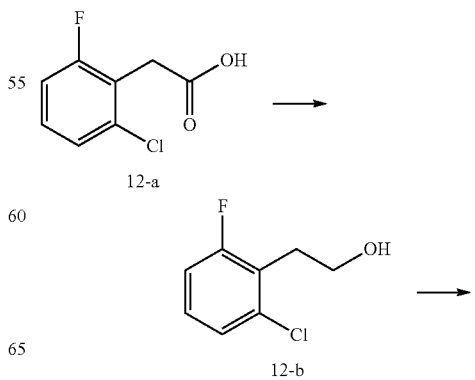

-continued

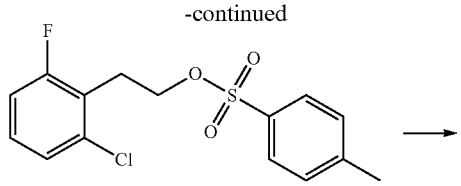

12-c

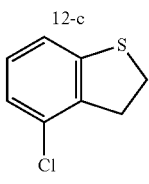

12-d

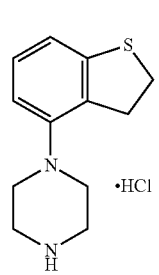

·HCl

Step 1:

Lithium aluminium hydride (4.6 g, 121 mmol) was added to a flask containing dry tetrahydrofuran (20 ml). Compound 12-a (10 g, 53.2 mmol) dissolved in tetrahydrofuran (100 ml) was added dropwise under ice bath condition. The mixture was stirred for 20 minutes at room temperature, then at reflux for 3 hours. Sodium sulfate decahydrate was added slowly until no bubbles appear. The mixture was filtered, the filtrate was dried, concentrated, subjected to column chromatography to obtain the product 12-b (7.8 g, yield: 85%).

Step 2:

Compound 12-b (6.7 g, 38.5 mmol), triethylamine (4.66 g, 46.2 mmol) and dichloromethane (80 ml) were added to the flask, p-toluenesulfonyl chloride (7.34 g, 38.5 mmol) in dichloromethane (20 ml) was added dropwise at room temperature and the mixture was stirred. After the reaction is complete, water and 1N hydrochloric acid was added, the mixture was extracted with dichloromethane. The organic phase was washed with water and saturated sodium bicarbonate solution, dried and concentrated to give the product 12-c (10 g, yield: 80%).

Step 3:

Compound 12-c (10 g, 30.4 mmol), sodium sulfide nonahydrate (8.75 g, 36.4 mmol) and N-methylpyrrolidinone (50 ml) were added to the flask and the mixture was stirred at 150° C. for 4 hours. The mixture was extracted with methyl t-butyl ether (80 ml×2) and water (100 ml). The organic phase was washed with saturated brine (100 ml×2), dried, concentrated, subjected to column chromatography to obtain the product 12-d (1.8 g, yield: 35%)

Step 4:

Compound 12-d (500 mg, 2.94 mmol), anhydrous piperazine (379 mg, 4.41 mmol), sodium tert-butoxide (423 mg, 4.41 mmol), 2,2'-bis(diphenylphosphino-1,1'-binaphthyl) (83 mg, 0.13 mmol), palladium acetate (10 mg, 0.044 mmol) and dry toluene (10 ml) were added to the flask under a nitrogen atmosphere and the mixture was stirred at 115° C. for 24 hours. The reaction mixture was concentrated, and subjected to column chromatography to obtain an oil. Hydrogen chloride-ethanol solution was added, the resulting hydrochloride salt was slurried in acetonitrile, filtered to give a white solid (280 mg, yield: 43%). ESI-MS (m/z): 221.1 [M+H]+.

Reference Example 13

Preparation of 4-(piperazin-1-yl)thieno[2,3-d]pyrimidine trifluoroacetate

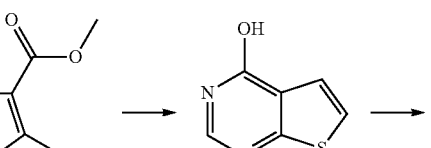

13-a        13-b

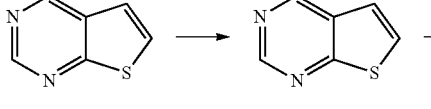

13-c        13-d

·CF₃CO₂H

Step 1:

Methyl 2-Amino-thiophene-3-carboxylate (2.0 g, 12.7 mmol) was dissolved in formamide (60 ml) and the mixture was stirred at 190° C. for 4 hours. The mixture was cooled, poured into water (200 ml) and extracted with n-butanol (50 ml×4). The combined organic phase was dried over anhydrous sodium sulfate, concentrated and subjected to column chromatography to give 13-b as a pale yellow solid (1.2 g, yield: 63%). ESI-MS (m/z): 153.0 [M+H]+. ¹H-NMR (300 Hz, DMSO-d₆): δ ppm 7.39(d, 1H), 7.57(d, 1H), 8.12(s, 1H), 12.49(brs, 1H).

Step 2:

Phosphorus oxychloride (10 ml) was added into compound 13-b (500 mg, 3.23 mmol) followed by stirring at reflux overnight. The reaction mixture was cooled to room temperature, poured into a vigorously stirred ice-water mixture and stirring was continued for 30 minutes. The mixture was extracted with dichloromethane (50 ml×3). The combined organic phase was washed with brine, dried over anhydrous sodium sulfate, and concentrated to give 13-c as a yellow solid (600 mg, yield: 100%). ESI-MS (m/z): 170.9 [M+H]+. ¹H-NMR (300 Hz, CDCl₃): δ ppm 7.46(d, 1H), 7.64(d, 1H), 8.87(s, 1H).

Step 3:

Compound 13-c (600 mg, 3.53 mmol) was dissolved in tetrahydrofuran (20 ml), 1-boc-piperazine (984 mg, 5.3 mmol) and N,N-diisopropylethylamine (910 mg, 7.06 mmol) were added thereto followed by stirring at reflux for 2 hours. The reaction mixture was cooled to room temperature, concentrated, subjected to column chromatography to obtain 13-d as a white solid (900 mg, yield: 79.4%). ESI-MS (m/z): 321.2 [M+H]+. 1H-NMR (300 Hz, CDCl3): δ ppm 1.48(s, 9H), 3.61(m, 4H), 3.92(m, 4H), 7.32(m, 2H), 8.50(s, 1H).

Step 4:

Compound 13-d (900 mg) was dissolved in dichloromethane (10 ml), trifluoroacetic acid (1 ml) was added at 0° C. and the mixture was stirred overnight at room temperature. The reaction mixture was concentrated to dryness under reduced pressure, the residue was slurried in methyl t-butyl ether/methanol system (V:V=15 ml:1 ml), filtered, and dried to give a yellow solid (606 mg, yield: 98%).

Reference Example 14

Preparation of 4-(benzo[b]thiophen-4-yl)-1,2,3,6-tetrahydropyridine hydrochloride

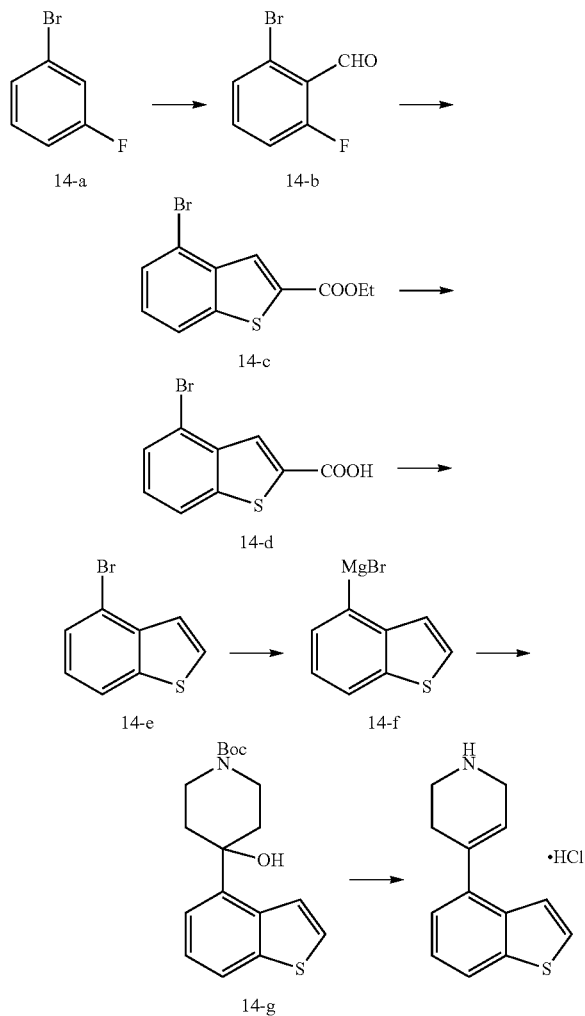

Step 1:

A 500 mL three-necked flask was charged with tetrahydrofuran (250 ml) and diisopropylamine (28 ml), n-butyllithium (78 ml) was added dropwise at −10° C.~0° C. under a nitrogen atmosphere. The mixture was stirred at 0° C. for 30 minutes and then cooled to −78° C. 3-Bromofluorobenzene (21 ml) was added dropwise, after stirring at −78° C. for 1 hour, N,N-dimethylformamide (17 ml) was added followed by stirring 20 minutes at the same temperature. Then glacial acetic acid (28 ml) and water (200 ml) was quickly added and the mixture was warmed to 15° C. The mixture was extracted with ethyl acetate (500 ml×2), the organic phase was washed with water (300 ml×2) and brine (200 ml×1), dried over anhydrous sodium sulfate, concentrated and subjected to column chromatography to obtain the target 14-b (32 g, yield: 81%).

Step 2:

A three-necked flask was charged with N,N-dimethylformamide (250 ml) and potassium carbonate (51.5 g, 373 mmol). Ethyl thioglycolate (13.7 ml) was added dropwise at room temperature under a nitrogen atmosphere followed by rapid addition of compound 14-b (25.2 g, 124 mmol). The mixture was stirred at 60° C. overnight, diluted with ethyl acetate (300 ml), filtered, and the filtrate was washed with water and saturated brine, dried, concentrated and subjected to column chromatography to obtain compound 14-c (23 g, yield: 66%).

Step 3:

A 500 mL single-neck flask was charged with compound 14-c (20 g, 70.4 mmol), tetrahydrofuran (120 ml) and water (100 ml). 4N aqueous sodium hydroxide solution (40 ml) was added under stirring followed by stirring at 70° C. for 1 hour. The reaction mixture was extracted with ethyl acetate (70 ml×2), the pH of the aqueous phase was adjusted with concentrated hydrochloric acid to 1~2, the precipitated solid was filtered and dried to give compound 14-d (16 g, yield: 88%).

Step 4:

Compound 14-d (14 g, 54.6 mmol) and dimethyl sulfoxide (140 ml) were placed in a 25 mL single neck flask, silver carbonate (15 g, 54.3 mmol) and acetic acid (163 mg) were added thereto under stirring. The mixture was stirred at 120° C. overnight, cooled to room temperature, filtered after ethyl acetate (100 ml) was added. The filtrate was extracted with ethyl acetate (200 ml×3) and water, the organic phase was dried, concentrated, subjected to column chromatography to obtain 14-e as a colorless transparent oil (1 g, yield: 95%).

Step 5:

Magnesium debris (113 mg, 4.7 mmol) was added to tetrahydrofuran (5 ml) under a nitrogen atmosphere, the mixture was stirred for 5 min and then heated to 60° C. Part of the tetrahydrofuran solution (1.0 g, 4.7 mmol, 5 ml) of compound 14-e (2 ml) was added dropwise to the above systems and stirred at 60° C. The Grignard reaction began as the system turned cyan blue. The remaining tetrahydrofuran solution of the compound 14-e was added dropwise under reflux and the system turned pale yellow. The reaction was continued at reflux until disappearance of magnesium debris (about 2 hours), which indicated the end of the Grignard reaction.

Step 6:

Tert-butyl 4-oxopiperidine-1-carboxylate (1.0 g, 5 mmol) in tetrahydrofuran (5 ml) was added dropwise into the fresh Grignard reagent 14-f at 0° C. followed by stirring at room temperature for 1 hour. The reaction was cooled to 0° C. and saturated ammonium chloride solution was added. The mixture was extracted with ethyl acetate, washed with brine, dried, concentrated and subjected to column chromatography to obtain compound 14-g (700 mg, 44% yield by two steps).

Step 7:

Compound 14-g (120 mg, 0.36 mmol) was dissolved in toluene (5 ml) and 6N hydrochloric acid (5 ml) and the mixture was stirred at 100° C. overnight. The reaction was cooled to room temperature, the pH value of the aqueous phase was adjusted to 9.0 with 10% sodium hydroxide solution at 0° C. The mixture was extracted with dichloromethane, dried, concentrated, the residue was dissolved in ethyl acetate and added with hydrogen chloride-ethanol solution. The resulting salt was filtered to give the target (50 mg, yield: 65%). ESI-MS (m/z): 216.1 [M+H]$^+$. $^1$H-NMR (300 Hz, MeOH-d$_4$): δ ppm 7.89(d, 1H), 7.64(d, 1H), 7.56(dd, 1H), 7.37(t, 1H), 7.28(dd, 1H), 5.96(m, 1H), 3.93 (m, 2H), 3.55(t, 2H), 2.85(m, 2H).

Reference Example 15

Preparation of 5-(2-chloroethyl)indolin-2-one

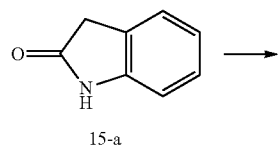

15-a

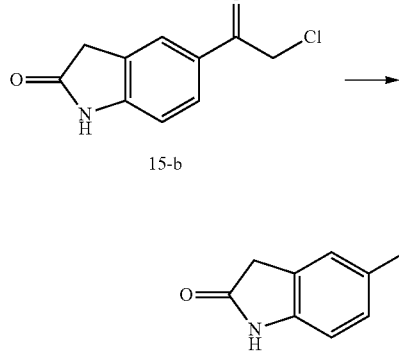

Step 1:

Indolin-2-one 15-a (2 g, 15.03 mmol) was dissolved in dichloromethane (10 ml), aluminum trichloride (7 g, 52.60 mmol) was added, then chloroacetyl chloride (2.26 ml, 30.06 mmol) dissolved in dichloromethane (10 ml) was slowly added dropwise under ice bath, the mixture was stirred at this temperature for 1 hour and at reflux for 2 hours. The mixture was cooled, poured into ice water, the aqueous layer was adjusted to be strongly acidic, the precipitated solid was filtered and dried to give a light gray white solid (2.811 g, yield: 90%).

Step 2:

Compound 15-b (1 g, 4.78 mmol) was dissolved in trifluoroacetic acid (10 ml), triethylsilane (1.5 ml) was added dropwise under ice-cooling followed by stirring at room temperature for 2 hours. The reaction solution was poured into water, extracted twice with ethyl acetate. The organic phase was washed with saturated sodium bicarbonate solution and brine, dried and concentrated to give a khaki solid (0.9 g, yield: 96%). ESI-MS (m/z): 195.9 [M+H]$^+$. $^1$H-NMR (300 Hz, CDCl$_3$): δ ppm 7.69(brs, 1H), 7.10(s, 1H), 7.07(d, 1H), 6.80(d, 1H), 3.68(t, 2H), 3.52(s, 2H), 3.02(t, 2H).

Reference Example 16

Preparation of 2-(6-chloro-2-oxo-1,2,3,4-tetrahydraquinolin-7-yl)ethyl methanesulfonate

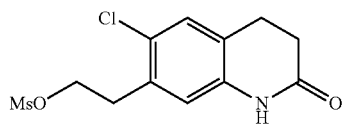

N,N-dimethylformamide (8 ml) and N-chlorosuccinimide (228 mg, 1.71 mmol) were added into the product of Reference Example 6(440 mg, 1.63 mmol) and the mixture was stirred at 100° C. for 4 hours. The mixture was extracted with dichloromethane and water, the organic phase was washed with brine, dried over anhydrous sodium sulfate, concentrated and subjected to column chromatography to give a white solid (330 mg, yield: 67%). ESI-MS (m/z): 304.0 [M+H]$^+$.

Reference Example 17

Preparation of 3-(2-chloroethyl)-9-fluoro-2-methyl-6,7,8,9-tetrahydro-4H-pyrido[1,2-a]pyrimidin-4-one

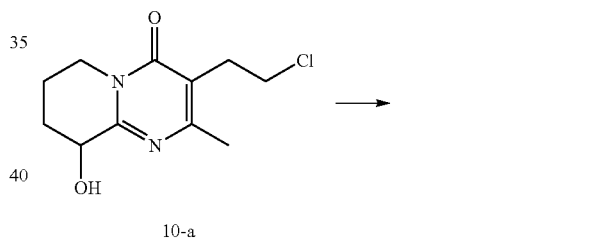

10-a

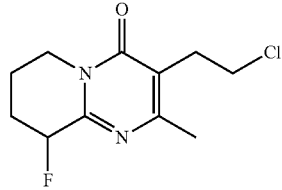

3-(2-chloroethyl)-9-hydroxy-2-methyl-6,7,8,9-tetrahydro-pyrido[1,2-a]pyrimidin-4-one 10-a (500 mg, 2.06 mmol) was dissolved in dichloromethane (10 ml), diethylaminosulfur trifluoride (0.32 ml, 2.47 mmol) dissolved in dichloromethane (8 ml) was added dropwise thereto under ice bath followed by stirring at room temperature for 3 hours. The mixture was quenched with water, saturated sodium bicarbonate solution was added to adjust pH to 7. The mixture was extracted with dichloromethane, dried over anhydrous sodium sulfate, concentrated and subjected to column chromatography to obtain the product as white crystal (370 mg, yield: 74%). ESI-MS (m z): 245.1 [M+H]$^+$. $^1$H-NMR (300 Hz, DMSO-d$_6$): δ ppm 1.92(m, 2H), 2.15(m, 2H), 2.29(s, 3H), 2.90(t, 2H), 3.55(m, 1H), 3.73(t, 2H), 4.00(dt, 1H), 5.26-5.47(dt, 1H).

Reference Example 18

Preparation of 5-(2-chloroethyl)-4-methylthiazole

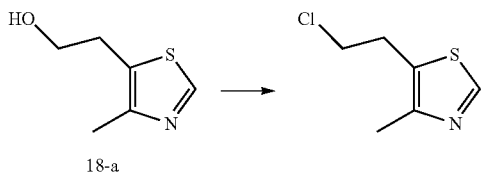

18-a 2-(4-methyl-thiazol-5-yl) ethanol 18-a (500 mg, 3.49 mmol) was added into thionyl chloride (4 ml) and the mixture was stirred at reflux for 3 hours. The mixture was concentrated to dryness to give a pale yellow solid (680 mg, yield: 98%). ESI-MS (m z): 162.0 [M+H]$^+$.

Reference Example 19

Preparation of 5-(2-chloroethyl)-1H-benzo[d]imidazol-2(3H)-one

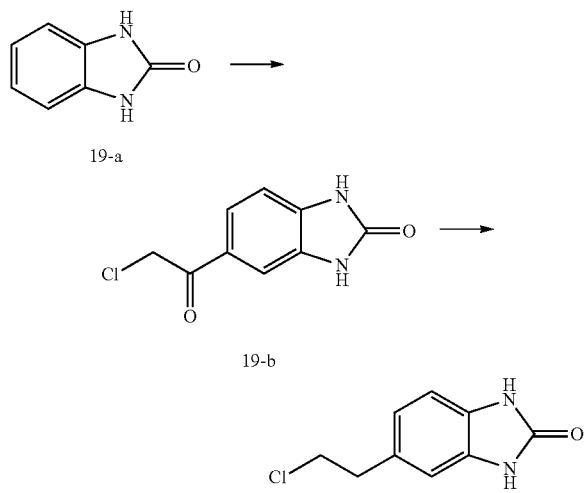

Step 1:

1H-benzimidazol-2(3H)-one 19-a (500 mg, 3.73 mmol) was added into anhydrous aluminum chloride (1.98 g, 14.9 mmol) and tetrachloroethane (3 ml). Chloroacetyl chloride (843 mg, 7.46 mmol) dissolved in tetrachloroethane (3 ml) was added dropwise thereto under ice bath followed by stirring at 100° C. for 1 hour. The mixture was cooled to room temperature, ice and 4N hydrochloric acid (20 ml) were added sequentially followed by stirring for 6 hours, the precipitated solid was filtered, the filter cake was slurried in isopropanol, filtered, and dried to give 19-b as an off-white solid (730 mg, yield: 93%). EI-MS (m/z): 210.

Step 2:

Compound 19-b (350 mg, 1.67 mmol) was dissolved in trifluoroacetic acid (5 ml), triethylsilane (0.66 ml, 4.17 mmol) was added dropwise under ice-cooling followed by stirring at room temperature overnight. The reaction mixture was concentrated, saturated sodium bicarbonate solution was added, the precipitated solid was filtered, the filter cake was washed three times with ice water and dried to give a pale yellow solid (310 mg, yield: 95%). EI-MS (m/z): 196.

Reference Example 20

Preparation of 6-(2-chloroethyl)benzo[d]thiazol-2(3H)-one

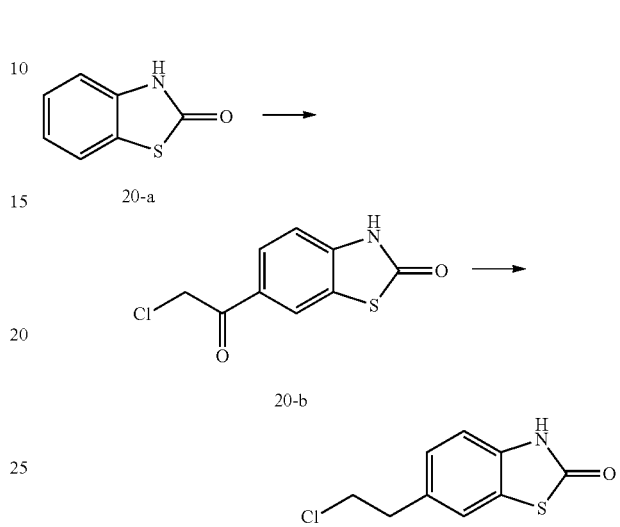

Step 1:

Benzothiazole-2(3H)-one 20-a (500 mg, 3.307 mmol) was suspended in carbon disulfide (8 ml), anhydrous aluminum chloride (2.65 g, 19.841 mmol) was added portionwise under ice bath, then chloroacetyl chloride (324 ul, 4.299 mmol) was slowly added dropwise. The reaction mixture was stirred at room temperature for 10 minutes and at reflux for 1.5 hours. The reaction was quenched with ice water and concentrated. Ice water (15 ml) and 4N hydrochloric acid (10 ml) was added thereto. The mixture was stirred for 2 hours at room temperature, filtered, the filter cake was washed with ice water twice, dried to give 20-b as a pink solid (740 mg, yield: 98%). ESI-MS (m/z): 227.9 [M+H]$^+$. $^1$H-NMR (300 Hz, DMSO-d$_6$): δ ppm 12.35(s, 1H), 8.25(d, 1H), 7.89(dd, 1H), 7.20(d, 1H), 5.13(s, 2H).

Step 2:

Compound 20-b (360 mg, 1.586 mmol) was dissolved in trifluoroacetic acid (5 ml), triethylsilane (630 ul, 3.965 mmol) was added dropwise followed by stirring at 10° C. overnight. The reaction mixture was concentrated, extracted with dichloromethane and water. The organic phase was dried over anhydrous sodium sulfate, filtered and concentrated to give a crude (385 mg), which was purified by column chromatography to obtain the target (280 mg, yield: 82.5%).

Reference Example 21

Preparation of 6-(2-chloroethyl)-2H-benzo[b][1,4]oxazin-3(4H)-one

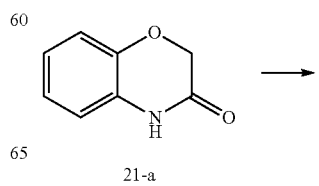

21-a

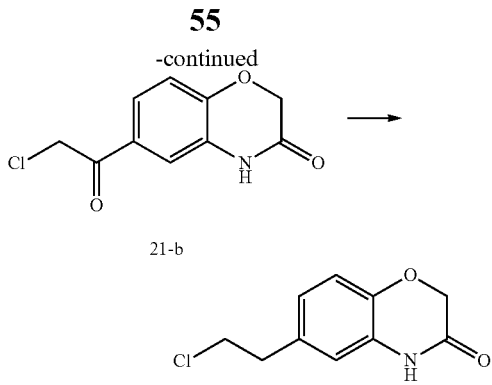

21-b

Step 1:

2H-1,4-benzoxazin-3(4H)-one 21-a (500 mg, 3.356 mmol) was suspended in dichloromethane (8 ml). Anhydrous aluminum chloride (895 mg, 6.712 mmol) was added portionwise under ice bath, then chloroacetyl chloride (330 ul, 4.363 mmol) was added slowly dropwise. The reaction mixture was stirred at room temperature for 10 minutes, then at reflux for 5 hours. The reaction was quenched with water, concentrated. The residue was added with ice water (10 ml), 4N hydrochloric acid (5 ml) and stirred for 2 hours at room temperature, then filtered, the filter cake was washed with ice water twice, dried to give 21-b as a pale yellow solid (690 mg, yield: 91%).

Step 2:

Compound 21-b (370 mg, 1.637 mmol) was dissolved in trifluoroacetic acid (4 ml), triethylsilane (640 ul, 4.093 mmol) was added dropwise under ice-bath followed by stirring at 10° C. overnight. The reaction solution was concentrated and extracted with dichloromethane and water. The organic phase was dried over anhydrous sodium sulfate, filtered and concentrated to give a crude (375 mg). The crude was slurried in petroleum ether, filtered and dried to give a pale yellow solid (316 mg, yield: 91%). $^1$H-NMR (300 Hz, DMSO-$d_6$): δ ppm 10.68(brs, 1H), 6.86(d, 1H), 6.81(dd, 1H), 6.74(d, 1H), 4.51(s, 2H), 3.75(t, 2H), 2.90(t, 2H).

Reference Example 22

Preparation of 6-(2-chloroethyl)-2H-benzo[b][1,4]thiazin-3(4H)-one

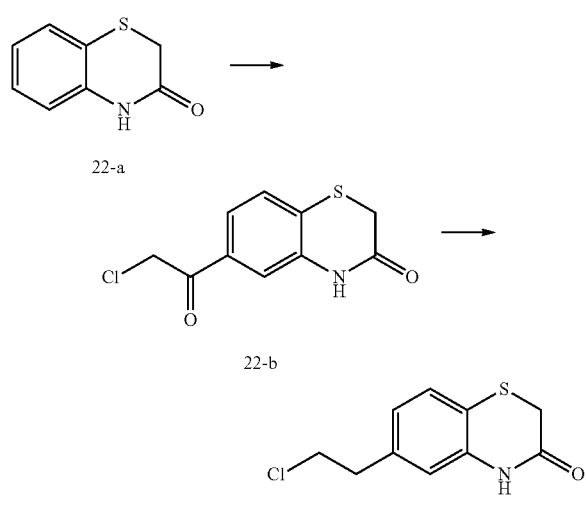

Step 1:

Anhydrous aluminum trichloride (1.62 g, 12.15 mmol) was added portionwise into chloroacetyl chloride (912 ul, 12.11 mmol) dissolved in methylene chloride (6 ml) under ice bath followed by stirring for 10 minutes at this temperature. Then 2H-1,4-benzothiazine-3(4H)-one 22-a (500 mg, 3.027 mmol) was added portionwise thereto, the reaction was stirred under ice bath for 4 hours and at room temperature overnight. Ice water (10 ml) and 4N hydrochloric acid (10 ml) was added sequentially. The mixture was stirred at room temperature for 2 hours. The precipitated solid was filtered, the filter cake was washed twice with ice water, dried to give 22-b as a pale yellow solid (700 mg, yield: 95.6%). $^1$H-NMR (300 Hz, DMSO-$d_6$): δ ppm 10.76(brs, 1H), 7.57(dd, 1H), 7.50(m, 2H), 5.11(s, 2H), 3.54(s, 2H).

Step 2:

Compound 22-b (350 mg, 1.446 mmol) was dissolved in trifluoroacetic acid (4 ml). triethylsilane (578 ul, 3.615 mmol) was added dropwise thereto under ice bath condition followed by stirring at 30° C. overnight. The reaction mixture was poured into ice water, extracted with dichloromethane, the organic phase was dried over anhydrous sodium sulfate, filtered, concentrated and subjected to column chromatography to give a pale yellow solid (285 mg, yield: 86.8%). EI-MS (m/z): 227.

Reference Example 23

Preparation of 5-(4-oxo-3,4-dihydroquinazolin-6-yl)pentyl methanesulfonate

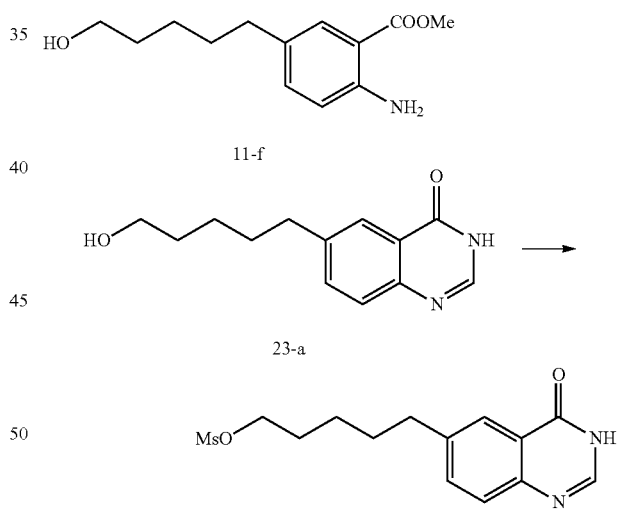

Step 1:

A mixture of compound 11-f (395 mg, 1.66 mmol), ammonium formate (1.04 g, 16.6 mmol) and formamide (5 ml) was stirred at 135° C. for 60 hours. The reaction mixture was poured into ice water and extracted with ethyl acetate three times. The combined organic layer was washed with brine, dried over anhydrous sodium sulfate, concentrated and subjected to column chromatography to obtain the target 23-a (150 mg, yield: 38%). ESI-MS (m/z): 233.2 [M+H]$^+$. $^1$H-NMR (300 Hz, DMSO-$d_6$): δ ppm 12.17(brs, 1H), 8.03(s, 1H), 7.90(d, 1H), 7.65(dd, 1H), 7.57(d, 1H), 4.36(t, 1H), 3.37(m, 2H), 2.70(t, 2H), 1.60(m, 2H), 1.43(m, 2H), 1.30(m, 2H).

Step 2:

Triethylamine (125 ul, 0.87 mmol) was added to the compound 23-a (100 mg, 0.43 mmol) in dichloromethane (5 ml). Methanesulfonyl chloride (51 ul, 0.65 mmol) was added thereto under ice-bath followed by stirring at room temperature for 2 hours. The reaction was diluted with dichloromethane, washed with saturated ammonium chloride solution, the organic phase was dried, concentrated and subjected to column chromatography to obtain a white solid (71 mg, yield: 53%). ESI-MS (m/z): 311.1 [M+H]+.

Reference Example 24

Preparation of 2-(2-chloroethyl)quinazolin-4(3H)-one

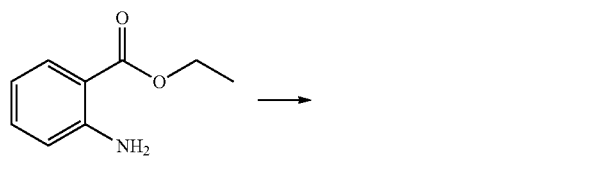

o-aminobenzoate 24-a (1.0 g, 6.62 mmol), acrylonitrile (0.88 ml, 13.24 mmol) were dissolved in 1,4-dioxane, hydrogen chloride-1,4-dioxane (10 ml) solution was slowly added thereto under ice bath condition. The mixture was stirred in a sealed tube at 80° C. overnight and concentrated. Water and dichloromethane was added thereto and the pH value of the aqueous layer was adjusted to 7-8 with ammonia. The mixture was filtered, the filter cake was slurried in methyl t-butyl ether, filtered and dried to give a pale yellow solid (660 mg, yield: 52%). ESI-MS (m/z): 209.1 [M+H]+.

Reference Example 25

Preparation of 3-(2-oxoindolin-5-yl)propyl methanesulfonate

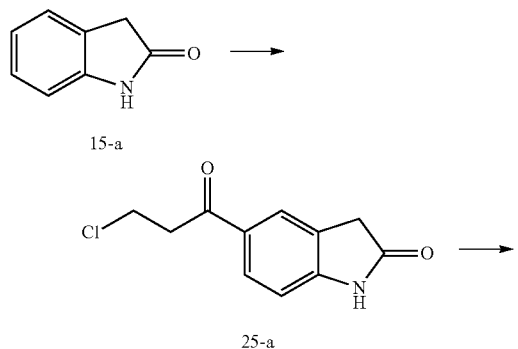

-continued

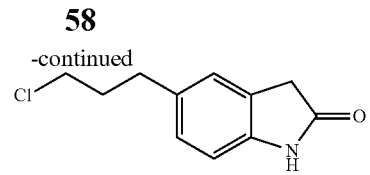

Step 1:

3-chloropropionyl chloride (538 ul, 5.63 mmol) was added dropwise to anhydrous aluminum chloride (2 g, 15.02 mmol) suspended in carbon disulfide under ice bath condition and stirred for 10 minutes, indolin-2-one 15-a (500 mg, 3.75 mmol) was added thereto. The mixture was stirred at room temperature for 15 minutes and at reflux for 3 hours. Carbon disulfide was removed, the reaction mixture was added with ice and 4N hydrochloric acid (5 ml) under stirring. The resulting solid was filtered, the filter cake was washed 3 times with ice water, dried to give a crude. The crude was slurried in ethyl acetate, filtered and dried to give 25-a as a pale pink solid (777 mg, yield: 92.4%). ¹HNMR (300 MHz, DMSO-d₆): δ ppm 10.77(s, 1H), 7.86(d, 1H), 7.81(s, 1H), 6.89(d, 1H), 3.89(t, 2H), 3.54(s, 2H), 3.44(t, 2H).

Step 2:

Triethylsilane (900 ul, 5.58 mmol) was added dropwise to compound 25-a (500 mg, 2.32 mmol) dissolved in trifluoroacetic acid and the mixture was stirred at 30° C. overnight. The reaction mixture was poured into ice water, and extracted three times with dichloromethane, the combined organic phase was dried and concentrated. The residue was slurried in petroleum ether/acetone system (V:V=30:1), filtered and dried to give a light pink solid (430 mg, yield: 92%).

Reference Example 26

Preparation of 4-(piperazin-1-yl)thieno[2,3-c]pyridine trifluoroacetate

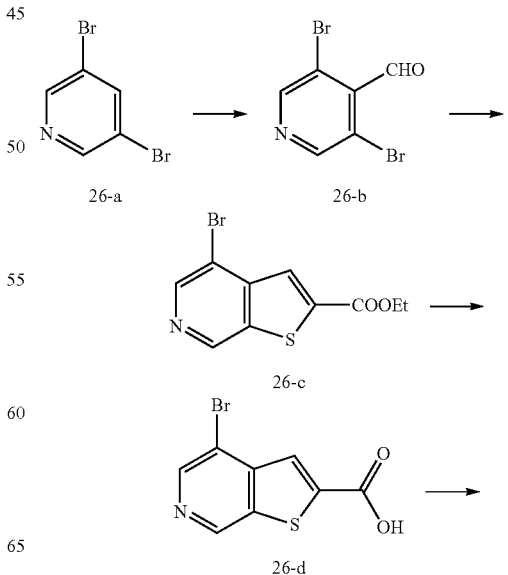

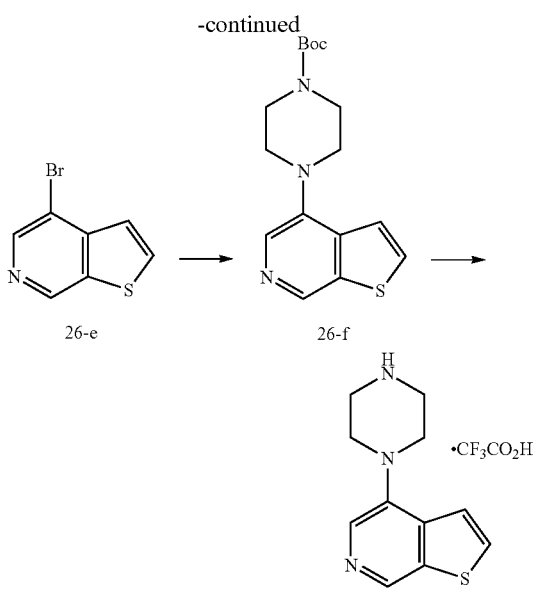

Step 1:

Diisopropylamine (2.4 g, 24.0 mmol) was dissolved in dry tetrahydrofuran (20 ml) under a nitrogen atmosphere, n-butyllithium in n-hexane (9.6 ml, 24.0 mmol) was added dropwise thereto at 0° C. followed by stirring at this temperature for 30 minutes, dry tetrahydrofuran (30 ml) was added and the mixture was cooled to −78° C., 3,5-dibromopyridine 26-a (4.7 g, 20 mml) in dry tetrahydrofuran (50 ml) was added dropwise thereto followed by stirring for 30 minutes. Methyl formate (2.4 g, 40 mml) was added followed by stirring for 30 minutes, The mixture was warmed to room temperature, extracted with saturated sodium bicarbonate (100 ml) and ethyl acetate (50 ml×3). The combined organic phase was dried over anhydrous sodium sulfate, concentrated and subjected to column chromatography to give 26-b as a pale yellow solid (4.0 g, yield: 75%). $^1$HNMR (300 MHz, DMSO-$d_6$): δ ppm 10.06(s, 1H), 8.87(s, 2H).

Step 2:

Compound 26-b (2.0 g, 7.5 mmol) was dissolved in tetrahydrofuran (10 ml), ethyl thioglycolate (0.68 ml, 7.5 mmol) was added thereto at 0° C. and the mixture was stirred for 1 hour. Cesium carbonate (2.46 g, 7.5 mmol) was added thereto followed by stirring at room temperature overnight. The reaction mixture was filtered, concentrated and subjected to column chromatography to give 26-c as a white solid (1.6 g, yield: 74%). ESI-MS (m/z): 286.1 [M+H]$^+$. $^1$HNMR (300 MHz, DMSO-$d_6$): δ ppm 9.36(s, 1H), 8.71(s, 1H), 8.01(s, 1H), 4.39(q, 2H), 1.34(t, 3H).

Step 3:

Compound 26-c (2.0 g, 7.0 mmol) was dissolved in tetrahydrofuran (40 ml), lithium hydroxide monohydrate (588 mg, 14.0 mmol) and methanol (5 ml) were added thereto followed by stirring at room temperature for 2 hours. The pH value of the mixture was adjusted to 4 with 2N hydrochloric acid. The mixture was concentrated to remove tetrahydrofuran and methanol, filtered, and dried in vacuum to give 26-d as a white solid (1.0 g, yield: 55%). $^1$HNMR (300 MHz, DMSO-$d_6$): δ ppm 9.33(s, 1H), 8.69(s, 1H), 7.94(s, 1H).

Step 4:

Compound 26-d (500 mg, 1.9 mol) was added into diphenyl ether (6 ml) and stirred at 230° C. for 2 hours. The mixture was cooled to room temperature, concentrated and subjected to silica gel column chromatography to obtain 26-e as a white solid (300 mg, yield: 73%). ESI-MS (m/z): 213.8 [M+H]$^+$. $^1$HNMR (300 MHz, CDCl$_3$): δ ppm 9.10(s, 1H), 8.60(s, 1H), 7.89(d, 1H), 7.54(d, 1H).

Step 5:

Compound 26-e (1.5 g, 7.0 mmol), 1-boc-piperazine (2.6 g, 14.0 mml), 2,2'-bis(diphenylphosphino-1,1'-binaphthyl) (436 mg, 0.7 mml), tris(dibenzylideneacetone) dipalladium (320.3 mg, 0.35 mmol) and sodium tert-butoxide (1.34 g, 14.0 mml) were dispersed in anhydrous toluene (50 ml) and stirred at 100° C. overnight under a nitrogen atmosphere. The reaction was cooled to room temperature, filtered, concentrated and subjected to silica gel column chromatography to obtain 26-f as a pale yellow solid (1.7 g, yield: 77%). ESI-MS (m/z): 320.3 [M+H]$^+$.

Step 6:

Compound 26-f (687 mg) was dissolved in dichloromethane (10 ml), trifluoroacetic acid (3.0 ml) was added thereto under 0° C. followed by stirring at room temperature overnight. The reaction mixture was concentrated to dryness under reduced pressure, the residual oil was slurried in methyl t-butyl ether/methanol (V:V=15 ml:1 ml) system, filtered, and dried to give a yellow solid (941 mg, yield: 98%). $^1$HNMR (300 MHz, CDCl$_3$): δ ppm 8.90(s, 1H), 8.06(s, 1H), 7.89(d, 1H), 7.51(d, 1H), 3.68(t, 4H), 3.21(t, 4H), 1.49(s, 9H).

Reference Example 27

Preparation of 3-(2-oxo-1,2,3,4-tetrahydroquinolin-7-yl)propyl methanesulfonate

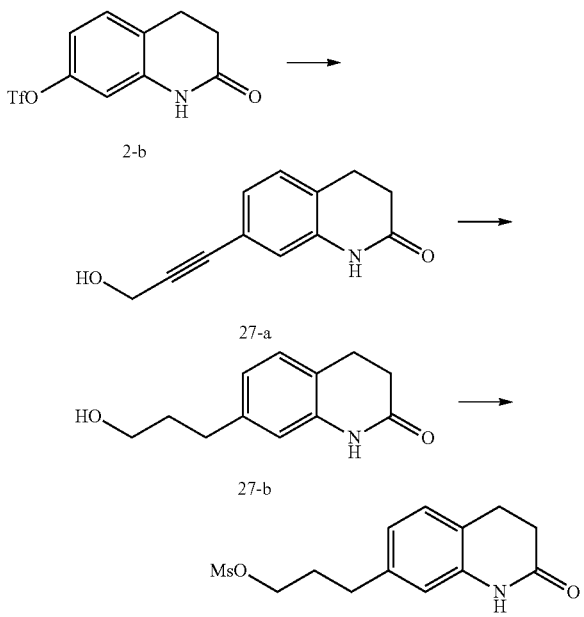

Step 1:

Compound 2-b (10.0 g, 33.9 mmol), Bis(triphenylphosphine) palladium dichloride (1.2 g, 1.7 mmol), triphenylphosphine (888.2 mg, 3.39 mmol), cuprous iodide (644 mg, 3.39 mol) and diisopropylamine (17.17 g, 170.0 mmol) were dispersed in N,N-dimethylformamide (100 ml) and the mixture was heated to 80° C. under a nitrogen atmosphere.

Propargyl alcohol (9.5 g, 170.0 mmol) was added dropwise followed by stirring for 4 hours. The reaction mixture was cooled, concentrated, subjected to column chromatography to give a pale yellow solid (4.0 g, yield: 58%). ESI-MS (m/z): 202.1 [M+H]$^+$. $^1$HNMR (300 MHz, DMSO-d$_6$): δ ppm 10.14(s, 1H), 7.14(d, 1H), 6.93(dd, 1H), 6.85(d, 1H), 5.30(t, 1H), 4.25(d, 2H), 2.85(t, 2H), 2.42(t, 2H).

Step 2:

Compound 27-a (2.0 g, 10.0 mmol) was dissolved in methanol (50 ml), 10% Pd/C (200 mg) was added and the mixture was stirred under a hydrogen atmosphere overnight. The reaction mixture was cooled, filtered, concentrated and subjected to column chromatography to give 27-b as a white solid (1.2 g, yield: 58%). ESI-MS (m/z): 206.2 [M+H]$^+$. $^1$HNMR (300 MHz, DMSO-d$_6$): δ ppm 9.98(s, 1H), 7.02(d, 1H), 6.71(dd, 1H), 6.64(d, 1H), 4.44(t, 1H), 3.37(q, 2H), 2.78(t, 2H), 2.49(t, 2H), 2.39(t, 2H), 1.63(m, 2H).

Step 3:

Compound 27-b (600 mg, 2.93 mmol) was dissolved in dichloromethane (10 ml) and trimethylamine (443.9 mg, 4.4 mmol) was added. Methanesulfonyl chloride (404 mg, 3.51 mmol) was added dropwise under ice bath condition followed by stirring at room temperature for 2 hours. Dichloromethane (100 ml) was added thereto, the organic phase was separated, washed with 1N hydrochloric acid and saturated sodium bicarbonate solution, dried over anhydrous sodium sulfate, concentrated and the residue was purified by column chromatography to give a white solid (745 mg, yield: 90.5%). ESI-MS (m/z): 284.1 [M+H]$^+$. $^1$HNMR (300 MHz, CDCl$_3$): δ ppm 8.76(s, 1H), 7.08(d, 1H), 6.81(d, 1H), 6.63(s, 1H), 4.21(t, 2H), 3.01(s, 3H), 2.93(t, 2H), 2.70(t, 2H), 2.63(t, 2H), 2.04(m, 2H).

Reference Example 28

Preparation of 3-(2-oxo-1,2-dihydroquinolin-7-yl)propyl methanesulfonate

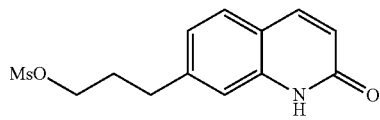 [SMILES: CS(=O)(=O)OCCCc1ccc2ccc(=O)[nH]c2c1]

By a similar method as in Reference Example 3, 3-(2-oxo-1,2-dihydroquinolin-7-yl)propyl methanesulfonate was prepared from the product of Reference Example 27 as a gray solid, yield 37.5%. ESI-MS (m/z): 282.2 [M+H]$^+$. $^1$HNMR (300 MHz, DMSO-d$_6$): δ ppm 11.67(s, 1H), 7.83(d, 1H), 7.56(d, 1H), 7.10(s, 1H), 7.04(d, 1H), 6.40(d, 1H), 4.19(t, 2H), 3.16(s, 3H), 2.71(t, 2H), 1.96(m, 2H).

Reference Example 29

Preparation of 7-(2-chloroethyl)-4,5-dihydro-1H-benzo[b]azepin-2(3H)-one

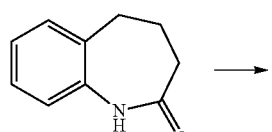

29-a

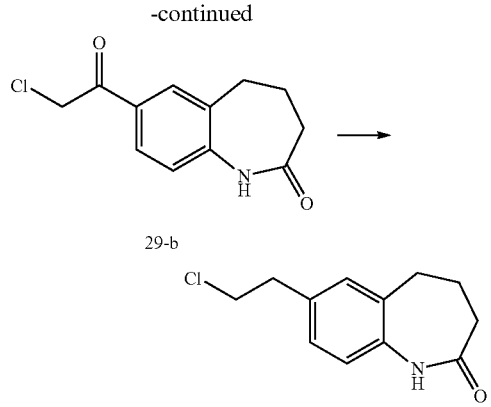

Step 1:

Chloroacetyl chloride (470 μl, 6.20 mmol) was added dropwise into anhydrous aluminum chloride (2.48 g, 18.60 mmol) suspended in carbon disulfide under ice bath condition and stirred for 10 minutes. 4,5-dihydro-benzo-1H-azepine-2(3H)-one 29-a (500 mg, 3.10 mmol) was added and the mixture was stirred at room temperature for 15 minutes and at reflux for 3 hours. Carbon disulfide was removed, ice and 4N hydrochloric acid (5 ml) was added sequentially under stirring. The precipitated pale yellow solid was filtered, washed 3 times with ice water, dried to give a crude. The crude was recrystallized in water-methanol system (11 ml:11 ml) to give the product as tan needles (640 mg, yield: 86.7%). $^1$HNMR (300 MHz, CDCl$_3$): δ ppm 8.31(s, 1H), 7.86(d, 1H), 7.84(dd, 1H), 7.07(d, 1H), 4.67(s, 2H), 2.88(t, 2H), 2.41(t, 2H), 2.29(m, 2H).

Step 2:

Triethylsilane (840 μL, 5.25 mmol) was added dropwise into compound 29-b (500 mg, 2.10 mmol) dissolved in trifluoroacetic acid (5 ml) and the mixture was stirred at 50° C. overnight. The reaction mixture was poured into ice water, extracted three times with dichloromethane. The combined organic phase was dried and concentrated. The residue was slurried in isopropyl ether, filtered and dried to give a pale yellow solid (430 mg, yield: 91.4%).

Reference Example 30

Preparation of 2-(2-oxoindolin-6-yl)ethyl methanesulfonate

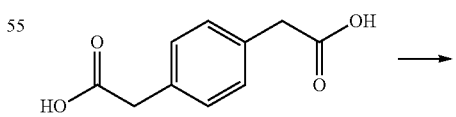

30-a

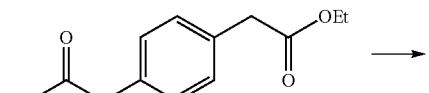

30-b

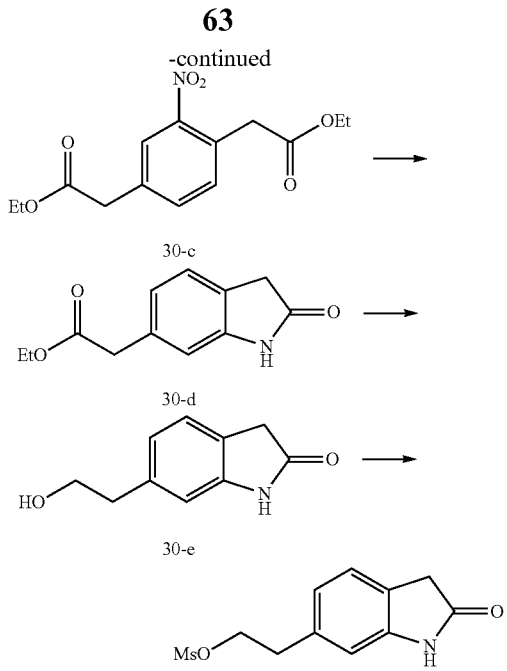

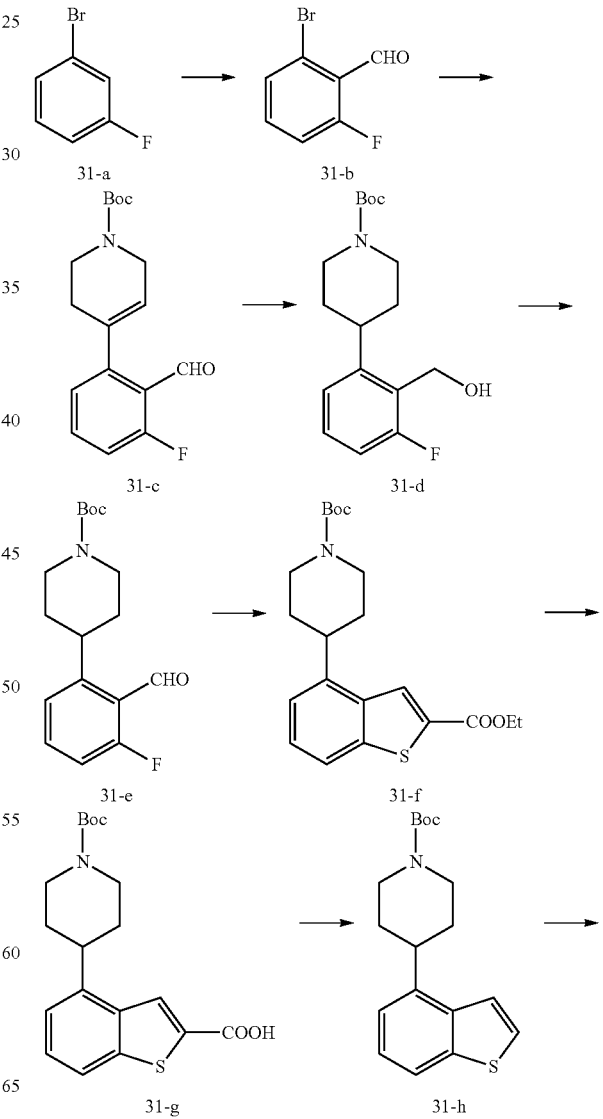

Step 1:

The reaction flask was charged with 2,2'-(1,4-phenylene)diacetic acid 30-a (9.2 g, 47.4 mmol) and ethanol (50 ml), concentrated sulfuric acid (5 ml, 94.8 mmol) was slowly added dropwise under stirring. The mixture was stirred at 80° C. overnight and then concentrated under reduced pressure to remove ethanol. Dichloromethane was added and the pH value of the aqueous layer was adjusted to 8 with saturated sodium bicarbonate solution. The aqueous phase was separated and extracted again with dichloromethane. The combined organic phase was dried and concentrated to give 30-b as solid (10.3 g, yield: 87%). ESI-MS (m/z): 251.2 [M+H]$^+$.

Step 2:

The reaction flask was charged with compound 30-b (10 g, 40 mmol) and concentrated sulfuric acid (30 ml), fuming nitric acid (1.7 ml, 40.4 mmol) was added dropwise thereto at 0° C. followed by stirring at room temperature for 1 hour. The reaction mixture was poured into ice water, the precipitated solid was filtered, washed with water and dried to give 30-c as solid (11 g, yield: 93%).

Step 3:

Ethanol (25 ml) and 10% Pd/C (850 mg) were added into compound 30-c (4.7 g, 15.9 mmol) and the mixture was stirred at 40° C. under a hydrogen atmosphere overnight. The mixture was filtered at 40° C., the filtrate was concentrated to give a crude (3.1 g). The crude was slurried in petroleum ether/ethyl acetate (V:V=6:1) system, filtered to obtain 30-d (2.4 g, yield: 71%). EI-MS (m/z): 219. $^1$HNMR (300 MHz, CDCl$_3$): δ ppm 8.80(brs, 1H), 7.17(d, 1H), 6.93(d, 1H), 6.86(s, 1H), 4.17(q, 2H), 3.60(s, 2H), 3.52(s, 2H), 1.28(t, 3H).

Step 4:

The reaction flask was charged with compound 30-d (2.86 g, 13.0 mmol) and tetrahydrofuran (200 ml), lithium aluminum hydride (2.5 g, 65.3 mmol) was added portionwise at 0° C. followed by stirring for 30 minutes. Water (1.24 ml), 15% aqueous sodium hydroxide solution (1.24 ml) and water (3.72 ml) were slowly added dropwise successively. The mixture was filtered and concentrated. The residue was slurried in dichloromethane, filtered to give a crude (1.28 g).

The crude was slurried in petroleum ether/dichloromethane system, filtered and dried to give 30-e as a white solid (1.17 g, yield: 50%). ESI-MS (m/z): 178.1 [M+H]$^+$. $^1$HNMR (300 MHz, DMSO-d$_6$): δ ppm 10.31(brs, 1H), 7.07(d, 1H), 6.76 (d, 1H), 6.68(s, 1H), 4.64(t, 1H), 3.57(q, 2H), 3.39(s, 2H), 2.67(t, 2H).

Step 5:

Compound 30-e (200 mg, 1.1 mmol) and pyridine (0.24, 3.3 mmol) were suspended in dichloromethane. Methanesulfonyl chloride (0.12 ml, 1.21 mmol) was slowly added thereto dropwise under ice bath followed by stirring at room temperature for 4 hours. The reaction mixture was poured into water, washed with 1N hydrochloric acid and saturated brine, the organic phase was dried, filtered and concentrated to give the target (220 mg, yield: 76%). ESI-MS (m/z): 256.0 [M+H]$^+$.

Reference Example 31

Preparation of 4-(benzo[b]thiophen-4-yl)piperidine trifluoroacetate

-continued

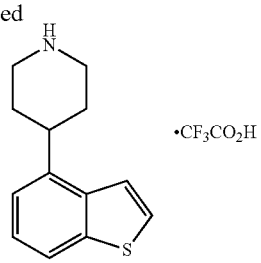

Step 1:

Diisopropylamine (5.14 g, 50.8 mmol) was dissolved in dry tetrahydrofuran (50 ml) under a nitrogen atmosphere, n-butyllithium in hexane (20.3 ml, 50.8 mml) was added dropwise thereto at 0° C. followed by stirring for 30 minutes. The reaction mixture was cooled to −78° C., 1-bromo-3-fluorobenzene 31-a (10.0 g, 42.4 mml) in dry tetrahydrofuran (100 ml) solution was added dropwise thereto followed by stirring for 30 minutes. Methyl formate (7.63 g, 127.2 mml) was added dropwise thereto followed by stirring for 30 minutes. The mixture was warmed to room temperature, extracted with ethyl acetate (100 ml×3) and 1N hydrochloric acid (100 ml). The combined organic phase was dried over anhydrous sodium sulfate, filtered, concentrated, subjected to column chromatography to give 31-b as a white solid (8.0 g, yield: 93%).

Step 2:

Compound 31-b (4.1 g, 20.4 mmol), tert-butyl 4-(4,4,5,5-tetramethyl-1,3,2-dioxaborolan-2-yl)-5,6-dihydropyridine-1(2H)-carboxylate (6.3 g, 20.4 mmol), 1,1'-Bis(diphenylphosphino)ferrocene-palladium(II)dichloride-dichloromethane complex (Pd(dppf)Cl$_2$.CH$_2$Cl$_2$, 1.7 g, 2.04 mmol) and potassium carbonate (7.04 g, 51.0 mmol) were dispersed in anhydrous N,N-dimethylformamide (80 ml) and stirred at 80° C. under a nitrogen atmosphere overnight. The reaction was cooled to room temperature, poured into water (200 ml) and extracted with ethyl acetate (100 ml×3). The combined organic phase was washed with brine, dried over anhydrous sodium sulfate, filtered, concentrated, subjected to column chromatography to give 31-c as a colorless oil (3.5 g, yield: 55.5%). $^1$HNMR (300 MHz, CDCl$_3$): δ ppm 10.26(s, 1H), 7.50(m, 1H), 7.09(t, 1H), 7.03(d, 1H), 5.55(s, 1H), 4.05(m, 2H), 3.67(m, 2H), 2.33(s, 2H), 1.49(s, 9H).

Step 3:

Compound 31-c (3.5 g, 11.5 mmol) was dissolved in ethyl acetate (50 ml), 10% Pd/C (1.0 g) was added and the mixture was stirred at room temperature under a hydrogen atmosphere for 5 hours. The mixture was filtered, the filtrate was concentrated to give 31-d as a colorless oil (3.5 g, 100%). ESI-MS (m/z): 310.1 [M+H]$^+$. $^1$HNMR (300 MHz, DMSO-d$_6$): δ ppm 7.26(dd, 1H), 7.04(d, 1H), 6.93(t, 1H), 4.80(s, 2H), 4.24(d, 2H), 3.08(t, 1H), 2.82(t, 2H), 1.78(d, 2H), 1.72-1.53(m, 4H), 1.47(s, 9H).

Step 4:

Compound 31-d (3.5 g, 11.5 mmol) was dissolved in dichloromethane (50 ml), pyridinium chlorochromate (PCC, 3.0 g, 13.8 mmol) was added thereto at room temperature followed by stirring for 1 hour. The mixture was filtered, concentrated and subjected to column chromatography to obtain 31-e as a white solid (3.0 g, yield: 85%). ESI-MS (m/z): 308.1 [M+H]$^+$. $^1$HNMR (300 MHz, CDCl$_3$): δ ppm 10.54(s, 1H), 7.51(dd, 1H), 7.16(d, 1H), 7.02(t, 1H), 4.23(d, 2H), 3.78(t, 1H), 2.86(t, 2H), 1.78(d, 2H), 1.57(m, 2H), 1.47(s, 9H).

Step 5:

Compound 31-e (3.0 g, 9.4 mmol) was dissolved in acetonitrile (50 ml), potassium carbonate (1.95 g, 14.1 mmol) and ethyl thioglycolate (0.85 ml, 9.4 mmol) were added thereto followed by stirring at 80° C. overnight. The mixture was filtered, concentrated and subjected to column chromatography to give 31-f as a white solid (3.3 g, yield: 90.1%). ESI-MS (m/z): 390.0 [M+H]$^+$. $^1$HNMR (300 MHz, CDCl$_3$): δ ppm 8.20(s, 1H), 7.71(d, 1H), 7.41(t, 1H), 7.22(d, 1H), 4.41(q, 2H), 4.30(d, 2H), 3.22(m, 1H), 2.90(t, 2H), 1.91(d, 2H), 1.75(m, 2H), 1.49(s, 9H), 1.42(t, 3H).

Step 6:

Lithium hydroxide monohydrate (698 mg, 16.6 mmol) and methanol (10 ml) were added into compound 31-f (3.24 g, 8.3 mmol) dissolved in tetrahydrofuran (60 ml) and the mixture was stirred at room temperature for 5 hours. The pH of the reaction mixture was adjusted to 4-5 with 1N hydrochloric acid, the precipitated solid was filtered, dried in vacuo to give 31-g as a white solid (2.8 g, yield: 96.5%).

Step 7:

Cuprous oxide (966 mg, 0.676 mml) was added into compound 31-g (2.44 g, 6.76 mmol) dispersed in quinoline (30 ml) and the mixture was stirred at 140° C. for 5 hours, then cooled to room temperature. The pH value of the mixture was adjusted to 4-5 with 1N hydrochloric acid. The mixture was extracted with ethyl acetate (100 ml×3). The combined organic phase was dried over anhydrous sodium sulfate, filtered, concentrated, subjected to column chromatography to give 31-h as a white solid (1.0 g, yield: 46.7%). ESI-MS (m/z): 318.2 [M+H]$^+$. $^1$HNMR (300 MHz, CDCl$_3$): δ ppm 7.76(d, 1H), 7.47(s, 2H), 7.32(t, 1H), 7.19(d, 1H), 4.31(s, 2H), 3.20(t, 1H), 2.89(t, 2H), 1.93(d, 2H), 1.77(m, 2H), 1.49(s, 9H).

Step 8:

Compound 31-h (400 mg, 1.26 mmol) was dissolved in dichloromethane (1 ml), trifluoroacetic acid (1 ml) was added followed by stirring at room temperature overnight. The reaction mixture was concentrated to dryness, the residual oil was slurried in methyl tert-butyl ether/methanol (V:V=15 ml:1 ml) system, filtered, and dried to give a yellow solid (219 mg, yield: 80%). ESI-MS (m/z): 218.0 [M+H]$^+$.

Reference Example 32

Preparation of 2-(6-chloro-2-oxo-1,2-dihydroquinolin-7-yl)ethyl methanesulfonate

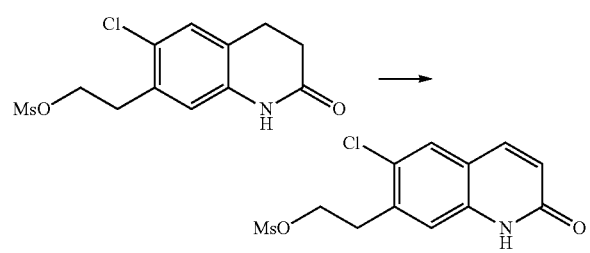

A reaction flask was charged with the product of Reference Example 16 2-(6-chloro-2-oxo-1,2,3,4-tetrahydro-quinolin-7-yl) ethyl methanesulfonate (330 mg, 1.09 mmol), 1,4-dioxane (5 ml) and 2,3-dichloro-5,6-dicyano-1,4-benzoquinone (DDQ, 740 mg, 3.26 mmol) were added thereto followed by stirring at reflux overnight. After completion of the reaction, the mixture was concentrated and dichloromethane (25 ml) was added. The mixture was washed with saturated sodium bicarbonate solution, saturated sodium thiosulfate solution and brine sequentially. The organic phase was dried, concentrated and purified by column chromatography to obtain the target (180 mg, yield: 55%). ESI-MS (m/z): 301.9 [M+H]$^+$.

Reference Example 33

Preparation of 6-(2-chloroethyl)-3-methyl-3,4-dihydroquinazolin-2(1H)-one

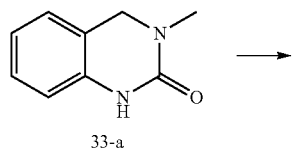

33-a

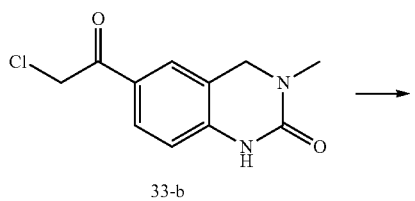

33-b

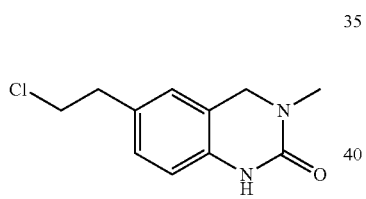

Step 1:

Chloroacetyl chloride (460 μL, 6.16 mmol) was added into anhydrous aluminum chloride (1.03 g, 7.7 mmol) suspended in 1,2-dichloroethane under ice bath condition and stirred for 10 minutes. 3-methyl 3,4-dihydro-quinazolin-2(1H)-one 33-a (500 mg, 3.08 mmol) was added and the mixture was stirred at room temperature for 15 minutes and at 48° C. for 3 hours. The reaction mixture was cooled to room temperature and poured into ice. The precipitated pale yellow solid was filtered, the filter cake was washed 3 times with ice water, dried to give compound 33-b as a pale yellow solid (710 mg, yield: 97%). $^1$HNMR (300 MHz, DMSO-d$_6$): δ ppm 9.72(s, 1H), 7.82-7.73(m, 2H), 6.84(d, 1H), 5.06(s, 2H), 4.47(s, 2H), 2.87(s, 3H).

Step 2:

Triethylsilane (5871 μl, 3.68 mmol) was added dropwise into compound 33-b (350 mg, 1.47 mmol) dissolved in trifluoroacetic acid (4 ml) and the mixture was stirred at 35° C. for 2.5 hours. The reaction solution was poured into ice water, the precipitated solid was filtered, the filter cake was washed 3 times with ice water, dried to give a pale yellow solid (320 mg, yield: 97%).

Reference Example 34

Preparation of 2-(1H-indol-3-yl)ethyl methanesulfonate

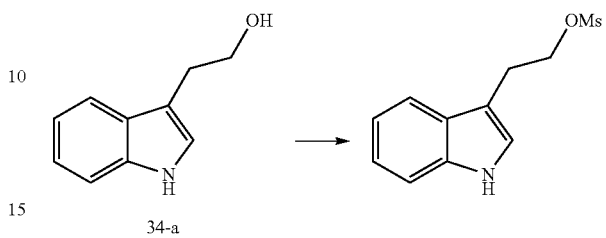

34-a

Compound 34-a (200 mg, 1.24 mmol) was dissolved in dichloromethane (5 ml), triethylamine (0.206 ml, 1.49 mmol) was added, methanesulfonyl chloride (0.105 ml, 1.36 mmol) was added dropwise under ice bath condition and the mixture was stirred at room temperature for 3 hours. The mixture was extracted with dichloromethane and water. The organic phase was washed with brine, dried and concentrated to give the target (260 mg, yield: 87%). ESI-MS (m/z): 240.0 [M+H]$^+$.

Reference Example 35

Preparation of 6-(2-chloroethyl)-3,4-dihydroquinolin-2(1H)-one

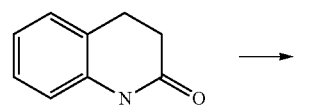

35-a

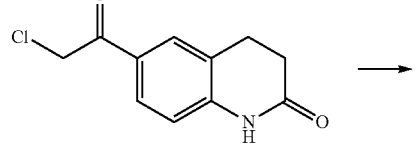

35-b

Step 1:

Chloroacetyl chloride (640 μl, 8.49 mmol) was added to anhydrous aluminum chloride (2.72 g, 20.38 mmol) suspended in carbon disulfide (10 ml) under ice bath. The mixture was stirred for 10 minutes and 3,4-dihydroquinoline-2(1H)-one 35-a (500 mg, 3.40 mmol) was added. The system was stirred at room temperature for 15 minutes and at reflux for 9 hours. Carbon disulfide was removed, ice and 4N hydrochloric acid (5 ml) were added under stirring. The precipitated solid was filtered, dried to give a crude. The crude was slurried in ethyl acetate, filtered, dried to give an off-white solid (710 mg, yield: 93%). $^1$HNMR (300 MHz, DMSO-d$_6$): δ ppm 10.46(s, 1H), 7.81(d, 1H), 7.78(dd, 1H), 6.92(d, 1H), 5.07(s, 2H), 2.93(t, 2H), 2.48(t, 2H).

Step 2:

Triethylsilane (900 μL, 5.58 mmol) was added dropwise into compound 35-b (500 mg, 2.32 mmol) dissolved in trifluoroacetic acid (5 ml) and the mixture was stirred at 30° C. overnight. The reaction mixture was poured into ice water (15 ml×3) and extracted with dichloromethane. The combined organic phase was dried, filtered and concentrated. The residue was slurried in petroleum ether, filtered, dried to give the target product as a brown solid (417 mg, yield: 89%).

Reference Example 36

Preparation of 2-(2-oxoindolin-4-yl)ethyl methanesulfonate

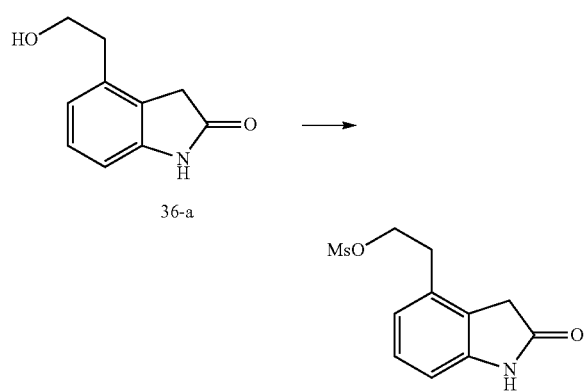

4-(2-hydroxyethyl)indolin-2-one 36-a (500 mg, 2.822 mmol) was dissolved in dichloromethane (15 ml) and pyridine (335 mg, 4.233 mmol) was added. Methanesulfonyl chloride (356 mg, 3.104 mmol) was added dropwise thereto at 0° C. followed by stirring at room temperature overnight. The mixture was diluted with dichloromethane (15 ml), washed with 1N hydrochloric acid, water, and brine sequentially. The organic phase was dried over anhydrous sodium sulfate, concentrated and subjected to column chromatography to obtain a yellow solid (460 mg, yield: 64%). ESI-MS (m/z): 256.0 [M+H]+.

Reference Example 37

Preparation of tert-butyl 4,5-diethyl-2-(2-((methylsulfonyl)oxy)ethyl)-6-oxopyrimidine-1(6H)-carboxylate

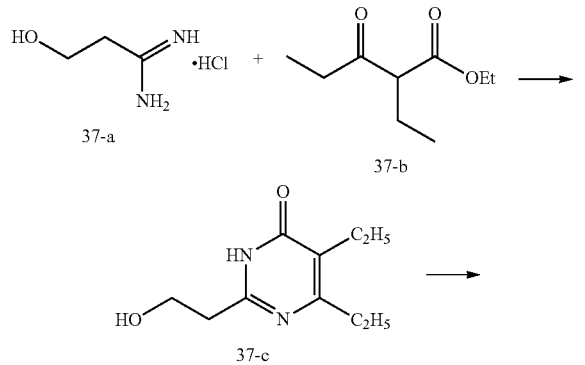

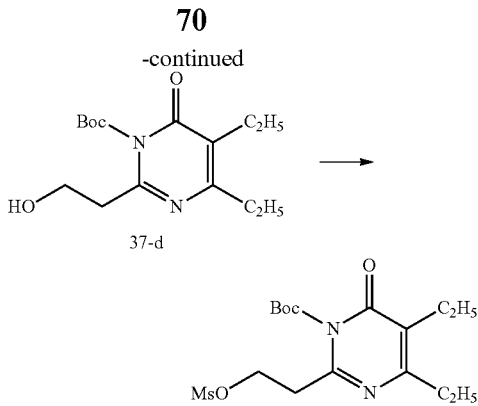

Step 1:

A mixture of compound 37-a (2.0 g, 16.3 mmol), ethyl 2-ethyl-3-oxopentanoate 37-b (6.0 g, 19.5 mmol), potassium carbonate (9.4 g, 48.9 mmol) and ethanol (20 ml) was stirred at reflux for 15 hours, then cooled and filtered. The filtrate was concentrated and subjected to column chromatography to obtain the target (198 mg). $^1$H-NMR (300 Hz, DMSO-$d_6$): δ ppm 12.09(brs, 1H), 4.75(brs, 1H), 3.72(t, 2H), 2.61(t, 2H), 2.45(q, 2H), 2.37(q, 2H), 1.11(t, 3H), 0.98(t, 3H).

Step 2:

Di-tert-butyl dicarbonate (317 mg, 1.45 mmol) was added into compound 37-c (250 mg, 1.32 mmol) suspended in tetrahydrofuran (15 ml) and the reaction mixture was stirred at 25~30° C. overnight. The mixture was concentrated and subjected to column chromatography to obtain a pale yellow oil (494 mg).

Step 3:

Compound 37-d (494 mg, 1.667 mmol) was dissolved in dichloromethane (20 ml) and triethylamine (253 mg, 2.5 mmol) was added. Methanesulfonyl chloride (210 mg, 1.834 mmol) was added thereto under 0~5° C. followed by stirring at room temperature for 1 hour. The reaction mixture was washed with water and brine, dried over anhydrous sodium sulfate and filtered. The filtrate was concentrated and subjected to column chromatography to obtain the target (520 mg). ESI-MS (m/z): 374.3 [M+H]+.

Reference Example 38

Preparation of tert-butyl 2-(2-((methylsulfonyl)oxy) ethyl)-6-oxopyrimidine-1(6H)-carboxylate

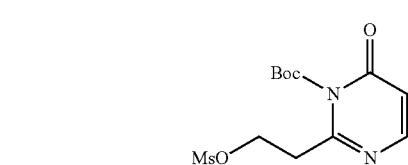 [SMILES: CC(C)(C)OC(=O)n1c(CCOS(C)(=O)=O)nccc1=O]

By a similar method as in Reference Example 37, tert-butyl 2-(2-((methylsulfonyl)oxy)ethyl)-6-oxopyrimidine-1 (6H)-carboxylate was prepared from Ethyl propiolate. ESI-MS (m/z): 319.1 [M+H]+.

EXAMPLE

Example 1

6-chloro-5-(2-(4-(2,3-dihydrobenzo[b]thiophen-4-yl) piperazin-1-yl)ethyl)indolin-2-one 6-chloro-5-(2-chloroethyl)indolin-2-one (120 mg, 0.52 mmol), the product of Reference Example 12(115 mg, 0.52 mmol), potassium carbonate (215 mg, 1.56 mmol), potassium iodide (86 mg, 0.52 mmol) and acetonitrile (5 ml) were added to the flask and the mixture was stirred at 85° C. overnight. The reaction mixture was concentrated and subjected to column chromatography to obtain a white solid (120 mg, yield: 56%). $^1$HNMR (300 MHz, DMSO-$d_6$): δ ppm 10.42(brs, 1H), 7.21(s, 1H), 7.07(t, 1H), 6.90(d, 1H), 6.80(s, 1H), 6.69(d, 1H), 3.45(s, 2H), 3.30(t, 2H), 3.14(t, 2H), 2.74-2.95(m, 6H), 2.59(brs, 4H), 2.50(t, 2H). ESI-MS (m/z): 414.2 [M+H]$^+$.

Example 2

3-(2-(4-(2,3-dihydrobenzo[b]thiophen-4-yl)piperazin-1-yl)ethyl)-9-hydroxy-2-methyl-6,7,8,9-tetrahydro-4H-pyrido[1,2-a]pyrimidin-4-one 3-(2-chloroethyl)-9-hydroxy-2-methyl-6,7,8,9-tetrahydro-4H-pyrido[1,2-a]pyrimidin-4-one 10-a (120 mg, 0.49 mmol), the product of Reference Example 12(109 mg, 0.49 mmol), potassium carbonate (202 mg, 1.47 mmol), potassium iodide (81 mg, 0.49 mmol) and acetonitrile (5 ml) were added to the flask and the mixture was stirred at 85° C. overnight. The reaction mixture was concentrated and subjected to column chromatography to give a pale yellow solid (120 mg, yield: 56%). $^1$HNMR (300 MHz, DMSO-$d_6$): δ ppm 7.07(t, 1H), 6.89(d, 1H), 6.69(d, 1H), 5.68(d, 1H), 4.44(m, 1H), 3.89(m, 1H), 3.66(m, 1H), 3.30(t, 2H), 3.14(t, 2H), 2.87(brt, 4H), 2.53-2.67(m, 6H), 2.39(t, 2H), 2.26(s, 3H), 1.73-2.06(m, 4H). ESI-MS (m/z): 427.2 [M+H]$^+$.

Example 3

3-(2-(4-(benzo[b]thiophen-4-yl)piperazin-1-yl)ethyl)-2-methyl-6,7,8,9-tetrahydro-4H-pyrido[1,2-a]pyrimidin-4-one 3-(2-chloroethyl)-2-methyl-6,7,8,9-tetrahydro-4H-pyrido[1,2-a]pyrimidin-4-one (120 mg, 0.53 mmol), the product of Reference Example 1(116 mg, 0.53 mmol), potassium carbonate (219 mg, 1.59 mmol), potassium iodide (88 mg, 0.53 mmol) and acetonitrile (5 ml) were added to the flask and the mixture was stirred at 85° C. overnight. The reaction mixture was concentrated and subjected to column chromatography to obtain a white solid (120 mg, yield: 55%). $^1$HNMR (300 MHz, DMSO-$d_6$): δ ppm 7.69(d, 1H), 7.61(d, 1H), 7.40(d, 1H), 7.27(t, 1H), 6.89(d, 1H), 3.78(t, 2H), 3.07(brs, 4H), 2.75(t, 2H), 2.68(brs, 4H), 2.63(t, 2H), 2.42(t, 2H), 2.22(s, 3H), 1.85(m, 2H), 1.76(m, 2H). ESI-MS (m/z): 409.1 [M+H]$^+$.

Example 4

3-(2-(4-(benzo[b]thiophen-4-yl)piperazin-1-yl)ethyl)-9-hydroxy-2-methyl-6,7,8,9-tetrahydro-4H-pyrido[1,2-a]pyrimidin-4-one A mixture of 3-(2-chloroethyl)-9-hydroxy-2-methyl-6,7,8,9-tetrahydro-4H-pyrido[1,2-a]pyrimidin-4-one 10-a (1 g, 4.13 mmol), the product of Reference Example 1(1.05 g, 4.13 mmol), potassium carbonate (1.7 g, 12.3 mmol), potassium iodide (0.68 g, 4.13 mmol) and acetonitrile (10 ml) was stirred at 85° C. overnight, the reaction was concentrated and subjected to column chromatography to obtain a pale yellow solid (1 g, yield: 58%). $^1$HNMR (300 MHz, DMSO-$d_6$): δ ppm 7.69(d, 1H), 7.61(d, 1H), 7.40(d, 1H), 7.27(t, 1H), 6.90(d, 1H), 5.69(d, 1H), 4.44(q, 1H), 3.91(m, 1H), 3.68(m, 1H), 3.08(brs, 4H), 2.69(brs, 4H), 2.66(t, 2H), 2.45(t, 2H), 2.28(s, 3H), 1.74-2.04(m, 4H). ESI-MS (m/z): 425.3 [M+H]$^+$.

A single isomer 4a and 4b was obtained respectively by HPLC chiral separation, the retention time is 13.2 minute and 16.3 minute respectively. Column type: AY-H 4.6×250 mm; mobile phase: ethanol:hexane=30:70(v/v); flow rate: 1.0 ml/min; detection wavelength: 277 nm.

Compound 4a:
(+)-3-(2-(4-(benzo[b]thiophen-4-yl)piperazin-1-yl)ethyl)-9-hydroxy-2-methyl-6,7,8,9-tetrahydro-4H-pyrido[1,2-a]pyrimidin-4-one, specific rotation: +8.82° (C=0.17, $CH_2Cl_2$).

Compound 4b:
(−)-3-(2-(4-(benzo[b]thiophen-4-yl)piperazin-1-yl)ethyl)-9-hydroxy-2-methyl-6,7,8,9-tetrahydro-4H-pyrido[1,2-a]pyrimidin-4-one, specific rotation: −7.98° (C=0.17, $CH_2Cl_2$).

Example 5

3-(2-(4-(benzo[b]thiophen-4-yl)piperazin-1-yl)ethyl)-2-methyl-7,8-dihydro-4H-pyrido[1,2-a]pyrimidine-4,9(6H)-dione The product of Example 4(120 mg, 0.28 mmol) was dissolved in dichloromethane (5 ml), Dess-Martin reagent (359 mg, 0.84 mmol) was added portionwise thereto and stirred at room temperature for 5 hours, then saturated sodium bicarbonate solution (2 ml) and sodium thiosulfate solution (1 ml) were added followed by stirring for 10 minutes. The mixture was extracted with dichloromethane, washed with brine, dried over anhydrous sodium sulfate, concentrated and subjected to column chromatography to give a pale yellow solid (70 mg, yield: 58%). $^1$HNMR (300 MHz, $CDCl_3$): δ ppm 7.54(d, 1H), 7.39(m, 2H), 7.27(t, 1H), 6.89(d, 1H), 4.20(t, 2H), 3.20(brs, 4H), 2.92-2.74(m, 8H), 2.62(t, 2H), 2.48(s, 3H), 2.33(m, 2H). ESI-MS (m/z): 423.2 [M+H]$^+$.

Example 6

3-(2-(4-(benzo[b]thiophen-4-yl)piperazin-1-yl)ethyl)-9-hydroxy-2,9-dimethyl-6,7,8,9-tetrahydro-4H-pyrido[1,2-a]pyrimidin-4-one hydrochloride The product of Example 5(120 mg, 0.28 mmol) was dissolved in dry tetrahydrofuran (3 ml), methyl magnesium bromide (2 ml, 1.99 mmol, 1M in THF) was added dropwise thereto under ice-cooling condition followed by stirring at room temperature for 3 hours. The reaction was quenched with saturated ammonium chloride, concentrated, extracted with dichloromethane, washed with brine, dried over anhydrous sodium sulfate, concentrated and subjected to column chromatography to give an oil. Hydrogen chloride-ethanol solution was added thereto under stirring, the resulting salt was slurried in acetonitrile, filtered to give a pale yellow solid (40 mg, yield: 32%). $^1$HNMR (300 MHz, MeOH-$d_6$): δ ppm 7.65(d, 1H), 7.58(d, 1H), 7.48(d, 1H), 7.31(t, 1H), 7.02(d, 1H), 4.37(d, 1H), 3.83(m, 1H), 3.66(m, 3H), 3.41(m, 2H), 3.19(m, 4H), 2.93-2.49(m, 4H), 2.22-1.60(m, 6H), 1.52(s, 3H).

Example 7

3-(2-(4-(benzo[b]thiophen-4-yl)piperazin-1-yl)ethyl)-9-fluoro-2-methyl-6,7,8,9-tetrahydro-4H-pyrido[1,2-a]pyrimidin-4-one The product of Reference Example 17(125 mg, 0.51 mmol), the product of Reference Example 1(112 mg, 0.51 mmol), potassium carbonate (213 mg, 1.54 mmol), potassium iodide (85 mg, 0.51 mmol) and acetonitrile (5 ml) were added to the flask and the mixture was stirred at 85° C. overnight. The reaction mixture was concentrated and subjected to column chromatography to obtain a pale yellow solid (150 mg, yield: 68%). $^1$HNMR (300 MHz, CDCl$_3$): δ ppm 7.54(d, 1H), 7.36-7.43(m, 2H), 7.27(t, 1H), 6.90(d, 1H), 5.25-5.46(dt, 1H), 4.18(dt, 1H), 3.75(m, 1H), 3.21(brt, 4H), 2.82(m, 6H), 2.60(t, 2H), 2.30-2.46(m, 1H), 2.39(s, 3H), 1.96-2.25(m, 3H). ESI-MS (m/z): 427.2 [M+H]$^+$.

Example 8

5-(2-(4-(benzo[b]thiophen-4-yl)piperazin-1-yl)ethyl)indolin-2-one

The product of Reference Example 15(79 mg, 0.40 mmol), the product of Reference Example 1(104 mg, 0.40 mmol), sodium carbonate (108 mg, 0.81 mmol), sodium iodide (60 mg, 0.40 mmol) and water (3 ml) were added to the flask and the mixture was stirred at 100° C. overnight. The mixture was extracted with dichloromethane and water, the organic phase was dried over anhydrous sodium sulfate, concentrated and subjected to column chromatography to give a crude. The crude was slurried in acetonitrile, filtered to give a white powder (90 mg, yield: 58%). $^1$HNMR (300 MHz, DMSO-d$_6$): δ ppm 10.28(brs, 1H), 7.69(d, 1H), 7.61 (d, 1H), 7.40(d, 1H), 7.27(t, 1H), 7.10(s, 1H), 7.04(d, 1H), 6.90(d, 1H), 6.72(d, 1H), 3.44(s, 2H), 3.07(brs, 4H), 2.72(t, 2H), 2.70(brs, 4H), 2.57(t, 2H). ESI-MS (m/z): 378.3 [M+H]$^+$.

Example 9

7-(2-(4-(benzo[b]thiophen-4-yl)piperazin-1-yl)ethyl)quinolin-2(1H)-one

The product of Reference Example 7(440 mg, 1.64 mmol), the product of Reference Example 1(418 mg, 1.64 mmol), potassium carbonate (682 mg, 4.94 mmol), potassium iodide (272 mg, 1.64 mmol) were dissolved in acetonitrile (10 ml) and stirred at reflux overnight. The reaction mixture was poured into ice water and extracted twice with ethyl acetate, the combined organic layer was washed with brine, dried over anhydrous sodium sulfate, concentrated to give a crude which was further purified by column chromatography to obtain a white solid (200 mg, yield: 31%). $^1$HNMR (400 MHz, DMSO-d$_6$): δ ppm 11.70(brs, 1H), 7.86(d, 1H), 7.70(d, 1H), 7.61(d, 1H), 7.57(d, 1H), 7.40(d, 1H), 7.27(t, 1H), 7.17(s, 1H), 7.09(dd, 1H), 6.90(d, 1H), 6.42(dd, 1H), 3.08(brs, 4H), 2.85(t, 2H), 2.71(brs, 4H), 2.64(t, 2H). ESI-MS (m/z): 390.2 [M+H]$^+$.

Example 10

7-(5-(4-(benzo[b]thiophen-4-yl)piperazin-1-yl)pentyl)-3,4-dihydroquinolin-2(1H)-one The product of Reference Example 2(250 mg, 0.80 mmol), the product of Reference Example 1(140 mg, 0.80 mmol), potassium carbonate (221 mg, 1.6 mmol), potassium iodide (132 mg, 0.80 mmol) and acetonitrile (5 ml) were added to the flask and the mixture was stirred at 85° C. overnight. The reaction mixture was concentrated, and the residue was purified by column chromatography to obtain a white powder (270 mg, yield: 77%). $^1$HNMR (300 MHz, DMSO-d$_6$): δ ppm 9.98(brs, 1H), 7.68(d, 1H), 7.60(d, 1H), 7.38(d, 1H), 7.26(t, 1H), 7.04(d, 1H), 6.88(d, 1H), 6.74(d, 1H), 6.67(s, 1H), 3.05(brs, 4H), 2.80(t, 2H), 2.58(brs, 4H), 2.49(t, 2H), 2.40(t, 2H), 2.34(t, 2H), 1.51(m, 4H), 1.30(m, 2H). ESI-MS (m/z): 434.3 [M+H]$^+$.

Example 11

7-(5-(4-(benzo[b]thiophen-4-yl)piperazin-1-yl)pentyl)quinolin-2(1H)-one

The product of Reference Example 3(180 mg, 0.58 mmol), the product of Reference Example 1(148 g, 0.58 mmol), anhydrous potassium carbonate (241 mg, 1.74 mmol), potassium iodide (96 mg, 0.58 mmol) and acetonitrile (5 ml) were added to the flask and the mixture was stirred at 85° C. overnight. The reaction mixture was concentrated, and the residue was purified by column chromatography to obtain a white powder (200 mg, yield: 79%). $^1$HNMR (300 MHz, DMSO-d$_6$): δ ppm 11.65(s, 1H), 7.84(d, 1H), 7.68(d, 1H), 7.60(d, 1H), 7.55(d, 1H), 7.38(d, 1H), 7.26(t, 1H), 7.11(s, 1H), 7.03(dd, 1H), 6.87(d, 1H), 6.41(d, 1H), 3.03(brs, 4H), 2.65(t, 2H), 2.57(brs, 4H), 2.34(t, 2H), 1.62(m, 2H), 1.49(m, 2H), 1.33(m, 2H). ESI-MS (m/z): 432.3 [M+H]$^+$.

Example 12

7-(5-(4-(2-chlorobenzo[b]thiophen-4-yl)piperazin-1-yl)pentyl)quinolin-2(1H)-one

A mixture of the product of Reference Example 3(108 mg, 0.35 mmol), the product of Reference Example 9(90 mg, 0.35 mmol), potassium carbonate (147 mg, 1.07 mmol), potassium iodide (58 mg, 0.35 mmol) and acetonitrile (5 ml) was stirred at 85° C. overnight. The reaction solution was concentrated, and subjected to column chromatography to obtain a white powder (75 mg, yield: 45%). $^1$HNMR (500 MHz, DMSO-d$_6$): δ ppm 11.66(brs, 1H), 7.84(d, 1H), 7.55 (m, 2H), 7.36(s, 1H), 7.29(t, 1H), 7.10(s, 1H), 7.03(d, 1H), 6.91(d, 1H), 6.41(d, 1H), 3.00(brs, 4H), 2.64(t, 2H), 2.56 (brs, 4H), 2.33(t, 2H), 1.61(m, 2H), 1.49(m, 2H), 1.32(m, 2H). ESI-MS (m/z): 466.2 [M+H]$^+$.

Example 13

7-(5-(4-(2-fluorobenzo[b]thiophen-4-yl)piperazin-1-yl)pentyl)quinolin-2(1H)-one hydrochloride A mixture of the product of Reference Example 3(104 mg, 0.33 mmol), the product of Reference Example 8(80 mg, 0.33 mmol), potassium carbonate (140 mg, 1.0 mmol), potassium iodide (56 mg, 0.33 mmol) and acetonitrile (5 ml) was stirred at 85° C. overnight. The reaction mixture was concentrated, subjected to column chromatography to obtain an oil. Hydrogen chloride-ethanol solution was added thereto under stirring, the resulting salt was filtered to give a white solid (95 mg, yield: 62%). $^1$HNMR (400 MHz, DMSO-d$_6$): δ ppm 11.70(s, 1H), 10.67(brs, 1H), 7.85(d, 1H), 7.61(d, 1H), 7.57(d, 1H), 7.31(t, 1H), 7.15(d, 1H), 7.12(s, 1H), 7.05(d, 1H), 7.01(d, 1H), 6.42(d, 1H), 3.55(d, 1H), 3.44(d, 1H), 3.05-3.29(m, 6H), 2.67(t, 2H), 1.77(m, 2H), 1.64(m, 2H), 1.35(m, 2H). ESI-MS (m/z): 450.2 [M+H]$^+$.

Example 14

7-(5-(4-(benzo[b]thiophen-4-yl)-5,6-dihydropyridin-1(2H)-yl)pentyl)quinolin-2(1H)-one A mixture of the product of Reference Example 3(114 mg, 0.37 mmol), the product of Reference Example 14(80 mg, 0.37 mmol), potassium carbonate (154 mg, 1.11 mmol), potassium iodide (61 mg, 0.37 mmol) and acetonitrile (5 ml) was stirred at 85° C. overnight. The reaction mixture was concentrated, and subjected to column chromatography to obtain a white powder (66 mg, yield: 60%). $^1$HNMR (500 MHz, DMSO-$d_6$): δ ppm 11.65(brs, 1H), 7.88(d, 1H), 7.84 (d, 1H), 7.73(d, 1H), 7.55(d, 1H), 7.48(d, 1H), 7.32(t, 1H), 7.21(d, 1H), 7.11(s, 1H), 7.04(d, 1H), 6.41(d, 1H), 5.86(s, 1H), 3.09(s, 2H), 2.65(m, 4H), 2.49(t, 2H), 2.40(t, 2H), 1.63(m, 2H), 1.53(m, 2H), 1.35(m, 2H). ESI-MS (m/z): 429.3 [M+H]$^+$.

Example 15

5-(2-(4-(benzo[b]thiophen-4-yl)piperazin-1-yl)ethyl)-6-chloroindolin-2-one hydrochloride A mixture of 6-chloro-5-(2-chloroethyl)indolin-2-one (332 mg, 1.45 mmol), the product of Reference Example 1(370 mg, 1.45 mmol), sodium carbonate (461 mg, 4.35 mmol), iodine sodium (216 mg, 1.45 mmol) and water (5 ml) was stirred under reflux for 24 hours. The reaction was cooled to room temperature, extracted with methylene chloride and water. The organic phase was dried over anhydrous sodium sulfate, filtered, concentrated and subjected to column chromatography to obtain an oil. Hydrogen chloride-ethanol solution was added thereto under stirring, the resulting salt was slurried in isopropanol, filtered to give a pale yellow solid (308 mg, yield: 51%). $^1$HNMR (400 MHz, DMSO-$d_6$): δ ppm 11.04(brs, 1H), 10.55(s, 1H), 7.77(d, 1H), 7.71(d, 1H), 7.50(d, 1H), 7.32(t, 1H), 7.29(s, 1H), 6.98(d, 1H), 6.88(s, 1H), 3.71(d, 2H), 3.57(d, 2H), 3.50(s, 2H), 3.38(m, 4H), 3.21(m, 4H). ESI-MS (m/z): 412.2 [M+H]$^+$.

Example 16

3-(2-(4-(benzo[b]thiophen-4-yl)piperazin-1-yl)ethyl)-2-methyl-6,7-dihydro-4H-pyrido[1,2-a]pyrimidin-4-one hydrochloride A mixture of the product of Reference Example 10(100 mg, 0.44 mmol), the product of Reference Example 1(113 mg, 0.44 mmol), potassium carbonate (184 mg, 1.33 mmol), potassium iodide (74 mg, 0.44 mmol) and acetonitrile (5 ml) was stirred at 85° C. overnight. The reaction was cooled to room temperature, extracted with methylene chloride and water. The organic phase was dried over anhydrous sodium sulfate, filtered, concentrated and subjected to column chromatography to obtain an oil. Hydrogen chloride-ethanol solution was added thereto under stirring, the resulting salt was slurried in isopropanol, filtered to give a white powder (60 mg, yield: 33%). $^1$HNMR (300 MHz, DMSO-$d_6$): δ ppm 11.34(brs, 1H), 7.77(d, 1H), 7.70(d, 1H), 7.50(d, 1H), 7.32(t, 1H), 7.00(m, 2H), 6.60(d, 1H), 4.04(t, 2H), 3.71(d, 2H), 3.56(d, 2H), 3.14-3.47(m, 6H), 3.02(m, 2H), 2.61(m, 2H), 2.42(s, 3H). ESI-MS (m/z): 407.1 [M+H]$^+$.

Example 17

3-(2-(4-(benzo[b]thiophen-4-yl)piperazin-1-yl)ethyl)-9-(benzyloxy)-2-methyl-4H-pyrido[1,2-a]pyrimidin-4-one hydrochloride The product of Reference Example 1(155 mg, 0.60 mmol), 9-(benzyloxy)-3-(2-chloroethyl)-2-methyl-4H-pyrido[1,2-a]pyrimidin-4-one (200 mg, 0.60 mmol), potassium carbonate (673 mg, 4.87 mmol), potassium iodide (101 mg, 0.60 mmol) and acetonitrile (5 ml) were added to the flask and the mixture was stirred at 85° C. for 24 hours. The reaction mixture was cooled to room temperature, extracted with dichloromethane and water. The organic layer was dried over anhydrous sodium sulfate, filtered, concentrated and subjected to column chromatography to obtain an oil. Hydrogen chloride-ethanol solution was added thereto under stirring, the resulting salt was filtered to give a white powder (200 mg, yield: 64%). $^1$HNMR (300 MHz, CDCl$_3$): δ ppm 8.61(dd, 1H), 7.54(d, 1H), 7.24-7.49(m, 8H), 6.86-6.93(m, 3H), 5.39(s, 2H), 3.23(brs, 4H), 3.01(t, 2H), 2.87(brs, 4H), 2.69(t, 2H), 2.64(s, 3H). ESI-MS (m/z): 511.3 [M+H]$^+$.

Example 18

3-(2-(4-(benzo[b]thiophen-4-yl)piperazin-1-yl)ethyl)-9-hydroxy-2-methyl-4H-pyrido[1,2-a]pyrimidin-4-one The product of Example 17(180 mg, 0.35 mmol) was added into concentrated hydrochloric acid (5 ml) and stirred at 80° C. for 2 hours. The reaction mixture was cooled and isopropanol (5 ml) was added dropwise thereto. The precipitated solid was filtered to give a pale yellow solid (130 mg, yield 87%). $^1$HNMR (300 MHz, DMSO-$d_6$): δ ppm 11.64(brs, 1H), 8.63(d, 1H), 7.88(m, 1H), 7.77(d, 1H), 7.69(d, 1H), 7.57(td, 1H), 7.50(d, 1H), 7.31(t, 1H), 6.96(d, 1H), 3.75(d, 1H), 3.56(d, 1H), 3.50-3.12(m, 8H), 2.70(s, 3H). ESI-MS (m/z): 421.2 [M+H]$^+$.

Example 19

7-(2-(4-(benzo[b]thiophen-4-yl)piperazin-1-yl)ethyl)-3,4-dihydroquinolin-2(1H)-one The product of Reference Example 6(100 mg, 0.37 mmol), the product of Reference Example 1(95 mg, 0.37 mmol), potassium carbonate (153 mg, 1.11 mmol), potassium iodide (61 mg, 0.37 mmol) were dissolved in acetonitrile (10 ml) and the mixture was stirred at reflux overnight. The reaction mixture was concentrated, the residue was subjected to column chromatography to obtain a white solid (70 mg, yield 48%). $^1$HNMR (400 MHz, DMSO-$d_6$): δ ppm 10.02(brs, 1H), 7.70(d, 1H), 7.62(d, 1H), 7.41(d, 1H), 7.28(t, 1H), 7.07(d, 1H), 6.91(d, 1H), 6.80(dd, 1H), 6.74(d, 1H), 3.08(brs, 4H), 2.82(t, 2H), 2.69(m, 6H), 2.58(t, 2H), 2.43(t, 2H). ESI-MS (m/z): 392.1 [M+H]$^+$.

Example 20

9-hydroxy-2-methyl-3-(2-(4-(thieno[2,3-d]pyrimidin-4-yl)piperazin-1-yl)ethyl)-6,7,8,9-tetrahydro-4H-pyrido[1,2-a]pyrimidin-4-one The product of Reference Example 13(77 mg, 0.30 mmol), 3-(2-chloroethyl)-9-hydroxy-2-methyl-6,7,8,9-tetrahydro-4H-pyrido[1,2-a]pyrimidin-4-one 10-a (73 mg, 0.30 mmol), potassium carbonate (145 mg, 1.05 mmol), potassium iodide (50 mg, 0.30 mmol) were dissolved in acetonitrile (7.5 ml) and the mixture was stirred at reflux overnight. The reaction mixture was concentrated and subjected to column chromatography to obtain a white solid (53 mg, yield: 41%). $^1$HNMR (300 MHz, DMSO-d$_6$): δ ppm 8.40(s, 1H), 7.63(s, 2H), 5.71(d, 1H), 4.44(m, 1H), 3.87(brs, 5H), 3.66(m, 1H), 2.53-2.70(m, 6H), 2.39(t, 2H), 2.26(s, 3H), 1.73-2.06(m, 4H). ESI-MS (m/z): 427.2 [M+H]$^+$.

Example 21

2-methyl-3-(2-(4-(thieno[2,3-d]pyrimidin-4-yl)piperazin-1-yl)ethyl)-6,7,8,9-tetrahydro-4H-pyrido[1,2-a]pyrimidin-4-one The product of Reference Example 13(93 mg, 0.36 mmol), 3-(2-chloroethyl)-2-methyl-6,7,8,9-tetrahydro-4H-pyrido[1,2-a]pyrimidin-4-one (82 mg, 0.36 mmol), potassium carbonate (173 mg, 1.26 mmol), potassium iodide (60 mg, 0.36 mmol) were dissolved in acetonitrile (7.5 ml) and the mixture was stirred at reflux overnight. The reaction mixture was concentrated and subjected to column chromatography to obtain a white solid (80 mg, yield: 54%). $^1$HNMR (300 MHz, DMSO-d$_6$): δ pmm 8.40(s, 1H), 7.62(s, 2H), 3.87 (brs, 4H), 3.77(t, 2H), 2.74(t, 2H), 2.58(brs, 6H), 2.38(t, 2H), 1.84(m, 2H), 1.74(m, 2H). ESI-MS (m/z): 411.1 [M+H]$^+$.

Example 22

7-(4-(4-(benzo[b]thiophen-4-yl)piperazin-1-yl)butyl)-3,4-dihydroquinolin-2(1H)-one The product of Reference Example 4(154 mg, 0.52 mmol), the product of Reference Example 1(133 mg, 0.52 mmol), potassium carbonate (215 mg, 1.56 mmol) and potassium iodide (86 mg, 0.52 mmol) were dissolved in acetonitrile (7.5 ml) and the mixture was stirred at reflux overnight. The reaction mixture was concentrated and subjected to column chromatography to obtain a yellow solid (110 mg, yield: 50%). $^1$HNMR (300 MHz, DMSO-d$_6$): δ ppm 10.02 (brs, 1H), 7.69(d, 1H), 7.61(d, 1H), 7.39(d, 1H), 7.27(t, 1H), 7.05(d, 1H), 6.88(d, 1H), 6.74(d, 1H), 6.68(s, 1H), 3.05(brs, 4H), 2.81(t, 2H), 2.58(brs, 4H), 2.50(t, 2H), 2.41(t, 4H), 1.39-1.64(m, 4H). ESI-MS (m/z): 420.2 [M+H]$^+$.

Example 23

7-(2-(4-(benzo[b]thiophen-4-yl)piperazin-1-yl)ethyl)-6-chloro-3,4-dihydroquinolin-2(1H)-one The product of Reference Example 16(100 mg, 0.33 mmol), the product of Reference Example 1(84 mg, 0.33 mmol), potassium carbonate (114 mg, 0.82 mmol), potassium iodide (55 mg, 0.33 mmol) were dissolved in acetonitrile (10 ml) and the mixture was stirred at reflux overnight. The mixture was concentrated and subjected to column chromatography to obtain a white solid (45 mg, yield: 32%). $^1$HNMR (300 MHz, DMSO-d$_6$): δ ppm 10.17(brs, 1H), 7.69(d, 1H), 7.62(d, 1H), 7.41(d, 1H), 7.20-7.33(m, 2H), 6.90(d, 1H), 6.84(s, 1H), 3.08(brs, 4H), 2.83(m, 4H), 2.70 (brs, 4H), 2.56(t, 2H), 2.42(t, 2H). ESI-MS (m/z): 426.3 [M+H]$^+$.

Example 24

6-(5-(4-(benzo[b]thiophen-4-yl)piperazin-1-yl)pentyl)-2-methylquinazolin-4(3H)-one The product of Reference Example 11(77 mg, 0.29 mmol), the product of Reference Example 1(74 mg, 0.29 mmol), potassium carbonate (120 mg, 0.87 mmol), potassium iodide (48 mg, 0.29 mmol) were added to acetonitrile (3 ml) and the mixture was stirred at reflux for 50 hours. The reaction mixture was concentrated and subjected to column chromatography to give a pale yellow solid (35 mg, yield: 27%). $^1$H-NMR (300 Hz, CDCl$_3$): δ ppm 10.84(brs, 1H), 8.05(s, 1H), 7.51-7.63(m, 3H), 7.38(m, 2H), 7.27(t, 1H), 6.91(d, 1H), 3.27(brs, 4H), 2.83(brs, 4H), 2.77(t, 2H), 2.57(t, 2H), 2.54(s, 3H), 1.72(m, 4H), 1.41(m, 2H). ESI-MS (m/z): 447.3 [M+H]$^+$.

Example 25

7-(2-(4-(2,3-dihydrobenzo[b]thiophen-4-yl)piperazin-1-yl)ethyl)quinolin-2(1H)-one The product of Reference Example 12(85 mg, 0.38 mmol), the product of Reference Example 7(103 mg, 0.38 mmol), potassium carbonate (157 mg, 1.14 mmol), potassium iodide (63 mg, 0.38 mmol) and acetonitrile (5 ml) were added to the flask and the mixture was stirred at 85° C. overnight. The reaction mixture was concentrated and subjected to column chromatography to obtain a crude. The crude was slurried in acetonitrile, filtered to give the product as a white solid (70 mg, yield: 46%). $^1$H-NMR (300 Hz, DMSO-d$_6$): δ ppm 11.67(brs, 1H), 7.85(d, 1H), 7.56(d, 1H), 7.16(s, 1H), 7.07(m, 2H), 6.90(d, 1H), 6.69(d, 1H), 6.42(d, 1H), 3.30(t, 2H), 3.14(t, 2H), 2.88(brs, 4H), 2.83(t, 2H), 2.61(m, 6H). ESI-MS (m/z): 392.2 [M+H]$^+$.

Example 26

5-(2-(4-(benzo[b]thiophen-4-yl)piperazin-1-yl)ethyl)-4-methylthiazole hydrochloride The product of Reference Example 18, The product of Reference Example 1, potassium carbonate (836 mg, 6.058 mmol), potassium iodide (87 mg, 0.529 mmol) were added to acetonitrile (6 ml) and the mixture was stirred at reflux overnight. The reaction mixture was concentrated and extracted with dichloromethane and water. The organic layer was dried, concentrated and subjected to column chromatography to give an oil (140 mg). Hydrogen chloride-ethanol solution was added thereto under stirring, the resulting salt was filtered and dried to give a white solid (78 mg, yield: 39%). $^1$H-NMR (300 Hz, DMSO-d$_6$): δ ppm 8.79(s, 1H), 7.70(d, 1H), 7.62(d, 1H), 7.40(d, 1H), 7.28(t, 1H), 6.91(d, 1H), 3.09(brs, 4H), 2.95(t, 2H), 2.70(brs, 4H), 2.60(t, 2H), 2.33(s, 3H). ESI-MS (m/z): 344.2 [M+H]$^+$.

Example 27

5-(2-(4-(benzo[b]thiophen-4-yl)piperazin-1-yl)ethyl)-1H-benzo[d]imidazol-2(3H)-one The product of Reference Example 19(150 mg, 0.76 mmol), the product of Reference Example 1(178 mg, 0.61 mmol), potassium carbonate (42 mg, 3.04 mmol), potassium iodide (126 mg, 0.76 mmol) were added to N,N-dimethylformamide (6 ml) and the mixture was stirred at 105° C.

overnight. The reaction mixture was extracted with dichloromethane and water. The organic phase was dried, concentrated and subjected to column chromatography to give a pale yellow solid (59 mg, yield: 20%). $^1$H-NMR (300 Hz, DMSO-$d_6$): δ ppm 10.53(s, 1H), 10.49(s, 1H), 7.70(d, 1H), 7.62(d, 1H), 7.40(d, 1H), 7.28(t, 1H), 6.90(d, 1H), 6.81(m, 3H), 3.08(brs, 4H), 2.75(t, 2H), 2.69(brs, 4H), 2.58(t, 2H). ESI-MS (m/z): 379.2 [M+H]$^+$.

Example 28

3-(2-(4-(benzo[b]thiophen-4-yl)piperazin-1-yl) ethyl)-9,9-difluoro-2-methyl-6,7,8,9-tetrahydro-4H-pyrido[1,2-a]pyrimidin-4-one hydrochloride The product of Example 5(120 mg, 0.28 mmol) was dissolved in dichloromethane (3 ml), diethylaminosulfur trifluoride (0.079 ml, 0.59 mmol) dissolved in dichloromethane (3 ml) was added dropwise thereto under ice bath condition followed by stirring at room temperature overnight. The mixture was extracted with dichloromethane and saturated sodium bicarbonate solution. The organic phase was washed with brine, dried over anhydrous sodium sulfate, filtered, concentrated and the residue was purified by column chromatography to obtain a crude. Hydrogen chloride-ethanol solution was added thereto under stirring, the resulting salt was filtered to give a pale yellow solid (50 mg, yield: 39%). $^1$HNMR (300 MHz, DMSO-$d_6$): δ ppm 10.91 (brs, 1H), 7.77(d, 1H), 7.71(d, 1H), 7.51(d, 1H), 7.32(t, 1H), 6.98(d, 1H), 3.88(t, 2H), 3.73(d, 2H), 3.58(d, 2H), 3.40(m, 2H), 3.23(m, 4H), 3.02(m, 2H), 2.43(m, 2H), 2.40(s, 3H), 2.07(m, 2H). ESI-MS (m/z): 445.3 [M+H]$^+$.

Example 29

6-(2-(4-(benzo[b]thiophen-4-yl)piperazin-1-yl)ethyl) benzo[d]thiazol-2(3H)-one hydrochloride The product of Reference Example 1(228 mg, 0.784 mmol), the product of Reference Example 20(186 mg, 0.869 mmol), sodium carbonate (333 mg, 3.142 mmol), sodium iodide (5 mg) were added to 4-methyl-2-pentanone (MIBK, 6 ml) under a nitrogen atmosphere and the mixture was stirred at reflux for 24 h. The reaction mixture was concentrated and the residue was purified by column chromatography to obtain a yellow oil. Hydrogen chloride-ethanol solution was added thereto under stirring. The resulting hydrochloride salt was slurried in acetone/isopropyl ether system (V:V=1:1), filtered, and dried to give the product as a pale yellow solid (58 mg, yield: 17%). $^1$H-NMR (400 Hz, DMSO-$d_6$): δ ppm 11.98(s, 1H), 11.05(brs, 1H), 7.78(d, 1H), 7.72(d, 1H), 7.53(s, 1H), 7.50(d, 1H), 7.33(t, 1H), 7.23(dd, 1H), 7.12(d, 1H), 6.99(d, 1H), 3.68(d, 2H), 3.57(d, 2H), 3.39(m, 4H), 3.24(t, 2H), 3.14(m, 2H). ESI-MS (m/z): 396.2 [M+H]$^+$.

Example 30

6-(2-(4-(benzo[b]thiophen-4-yl)piperazin-1-yl) ethyl)-2H-benzo[b][1,4]oxazin-3(4H)-one hydrochloride The product of Reference Example 1(224 mg, 0.77 mmol), the product of Reference Example 22(196 mg, 0.925 mmol), sodium carbonate (328 mg, 3.094 mmol), sodium iodide (5 mg) were added to N-methylpyrrolidone (NMP, 6 ml) under a nitrogen atmosphere and the mixture was stirred at 120° C. for 11 hours. The reaction solution was poured into ice water, the precipitated red-brown solid was filtered. The filter cake was washed three times with ice water, dried and subjected to silica gel column chromatography to give a crude (112 mg). Hydrogen chloride-ethanol solution was added thereto under stirring, the resulting salt was slurried in acetone, filtered and dried to give a pale yellow solid (105 mg, yield: 31.7%). $^1$H-NMR (300 Hz, DMSO-$d_6$): δ ppm 10.67(s, 1H), 7.69(d, 1H), 7.62(d, 1H), 7.40(d, 1H), 7.28(t, 1H), 6.90(d, 1H), 6.88-6.76(m, 3H), 4.52(s, 2H), 3.08(brt, 4H), 2.69(m, 6H), 2.56(t, 2H). ESI-MS (m/z): 394.3 [M+H]$^+$.

Example 31

6-(2-(4-(benzo[b]thiophen-4-yl)piperazin-1-yl) ethyl)-2H-benzo[b][1,4]thiazin-3(4H)-one The product of Reference Example 1(204 mg, 0.701 mmol), the product of Reference Example 22(200 mg, 0.881 mmol), sodium carbonate (300 mg, 2.83 mmol), sodium iodide (132 mg, 0.881 mmol) were added to N-methylpyrrolidone (NMP, 6 ml) under a nitrogen atmosphere and the mixture was stirred at 120° C. overnight. The reaction mixture was poured into ice water under stirring, the precipitated tan solid was filtered, the filter cake was washed three times with ice water, dried, subjected to silica gel column chromatography to give an oil. The oil was slurried in ethyl acetate, filtered, and dried to give a pale yellow solid (43 mg, yield: 15%). $^1$H-NMR (300 Hz, DMSO-$d_6$): δ ppm 10.54(brs, 1H), 7.71(d, 1H), 7.64(d, 1H), 7.43(d, 1H), 7.27 (m, 2H), 6.90(m, 3H), 3.44(s, 2H), 3.11(brt, 4H), 2.74(m, 6H), 2.50(t, 2H). ESI-MS (m/z): 410.2 [M+H]$^+$.

Example 32

7-(2-(4-(thieno[2,3-d]pyrimidin-4-yl)piperazin-1-yl) ethyl)quinolin-2(1H)-one

The product of Reference Example 7(40 mg, 0.15 mmol), the product of Reference Example 13(50 mg, 0.15 mmol), potassium carbonate (41 mg, 0.3 mmol), potassium iodide (25 mg, 0.15 mmol) were suspended in water (3 ml) and stirred at 80° C. overnight. The reaction mixture was cooled to room temperature and filtered. The filter cake was washed with water and dried to give a gray solid (30 mg, yield: 51%). $^1$H-NMR (300 Hz, DMSO-$d_6$): δ ppm 11.68(s, 1H), 8.41(s, 1H), 7.85(d, 1H), 7.63(m, 2H), 7.56(d, 1H), 7.17(s, 1H), 7.08(d, 1H), 6.42(d, 1H), 3.89(brt, 4H), 2.84(t, 2H), 2.60(m, 6H). ESI-MS (m/z): 392.3 [M+H]$^+$.

Example 33

7-(4-(4-(benzo[b]thiophen-4-yl)piperazin-1-yl)butyl) quinolin-2(1H)-one

The product of Reference Example 5(100 mg, 0.34 mmol), the product of Reference Example 1(87 mg, 0.34 mmol), potassium carbonate (117 mg, 0.85 mmol), potassium iodide (56 mg, 0.34 mmol) were suspended in acetonitrile (7.5 ml) and the mixture was stirred at reflux overnight. The reaction mixture was concentrated and subjected to silica gel column chromatography to give a crude. The crude was slurried in methyl tert-butyl ether, filtered, and dried to obtain the product as an off-white solid (40 mg, yield: 28%). $^1$H-NMR (DMSO-d6): δ ppm 11.70(brs, 1H), 7.86(d, 1H), 7.73(d, 1H), 7.66(d, 1H), 7.58(d, 1H), 7.44(d, 1H), 7.29(t, 1H), 7.12(s, 1H), 7.06(d, 1H), 6.93(d, 1H), 6.43(d, 1H), 3.33(t, 2H), 3.07(m, 6H), 2.70(brs, 4H), 1.64(m, 4H). ESI-MS (m/z): 418.4 [M+H]$^+$.

Example 34

6-(5-(4-(benzo[b]thiophen-4-yl)piperazin-1-yl)pentyl)quinazolin-4(3H)-one hydrochloride The product of Reference Example 1(60 mg, 0.206 mmol), the product of Reference Example 23(71 mg, 0.229 mmol), potassium carbonate (95 mg, 0.688 mmol) were added to acetonitrile (3 ml) and the mixture was stirred at reflux overnight. The reaction mixture was concentrated and subjected to silica gel column chromatography to give an oil (60 mg). Hydrogen chloride-ethanol solution was added thereto under stirring. The resulting hydrochloride salt was slurried in acetone, filtered, and dried to give a pale yellow solid (55 mg, yield: 56.9%). $^1$H-NMR (300 Hz, DMSO-d$_6$): δ ppm 12.15(brs, 1H), 8.03(s, 1H), 7.93(d, 1H), 7.68(d, 1H), 7.66(d, 1H), 7.61(d, 1H), 7.58(d, 1H), 7.38(d, 1H), 7.27(t, 1H), 6.87(d, 1H), 3.03(brs, 4H), 2.74(t, 2H), 2.58(brs, 4H), 2.35(t, 2H), 1.65(m, 2H), 1.51(m, 2H), 1.33(m, 2H). ESI-MS (m/z): 433.4 [M+H]$^+$.

Example 35

2-(2-(4-(benzo[b]thiophen-4-yl)piperazin-1-yl)ethyl)quinazolin-4(3H)-one

The product of Reference Example 24(120 mg, 0.57 mmol), the product of Reference Example 1(145 mg, 0.57 mmol), potassium carbonate (236 mg, 1.71 mmol), potassium iodide (95 mg, 0.57 mmol) and water (10 ml) were added to the flask. The mixture was stirred at reflux overnight, concentrated and the residue was purified by column chromatography to give the product (100 mg, yield: 44%). $^1$H-NMR (400 Hz, DMSO-d$_6$): δ ppm 12.29(s, 1H), 8.09(dd, 1H), 7.79(td, 1H), 7.70(d, 1H), 7.62(d, 2H), 7.47(t, 1H), 7.41(d, 1H), 7.27(t, 1H), 6.90(d, 1H), 3.07(brs, 4H), 2.87(m, 4H), 2.73(brs, 4H). ESI-MS (m/z): 391.3 [M+H]$^+$.

Example 36

3-(2-(4-(benzo[b]thiophen-4-yl)piperidin-1-yl)ethyl)-9-hydroxy-2-methyl-6,7,8,9-tetrahydro-4H-pyrido[1,2-a]pyrimidin-4-one 3-(2-chloroethyl)-9-hydroxy-2-methyl-6,7,8,9-tetrahydro-4H-pyrido[1,2-a]pyrimidin-4-on e 10-a (133 mg, 0.55 mmol), the product of Reference Example 31(120 mg, 0.55 mmol), potassium carbonate (229 mg, 1.65 mmol), potassium iodide (92 mg, 0.55 mmol) and acetonitrile (5 ml) were added to the flask. The mixture was stirred at reflux for 12 hours, concentrated, and the residue was purified by column chromatography to obtain a white solid (115 mg, yield: 49%). $^1$H-NMR (400 Hz, DMSO-d$_6$): δ ppm 7.84(d, 1H), 7.76(d, 1H), 7.62(d, 1H), 7.33(t, 1H), 7.26(d, 1H), 5.71(d, 1H), 4.45(q, 1H), 3.91(m, 1H), 3.68(m, 1H), 3.08(m, 3H), 2.65(m, 2H), 2.41(t, 2H), 2.28(s, 3H), 2.21(t, 2H), 2.06-1.70 (m, 8H). ESI-MS (m/z): 424.4 [M+H]$^+$.

Example 37

5-(2-(4-(benzo[b]thiophen-4-yl)piperidin-1-yl)ethyl)-6-chloroindolin-2-one

The product of Reference Example 31(120 mg, 0.553 mmol), 6-chloro-5-(2-chloroethyl)indolin-2-one (150 mg, 0.663 mmol), potassium carbonate (230 mg, 1.66 mmol), potassium iodide (90 mg, 0.553 mmol) and water (5 ml) were added to the flask. The mixture was stirred at 105° C. for 12 hours, cooled, filtered. The filter cake was slurried in acetonitrile and filtered to give the product (155 mg, yield: 58%). $^1$H-NMR (400 Hz, DMSO-d$_6$): δ ppm 10.43(s, 1H), 7.84(d, 1H), 7.76(d, 1H), 7.62(d, 1H), 7.33(t, 1H), 7.26(d, 1H), 7.23(s, 1H), 6.81(s, 1H), 3.47(s, 2H), 3.08(d, 3H), 2.84(t, 2H), 2.51(m, 2H), 2.23(t, 2H), 1.79(m, 4H). ESI-MS (m/z): 411.3 [M+H]+.

Example 38

4-(2-(4-(benzo[b]thiophen-4-yl)piperazin-1-yl)ethyl)indolin-2-one

The product of Reference Example 36(180 mg, 0.706 mmol), the product of Reference Example 1(180 mg, 0.706 mmol), potassium carbonate (243 mg, 1.77 mmol), potassium iodide (176 mg, 1.06 mmol) were added to acetonitrile (7.5 ml) and the mixture was stirred at 80° C. overnight. The reaction mixture was concentrated and the residue was purified by column chromatography to obtain a yellow solid (126 mg, yield: 47%). $^1$H-NMR (300 Hz, DMSO-d$_6$): δ ppm 10.35(s, 1H), 7.69(d, 1H), 7.61(d, 1H), 7.40(d, 1H), 7.27(t, 1H), 7.10(t, 1H), 6.89(d, 1H), 6.82(d, 1H), 6.66(d, 1H), 3.49(s, 2H), 3.07(brs, 4H), 2.70(m, 6H), 2.60(t, 2H). ESI-MS (m/z): 378.4 [M+H]$^+$.

Example 39

6-(2-(4-(benzo[b]thiophen-4-yl)piperazin-1-yl)ethyl)indolin-2-one hydrochloride

The product of Reference Example 30(110 mg, 0.412 mmol), the product of Reference Example 1(100 mg, 0.344 mmol), potassium carbonate (200 mg, 1.376 mmol), potassium iodide (73 mg, 0.344 mmol) were suspended in acetonitrile (5 ml) and the mixture was stirred at reflux overnight. The reaction solution was concentrated, and the residue was purified by column chromatography to obtain a crude. Hydrogen chloride-ethanol solution was added thereto under stirring, the resulting salt was filtered to give an off-white solid (100 mg, yield: 61%). $^1$H-NMR (400 Hz, DMSO-d$_6$): δ ppm 11.05(brs, 1H), 10.52(s, 1H), 7.79(d, 1H), 7.72(d, 1H), 7.50(d, 1H), 7.33(t, 1H), 7.19(d, 1H), 6.99(d, 1H), 6.87(dd, 1H), 6.77(d, 1H), 3.69(d, 2H), 3.58(d, 2H), 3.46(s, 2H), 3.38(m, 4H), 3.24(t, 2H), 3.09(m, 2H). ESI-MS (m/z): 378.2 [M+H]$^+$.

Example 40

7-(2-(4-(benzo[b]thiophen-4-yl)piperazin-1-yl)ethyl)-6-chloroquinolin-2(1H)-one

The product of Reference Example 32(24 mg, 0.079 mmol), the product of Reference Example 1(20 mg, 0.079 mmol), potassium carbonate (22 mg, 0.158 mmol), potassium iodide (13 mg) were suspended in water (3 ml) and the reaction was stirred at 80° C. overnight. The reaction mixture was cooled to room temperature, filtered, the filter cake was washed with water and dried to give a gray solid (23 mg, yield: 69%). $^1$H-NMR (300 Hz, DMSO-d$_6$): δ ppm 11.77 (brs, 1H), 7.80(m, 1H), 7.67(d, 1H), 7.59(d, 1H), 7.39(d, 1H), 7.26(m, 2H), 6.88(d, 1H), 6.48(d, 1H), 3.08(brs, 4H), 2.94(t, 2H), 2.71(brs, 4H), 2.63(t, 2H). ESI-MS (m/z): 424.2 [M+H]$^+$.

Example 41

9-hydroxy-2-methyl-3-(2-(4-(thieno[2,3-c]pyridin-4-yl)piperazin-1-yl)ethyl)-6,7,8,9-tetrahydro-4H-pyrido[1,2-a]pyrimidin-4-one The product of Reference Example 26(200 mg, 0.632 mmol), 3-(2-chloroethyl)-9-hydroxy-2-methyl-6,7,8,9-tetrahydro-4H-pyrido[1,2-a]pyrimidin-4-one 10-a (158 mg, 0.695 mmol), potassium carbonate (218 mg, 1.58 mmol), potassium iodide (157 mg, 0.948 mmol) were added to acetonitrile (7.5 ml) and the mixture was stirred at 80° C. overnight. The reaction mixture was concentrated and subjected to column chromatography to obtain a yellow solid (125 mg, yield: 46.6%). $^1$H-NMR (300 Hz, DMSO-$d_6$): δ ppm 8.91(s, 1H), 8.06(m, 2H), 7.53(d, 1H), 5.71(d, 1H), 4.45(q, 1H), 3.91(m, 1H), 3.68(m, 1H), 3.21(brs, 4H), 2.95-2.61(m, 6H), 2.50(t, 2H), 2.29(s, 3H), 2.10-1.70(m, 4H). ESI-MS (m/z): 426.3 [M+H]$^+$.

Example 42

6-chloro-5-(2-(4-(thieno[2,3-c]pyridin-4-yl)piperazin-1-yl)ethyl)indolin-2-one

The product of Reference Example 26(200 mg, 0.632 mmol), 6-chloro-5-(2-chloroethyl)indolin-2-one (160 mg, 0.695 mmol), potassium carbonate (218 mg, 1.58 mmol), potassium iodide (157 mg, 0.948 mmol) were added to acetonitrile (7.5 ml) and the mixture was stirred at 80° C. overnight. The reaction mixture was concentrated and subjected to column chromatography to obtain a white solid (25 mg, yield: 8.7%). $^1$H-NMR (300 Hz, DMSO-$d_6$): δ ppm 10.41(s, 1H), 8.89(s, 1H), 8.04(m, 2H), 7.51(d, 1H), 7.23(s, 1H), 6.81(s, 1H), 3.46(s, 2H), 3.18(brs, 4H), 2.85(t, 2H), 2.71(brs, 4H), 2.56(t, 2H). ESI-MS (m/z): 413.3 [M+H]$^+$.

Example 43

7-(2-(4-(thieno[2,3-c]pyridin-4-yl)piperazin-1-yl)ethyl)quinolin-2(1H)-one

The product of Reference Example 26(177 mg, 0.56 mmol), the product of Reference Example 7(150 mg, 0.56 mmol), potassium carbonate (271 mg, 1.96 mmol), potassium iodide (140 mg, 0.84 mmol) were added to acetonitrile (7.5 ml) and the mixture was stirred at 80° C. overnight. The reaction mixture was concentrated and subjected to column chromatography to give a white solid (75 mg, yield: 34.4%). $^1$H-NMR (DMSO-$d_6$): δ ppm 11.68(s, 1H), 8.90(s, 1H), 8.05(s, 2H), 7.85(d, 1H), 7.54(m, 2H), 7.18(s, 1H), 7.09(m, 1H), 6.42(d, 1H), 3.19(brs, 4H), 2.86(t, 2H), 2.74(brs, 6H). ESI-MS (m/z): 391.3 [M+H]$^+$.

Example 44

7-(3-(4-(benzo[b]thiophen-4-yl)piperazin-1-yl)propyl)quinolin-2(1H)-one

The product of Reference Example 28(100 mg, 0.355 mmol), the product of Reference Example 1(91 mg, 0.355 mmol), potassium carbonate (172 mg, 1.24 mmol), potassium iodide (88 mg, 0.53 mmol) were added to acetonitrile (7.5 ml) and the mixture was stirred at 80° C. overnight. The reaction mixture was cooled to room temperature, poured into water (30 ml). The precipitated solid was filtered, washed with water and dried to give a crude. The crude was slurried in ethyl acetate (2.0 ml), filtered, dried to give the product as an off-white solid (88 mg, yield: 61.5%). $^1$H-NMR (DMSO-$d_6$): δ ppm 11.68(s, 1H), 7.85(d, 1H), 7.69(d, 1H), 7.61(d, 1H), 7.56(d, 1H), 7.38(d, 1H), 7.27(t, 1H), 7.14(s, 1H), 7.06(d, 1H), 6.89(d, 1H), 6.42(d, 1H), 3.07(brs, 4H), 2.69(t, 2H), 2.60(brs, 4H), 2.38(t, 2H), 1.79(m, 2H). ESI-MS (m/z): 404.4 [M+H]$^+$.

Example 45

7-(3-(4-(benzo[b]thiophen-4-yl)piperazin-1-yl)propyl)-3,4-dihydroquinolin-2(1H)-one The product of Reference Example 27(120 mg, 0.424 mmol), the product of Reference Example 1(108 mg, 0.424 mmol), potassium carbonate (205 mg, 1.484 mmol), potassium iodide (106 mg, 0.636 mmol) were added to acetonitrile (7.5 ml) and the mixture was stirred at 80° C. overnight. The reaction mixture was cooled to room temperature, poured into water (30 ml). The precipitated solid was filtered, washed with water and dried to give a crude. The crude was slurried in petroleum ether-ethyl acetate system, filtered, dried to give the product as an off-white solid (58 mg, yield: 34%). $^1$H-NMR (DMSO-$d_6$): δ ppm 10.01(s, 1H), 7.69(d, 1H), 7.61(d, 1H), 7.39(d, 1H), 7.27(t, 1H), 7.05(d, 1H), 6.89(d, 1H), 6.76(d, 1H), 6.70(s, 1H), 3.07(brs, 4H), 2.81(t, 2H), 2.59(brs, 4H), 2.54(t, 2H), 2.39(m, 4H), 1.72(m, 2H). ESI-MS (m/z): 406.3 [M+H]$^+$.

Example 46

3-(2-(4-(benzo[b]thiophen-4-yl)piperazin-1-yl)ethyl)-1H-indole

The product of Reference Example 34(200 mg, 0.83 mmol), the product of Reference Example 1(182 mg, 0.83 mmol), potassium carbonate (347 mg, 2.5 mmol), potassium iodide (139 mg, 0.83 mmol) were added to acetonitrile (5 ml) and the mixture was stirred at 80° C. overnight. The reaction mixture was concentrated and subjected to column chromatography to give a white solid (120 mg, yield: 39%). $^1$H-NMR (DMSO-$d_6$): δ ppm 10.85(s, 1H), 7.71(d, 1H), 7.63(d, 1H), 7.56(d, 1H), 7.43(d, 1H), 7.35(d, 1H), 7.29(t, 1H), 7.20(s, 1H), 7.07(t, 1H), 6.98(t, 1H), 6.92(d, 1H), 3.16(brs, 4H), 3.04-2.63(m, 8H). ESI-MS (m/z): 362.1 [M+H]$^+$.

Example 47

6-(2-(4-(benzo[b]thiophen-4-yl)piperazin-1-yl)ethyl)-3,4-dihydroquinolin-2(1H)-one hydrochloride The product of Reference Example 35(120 mg, 0.57 mmol), the product of Reference Example 1(163 mg, 0.56 mmol), sodium carbonate (238 mg, 2.23 mmol), sodium iodide (2 mg) were added to N,N-dimethylformamide (3 ml) under a nitrogen atmosphere and the mixture was stirred at 120° C. for 9 hours. The reaction mixture was poured into ice water. The precipitated pale yellow solid was filtered, washed three times with ice water, dried, subjected to column chromatography to give a crude. Hydrogen chloride-ethanol solution was added thereto under stirring. The resulting hydrochloride salt was slurried in acetonitrile/methanol system, filtered, and dried to give a pale yellow solid (80 mg, yield: 33%). $^1$H-NMR (300 Hz, DMSO-$d_6$): δ ppm 9.99(s, 1H), 7.69(d, 1H), 7.61(d, 1H), 7.40(d, 1H), 7.27(t, 1H), 7.05(d, 1H), 7.01(d, 1H), 6.90(d, 1H), 6.76(d, 1H), 3.07(brt, 4H), 2.83(t, 2H), 2.69(m, 6H), 2.56(t, 2H), 2.42(t, 2H). ESI-MS (m/z): 392.1 [M+H]$^+$.

Example 48

5-(3-(4-(benzo[b]thiophen-4-yl)piperazin-1-yl)propyl)indolin-2-one hydrochloride The product of Reference Example 25(100 mg, 0.48 mmol), the product of Reference Example 1(136 mg, 0.47 mmol), sodium carbonate (198 mg, 1.87 mmol), sodium iodide (71 mg, 0.48 mmol) were added to water (4 ml) under a nitrogen atmosphere and the mixture was stirred at reflux for 9 hours. The reaction mixture was extracted twice with dichloromethane. The combined organic layer was dried, concentrated, subjected to column chromatography to obtain a crude. Hydrogen chloride-ethanol solution was added thereto under stirring. The resulting hydrochloride salt was slurried in ethyl acetate-methanol system, filtered, dried to give a white solid (135 mg, yield: 68%). $^1$H-NMR (300 Hz, DMSO-d$_6$): δ ppm 10.27(s, 1H), 7.69(d, 1H), 7.61(d, 1H), 7.39(d, 1H), 7.27(t, 1H), 7.07(s, 1H), 7.00(d, 1H), 6.89(d, 1H), 6.71(d, 1H), 3.43(s, 2H), 3.07(brs, 4H), 2.59(brs, 4H), 2.55(t, 2H), 2.37(t, 2H), 1.73(m, 2H). ESI-MS (m/z): 392.2 [M+H]$^+$.

Example 49

7-(2-(4-(benzo[b]thiophen-4-yl)piperazin-1-yl)ethyl)-4,5-dihydro-1H-benzo[b]azepin-2(3H)-one hydrochloride The product of Reference Example 29(100 mg, 0.45 mmol), the product of Reference Example 1(130 mg, 0.45 mmol), potassium carbonate (246 mg, 1.79 mmol), potassium iodide (74 mg, 0.45 mmol) were added to acetonitrile (4 ml) and the mixture was stirred at reflux for 20 hours. The reaction mixture was extracted with dichloromethane and water. The combined organic layer was dried, concentrated, subjected to column chromatography to obtain a crude. Hydrogen chloride-ethanol solution was added thereto under stirring. The resulting hydrochloride salt was slurried in ethyl acetate, filtered, dried to give a pale yellow solid (90 mg, yield: 45.6%). $^1$H-NMR (300 Hz, DMSO-d$_6$): δ ppm 9.45(s, 1H), 7.69(d, 1H), 7.61(d, 1H), 7.40(d, 1H), 7.27(t, 1H), 7.11(m, 2H), 6.89(m, 2H), 3.08(brs, 4H), 2.80-2.54(m, 10H), 2.11(m, 4H). ESI-MS (m/z): 406.3 [M+H]$^+$.

Example 50

3-(2-(4-(benzo[b]thiophen-4-yl)piperazin-1-yl)ethyl)-2-methyl-4H-pyrido[1,2-a]pyrimidin-4-one hydrochloride The product of Reference Example 1(50 mg, 0.17 mmol), 3-(2-chloroethyl)-2-methyl-4H-pyrido[1,2-a]pyrimidin-4-one (40 mg, 0.18 mmol), potassium carbonate (82 mg, 0.60 mmol), potassium iodide (2 mg) were added to acetonitrile (2 ml) and the mixture was stirred at reflux overnight. The reaction mixture was extracted with dichloromethane and water. The organic layer was combined, dried, concentrated, subjected to column chromatography to obtain a crude. Hydrogen chloride-ethanol solution was added thereto under stirring. The resulting hydrochloride salt was slurried in ethyl acetate/n-hexane system, filtered, dried to give a white solid (40 mg, yield: 49%). $^1$H-NMR (300 Hz, DMSO-d$_6$): δ ppm 8.89(d, 1H), 7.85(t, 1H), 7.69(d, 1H), 7.60(t, 2H), 7.42(d, 1H), 7.28(t, 2H), 6.91(d, 1H), 3.09(brs, 4H), 2.85(t, 2H), 2.73(brs, 4H), 2.54(t, 2H), 2.50(s, 3H). ESI-MS (m/z): 405.3 [M+H]$^+$.

Example 51

6-(2-(4-(benzo[b]thiophen-4-yl)piperazin-1-yl)ethyl)-3-methyl-3,4-dihydroquinazolin-2(1H)-one The product of Reference Example 33(180 mg, 0.80 mmol), the product of Reference Example 1(230 mg, 0.79 mmol), sodium carbonate (335 mg, 3.16 mmol), sodium iodide (4 mg) were added to N,N-dimethylformamide (4 ml) under a nitrogen atmosphere and the mixture was stirred at 120° C. for 16 hours. The reaction mixture was poured into ice water, the precipitated solid was filtered, washed 3 times with ice water, dried, subjected to column chromatography to give a crude (110 mg). The crude was slurried in ethyl acetate, filtered, dried to give a pale yellow solid (80 mg, yield: 25%). $^1$H-NMR (300 Hz, DMSO-d$_6$): δ ppm 9.12(s, 1H), 7.69(d, 1H), 7.61(d, 1H), 7.40(d, 1H), 7.27(t, 1H), 7.00(d, 1H), 6.96(s, 1H), 6.89(d, 1H), 6.68(d, 1H), 4.36(s, 2H), 3.07(brs, 4H), 2.84(s, 3H), 2.67(m, 6H), 2.55(t, 2H). ESI-MS (m/z): 407.3 [M+H]+.

Example 52

3-(2-(4-(benzo[b]thiophen-4-yl)piperazin-1-yl)ethyl)-9-chloro-2-methyl-6,7,8,9-tetrahydro-4H-pyrido[1,2-a]pyrimidin-4-one Thionyl chloride (6.8 ul, 0.094 mmol) in dichloromethane was added dropwise to the product of Example 4(20 mg, 0.047 mmol) dissolved in dichloromethane under ice bath followed by stirring at 10° C. for 1 hour. The reaction solution was diluted with dichloromethane, washed with saturated aqueous sodium bicarbonate solution. The organic phase was dried, concentrated and subjected to column chromatography to obtain the target (19 mg, yield: 91%). $^1$H-NMR (300 Hz, MeOH-d$_4$): δ ppm 7.66(d, 1H), 7.60(d, 1H), 7.50(d, 1H), 7.33(t, 1H), 7.03(d, 1H), 5.18(m, 1H), 4.30(m, 1H), 3.71(m, 1H), 3.49(brs, 4H), 3.41(brs, 4H), 3.21(t, 2H), 3.03(m, 2H), 2.43(s, 3H), 2.35(m, 3H), 2.14(m, 1H). ESI-MS (m/z): 443.3 [M+H]$^+$.

Example 53

5-(2-(4-(benzo[b]thiophen-4-yl)piperazin-1-yl)ethyl)indoline-2-thione hydrochloride The product of Example 8(500 mg, 1.325 mmol) was suspended in toluene (15 ml), Lawesson's reagent was added (642 mg, 1.59 mmol) and the mixture was stirred at 80° C. overnight. The reaction solution was concentrated, and the residue was purified by column chromatography to obtain a crude. Hydrogen chloride-ethanol solution was added thereto under stirring, the resulting salt was slurried in isopropyl ether/methanol system, filtered to give a yellow solid (40 mg, yield: 7.6%). $^1$H-NMR (300 Hz, DMSO-d$_6$): δ ppm 12.66(s, 1H), 10.96(brs, 1H), 7.77(d, 1H), 7.71(d, 1H), 7.49(d, 1H), 7.32(t, 1H), 7.25(s, 1H), 7.19(d, 1H), 6.99(d, 1H), 6.96(d, 1H), 4.06(s, 2H), 3.02-3.74(m, 12H).

Example 54

7-(2-(4-(benzo[b]thiophen-4-yl)piperazin-1-yl)ethyl)quinoline-2(1H)-thione

The product of Example 9(200 mg, 0.51 mmol) was suspended in toluene (20 ml), Lawesson's reagent (416 mg, 1.02 mmol) was added and the mixture was stirred at 80° C. for 14 hours. The reaction mixture was concentrated, and the residue was purified by column chromatography to obtain a yellow solid (60 mg, yield: 28.8%). $^1$H-NMR (300 Hz, DMSO-d6): δ ppm 13.64(s, 1H), 7.80(d, 1H), 7.72(m, 2H), 7.63(d, 1H), 7.51(s, 1H), 7.43(d, 1H), 7.28(m, 2H), 7.21(d, 1H), 6.92(d, 1H), 3.14(brt, 4H), 2.64-3.06(m, 8H). ESI-MS (m/z): 406.2 [M+H]$^+$.

Example 55

2-(2-(4-(benzo[b]thiophen-4-yl)piperazin-1-yl)ethyl)-5,6-diethylpyrimidin-4(3H)-one hydrochloride The product of Reference Example 37(270 mg, 0.72 mmol), the product of Reference Example 1(314 mg, 1.44 mmol) were dissolved in acetonitrile (10 ml) under a nitrogen atmosphere and the mixture was stirred at reflux overnight. The reaction mixture was cooled to room temperature, concentrated, subjected to column chromatography to obtain a crude (160 mg). The crude was dissolved in methanol (5 ml), added with hydrogen chloride-methanol solution (1.0 ml), stirred for 3 hours at room temperature, concentrated and the residue was purified by column chromatography to give the target (35 mg, yield: 12.2%). $^1$H-NMR (300 Hz, DMSO-d$_6$): δ ppm 12.23(brs, 1H), 7.69(d, 1H), 7.61(d, 1H), 7.40(d, 1H), 7.27(t, 1H), 6.89(d, 1H), 3.05(brt, 4H), 2.61-2.86(m, 8H), 2.31-2.57(m, 4H), 1.13(t, 3H), 0.99(t, 3H). ESI-MS (m/z): 397.2 [M+H]$^+$.

Example 56

2-(2-(4-(benzo[b]thiophen-4-yl)piperazin-1-yl)ethyl)pyrimidin-4(3H)-one hydrochloride By a similar method as in example 55, 2-(2-(4-(benzo[b]thiophen-4-yl)piperazin-1-yl)ethyl)pyrimidin-4(3H)-one hydrochloride was prepared from Reference Example 38 and Reference Example 1. $^1$H-NMR (300 Hz, DMSO-d$_6$): δ ppm 9.45(brs, 1H), 7.96(d, 1H), 7.77(d, 1H), 7.70(d, 1H), 7.50(d, 1H), 7.31(t, 1H), 6.96(d, 1H), 6.36(d, 1H), 3.63(t, 2H), 3.17-3.57(m, 10H). ESI-MS (m/z): 341.0 [M+H]$^+$.

The table below shows compounds of Examples 57 to 154, these compounds can be prepared by a similar method as in example 1-55, using the corresponding starting materials and intermediates.

| Example No. | name | $^1$H NMR 和 ESI-MS |
|---|---|---|
| 57 | 7-(2-(4-(2-fluorobenzo[b]thiophen-4-yl)piperazin-1-yl)ethyl)quinolin-2(1H)-one hydrochloride | $^1$H NMR (300 MHz, DMSO-d$_6$) δ 3.12-3.55 (m, 6H), 3.66 (d, 2H), 4.94 (br, 4H), 6.47 (d, 1H), 7.03 (d, 1H), 7.16 (m, 3H), 7.32 (t, 1H), 7.61 (d, 1H), 7.65 (d, 1H), 7.89 (d, 1H), 11.59 (s, 1H), 11.83 (s, 1H). ESI-MS m/z 408.7 [M + H]$^+$. |
| 58 | 2-((4-(benzo[b]thiophen-4-yl)piperazin-1-yl)methyl)-1H-benzo[d]imidazole | $^1$H NMR (300 MHz, DMSO-d$_6$) δ 2.73 (br, 4H), 3.11 (br, 4H), 3.83 (s, 2H), 6.90 (d, 1H), 7.14 (m, 2H), 7.27 (t, 1H), 7.40 (d, 1H), 7.45 (d, 1H), 7.57 (d, 1H), 7.61 (d, 1H), 7.68 (d, 1H), 12.35 (s, 1H). ESI-MS m/z 349.3 [M + H]$^+$. |
| 59 | 6-(2-(4-(benzo[b]thiophen-4-yl)piperazin-1-yl)ethyl)benzo[d]thiazole | $^1$H NMR (300 MHz, DMSO-d$_6$) δ 3.20-3.63 (m, 10H), 3.70 (d, 2H), 6.98 (d, 1H), 7.32 (t, 1H), 7.50 (m, 2H), 7.70 (d, 1H), 7.77 (d, 1H), 8.09 (m, 2H), 9.38 (s, 1H), 11.45 (s, 1H). ESI-MS m/z 380.0 [M + H]$^+$. |
| 60 | 7-(2-(4-(2-fluorobenzo[b]thiophen-4-yl)piperazin-1-yl)ethyl)benzo[d]thiazol-2-amine | $^1$H NMR (300 MHz, DMSO-d$_6$) δ 2.69 (m, 6H), 2.85 (t, 2H), 3.02 (br, 4H), 6.89-7.01 (m, 3H), 7.17 (m, 2H), 7.28 (t, 1H), 7.43 (s, 2H), 7.52 (d, 1H). ESI-MS m/z 413.7 [M + H]$^+$. |
| 61 | N-(7-(2-(4-(2-fluorobenzo[b]thiophen-4-yl)piperazin-1-yl)ethyl)benzo[d]thiazol-2-yl)acetamide | $^1$H NMR (300 MHz, DMSO-d$_6$) δ 2.20 (s, 3H), 2.72 (m, 6H), 3.02 (m, 6H), 6.95 (d, 1H), 7.00 (d, 1H), 7.21 (d, 1H), 7.27 (t, 1H), 7.38 (t, 1H), 7.52 (d, 1H), 7.60 (d, 1H), 12.33 (s, 1H). ESI-MS m/z 455.0 [M + H]$^+$. |
| 62 | 5-(2-(4-(2-fluorobenzo[b]thiophen-4-yl)piperazin-1-yl)ethyl)benzo[d]thiazol-2-amine hydrochloride | $^1$H NMR (300 MHz, DMSO-d$_6$) δ 2.90-3.78 (m, 12H), 6.94 (d, 1H), 7.02 (d, 1H), 7.13 (s, 1H), 7.30 (m, 2H), 7.48 (s, 2H), 7.60 (d, 2H), 10.70 (s, 1H). ESI-MS m/z 413.1 [M + H]$^+$. |
| 63 | N-(5-(2-(4-(2-fluorobenzo[b]thiophen-4-yl)piperazin-1-yl)ethyl)benzo[d]thiazol-2-yl)acetamide | $^1$H NMR (300 MHz, DMSO-d$_6$) δ 2.19 (s, 3H), 2.69 (m, 6H), 2.91 (t, 2H), 3.02 (br, 4H), 6.97 (m, 2H), 7.21 (d, 1H), 7.28 (t, 1H), 7.52 (d, 1H), 7.63 (s, 1H), 7.85 (d, 1H), 12.30 (s, 1H). ESI-MS m/z 454.9 [M + H]$^+$. |
| 64 | 7-(2-(4-(2-fluorobenzo[b]thiophen-4-yl)piperazin-1-yl)ethyl)-3,4-dihydroquinolin-2(1H)-onehydrochloride | $^1$H NMR (300 MHz, DMSO-d$_6$) δ 2.43 (t, 2H). 2.84 (t, 2H), 2.99-3.53 (m, 10H), 3.65 (d, 2H), 6.75 (s, 1H), 6.85 (d, 1H), 7.02 (d, 1H), 7.15 (m, 2H), 7.32 (t, 1H), 7.61 (d, 1H), 10.15 (s, 1H), 11.32 (s, 1H). ESI-MS m/z 410 [M + H]$^+$. |
| 65 | 6-(2-(4-(2-fluorobenzo[b]thiophen-4-yl)piperazin-1-yl)ethyl)-3,4-dihydroquinolin-2(1H)-one | $^1$H NMR (300 MHz, DMSO-d$_6$) δ 2.42 (t, 2H), 2.55 (t, 2H), 2.66 (m, 6H), 2.83 (t, 2H), 3.01 (br, 4H), 6.76 (d, 1H), 6.99 (m, 4H), 7.27 (t, 1H), 7.52 (d, 1H), 9.99 (s, 1H). ESI-MS m/z 410.5 [M + H]$^+$. |
| 66 | 6-(2-(4-(benzo[b]thiophen-4-yl)piperazin-1-yl)ethyl)-7-fluoro-2H-benzo[b][1,4]oxazin-3(4H)-one | $^1$H NMR (300 MHz, DMSO-d$_6$) δ 2.55 (t, 2H), 2.70 (m, 6H), 3.08 (br, 4H), 4.56 (s, 2H), 6.87 (m, 3H), 7.27 (t, 1H), 7.40 (d, 1H), 7.61 (d, 1H), 7.69 (d, 1H), 10.70 (s, 1H). ESI-MS m/z 412.1 [M + H]$^+$. |

| Example No. | name | ¹H NMR 和 ESI-MS |
|---|---|---|
| 67 | 7-(2-(4-(3-methylbenzo[b]thiophen-4-yl)piperazin-1-yl)ethyl)-3,4-dihydroquinolin-2(1H)-one | ¹H NMR (300 MHz, DMSO-d$_6$) δ 2.26-2.60 (m, 6H), 2.63-3.09 (m, 13H), 6.73 (s, 1H), 6.79 (d, 1H), 7.06 (d, 1H), 7.11 (d, 1H), 7.27 (m, 2H), 7.64 (d, 1H), 10.01 (s, 1H). ESI-MS m/z 406.1 [M + H]$^+$. |
| 68 | 6-(2-(4-(benzo[b]thiophen-4-yl)piperazin-1-yl)ethyl)benzo[d]oxazol-2(3H)-one | ¹H NMR (300 MHz, DMSO-d$_6$) δ 2.60 (t, 2H), 2.68 (br, 4H), 2.79 (t, 2H), 3.06 (br, 4H), 6.90 (d, 1H), 7.01 (m, 2H), 7.22 (s, 1H), 7.27 (t, 1H), 7.39 (d, 1H), 7.61 (d, 1H), 7.69 (d, 1H), 11.52 (s, 1H). ESI-MS m/z 380.2 [M + H]$^+$. |
| 69 | 4-((4-(benzo[b]thiophen-4-yl)piperazin-1-yl)methyl)quinolin-2(1H)-one | ¹H NMR (300 MHz, DMSO-d$_6$) δ 2.73 (br, 4H), 3.08 (br, 4H), 3.78 (s, 2H), 6.56 (s, 1H), 6.90 (d, 1H), 7.15-7.36 (m, 3H), 7.41 (d, 1H), 7.50 (t, 1H), 7.61 (d, 1H), 7.70 (d, 1H), 7.96 (d, 1H), 11.71 (s, 1H). ESI-MS m/z 376.2 [M + H]$^+$. |
| 70 | 3-(4-(4-(benzo[b]thiophen-4-yl)piperazin-1-yl)butyl)-1H-indole-5-carbonitrile | ¹H NMR (300 MHz, DMSO-d$_6$) δ 1.75 (m, 4H), 2.79 (t, 2H), 3.23 (m, 6H), 3.55 (t, 4H), 6.96 (d, 1H), 7.31 (t, 1H), 7.41 (m, 2H), 7.50 (m, 2H), 7.70 (d, 1H), 7.77 (d, 1H), 8.12 (s, 1H), 11.49 (s, 1H). ESI-MS m/z 415.3 [M + H]$^+$. |
| 71 | 7-(5-(4-(6-fluorobenzo[b]thiophen-4-yl)piperazin-1-yl)pentyl)quinolin-2(1H)-one | ¹H NMR (300 MHz, DMSO-d$_6$) δ 1.33 (m, 2H), 1.49 (m, 2H), 1.62 (m, 2H), 2.35 (t, 2H), 2.57 (br, 4H), 2.64 (t, 2H), 3.06 (br, 4H), 6.41 (d, 1H), 6.73 (d, 1H), 7.03 (d, 1H), 7.10 (s, 1H), 7.35 (d, 1H), 7.49 (d, 1H), 7.55 (d, 1H), 7.65 (d, 1H), 7.84 (d, 1H), 11.65 (s, 1 H). ESI-MS m/z 449.9 [M + H]$^+$. |
| 72 | 6-(4-(4-(benzo[b]thiophen-4-yl)piperazin-1-yl)butyl)-8-fluoro-2H-benzo[b][1,4]oxazin-3(4H)-one | ¹H NMR (300 MHz, DMSO-d$_6$) δ 1.48 (m, 2H), 1.56 (m, 2H), 2.38 (t, 2H), 2.52 (t, 2H), 2.58 (br, 4H), 3.06 (br, 4H), 4.61 (s, 2H), 6.55 (s, 1H), 6.75 (d, 1H), 6.89 (d, 1H), 7.27 (t, 1H), 7.39 (d, 1H), 7.61 (d, 1H), 7.69 (d, 1H), 10.83 (s, 1H). ESI-MS m/z 440.2 [M + H]$^+$. |
| 73 | 1-(benzo[b]thiophen-4-yl)-4-((2,3-dihydrobenzo[b][1,4]dioxin-2-yl)methyl)piperazine | ¹H NMR (300 MHz, DMSO-d$_6$) δ 2.63-2.83 (m, 6H), 3.08 (brt, 4H), 4.00 (dd, 1H), 4.33 (dd, 1H), 4.40 (m, 1H), 6.78-6.93 (m, 5H), 7.27 (t, 1H), 7.40 (d, 1H), 7.61 (d, 1H), 7.68 (d, 1H). ESI-MS m/z 366.7 [M + ]$^+$. |
| 74 | 6-(4-(4-(2-fluorobenzo[b]thiophen-4-yl)piperazin-1-yl)butyl)-3,4-dihydroquinolin-2(1H)-one | ¹H NMR (300 MHz, DMSO-d$_6$) δ 1.47 (m, 2H), 1.56 (m, 2H), 2.39 (m, 4H), 2.54 (m, 6H), 2.83 (t, 2H), 2.99 (br, 4H), 6.75 (d, 1H), 6.96 (m, 4H), 7.27 (t, 1H), 7.51 (d, 1H), 9.97 (s, 1H). ESI-MS m/z 438.6 [M + H]$^+$. |
| 75 | 2-(2-(4-(benzo[b]thiophen-4-yl)piperazin-1-yl)ethyl)-1H-benzo[d]imidazole | ¹H NMR (300 MHz, DMSO-d$_6$) δ 2.72 (br, 4H), 2.89 (t, 2H), 3.06 (m, 6H), 6.89 (d, 1H), 7.11 (m, 2H), 7.26 (t, 1H), 7.41 (d, 1H), 7.48 (m, 2H), 7.61 (d, 1H), 7.69 (d, 1H), 12.20 (s, 1H). ESI-MS m/z 362.9 [M + H]$^+$. |
| 76 | N-(6-(2-(4-(2-fluorobenzo[b]thiophen-4-yl)piperazin-1-yl)ethyl)benzo[d]thiazol-2-yl)acetamide hydrochloride | ¹H NMR (300 MHz, DMSO-d$_6$) δ 2.20 (s, 3H), 3.14-3.75 (m, 12H), 7.04 (d, 1H), 7.17 (d, 1H), 7.35 (m, 2H), 7.62 (d, 1H), 7.73 (d, 1H), 7.90 (s, 1H), 11.03 (s, 1H), 12.36 (s, 1H). ESI-MS m/z 455.5 [M + H]$^+$. |
| 77 | 5-(2-(4-(2-fluorobenzo[b]thiophen-4-yl)piperazin-1-yl)ethyl)-1H-benzo[d]imidazol-2(3H)-one | ¹H NMR (300 MHz, DMSO-d$_6$) δ 2.57 (t, 2H), 2.66 (br, 4H), 2.74 (t, 2H), 3.01 (br, 4H), 6.81 (m, 3H), 6.96 (m, 2H), 7.27 (t, 1H), 7.52 (d, 1H), 10.46 (s, 1H), 10.50 (s, 1H). ESI-MS m/z 397.1 [M + H]$^+$. |
| 78 | 6-(2-(4-(6-fluorobenzo[b]thiophen-4-yl)piperazin-1-yl)ethyl)-2H-benzo[b][1,4]oxazin-3(4H)-one | ¹H NMR (300 MHz, DMSO-d$_6$) δ 2.57 (t, 2H), 2.69 (m, 6H), 3.11 (br, 4H), 4.53 (s, 2H), 6.72-6.89 (m, 4H), 7.37 (d, 1H), 7.50 (dd, 1H), 7.66 (d, 1H), 10.65 (s, 1H). ESI-MS m/z 412.1 [M + H]$^+$. |
| 79 | 5-(2-(4-(2-fluorobenzo[b]thiophen-4-yl)piperazin-1-yl)ethyl)indolin-2-one | ¹H NMR (300 MHz, DMSO-d$_6$) δ 2.55 (t, 2H), 2.68 (m, 6H), 3.01 (br, 4H), 3.43 (s, 2H), 6.72 (d, 1H), 6.96 (m, 2H), 7.03 (d, 1H), 7.09 (s, 1H), 7.27 (t, 1H), 7.52 (d, 1H), 10.28 (s, 1H). ESI-MS m/z 396.0 [M + H]$^+$. |
| 80 | 6-(2-(4-(benzo[b]thiophen-4-yl)piperazin-1-yl)ethyl)-2-methylquinazolin-4(3H)-one | ¹H NMR (300 MHz, DMSO-d$_6$) δ 2.33 (s, 3H), 2.75 (m, 6H), 2.95 (t, 2H), 3.08 (br, 4H), 6.90 (d, 1H), 7.27 (t, 1H), 7.39 (m, 2H), 7.47 (s, 1H), 7.62 (d, 1H), 7.70 (d, 1H), 7.99 (d, 1H), 12.13 (s, 1H). ESI-MS m/z 405.1 [M + H]$^+$. |

-continued

| Example No. | name | ¹H NMR 和 ESI-MS |
|---|---|---|
| 81 | 7-(2-(4-(benzo[b]thiophen-4-yl)piperazin-1-yl)ethyl)-1,1-dioxide-3,4-dihydro-2H-benzo[e][1,2]thiazine hydrochloride | ¹H NMR (300 MHz, DMSO-$d_6$) δ 2.90 (t, 2H), 3.14-3.49 (m, 8H), 3.57 (m, 4H), 3.69 (d, 2H), 6.98 (d, 1H), 7.33 (m, 2H), 7.48 (m, 3H), 7.70 (m, 2H), 7.77 (d, 1H), 11.26 (s, 1H). ESI-MS m/z 428.0 [M + H]⁺. |
| 82 | 5-(2-(4-(benzo[b]thiophen-4-yl)piperidin-1-yl)ethyl)indolin-2-one | ¹H NMR (300 MHz, DMSO-$d_6$) δ 1.83 (m, 4H), 2.31 (m, 1H), 2.69 (m, 4H), 3.14 (m, 4H), 3.44 (s, 2H), 6.73 (d, 1H), 7.04 (d, 1H), 7.10 (s, 1H), 7.25 (d, 1H), 7.32 (t, 1H), 7.62 (d, 1H), 7.76 (d, 1H), 7.84 (d, 1H), 10.31 (s, 1H). ESI-MS m/z 377.0 [M + H]⁺. |
| 83 | 7-(2-(4-(benzo[b]thiophen-4-yl)piperidin-1-yl)ethyl)-3,4-dihydroquinolin-2(1H)-one | ¹H NMR (300 MHz, DMSO-$d_6$) δ 1.79 (m, 5H), 2.21 (m, 2H), 2.40 (t, 2H), 2.53 (m, 2H), 2.69 (br, 2H), 2.80 (t, 2H), 3.09 (br, 2H), 6.70 (s, 1H), 6.78 (d, 1H), 7.05 (d, 1H), 7.23 (d, 1H), 7.31 (t, 1H), 7.60 (d, 1H), 7.75 (d, 1H), 7.82 (d, 1H), 10.03 (s, 1H). ESI-MS m/z 391.1 [M + H]⁺. |
| 84 | 5-(2-(4-(6-fluorobenzo[b]thiophen-4-yl)piperazin-1-yl)ethyl)indolin-2-one | ¹H NMR (300 MHz, DMSO-$d_6$) δ 2.56 (t, 2H), 2.69 (m, 6H), 3.09 (br, 4H), 3.43 (s, 2H), 6.73 (m, 2H), 7.03 (d, 1H), 7.09 (s, 1H), 7.37 (d, 1H), 7.49 (d, 1H), 7.65 (d, 1H), 10.27 (s, 1H). ESI-MS m/z 396.5 [M + H]⁺. |
| 85 | 7-(2-(4-(6-fluorobenzo[b]thiophen-4-yl)piperazin-1-yl)ethyl)-3,4-dihydroquinolin-2(1H)-one | ¹H NMR (300 MHz, DMSO-$d_6$) δ 2.42 (t, 2H), 2.57 (t, 2H), 2.68 (m, 6H), 2.82 (t, 2H), 3.10 (br, 4H), 6.76 (m, 3H), 7.06 (d, 1H), 7.37 (d, 1H), 7.49 (d, 1H), 7.66 (d, 1H), 10.01 (s, 1H). ESI-MS m/z 410.5 [M + H]⁺. |
| 86 | 6-(2-(4-(benzo[b]thiophen-4-yl)piperazin-1-yl)ethyl)-1-methyl-1H-benzo[d]imidazol-2(3H)-one | ¹H NMR (300 MHz, DMSO-$d_6$) δ 2.62 (t, 2H), 2.70 (br, 4H), 2.80 (t, 2H), 3.08 (br, 4H), 3.26 (s, 3H), 6.89 (m, 3H), 6.99 (s, 1H), 7.27 (t, 1H), 7.40 (d, 1H), 7.61 (d, 1H), 7.69 (d, 1H), 10.70 (s, 1H). ESI-MS m/z 393.5 [M + H]⁺. |
| 87 | 5-(2-(4-(benzo[b]thiophen-4-yl)piperazin-1-yl)ethyl)-1,3-dimethyl-1H-benzo[d]imidazol-2(3H)-one hydrochloride | ¹H NMR (300 MHz, DMSO-$d_6$) δ 3.13-3.47 (m, 14H), 3.56 (d, 2H), 3.68 (d, 2H), 6.99 (t, 2H), 7.12 (m, 2H), 7.32 (t, 1H), 7.49 (d, 1H), 7.70 (d, 1H), 7.77 (d, 1H), 11.44 (s, 1H). ESI-MS m/z 407.0 [M + H]⁺. |
| 88 | 5-(2-(4-(benzo[b]thiophen-4-yl)piperazin-1-yl)ethyl)-1-methyl-1H-benzo[d]imidazol-2(3H)-one | ¹H NMR (300 MHz, DMSO-$d_6$) δ 2.59 (t, 2H), 2.69 (br, 4H), 2.78 (t, 2H), 3.07 (br, 4H), 3.25 (s, 3H), 6.89 (m, 3H), 6.98 (d, 1H), 7.27 (t, 1H), 7.40 (d, 1H), 7.61 (d, 1H), 7.69 (d, 1H), 10.74 (s, 1H). ESI-MS m/z 393.5 [M + H]⁺. |
| 89 | 6-(2-(4-(2-methoxybenzo[b]thiophen-4-yl)piperazin-1-yl)ethyl)-3,4-dihydroquinolin-2(1H)-one | ¹H NMR (300 MHz, DMSO-$d_6$) δ 2.42 (t, 2H), 2.53-2.93 (m, 10H), 3.05 (br, 4H), 6.43 (s, 1H), 6.78 (d, 1H), 6.89 (d, 1H), 7.03 (m, 2H), 7.13 (t, 1H), 7.40 (d, 1H), 10.01 (s, 1H). ESI-MS m/z 422.0 [M + H]⁺. |
| 90 | 3-(2-(4-(6-fluorobenzo[b]thiophen-4-yl)piperazin-1-yl)ethyl)-2-methyl-6,7,8,9-tetrahydro-4H-pyrido[1,2-a]pyrimidin-4-one | ¹H NMR (300 MHz, DMSO-$d_6$) δ 1.76 (m, 2H), 1.85 (m, 2H), 2.22 (s, 3H), 2.43 (t, 2H), 2.57-2.82 (m, 8H), 3.10 (br, 4H), 3.78 (t, 2H), 6.75 (d, 1H), 7.37 (d, 1H), 7.49 (d, 1H), 7.65 (d, 1H). ESI-MS m/z 427.5 [M + H]⁺. |
| 91 | 7-(2-(4-(2-oxo-2,3-dihydrobenzo[b]thiophen-4-yl)piperazin-1-yl)ethyl)-3,4-dihydroquinolin-2(1H)-one | ¹H NMR (300 MHz, DMSO-$d_6$) δ 2.42 (t, 2H), 2.84 (t, 2H), 2.98-3.45 (m, 12H), 3.59 (d, 2H), 4.15 (s, 2H), 6.74 (s, 1H), 6.83 (d, 1H), 6.99 (d, 1H), 7.14 (d, 1H), 7.26 (d, 1H), 7.35 (t, 1H), 10.14 (s, 1H), 11.34 (s, 1H). ESI-MS m/z 408.1 [M + H]⁺. |
| 92 | 6-(2-(4-(2-fluorobenzo[b]thiophen-4-yl)piperazin-1-yl)ethyl)-2H-benzo[b][1,4]oxazin-3(4H)-one | ¹H NMR (300 MHz, DMSO-$d_6$) δ 2.55 (t, 2H), 2.67 (m, 6H), 3.02 (br, 4H), 4.52 (s, 2H), 6.82 (m, 3H), 6.97 (m, 2H), 7.28 (t, 2H), 7.52 (d, 1H), 10.66 (s, 1H). ESI-MS m/z 412.2 [M + H]⁺. |
| 93 | 5-(2-(4-(2-fluorobenzo[b]thiophen-4-yl)piperazin-1-yl)ethyl)-1,3-dimethyl-1H-benzo[d]imidazol-2(3H)-one hydrochloride | ¹H NMR (300 MHz, DMSO-$d_6$) δ 3.03-3.55 (m, 16H), 3.62 (d, 2H), 7.00 (m, 2H), 7.11 (m, 3H), 7.30 (t, 1H), 7.59 (d, 1H), 8.59 (br, 2H), 11.53 (s, 1H). ESI-MS m/z 425.1 [M + H]⁺. |
| 94 | 6-fluoro-5-(2-(4-(2-fluorobenzo[b]thiophen-4-yl)piperazin-1-yl)ethyl)indolin-2-one | ¹H NMR (300 MHz, DMSO-$d_6$) δ 2.54 (t, 2H), 2.66 (br, 4H), 2.73 (t, 2H), 3.01 (br, 4H), 3.42 (s, 2H), 6.58 (d, 1H), 6.95 (d, 1H), 6.98 (d, 1H), 7.16 (d, 1H), 7.27 (t, 1H), 7.52 (d, 1H), 10.40 (s, 1H). ESI-MS m/z 414.1 [M + H]⁺. |
| 95 | 5-(2-(4-(benzo[b]thiophen-4-yl)piperazin-1-yl)ethyl)-6-fluoroindolin-2-one | ¹H NMR (300 MHz, DMSO-$d_6$) δ 2.55 (t, 2H), 2.70 (m, 6H), 3.07 (br, 4H), 3.42 (s, 2H), 6.59 (d, 1H), 6.89 (d, 1H), 7.16 (d, 1H), 7.27 (t, 1H), 7.40 (d, 1H), 7.61 (d, 1H), 7.68 (d, 1H), 10.41 (s, 1H). ESI-MS m/z 396.0 [M + H]⁺. |

| Example No. | name | ¹H NMR 和 ESI-MS |
|---|---|---|
| 96 | 7-(2-(4-(benzo[b]thiophen-4-yl)piperazin-1-yl)ethyl)-1-benzyl-3-methylquinazoline-2,4(1H,3H)-dione | ¹H NMR (300 MHz, DMSO-$d_6$) δ 3.11-3.46 (m, 11H), 3.53 (d, 2H), 3.62 (d, 2H), 5.40 (s, 2H), 6.97 (d, 1H), 7.21-7.39 (m, 8H), 7.48 (d, 1H), 7.70 (d, 1H), 7.77 (d, 1H), 8.07 (d, 1H), 11.18 (s, 1H). ESI-MS m/z 511.7 [M + H]⁺. |
| 97 | 6-(2-(4-(benzo[b]thiophen-4-yl)piperidin-1-yl)ethyl)-2H-benzo[b][1,4]oxazin-3(4H)-one | ¹H NMR (300 MHz, DMSO-$d_6$) δ 1.54 (m, 1H), 1.84 (br, 4H), 2.72 (br, 4H), 3.14 (brt, 4H), 4.51 (s, 2H), 6.81 (m, 3H), 7.23 (d, 1H), 7.32 (t, 1H), 7.61 (d, 1H), 7.75 (d, 1H), 7.83 (d, 1H), 10.66 (s, 1H). ESI-MS m/z 393.0 [M + H]⁺. |
| 98 | 6-(2-(4-(benzo[b]thiophen-4-yl)piperidin-1-yl)ethyl)-3,4-dihydroquinolin-2(1H)-one | ¹H NMR (300 MHz, DMSO-$d_6$) δ 1.54 (m, 1H), 1.79 (m, 4H), 2.25 (br, 2H), 2.40 (t, 2H), 2.63 (m, 4H), 2.81 (t, 2H), 3.34 (br, 2H), 6.75 (d, 1H), 6.99 (d, 1H), 7.02 (s, 1H), 7.23 (d, 1H), 7.31 (t, 1H), 7.59 (d, 1H), 7.74 (d, 1H), 7.82 (d, 1H), 9.97 (s, 1H). ESI-MS m/z 391.0 [M + H]⁺. |
| 99 | 3-(2-(4-(benzo[b]thiophen-4-yl)piperidin-1-yl)ethyl)-2-methyl-6,7,8,9-tetrahydro-4H-pyrido[1,2-a]pyrimidin-4-one hydrochloride | ¹H NMR (300 MHz, DMSO-$d_6$) δ 1.83 (m, 4H), 2.05 (m, 4H), 2.29 (s, 3H), 2.84 (m, 4H), 3.07-3.55 (m, 5H), 3.79 (m, 4H), 7.24 (d, 1H), 7.38 (t, 1H), 7.70 (d, 1H), 7.85 (d, 1H), 7.92 (d, 1H), 9.28 (s, 1H). ESI-MS m/z 408.2 [M + H]⁺. |
| 100 | 6-(2-(4-(2-fluorobenzo[b]thiophen-4-yl)piperazin-1-yl)ethyl)quinolin-2(1H)-one | ¹H NMR (300 MHz, DMSO-$d_6$) δ 2.65 (m, 6H), 2.82 (t, 2H), 3.01 (br, 4H), 6.47 (d, 1H), 6.95 (d, 1H), 6.98 (d, 1H), 7.23 (d, 1H), 7.27 (t, 1H), 7.40 (d, 1H), 7.51 (m, 2H), 7.84 (d, 1H), 11.66 (s, 1H). ESI-MS m/z 408.3 [M + H]⁺. |
| 101 | 5-(4-(4-(2-fluorobenzo[b]thiophen-4-yl)piperazin-1-yl)butyl)indolin-2-one | ¹H NMR (300 MHz, DMSO-$d_6$) δ 1.52 (m, 4H), 2.36 (t, 2H), 2.54 (m, 6H), 2.99 (br, 4H), 3.31 (s, 2H), 6.71 (d, 1H), 6.96 (m, 3H), 7.04 (s, 1H), 7.27 (t, 1H), 7.51 (d, 1H), 10.25 (s, 1H). ESI-MS m/z 424.5 [M + H]⁺. |
| 102 | 7-(2-(4-(6-fluorobenzo[b]thiophen-4-yl)piperazin-1-yl)ethyl)quinolin-2(1H)-one | ¹H NMR (300 MHz, DMSO-$d_6$) δ 2.66 (m, 6H), 2.85 (t, 2H), 3.10 (br, 4H), 6.42 (d, 1H), 6.75 (d, 1H), 7.09 (d, 1H), 7.18 (s, 1H), 7.37 (d, 1H), 7.49 (d, 1H), 7.57 (d, 1H), 7.66 (d, 1H), 7.85 (d, 1H), 11.68 (s, 1H). ESI-MS m/z 408.7 [M + H]⁺. |
| 103 | 3-(4-(4-(benzo[b]thiophen-4-yl)piperazin-1-yl)butyl)-6,7-dimethoxy-4H-chromen-4-one | ¹H NMR (300 MHz, DMSO-$d_6$) δ 1.53 (m, 4H), 2.40 (t, 4H), 2.60 (br, 4H), 3.06 (br, 4H), 3.85 (s, 3H), 3.90 (s, 3H), 6.89 (d, 1H), 7.17 (s, 1H), 7.27 (t, 1H), 7.38 (s, 1H), 7.39 (d, 1H), 7.61 (d, 1H), 7.69 (d, 1H), 8.19 (s, 1H). ESI-MS m/z 479.0 [M + H]⁺. |
| 104 | 6-(4-(4-(benzo[b]thiophen-4-yl)piperidin-1-yl)butyl)-3,4-dihydroquinolin-2(1H)-one | ¹H NMR (300 MHz, DMSO-$d_6$) δ 1.46 (m, 2H), 1.55 (m, 2H), 1.76 (m, 4H), 2.07 (t, 2H), 2.33 (t, 2H), 2.41 (t, 2H), 2.51 (d, 2H), 2.83 (t, 2H), 2.96 (d, 2H), 3.05 (m, 1H), 6.75 (d, 1H), 6.95 (d, 1H), 6.99 (s, 1H), 7.24 (d, 1H), 7.31 (t, 1H), 7.59 (d, 1H), 7.74 (d, 1H), 7.82 (d, 1H), 9.96 (s, 1H). ESI-MS m/z 419.5 [M + H]⁺. |
| 105 | 3-(2-(4-(benzo[b]thiophen-4-yl)piperazin-1-yl)ethyl)-5-methoxy-1H-indole | ¹H NMR (300 MHz, DMSO-$d_6$) δ 2.72 (m, 6H), 2.87 (t, 2H), 3.11 (br, 4H), 3.77 (s, 3H), 6.71 (dd, 1H), 6.91 (d, 1H), 7.01 (d, 1H), 7.14 (d, 1H), 7.22 (d, 1H), 7.28 (t, 1H), 7.42 (d, 1H), 7.62 (d, 1H), 7.69 (d, 1H), 10.61 (s, 1H). ESI-MS m/z 392.1 [M + H]⁺. |
| 106 | 3-(3-(4-(benzo[b]thiophen-4-yl)piperazin-1-yl)propyl)-5-methoxy-1H-indole | ¹H NMR (300 MHz, DMSO-$d_6$) δ 1.84 (m, 2H), 2.45 (t, 2H), 2.62 (br, 4H), 2.69 (t, 2H), 3.08 (br, 4H), 3.76 (s, 3H), 6.70 (dd, 1H), 6.90 (d, 1H), 6.98 (d, 1H), 7.08 (d, 1H), 7.21 (d, 1H), 7.27 (t, 1H), 7.39 (d, 1H), 7.61 (d, 1H), 7.68 (d, 1H), 10.57 (s, 1H). ESI-MS m/z 406.8 [M + H]⁺. |
| 107 | 3-(4-(4-(benzo[b]thiophen-4-yl)piperazin-1-yl)butyl)-5-methoxy-1H-indole | ¹H NMR (300 MHz, DMSO-$d_6$) δ 1.55 (m, 2H), 1.68 (m, 2H), 2.41 (t, 2H), 2.59 (br, 4H), 2.68 (t, 2H), 3.05 (br, 4H), 3.75 (s, 3H), 6.70 (dd, 1H), 6.88 (d, 1H), 6.98 (d, 1H), 7.06 (d, 1H), 7.21 (d, 1H), 7.27 (t, 1H), 7.38 (d, 1H), 7.60 (d, 1H), 7.68 (d, 1H), 10.56 (s, 1H). ESI-MS m/z 420.1 [M + H]⁺. |
| 108 | 3-(3-(4-(benzo[b]thiophen-4-yl)piperazin-1-yl)propyl)-1H-indole-5-carbonitrile | ¹H NMR (300 MHz, DMSO-$d_6$) δ 1.85 (m, 2H), 2.41 (t, 2H), 2.61 (br, 4H), 2.76 (t, 2H), 3.09 (br, 4H), 6.90 (d, 1H), 7.27 (t, 1H), 7.38 (m, 3H), 7.49 (d, 1H), 7.61 (d, 1H), 7.69 (d, 1H), 8.11 (s, 1H), 11.38 (s, 1H). ESI-MS m/z 401.0 [M + H]⁺. |

-continued

| Example No. | name | ¹H NMR 和 ESI-MS |
|---|---|---|
| 109 | 3-(2-(4-(benzo[b]thiophen-4-yl)piperazin-1-yl)ethyl)-1H-indole-5-carbonitrile | ¹H NMR (300 MHz, DMSO-$d_6$) δ 2.72 (m, 6H), 2.94 (t, 2H), 3.10 (br, 4H), 6.91 (d, 1H), 7.28 (t, 1H), 7.41 (m, 3H), 7.50 (d, 1H), 7.62 (d, 1H), 7.70 (d, 1H), 8.13 (s, 1H), 11.41 (s, 1H). ESI-MS m/z 387.6 [M + H]⁺. |
| 110 | 1-acetyl-3-(4-(4-(benzo[b]thiophen-4-yl)piperazin-1-yl)butyl)-1H-indole-5-carbonitrile | ¹H NMR (300 MHz, DMSO-$d_6$) δ 1.58 (m, 2H), 1.72 (m, 2H), 2.44 (t, 2H), 2.60 (br, 4H), 2.66 (s, 3H), 2.74 (t, 2H), 3.06 (br, 4H), 6.89 (d, 1H), 7.26 (t, 1H), 7.39 (d, 1H), 7.60 (d, 1H), 7.68 (d, 1H), 7.72 (dd, 1H), 7.84 (s, 1H), 8.22 (d, 1H), 8.45 (d, 1H). ESI-MS m/z 457.6 [M + H]⁺. |
| 111 | 6-(4-(4-(benzo[b]thiophen-4-yl)piperazin-1-yl)butyl)-3,4-dihydroquinolin-2(1H)-one | ¹H NMR (300 MHz, DMSO-$d_6$) δ 1.52 (m, 4H), 2.41 (t, 4H), 2.57 (m, 6H), 2.83 (t, 2H), 3.05 (br, 4H), 6.76 (d, 1H), 6.89 (d, 1H), 6.96 (d, 1H), 7.00 (s, 1H), 7.27 (t, 1H), 7.39 (d, 1H), 7.61 (d, 1H), 7.69 (d, 1H), 9.97 (s, 1H). ESI-MS m/z 420.5 [M + H]⁺. |
| 112 | 5-(4-(4-(benzo[b]thiophen-4-yl)piperazin-1-yl)butyl)indolin-2-one | ¹H NMR (300 MHz, DMSO-$d_6$) δ 1.52 (m, 4H), 2.37 (t, 2H), 2.56 (m, 6H), 3.05 (br, 4H), 3.42 (s, 2H), 6.71 (d, 1H), 6.88 (d, 1H), 6.98 (d, 1H), 7.04 (s, 1H), 7.26 (t, 1H), 7.38 (d, 1H), 7.60 (d, 1H), 7.68 (d, 1H), 10.25 (s, 1H). ESI-MS m/z 405.8 [M + H]⁺. |
| 113 | 6-chloro-5-(2-(4-(2-fluorobenzo[b]thiophen-4-yl)piperazin-1-yl)ethyl)indolin-2-one | ¹H NMR (300 MHz, DMSO-$d_6$) δ 2.55 (t, 2H), 2.68 (br, 4H), 2.84 (t, 2H), 3.02 (br, 4H), 3.46 (s, 2H), 6.81 (s, 1H), 6.97 (m, 2H), 7.23 (s, 1H), 7.28 (t, 1H), 7.52 (d, 1H), 10.40 (s, 1H). ESI-MS m/z 430.1 [M + H]⁺. |
| 114 | 6-(2-(4-(benzo[b]thiophen-4-yl)piperazin-1-yl)ethyl)-4-methyl-2H-benzo[b][1,4]oxazin-3(4H)-one | ¹H NMR (300 MHz, DMSO-$d_6$) δ 2.62 (t, 2H), 2.71 (br, 4H), 2.78 (t, 2H), 3.08 (br, 4H), 3.28 (s, 3H), 4.60 (s, 2H), 6.91 (m, 2H), 7.08 (s, 1H), 7.27 (t, 1H), 7.40 (d, 1H), 7.61 (d, 1H), 7.69 (d, 1H). ESI-MS m/z 408.2 [M + H]⁺. |
| 115 | 7-(2-(4-(benzo[b]thiophen-4-yl)piperazin-1-yl)ethyl)-1-methyl-3,4-dihydroquinolin-2(1H)-one | ¹H NMR (300 MHz, DMSO-$d_6$) δ 2.51 (t, 2H), 2.63 (t, 2H), 2.71 (br, 4H), 2.80 (m, 4H), 3.08 (br, 4H), 3.26 (s, 3H), 6.90 (m, 2H), 7.00 (s, 1H), 7.11 (d, 1H), 7.27 (t, 1H), 7.40 (d, 1H), 7.61 (d, 1H), 7.69 (d, 1H). ESI-MS m/z 406.0 [M + H]⁺. |
| 116 | 5-(2-(4-(benzo[b]thiophen-4-yl)piperazin-1-yl)ethyl)benzo[d]thiazol-2-amine | ¹H NMR (300 MHz, DMSO-$d_6$) δ 2.66 (m, 6H), 2.79 (t, 2H), 3.08 (br, 4H), 6.90 (m, 2H), 7.26 (m, 2H), 7.41 (m, 3H), 7.53 (d, 1H), 7.61 (d, 1H), 7.69 (d, 1H). ESI-MS m/z 395.0 [M + H]⁺. |
| 117 | 7-(2-(4-(benzo[b]thiophen-4-yl)piperazin-1-yl)ethyl)benzo[d]thiazol-2-amine | ¹H NMR (300 MHz, DMSO-$d_6$) δ 2.70 (m, 6H), 2.86 (t, 2H), 3.09 (br, 4H), 6.91 (t, 2H), 7.17 (m, 2H), 7.27 (t, 1H), 7.41 (d, 1H), 7.44 (s, 2H), 7.61 (d, 1H), 7.69 (d, 1H). ESI-MS m/z 395.0 [M + H]⁺. |
| 118 | N-(5-(2-(4-(benzo[b]thiophen-4-yl)piperazin-1-yl)ethyl)benzo[d]thiazol-2-yl)acetamide | ¹H NMR (300 MHz, DMSO-$d_6$) δ 2.19 (s, 3H), 2.70 (m, 6H), 2.91 (t, 2H), 3.08 (br, 4H), 6.90 (d, 1H), 7.21 (dd, 1H), 7.27 (t, 1H), 7.40 (d, 1H), 7.61 (d, 1H), 7.63 (d, 1H), 7.69 (d, 1H), 7.85 (d, 1H), 12.30 (s, 1H). ESI-MS m/z 437.1 [M + H]⁺. |
| 119 | N-(7-(2-(4-(benzo[b]thiophen-4-yl)piperazin-1-yl)ethyl)benzo[d]thiazol-2-yl)acetamide | ¹H NMR (300 MHz, DMSO-$d_6$) δ 2.20 (s, 3H), 2.74 (m, 6H), 3.03 (t, 2H), 3.09 (br, 4H), 6.90 (d, 1H), 7.21 (d, 1H), 7.27 (t, 1H), 7.38 (t, 1H), 7.42 (d, 1H), 7.60 (t, 2H), 7.69 (d, 1H), 12.33 (s, 1H). ESI-MS m/z 437.1 [M + H]⁺. |
| 120 | 4-(2-(4-(benzo[b]thiophen-4-yl)piperazin-1-yl)ethyl)benzo[d]thiazol-2-amine | ¹H NMR (300 MHz, DMSO-$d_6$) δ 2.69 (m, 6H), 3.04 (t, 2H), 3.08 (br, 4H), 6.93 (m, 2H), 7.10 (d, 1H), 7.28 (t, 1H), 7.41 (d, 1H), 7.49 (m, 3H), 7.61 (d, 1H), 7.69 (d, 1H). ESI-MS m/z 395.0 [M + H]⁺. |
| 121 | N-(4-(2-(4-(benzo[b]thiophen-4-yl)piperazin-1-yl)ethyl)benzo[d]thiazol-2-yl)acetamide | ¹H NMR (300 MHz, DMSO-$d_6$) δ 2.20 (s, 3H), 2.72 (m, 6H), 3.09 (br, 4H), 3.19 (t, 2H), 6.90 (d, 1H), 7.26 (m, 3H), 7.40 (d, 1H), 7.61 (d, 1H), 7.69 (d, 1H), 7.79 (d, 1H), 12.38 (s, 1H). ESI-MS m/z 437.1 [M + H]⁺. |
| 122 | 7-(2-(4-(2-methylbenzo[b]thiophen-4-yl)piperazin-1-yl)ethyl)-3,4-dihydroquinolin-2(1H)-one | ¹H NMR (300 MHz, DMSO-$d_6$) δ 2.42 (t, 2H), 2.56 (m, 5H), 2.68 (m, 6H), 2.82 (t, 2H), 3.04 (br, 4H), 6.73 (s, 1H), 6.80 (d, 1H), 6.85 (d, 1H), 7.06 (d, 1H), 7.10 (s, 1H), 7.18 (t, 1H), 7.47 (d, 1H), 10.02 (s, 1H). ESI-MS m/z 406.1 [M + H]⁺. |

-continued

| Example No. | name | ¹H NMR 和 ESI-MS |
|---|---|---|
| 123 | 3-((4-(benzo[b]thiophen-4-yl)piperazin-1-yl)methyl)-1-methyl-1H-indole hydrochloride | ¹H NMR (300 MHz, DMSO-$d_6$) δ 3.16 (m, 2H), 3.37 (m, 2H), 3.52 (br, 4H), 3.85 (s, 3H), 4.57 (s, 2H), 6.94 (d, 1H), 7.13-7.34 (m, 3H), 7.47 (d, 1H), 7.51 (d, 1H), 7.68 (m, 2H), 7.74 (d, 1H), 7.91 (d, 1H), 10.67 (s, 1H). ESI-MS m/z 362.1 [M + H]⁺. |
| 124 | 1-(3-(2-(4-(benzo[b]thiophen-4-yl)piperazin-1-yl)ethyl)indolin-1-yl)ethanone hydrochloride | ¹H NMR (300 MHz, DMSO-$d_6$) δ 2.03 (m, 1H), 2.19 (s, 3H), 2.28 (m, 1H), 3.24 (m, 2H), 3.54 (d, 3H), 3.64 (d, 2H), 3.86 (m, 5H), 4.26 (t, 1H), 6.97 (d, 1H), 7.05 (t, 1H), 7.20 (t, 1H), 7.32 (m, 2H), 7.48 (d, 1H), 7.70 (d, 1H), 7.77 (d, 1H), 8.06 (d, 1H), 11.06 (s, 1H). ESI-MS m/z 406.5 [M + H]⁺. |
| 125 | 3-(2-(4-(benzo[b]thiophen-4-yl)piperazin-1-yl)ethyl)-1-tosyl-1H-indole-5-carbonitrile | ¹H NMR (300 MHz, DMSO-$d_6$) δ 2.29 (s, 3H), 2.70 (m, 6H), 2.91 (t, 2H), 3.05 (br, 4H), 6.90 (d, 1H), 7.29 (t, 1H), 7.39 (m, 3H), 7.62 (d, 1H), 7.70 (d, 1H), 7.73 (dd, 1H), 7.88 (m, 3H), 8.08 (d, 1H), 8.26 (d, 1H). ESI-MS m/z 541.1 [M + H]⁺. |
| 126 | 3-(3-(4-(benzo[b]thiophen-4-yl)piperazin-1-yl)propyl)-1-tosyl-1H-indole-5-carbonitrile | ¹H NMR (300 MHz, DMSO-$d_6$) δ 1.84 (m, 2H), 2.30 (s, 3H), 2.35 (t, 2H), 2.56 (br, 4H), 2.72 (t, 2H), 3.03 (br, 4H), 6.87 (d, 1H), 7.28 (t, 1H), 7.39 (m, 3H), 7.61 (d, 1H), 7.69 (d, 1H), 7.73 (dd, 1H), 7.81 (s, 1H), 7.90 (d, 2H), 8.08 (d, 1H), 8.25 (d, 1H). ESI-MS m/z 555.7 [M + H]⁺. |
| 127 | 3-(4-(4-(benzo[b]thiophen-4-yl)piperazin-1-yl)butyl)-5-methoxy-1-tosyl-1H-indole | ¹H NMR (300 MHz, DMSO-$d_6$) δ 1.47 (m, 2H), 1.65 (m, 2H), 2.28 (s, 3H), 2.38 (t, 2H), 2.55 (br, 4H), 2.64 (t, 2H), 3.03 (br, 4H), 3.76 (s, 3H), 6.88 (d, 1H), 6.93 (dd, 1H), 7.05 (d, 1H), 7.22-7.42 (m, 4H), 7.49 (s, 1H), 7.61 (d, 1H), 7.69 (d, 1H), 7.77 (m, 3H). ESI-MS m/z 573.9 [M + H]⁺. |
| 128 | 3-(3-(4-(benzo[b]thiophen-4-yl)piperazin-1-yl)propyl)-5-methoxy-1-tosyl-1H-indole | ¹H NMR (300 MHz, DMSO-$d_6$) δ 1.82 (m, 2H), 2.29 (s, 3H), 2.35 (t, 2H), 2.57 (br, 4H), 2.65 (t, 2H), 3.06 (br, 4H), 3.77 (s, 3H), 6.88 (d, 1H), 6.93 (dd, 1H), 7.04 (d, 1H), 7.27 (t, 1H), 7.34 (d, 2H), 7.39 (d, 1H), 7.50 (s, 1H), 7.61 (d, 1H), 7.69 (d, 1H), 7.79 (m, 3H). ESI-MS m/z 560.7 [M + H]⁺. |
| 129 | 3-(2-(4-(benzo[b]thiophen-4-yl)piperazin-1-yl)ethyl)-5-methoxy-1-tosyl-1H-indole | ¹H NMR (300 MHz, DMSO-$d_6$) δ 2.27 (s, 3H), 2.71 (m, 6H), 2.83 (t, 2H), 3.07 (br, 4H), 3.77 (s, 3H), 6.92 (m, 2H), 7.10 (d, 1H), 7.31 (m, 3H), 7.41 (d, 1H), 7.58 (s, 1H), 7.62 (d, 1H), 7.70 (d, 1H), 7.78 (m, 3H). ESI-MS m/z 545.9 [M + H]⁺. |
| 130 | 6-(2-(4-(2-oxo-2,3-dihydrobenzo[b]thiophen-4-yl)piperazin-1-yl)ethyl)-3,4-dihydroquinolin-2(1H)-one | ¹H NMR (300 MHz, DMSO-$d_6$) δ 2.41 (t, 2H), 2.52-2.73 (m, 8H), 2.83 (t, 2H), 2.95 (br, 4H), 4.09 (s, 2H), 6.76 (d, 1H), 6.93 (d, 1H), 7.00 (d, 1H), 7.03 (s, 1H), 7.17 (d, 1H), 7.29 (t, 1H), 9.98 (s, 1H). ESI-MS m/z 408.1 [M + H]⁺. |
| 131 | 3-(2-(4-(2-fluorobenzo[b]thiophen-4-yl)piperazin-1-yl)ethyl)-9-hydroxy-2-methyl-6,7,8,9-tetrahydro-4H-pyrido[1,2-a]pyrimidin-4-one hydrochloride | ¹H NMR (300 MHz, DMSO-$d_6$) δ 1.78-2.11 (m, 4H), 2.50 (s, 3H), 3.04 (m, 2H), 3.15-3.43 (m, 6H), 3.49 (d, 2H), 3.68 (d, 2H), 3.77 (m, 1H), 3.94 (m, 1H), 4.75 (t, 1H), 7.02 (d, 1H), 7.17 (d, 1H), 7.32 (t, 1H), 7.61 (d, 1H), 11.52 (s, 1H). ESI-MS m/z 443.0 [M + H]⁺. |
| 132 | 2-(2-(4-(benzo[b]thiophen-4-yl)piperazin-1-yl)ethyl)-2H-benzo[b][1,4]oxazin-3(4H)-one hydrochloride | ¹H NMR (300 MHz, DMSO-$d_6$) δ 3.16-3.71 (m, 10H), 3.84 (m, 2H), 4.78 (m, 1H), 6.97 (m, 5H), 7.31 (t, 1H), 7.49 (d, 1H), 7.70 (d, 1H), 7.76 (d, 1H), 10.87 (s, 1H), 11.06 (s, 1H). ESI-MS m/z 394.0 [M + H]⁺. |
| 133 | 7-(2-(4-(benzo[b]thiophen-4-yl)piperazin-1-yl)ethyl)-3,4-dihydroquinoline-2(1H)-thione hydrochloride | ¹H NMR (300 MHz, DMSO-$d_6$) δ 2.43 (t, 2H), 2.84 (t, 2H), 3.06 (m, 2H), 3.20-3.46 (m, 6H), 3.56 (d, 2H), 3.67 (d, 2H), 6.76 (s, 1H), 6.86 (d, 1H), 6.98 (d, 1H), 7.15 (d, 1H), 7.32 (t, 1H), 7.49 (d, 1H), 7.70 (d, 1H), 7.77 (d, 1H), 10.13 (s, 1H), 11.30 (s, 1H). ESI-MS m/z 408.0 [M + H]⁺. |
| 134 | (3aR,4R,6aS)-4-(5-(4-(benzo[b]thiophen-4-yl)piperazin-1-yl)pentyl)tetrahydro-1H-thieno[3,4-d]imidazol-2(3H)-one | ¹H NMR (300 MHz, CDCl$_3$) δ 1.44 (m, 4H), 1.68 (m, 4H), 2.60 (m, 2H), 2.74 (d, 1H), 2.88 (m, 5H), 3.16 (m, 1H), 3.28 (br, 4H), 4.31 (dd, 1H), 4.50 (dd, 1H), 6.91 (d, 1H), 7.27 (t, 1H), 7.39 (m, 2H), 7.56 (d, 1H). ESI-MS m/z 431.6 [M + H]⁺. |

-continued

| Example No. | name | ¹H NMR 和 ESI-MS |
|---|---|---|
| 135 | pentyl (6-(2-(4-(benzo[b]thiophen-4-yl)piperazin-1-yl)ethyl)benzo[d]thiazol-2-yl)carbamate | ¹H NMR (300 MHz, DMSO-$d_6$) δ 0.88 (t, 3H), 1.32 (m, 4H), 1.64 (m, 2H), 2.68 (m, 6H), 2.87 (t, 2H), 3.08 (br, 4H), 4.18 (t, 2H), 6.89 (d, 1H), 7.27 (m, 2H), 7.40 (d, 1H), 7.60 (m, 2H), 7.68 (d, 1H), 7.81 (s, 1H), 11.94 (s, 1H). ESI-MS m/z 509.1 [M + H]⁺. |
| 136 | 3-(2-(4-(benzo[b]thiophen-4-yl)piperazin-1-yl)ethyl)-2-methyl-4-oxo-6,7,8,9-tetrahydro-4H-pyrido[1,2-a]pyrimidin-9-yl benzoate | ¹H NMR (300 MHz, DMSO-$d_6$) δ 1.97-2.28 (m, 7H), 2.47 (t, 2H), 2.68 (m, 6H), 3.08 (br, 4H), 3.76 (m, 1H), 4.02 (m, 1H), 5.96 (t, 1H), 6.89 (d, 1H), 7.27 (t, 1H), 7.40 (d, 1H), 7.53 (t, 2H), 7.61 (d, 1H), 7.67 (m, 2H), 8.00 (d, 2H). ESI-MS m/z 529.1 [M + H]⁺. |
| 137 | 6-(4-(4-(benzo[b]thiophen-4-yl)piperazin-1-yl)butyl)-2H-benzo[b][1,4]oxazin-3(4H)-one | ¹H NMR (300 MHz, DMSO-$d_6$) δ 1.51 (m, 4H), 2.37 (t, 2H), 2.53 (t, 2H), 2.58 (br, 4H), 3.05 (br, 4H), 4.51 (s, 2H), 6.74 (m, 2H), 6.87 (m, 2H), 7.27 (t, 1H), 7.39 (d, 1H), 7.61 (d, 1H), 7.68 (d, 1H), 10.62 (s, 1H). ESI-MS m/z 422.0 [M + H]⁺. |
| 138 | 1-(benzo[b]thiophen-4-yl)-4-(4-(1-cyclohexyl-1H-tetrazol-5-yl)butyl)piperazine hydrochloride | ¹H NMR (300 MHz, DMSO-$d_6$) δ 1.16-2.04 (m, 14H), 2.98 (t, 2H), 3.25 (m, 6H), 3.56 (t, 4H), 4.43 (m, 1H), 6.96 (d, 1H), 7.32 (t, 1H), 7.49 (d, 1H), 7.70 (d, 1H), 7.77 (d, 1H), 10.82 (s, 1H). ESI-MS m/z 425.3 [M + H]⁺. |
| 139 | 6-(2-(4-(benzo[b]thiophen-4-yl)piperazin-1-yl)ethyl)-8-fluoro 2H-benzo[b][1,4]oxazin-3(4H)-one | ¹H NMR (300 MHz, DMSO-$d_6$) δ 3.07 (t, 2H), 3.33 (m, 6H), 3.56 (d, 2H), 3.66 (d, 2H), 4.65 (s, 2H), 6.65 (s, 1H), 6.88 (d, 1H), 6.98 (d, 1H), 7.32 (t, 1H), 7.48 (d, 1H), 7.70 (d, 1H), 7.76 (d, 1H), 11.00 (s, 1H), 11.26 (br, 1H). ESI-MS m/z 411.6 (M + H)⁺. |
| 140 | 7-(2-(4-(benzo[b]thiophen-4-yl)piperazin-1-yl)-1-hydroxyethyl)quinolin-2(1H)-one | ¹H NMR (300 MHz, DMSO-$d_6$) δ 2.54 (d, 1H), 2.60 (dd, 1H), 2.75 (brt, 4H), 3.07 (brt, 4H), 4.83 (m, 1H), 5.29 (d, 1H), 6.44 (d, 1H), 6.89 (d, 1H), 7.18 (d, 1H), 7.27 (t, 1H), 7.37 (s, 1H), 7.39 (d, 1H), 7.60 (t, 2H), 7.69 (d, 1H), 7.87 (d, 1H), 11.75 (s, 1H). ESI-MS m/z 406.1 [M + H]⁺. |
| 141 | 6-(2-(4-(benzo[b]thiophen-4-yl)piperazin-1-yl)-1-hydroxyethyl)-2H-benzo[b][1,4]oxazin-3(4H)-one | ¹H NMR (300 MHz, DMSO-$d_6$) δ 2.39-2.61 (m, 2H), 2.73 (brt, 4H), 3.07 (brt, 4H), 4.54 (s, 2H), 4.68 (m, 1H), 5.04 (d, 1H), 6.90 (m, 3H), 6.96 (s, 1H), 7.27 (t, 1H), 7.39 (d, 1H), 7.61 (d, 1H), 7.68 (d, 1H), 10.68 (s, 1H). ESI-MS m/z 410.1 [M + H]⁺. |
| 142 | 6-(2-(4-(benzo[b]thiophen-4-yl)piperazin-1-yl)-1-hydroxyethyl)-2H-benzo[b][1,4]thiazin-3(4H)-one | ¹H NMR (300 MHz, DMSO-$d_6$) δ 2.41-2.63 (m, 2H), 2.74 (brt, 4H), 3.07 (brt, 4H), 3.43 (s, 2H), 4.70 (m, 1H), 5.14 (d, 1H), 6.89 (d, 1H), 6.97 (dd, 1H), 7.04 (s, 1H), 7.27 (m, 2H), 7.39 (d, 1H), 7.60 (d, 1H), 7.68 (d, 1H), 10.54 (s, 1H). ESI-MS m/z 426.0 [M + H]⁺. |
| 143 | 5-(2-(4-(benzo[b]thiophen-4-yl)piperazin-1-yl)acetyl)indolin-2-one hydrochloride | ¹H NMR (300 MHz, DMSO-$d_6$) δ 3.30 (t, 2H), 3.40-3.75 (m, 8H), 5.16 (s, 2H), 7.01 (t, 2H), 7.33 (t, 1H), 7.50 (d, 1H), 7.72 (d, 1H), 7.78 (d, 1H), 7.88 (s, 1H), 7.93 (d, 1H), 10.49 (s, 1H), 11.05 (s, 1H). ESI-MS m/z 392.2 [M + H]⁺. |
| 144 | 8-(2-(4-(benzo[b]thiophen-4-yl)piperazin-1-yl)-1-methoxyethyl)-2H-benzo[b][1,4]oxazin-3(4H)-one | ¹H NMR (300 MHz, DMSO-$d_6$) δ 2.55 (d, 1H), 2.71 (m, 5H), 3.06 (brt, 4H), 3.18 (s, 3H), 4.60 (s, 2H), 4.77 (dd, 1H), 6.79-7.02 (m, 4H), 7.27 (t, 1H), 7.40 (d, 1H), 7.60 (d, 1H), 7.68 (d, 1H), 10.72 (s, 1H). ESI-MS m/z 424.1 [M + H]⁺. |
| 145 | 5-(2-(4-(benzo[b]thiophen-4-yl)piperazin-1-yl)-1-hydroxyethyl)indolin-2-one | ¹H NMR (300 MHz, DMSO-$d_6$) δ 2.45 (dd, 1H), 2.57 (dd, 1H), 2.73 (br, 4H), 3.06 (br, 4H), 3.46 (s, 2H), 4.70 (m, 1H), 4.95 (d, 1H), 6.75 (d, 1H), 6.89 (d, 1H), 7.15 (d, 1H), 7.22 (s, 1H), 7.27 (t, 1H), 7.39 (d, 1H), 7.61 (d, 1H), 7.68 (d, 1H), 10.33 (s, 1H). ESI-MS m/z 394.5 (M + H)⁺. |
| 146 | 6-(2-(4-(benzo[b]thiophen-4-yl)piperazin-1-yl)acetyl)benzo[d]thiazol-2(3H)-one | ¹H NMR (300 MHz, DMSO-$d_6$) δ 2.77 (brt, 4H), 3.08 (brt, 4H), 3.90 (s, 2H), 6.90 (d, 1H), 7.21 (d, 1H), 7.27 (t, 1H), 7.40 (dd, 1H), 7.61 (d, 1H), 7.69 (d, 1H), 7.98 (dd, 1H), 8.31 (d, 1H), 12.28 (s, 1H). ESI-MS m/z 410.2 [M + H]⁺. |
| 147 | 5-(2-(4-(benzo[b]thiophen-4-yl)piperazin-1-yl)acetyl)-1H-benzo[d]imidazol-2(3H)-one | ¹H NMR (300 MHz, DMSO-$d_6$) δ 2.76 (brt, 4H), 3.08 (brt, 4H), 3.89 (s, 2H), 6.90 (d, 1H), 7.02 (d, 1H), 7.27 (t, 1H), 7.40 (d, 1H), 7.57 (d, 1H), 7.61 (d, 1H), 7.69 (d, 1H), 7.75 (dd, 1H), 10.90 (s, 1H), 11.07 (s, 1H). ESI-MS m/z 393.2 [M + H]⁺. |

-continued

| Example No. | name | ¹H NMR 和 ESI-MS |
|---|---|---|
| 153 | N-(6-(2-(4-(benzo[b]thiophen-4-yl)piperazin-1-yl)ethyl)benzo[d]thiazol-2-yl)acetamide | ¹H NMR (300 MHz, DMSO-$d_6$) δ 2.19 (s, 3H), 2.69 (m, 6H), 2.90 (t, 2H), 3.08 (br, 4H), 6.90 (d, 1H), 7.27 (t, 1H), 7.32 (d, 1H), 7.41 (d, 1H), 7.63 (t, 2H), 7.70 (d, 1H), 7.84 (s, 1H), 12.29 (s, 1H). ESI-MS m/z 437.0 [M + H]⁺. |
| 154 | 6-(2-(4-(benzo[b]thiophen-4-yl)piperazin-1-yl)ethyl)benzo[d]thiazol-2-amine | ¹H NMR (300 MHz, DMSO-$d_6$) δ 2.61 (t, 2H), 2.69 (br, 4H), 2.79 (t, 2H), 3.08 (br, 4H), 6.90 (d, 1H), 7.09 (dd, 1H), 7.26 (m, 2H), 7.35 (s, 2H), 7.40 (d, 1H), 7.53 (d, 1H), 7.61 (d, 1H), 7.69 (d, 1H). ESI-MS m/z 396.2 [M + H]⁺. |

Pharmacological Test 1) 5-HT$_{1A}$ Receptor Agonism Activity Test

The 5-HT$_{1A}$ receptor agonism activity test (The agonism activity of test compounds on 5-HT$_{1A}$ receptor expressing human recombinant 5-HT$_{1A}$ receptor in HEK293 cells) was performed using LANCE™ cAMP 384 Kit (Product of USA PerkinElmer Inc.). The 5-HT$_{1A}$ receptor agonism activity of test compounds was evaluated through their inhibition on cAMP production in HEK293 cells. cAMP concentration test was performed according to the method documented in the kit instructions. The concentration of the test compounds was 0.1 nM-10000 nM, 8-OH-DPAT was used as a positive control, EC$_{50}$ value was calculated by the Excelfit software and the results are shown in Table 1.

2) D$_2$ Receptor Antagonism Activity Test

The D$_2$ receptor antagonism activity test (The antagonism activity of test compounds on D$_2$ receptor expressing human recombinant D$_2$ receptor in HEK293 cells) was performed using LANCE™ cAMP 384 Kit (Product of USA PerkinElmer Inc.). The D$_2$ antagonism activity of test compounds was evaluated through their inhibition on dopamine-induced decrease of cAMP production in HEK293 cells. cAMP concentration test was performed according to the method documented in the kit instructions. The concentration of the test compounds was 0.1 nM-10000 nM, risperidone was used as a positive control, IC$_{50}$ value was calculated by the Excelfit software and the results are shown in Table 1.

3) 5-HT$_{2A}$ Receptor Antagonism Activity Test

The 5-HT$_{2A}$ receptor antagonism activity test (The antagonism activity of test compounds on 5-HT$_{2A}$ receptor expressing human recombinant 5-HT$_{2A}$ receptor in CHO-K1 cells) was performed using FLIPR® Calcium 5 Assay Kit (Product of Molecular Devices USA Inc.) according to the method documented in the kit instructions. The concentration of the test compounds was 0.1 nM-10000 nM and risperidone was used as a positive control. Test method is as follows: On the first day the seed cells are placed in T-175 flask containing 25 ml growth medium (F-12 nutrient mixture+10% FBS+1% penicillin/streptomycin+1.2% 50 mg/ml Geneticin) at a density of 14 million per bottle, cells were cultured under 37° C./5% CO$_2$/humidified conditions for 24 hours; On the next day the seed cells were inoculated to the 384-well cell culture plate (each well containing 20,000 cells), the growth medium was replaced by 50 μL detecting medium (F-12 nutrient mixture+1.5% activated carbon-treated FBS), the cells were cultured under 37° C./5% CO$_2$/humidified conditions for 16 hours; On the third day the medium was removed, each well of the cells plates were added with 24 μL freshly prepared loading dye solution (formulated according to the instructions), the plates were placed in an incubator and incubated under 37° C./5% CO$_2$/humidified conditions for 120 minutes; transfer 6 μL test compound solution to the assay plate and gently shaking for one minute, incubated under 37° C./5% CO$_2$/humidified conditions for 30 minutes; each well of the assay plate was added with 10 μL freshly prepared α-methyl-5-hydroxytryptamine solution (1.2 M, the final concentration of α-methyl-5-hydroxytryptamine is 300 nM), data were detected and analyzed by FLIPR (Product of US Molecular Devices Corporation). Inhibition rate of the compounds at different concentrations was calculated, IC$_{50}$ value was calculated by the Excelfit software and the results are shown in Table 1.

TABLE 1

| Test compound | 5-HT$_{1A}$ receptor agonism (EC$_{50}$, mol/L) | D$_2$ receptor antagonism (IC$_{50}$, mol/L) | 5-HT$_{2A}$ receptor antagonism (IC$_{50}$, mol/L) |
|---|---|---|---|
| Compound of example 1 | 3.31E−09 | 5.69E−08 | 2.27E−07 |
| Compound of example 2 | 2.86E−08 | 1.18E−08 | 2.64E−08 |
| Compound of example 3 | 4.57E−09 | 2.61E−09 | 1.51E−08 |
| Compound of example 4 | 9.75E−09 | 5.43E−09 | 2.9E−09 |
| Compound of example 4a | 3.83E−08 | 6.89E−09 | 1.72E−09 |
| Compound of example 4b | 6.03E−08 | 2.1E−08 | 3.46E−09 |
| Compound of example 5 | 3.29E−08 | 5.7E−08 | 4.4E−08 |
| Compound of example 7 | 7.2E−09 | 3.32E−09 | 1.02E−08 |
| Compound of example 8 | 1.67E−09 | 8.83E−09 | 6.36E−09 |
| Compound of example 9 | 9.72E−10 | 7.06E−09 | 9.56E−08 |
| Compound of example 11 | 1.95E−09 | 1.02E−08 | 2.09E−07 |
| Compound of example 15 | 1.05E−09 | 1.29E−08 | 7.46E−08 |
| Compound of example 16 | 1.2E−08 | 1.67E−08 | 7.72E−08 |
| Compound of example 17 | 6.94E−09 | 2.07E−08 | 3.5E−07 |
| Compound of example 18 | 1.07E−08 | 2.67E−08 | 7.13E−08 |
| Compound of example 19 | 9.26E−10 | 8.62E−09 | 1.69E−07 |
| Compound of example 23 | 4.63E−07 | 8.12E−08 | 9.76E−08 |
| Compound of example 24 | 2.59E−08 | 5.07E−08 | 7.81E−07 |
| Compound of example 25 | 8.24E−10 | 8.51E−08 | 7.79E−08 |
| Compound of example 26 | 9.98E−09 | 4.82E−07 | 4.95E−08 |
| Compound of example 27 | 1.91E−08 | 1.95E−08 | 4.91E−09 |
| Compound of example 28 | 1.72E−08 | 3.51E−09 | 2.54E−08 |
| Compound of example 29 | 2.13E−09 | 4.88E−08 | 7.64E−09 |
| Compound of example 30 | 6.26E−10 | 3.42E−08 | 4.21E−08 |
| Compound of example 31 | 6.8E−10 | 9.27E−08 | 5.22E−08 |
| Compound of example 33 | 2.24E−09 | 3.56E−08 | 2.44E−07 |
| Compound of example 34 | 5.4E−08 | 3.24E−07 | 2.01E−07 |
| Compound of example 35 | 4.19E−08 | 2.16E−07 | 2.15E−08 |
| Compound of example 36 | 3.41E−08 | 7.54E−08 | 7.66E−09 |
| Compound of example 37 | 3.11E−09 | 5.19E−08 | 2.81E−08 |
| Compound of example 38 | 1.01E−09 | 6.98E−08 | 8.46E−09 |
| Compound of example 41 | 8.99E−07 | 9.6E−07 | 6.54E−08 |
| Compound of example 42 | 1E−07 | 2.7E−07 | 1.15E−07 |
| Compound of example 43 | 1.23E−08 | 2.41E−07 | 2.86E−07 |
| Compound of example 52 | 9.69E−09 | 5.49E−09 | 1.22E−08 |
| Compound of example 57 | 4.51E−09 | 8.4E−09 | 3.68E−07 |
| Compound of example 58 | 4.55E−09 | 1.01E−07 | 2.17E−06 |
| Compound of example 59 | 9.33E−09 | 2.67E−08 | 1.02E−08 |
| Compound of example 64 | 3.16E−08 | 2.94E−09 | 2.57E−07 |
| Compound of example 65 | 1.25E−09 | 7.76E−09 | 4.03E−08 |
| Compound of example 66 | 1.29E−09 | 6.17E−08 | 8.15E−08 |
| Compound of example 68 | 1.55E−08 | 5.46E−09 | 4.82E−09 |
| Compound of example 70 | 9.7E−09 | 7.97E−08 | 3.32E−07 |

TABLE 1-continued

| Test compound | 5-HT$_{1A}$ receptor agonism (EC$_{50}$, mol/L) | D$_2$ receptor antagonism (IC$_{50}$, mol/L) | 5-HT$_{2A}$ receptor antagonism (IC$_{50}$, mol/L) |
|---|---|---|---|
| Compound of example 72 | 2.53E−09 | 1.32E−08 | 9.51E−07 |
| Compound of example 74 | 2.08E−08 | 1.06E−09 | 8.74E−07 |
| Compound of example 77 | 4.80E−09 | 6.91E−09 | 1.57E−07 |
| Compound of example 78 | 5.99E−10 | 4.56E−08 | 3.28E−07 |
| Compound of example 79 | 7.7E−10 | 3.87E−09 | 1.68E−08 |
| Compound of example 80 | 1.74E−09 | 2.51E−08 | 1.19E−08 |
| Compound of example 81 | 1.05E−09 | 1.43E−08 | 1.67E−09 |
| Compound of example 82 | 2.8E−09 | 1.09E−08 | 1.15E−08 |
| Compound of example 83 | 4.91E−09 | 1.04E−08 | 2.5E−08 |
| Compound of example 84 | 2.35E−10 | 1.09E−08 | 1.75E−08 |
| Compound of example 85 | 1.38E−09 | 5.32E−09 | 7.75E−08 |
| Compound of example 86 | 2.16E−08 | 2.35E−08 | 9.33E−08 |
| Compound of example 87 | 4.5E−09 | 9.24E−09 | 8.8E−08 |
| Compound of example 88 | 6.31E−09 | 2.15E−07 | 3.56E−07 |
| Compound of example 89 | 1.29E−09 | 8.06E−09 | 1.05E−06 |
| Compound of example 90 | 2.77E−08 | 1.04E−08 | 1.36E−08 |
| Compound of example 97 | 2.23E−10 | 6.81E−09 | 1.73E−07 |
| Compound of example 98 | 2.9E−09 | 1.24E−08 | 1.85E−07 |
| Compound of example 99 | 7.62E−08 | 1.04E−08 | 5.12E−09 |
| Compound of example 101 | 1.68E−08 | 1.84E−08 | 7.59E−07 |
| Compound of example 102 | 3.29E−09 | 1.06E−07 | 1.90E−06 |
| Compound of example 104 | 1.23E−08 | 9.88E−08 | 1.06E−07 |
| Compound of example 105 | 5.64E−09 | 4.41E−07 | 2.55E−08 |
| Compound of example 106 | 1.04E−08 | 5.43E−07 | 6.62E−08 |
| Compound of example 107 | 7.95E−09 | 8.43E−09 | 3.93E−07 |
| Compound of example 108 | 4.49E−08 | 2.17E−08 | 8.19E−07 |
| Compound of example 109 | 9.99E−08 | 2.43E−07 | 2E−07 |
| Compound of example 110 | 8.4E−08 | 5.76E−08 | 1.76E−06 |
| Compound of example 111 | 2.95E−08 | 2.39E−08 | 4E−07 |
| Compound of example 112 | 3.46E−08 | 2.81E−08 | 2.57E−07 |
| Compound of example 113 | 9.09E−09 | 6.1E−08 | 7.16E−07 |
| Compound of example 114 | 8.08E−09 | 2.69E−08 | 4.61E−07 |
| Compound of example 115 | 8.52E−09 | 2.93E−08 | 5.37E−08 |
| Compound of example 116 | 3.79E−10 | 5.97E−09 | 9.03E−09 |
| Compound of example 117 | 3.97E−10 | 6.02E−09 | 1.59E−08 |
| Compound of example 118 | 6.02E−10 | 1.19E−07 | 7.5E−08 |
| Compound of example 119 | 7.87E−10 | 4.69E−09 | 3.43E−08 |
| Compound of example 120 | 7.61E−10 | 2.29E−07 | 7.33E−09 |
| Compound of example 121 | 3.2E−08 | 2.16E−07 | 4.1E−08 |
| Compound of example 124 | 1.42E−08 | 1.21E−08 | 5.36E−07 |
| Compound of example 131 | 2.60E−08 | 1.91E−07 | 5.13E−08 |
| Compound of example 132 | 1.18E−08 | 1.14E−07 | 9.92E−07 |
| Compound of example 133 | 1.02E−09 | 1.09E−08 | 5.54E−08 |
| Compound of example 134 | 7.5E−10 | 3.79E−08 | 1.67E−08 |
| Compound of example 137 | 1.81E−09 | 3.02E−08 | 7.11E−07 |
| Compound of example 138 | 1.02E−09 | 9.4E−09 | 4.18E−08 |
| Compound of example 139 | 7.66E−10 | 7.96E−08 | 1.04E−07 |
| Compound of example 144 | 8.93E−09 | 6.58E−08 | 1.7E−08 |
| Compound of example 145 | 6.3E−09 | 1.92E−07 | 1.47E−08 |
| Compound of example 150 | 1.57E−08 | 4.54E−09 | 1.08E−07 |
| Compound of example 153 | 2.35E−09 | 3.8E−09 | 1.89E−08 |
| Compound of example 154 | 1.32E−09 | 2.01E−09 | 1.61E−09 |
| risperidone | >1.0E−04 | 1.33E−08 | 4.67E−09 |
| aripiprazole | 1.88E−06 | / | 2.79E−06 |

4) D$_2$ Receptor Agonism Activity Test

The D$_2$ receptor agonism activity test (The agonism activity of test compounds on D$_2$ receptor expressing human recombinant D$_2$ receptor in HEK293 cells) was performed using LANCE™ cAMP 384 Kit (Product of USA PerkinElmer Inc.). The D$_2$ agonism of test compounds was evaluated through their inhibition on cAMP production in HEK293 cells. cAMP concentration test was performed according to the method documented in the kit instructions. The concentration of the test compound is 0.1 nM-10000 nM, dopamine was used as a positive control, EC$_{50}$ value was calculated by the Excelfit software and the results are shown in Table 2.

TABLE 2

| Test compound | D$_2$ receptor agonism (IC$_{50}$, mol/L) |
|---|---|
| Compound of example 9 | 3.39E−09 |
| Compound of example 11 | 2.06E−09 |
| Compound of example 19 | 2.23E−09 |
| Compound of example 22 | 2.16E−09 |
| Compound of example 27 | 3.84E−10 |
| Compound of example 57 | 4.8E−10 |
| Compound of example 64 | 2.42E−10 |
| Compound of example 65 | 9.21E−11 |
| Compound of example 72 | 6.72E−10 |
| Compound of example 74 | 3.20E−10 |
| Compound of example 77 | 2.19E−10 |
| Compound of example 79 | 1.2E−09 |
| Compound of example 83 | 7.4E−09 |
| Compound of example 101 | 1.30E−09 |
| Compound of example 131 | 3.53E−09 |
| risperidone | >1E−4 |
| aripiprazole | 1.01E−08 |

5) In Vivo Efficacy Test (PCP-Induced High Locomotor Activity in Mice)

PCP solution was prepared in a suitable concentration for 7 mg/kg dosage with saline. Solutions of aripiprazole and all the test compounds in a suitable concentration were prepared with 0.5% CMC-Na solution respectively. Male ICR mice (18-22 g) were used as test animals. All the test mice were randomly divided into vehicle control group, model control group, positive control group, and treatment group(8 mice per group). Mice of each group were orally administered test compounds or vehicle. After 45 minutes PCP solution was administered (7 mg/kg) through intraperitoneal injection. The mice track after drug or saline administration was recorded and analyzed by the spontaneous, open-field video analysis system. Then the mice track in 75 min after PCP administration was recorded. The mice track was recorded and analyzed by the spontaneous, open-field video analysis system. The total distance in each group was calculate and expressed as mean+SD and statistical evaluation was performed by one way ANOVA. After PCP was administered, a significant increase in locomotor activity was observed compared with the saline group. The test compound can significantly reduce PCP-induced hyperactivity in mice at following doses (Table 3), and showed statistical significances compared with the model group.

TABLE 3

| Test ompound | Effective dose (mg/kg) |
|---|---|
| Compound of example 3 | 0.03-0.1 |
| Compound of example 4 | 0.1-3 |
| Compound of example 5 | 0.1-0.3 |
| Compound of example 7 | 0.1-0.3 |
| Compound of example 8 | 0.1-0.3 |
| Compound of example 15 | 0.1-1 |
| Compound of example 19 | 0.1 |
| Compound of example 27 | 0.3 |
| Compound of example 29 | 0.3 |
| Compound of example 30 | 0.3 |
| Compound of example 31 | 1 |
| Compound of example 33 | 1 |
| Compound of example 46 | 1 |
| Compound of example 47 | 0.3 |
| Compound of example 49 | 1 |
| Compound of example 50 | 1 |
| Compound of example 51 | 1 |
| Compound of example 57 | 1 |
| Compound of example 59 | 0.3 |
| Compound of example 64 | 1 |
| Compound of example 65 | 3 |

TABLE 3-continued

| Test ompound | Effective dose (mg/kg) |
| --- | --- |
| Compound of example 68 | 0.3 |
| Compound of example 71 | 3 |
| Compound of example 72 | 3 |
| Compound of example 74 | 3 |
| Compound of example 77 | 3 |
| Compound of example 78 | 3 |
| Compound of example 79 | 1 |
| Compound of example 80 | 1 |
| Compound of example 81 | 1 |
| Compound of example 82 | 1 |
| Compound of example 83 | 1 |
| Compound of example 85 | 1 |
| Compound of example 87 | 1 |
| Compound of example 88 | 1 |
| Compound of example 89 | 1 |
| Compound of example 102 | 3 |
| Compound of example 112 | 1 |
| Compound of example 124 | 3 |
| Compound of example 131 | 3 |
| Compound of example 133 | 1 |
| Compound of example 137 | 3 |
| Compound of example 4a | 0.03 |
| Compound of example 4b | 0.03 |
| aripiprazole | 3 |

The invention claimed is:

1. A heterocyclic compound represented by formula(I), a stereoisomer or a pharmaceutically acceptable salt thereof:

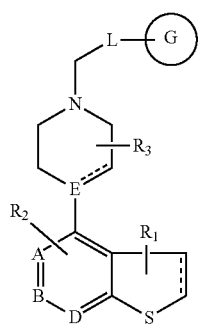

(I)

wherein,

A is C, B and D and are each independently C or N;

═══ represents a single or double bond;

E is CH, N or C; when E is CH or N, the bond ═══ connected to E represents a single bond; and when E is C, the bond ═══ connected to E represents a double bond;

$R_1$ is hydrogen or 1 to 4 substituents each independently selected from the group consisting of halogen, hydroxy, mercapto, oxo(═O), thioxo(═S), C1-C6 alkoxy, halogenated C1~C6 alkoxy, C1~C6 alkylthio, C1~C6 alkyl, halogenated C1~C6 alkyl, nitro, amino, C1~C6 alkyl-substituted amino, cyano, carboxyl, aldehyde group, amino C1~C6 alkyl, hydroxyl C1~C6 alkyl, cyano C1~C6 alkyl, C1~C6 alkanoyl, halogenated C1~C6 alkanoyl, sulfonic group(—SO$_2$OH), aminosulfonyl(—SO$_2$NH$_2$), carbamoyl(—CONH$_2$), C1~C6 alkyl-substituted carbamoyl, carboxyl C1~C6 alkyl, C1~C6 alkylsulfonyl, halogenated C1~C6 alkylsulfonyl, C1~C6 alkyl-substituted amino C1~C6 alkyl, carbamoyl C1~C6 alkyl and C1~C6 alkyl-substituted carbamoyl C1~C6 alkyl;

$R_2$ does not exist, or is 1 to 3 substituents each independently selected from the group consisting of halogen, hydroxy, mercapto, C1~C6 alkoxy, halogenated C1~C6 alkoxy, C1~C6 alkylthio, C1~C6 alkyl, halogenated C1~C6 alkyl, nitro, amino, C1~C6 alkyl-substituted amino, cyano, carboxyl, aldehyde group, amino C1~C6 alkyl, hydroxyl C1~C6 alkyl, cyano C1~C6 alkyl, C1~C6 alkanoyl, halogenated C1~C6 alkanoyl, sulfonic group(—SO$_2$OH), aminosulfonyl(—SO$_2$NH$_2$), carbamoyl(—CONH$_2$), C1~C6 alkyl-substituted carbamoyl, carboxy C1~C6 alkyl, C1~C6 alkylsulfonyl, halogenated C1~C6 alkylsulfonyl, C1~C6 alkyl-substituted amino C1~C6 alkyl, carbamoyl C1~C6 alkyl and C1~C6 alkyl-substituted carbamoyl C1~C6 alkyl;

$R_3$ is hydrogen or 1 to 4 substituents each independently selected from the group consisting of hydroxyl and C1~C6 alkyl;

L does not exist or is C1~C5 alkylene;

ring G is a heteromonocyclic or heterobicyclic group, wherein the heterobicyclic group is a phenyl-fused heteromonocyclic group, a cyclohydrocarbyl-fused heteromonocyclic group or a heteromonocycle-fused heteromonocyclic group, wherein the heteromonocyclic group contains at least one heteroatom selected from the group consisting of N, S and O;

ring G is connected to L through a carbon atom on ring G; and ring G is optionally substituted with one or more substituents which are identical or different, the substituent on the ring G is selected from the group consisting of halogen, C1~C6 alkyl, halogenated C1~C6 alkyl, C1~C6 alkoxy, halogenated C1~C6 alkoxy, nitro, cyano, hydroxy, mercapto, amino, C1~C6 alkyl-substituted amino, azido, C1~C6 alkanoyl, halogenated C1~C6 alkanoyl, C2~C6 alkenyl, C2~C6 alkynyl, carboxy C1~C6 alkyl, cyano C1~C6 alkyl, C2~C6 alkenyloxy, C2~C6 alkynyloxy, carbamoyl(—CONH$_2$), C1~C6 alkyl-substituted carbamoyl, carboxyl, hydroxyl C1~C6 alkyl, oxo(═O), thioxo(═S), aminosulfonyl(—SO$_2$NH$_2$), C1~C6 alkylthio, C1~C6 alkylsulfonyl, halogenated C1~C6 alkylsulfonyl, sulfonic group(—SO$_2$OH), aldehyde group, amino C1~C6 alkyl, C1~C6 alkyl-substituted amino C1~C6 alkyl, carbamoyl C1~C6 alkyl, C1~C6 alkyl-substituted carbamoyl C1~C6 alkyl, C3~C10 cyclohydrocarbyl, C3~C10 cyclohydrocarbyl C1~C6 alkyl, C3~C10 cyclohydrocarbyl-formamido, furanyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C10 cyclohydrocarbyl C1~C6 alkoxy, furanyl C1~C6 alkyl, furanyl C1~C6 alkoxy, thienyl C1~C6 alkyl, thienyl C1~C6 alkoxy, pyrrolyl C1~C6 alkyl, pyrrolyl C1~C6 alkoxy, pyrrolidinyl C1~C6 alkyl, pyrrolidinyl C1~C6 alkoxy, pyrazolyl C1~C6 alkyl, pyrazolyl C1~C6 alkoxy, triazolyl C1~C6 alkyl, triazolyl C1~C6 alkoxy, thiazolyl C1~C6 alkyl, thiazolyl C1~C6 alkoxy, isothiazolyl C1~C6 alkyl, isothiazolyl C1~C6 alkoxy, oxazolyl C1~C6 alkyl, oxazolyl C1~C6 alkoxy, isoxazolyl C1~C6 alkyl, isoxazolyl C1~C6 alkoxy, pyrazinyl C1~C6 alkyl, pyrazinyl C1~C6 alkoxy, pyridazinyl C1~C6 alkyl, pyridazinyl C1~C6 alkoxy, pyridyl C1~C6 alkyl, pyridyl C1~C6 alkoxy, pyrimidinyl C1~C6 alkyl, pyrimidinyl C1~C6 alkoxy, phenyl, phenoxy, phenylsulfonyl, phenyl C1~C6 alkyl, phenyl C1~C6 alkoxy, phenyl C1~C6 alkanoyl, and phenyl C1~C6 alkanoyloxy; said C3~C10 cyclohydrocarbyl, C3~C10 cyclohydrocarbyl C1~C6 alkyl, furanyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C10 cyclohydrocarbyl C1~C6 alkoxy, furanyl C1~C6 alkyl, furanyl C1~C6 alkoxy, thienyl C1~C6 alkyl, thienyl C1~C6 alkoxy, pyrrolyl C1~C6 alkyl, pyrrolyl C1~C6 alkoxy, pyrrolidinyl C1~C6 alkyl, pyrrolidinyl C1~C6alkoxy, pyrazolyl C1~C6 alkyl, pyrazolyl C1~C6 alkoxy, triazolyl C1~C6 alkyl, triazolyl C1~C6 alkoxy, thiazolyl C1~C6 alkyl, thiazolyl C1~C6 alkoxy, isothiazolyl C1~C6 alkyl, isothiazolyl C1~C6 alkoxy, oxazolyl C1~C6 alkyl, oxazolyl C1~C6 alkoxy, isoxazolyl C1~C6 alkyl, isoxazolyl C1~C6 alkoxy, pyrazinyl C1~C6 alkyl, pyrazinyl C1~C6 alkoxy, pyridazinyl C1~C6 alkyl, pyridazinyl C1~C6 alkoxy, pyridyl C1~C6 alkyl, pyridyl C1~C6 alkoxy, pyrimidinyl C1~C6 alkyl, pyrimidinyl C1~C6 alkoxy, phenyl, phenoxy, phenylsulfonyl, phenyl C1~C6alkyl, phenyl C1~C6alkoxy, phenyl C1~C6alkanoyl and phenyl C1~C6alkanoyloxy are optionally substituted with one or more substituents selected from the group consisting of halogen, C1~C6 alkyl, halogenated C1~C6 alkyl, C1~C6 alkoxy, C1~C6 alkoxycarbonyl, halogenated C1~C6 alkoxy, nitro, cyano, hydroxy, amino, C1~C6alkanoyl, halogenated C1~C6alkanoyl, carbamoyl, and carboxyl;
provided that the following compounds are excluded:
1-(2-(4-(2-cyano-7-fluorobenzo[b]thiophen-4-yl)-2-methylpiperazin-1-yl)ethyl)isochroman-6-carboxamide; and
1-(2-(4-(7-fluorobenzo[b]thiophen-4-yl)-2-methylpiperazin-1-yl)ethyl)isochroman-6-carboxamide.

2. The heterocyclic compound, stereoisomer or pharmaceutically acceptable salt thereof according to claim 1, wherein ring G is a 3- to 10-membered heteromonocyclic group, a phenyl-fused 3- to 10-membered heteromonocyclic group, a C3~C10 cyclohydrocarbyl-fused 3- to 10-membered heteromonocyclic group or a 3- to 10-membered heteromonocycle-fused 3- to 10-membered heteromonocyclic group.

3. The heterocyclic compound, stereoisomer or pharmaceutically acceptable salt thereof according to claim 2, wherein ring G is a 5- b4 to 7-membered heteromonocyclic group, a phenyl-fused 5- to 7-membered heteromonocyclic group, a C5-C7 cyclohydrocarbyl-fused 5- to 7-membered heteromonocyclic group or a 5- to 7-membered heteromonocycle-fused 5- to 7-membered heteromonocyclic group.

4. The heterocyclic compound, stereoisomer or pharmaceutically acceptable salt thereof according to claim 3, wherein ring G is a heterocyclic group selected from the group consisting of furanyl, dihydrofuranyl, tetrahydrofuranyl, thienyl, dihydrothienyl, tetrahydrothienyl, pyrrolyl, dihydro-pyrrolyl, pyrrolidinyl, pyrazolyl, dihydro-pyrazolyl, pyrazolidinyl, triazolyl, dihydrotriazole, triazolidinyl, thiazolyl, dihydro-thiazolyl, thiazolidinyl, isothiazolyl, dihydro-isothiazolyl, isothiazolidinyl, oxazolyl, dihydro-oxazolyl, oxazolidinyl, isoxazolyl, dihydro-isoxazolyl, isoxazolidinyl, pyranyl, dihydro-pyranyl, tetrahydropyranyl, pyrazinyl, dihydro-pyrazinyl, tetrahydro-pyrazinyl, piperazinyl, pyridazinyl, dihydro-pyridazinyl, tetrahydropyridazinyl,

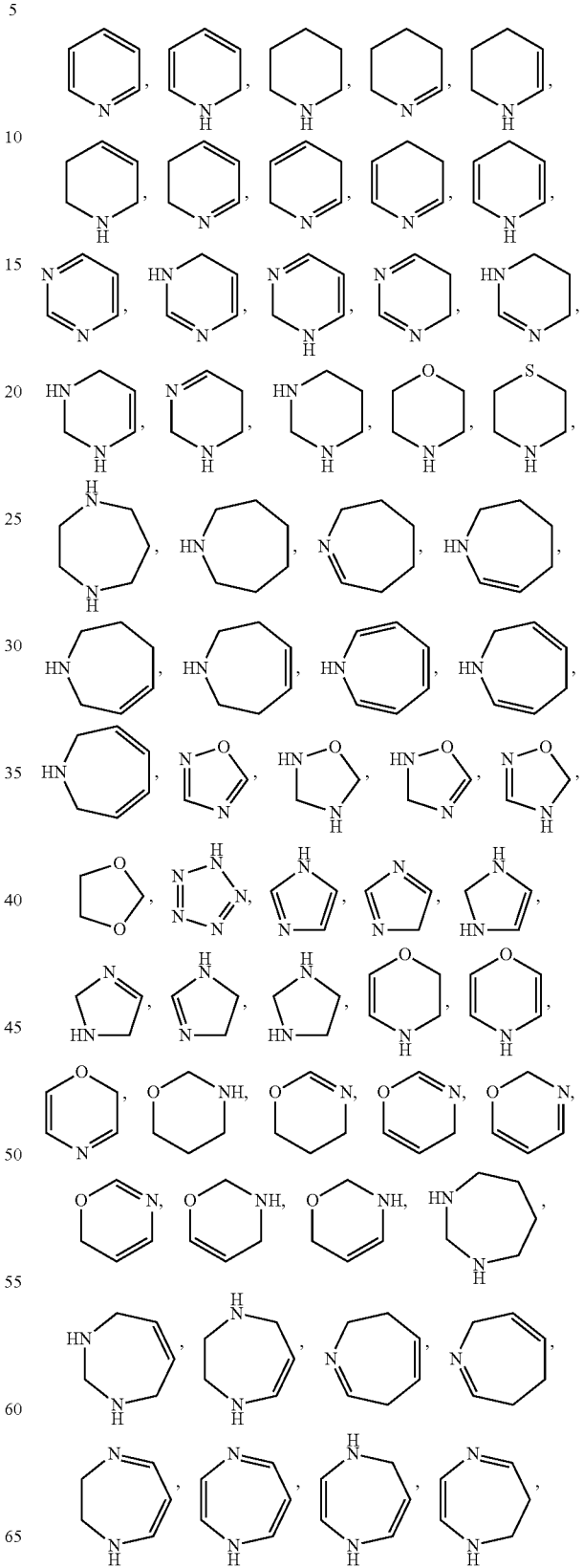

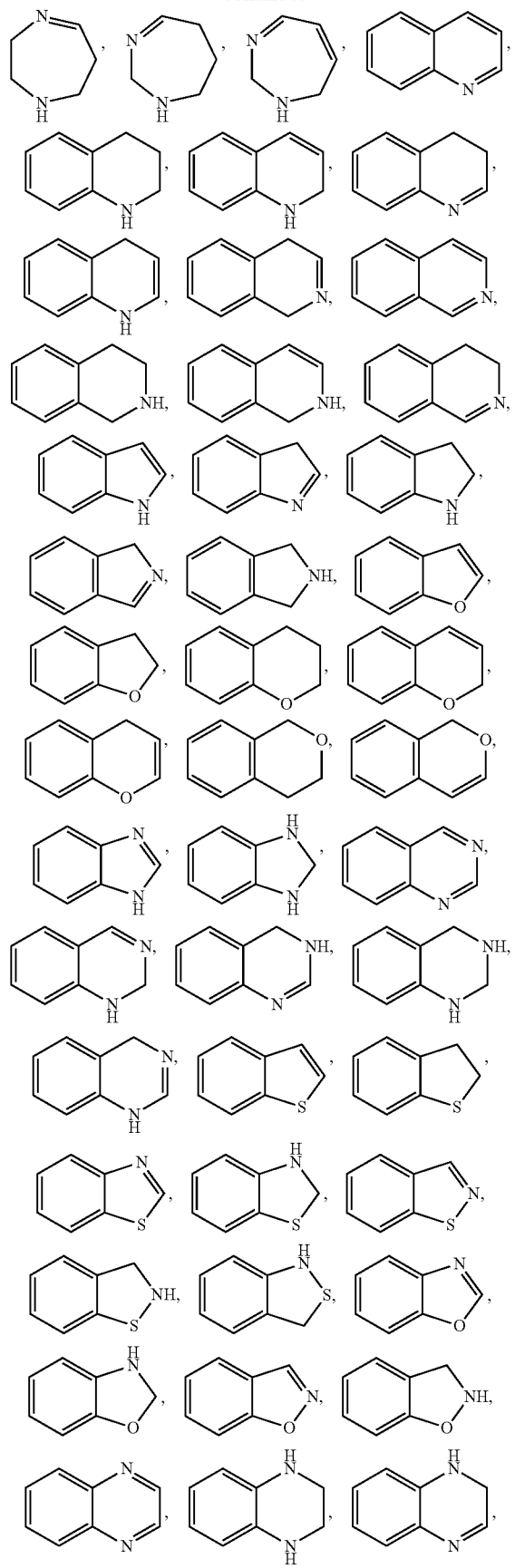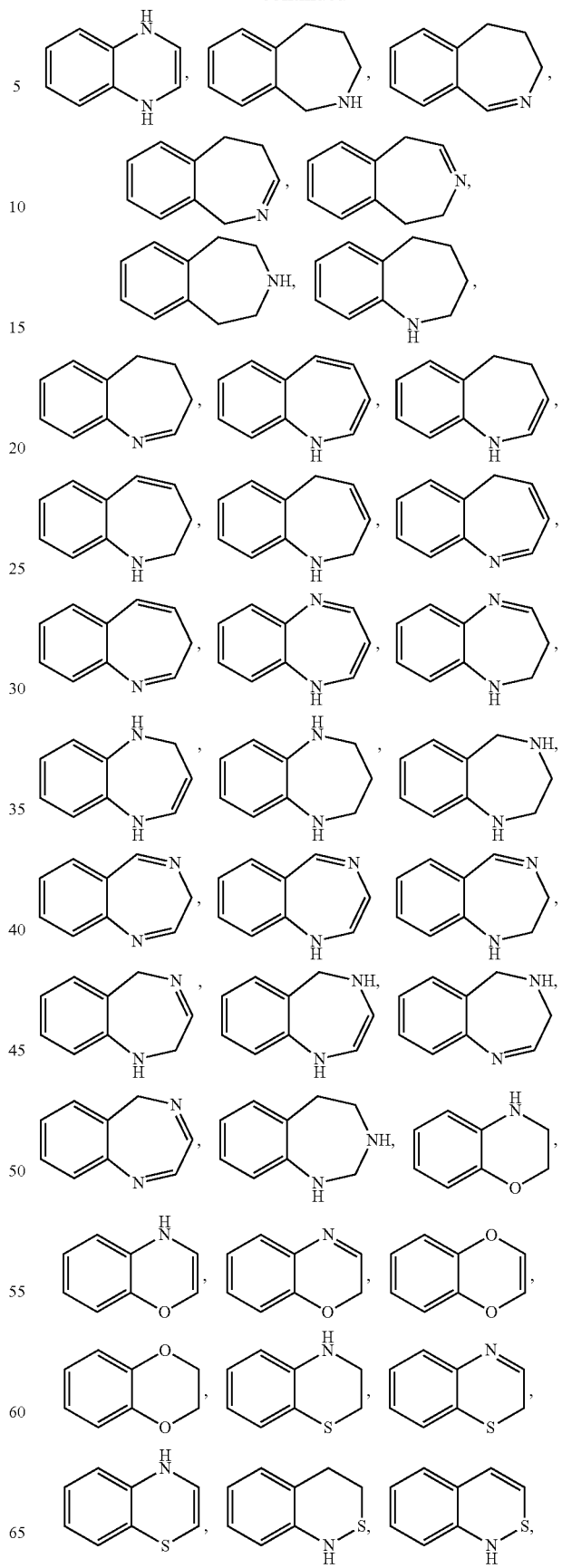

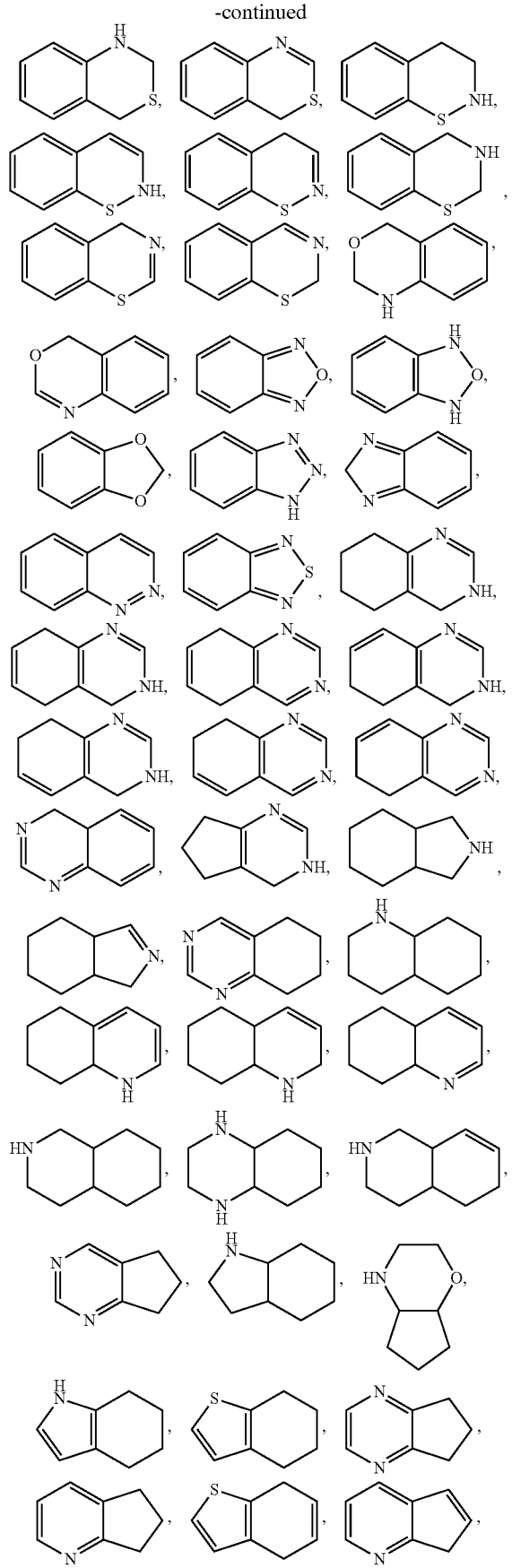
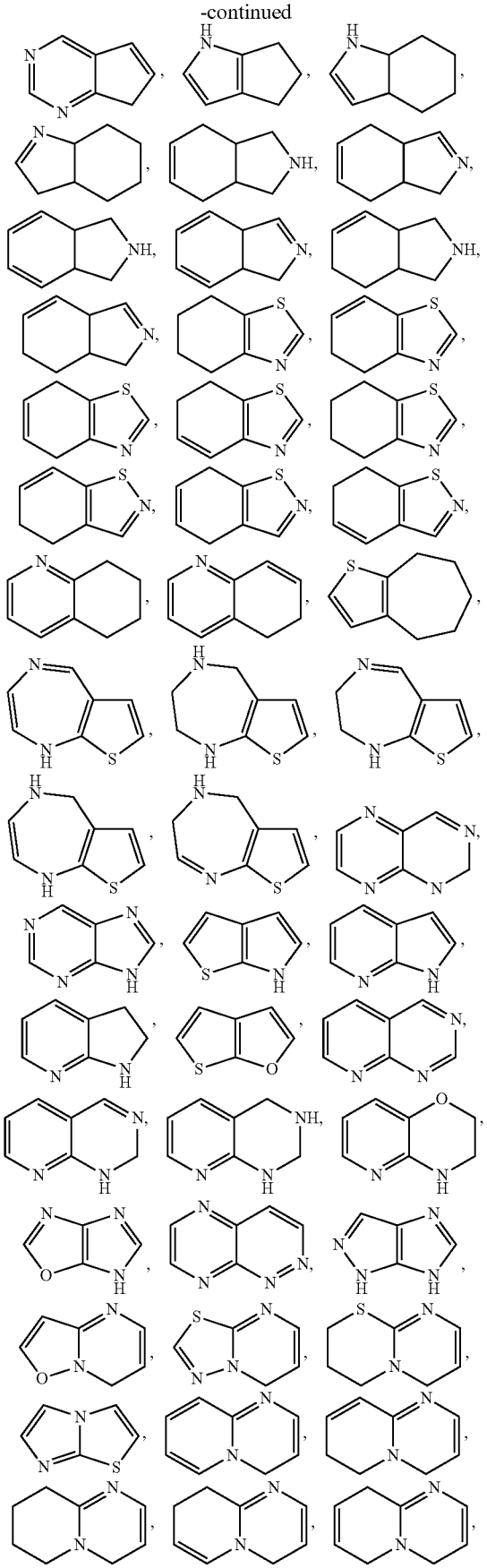

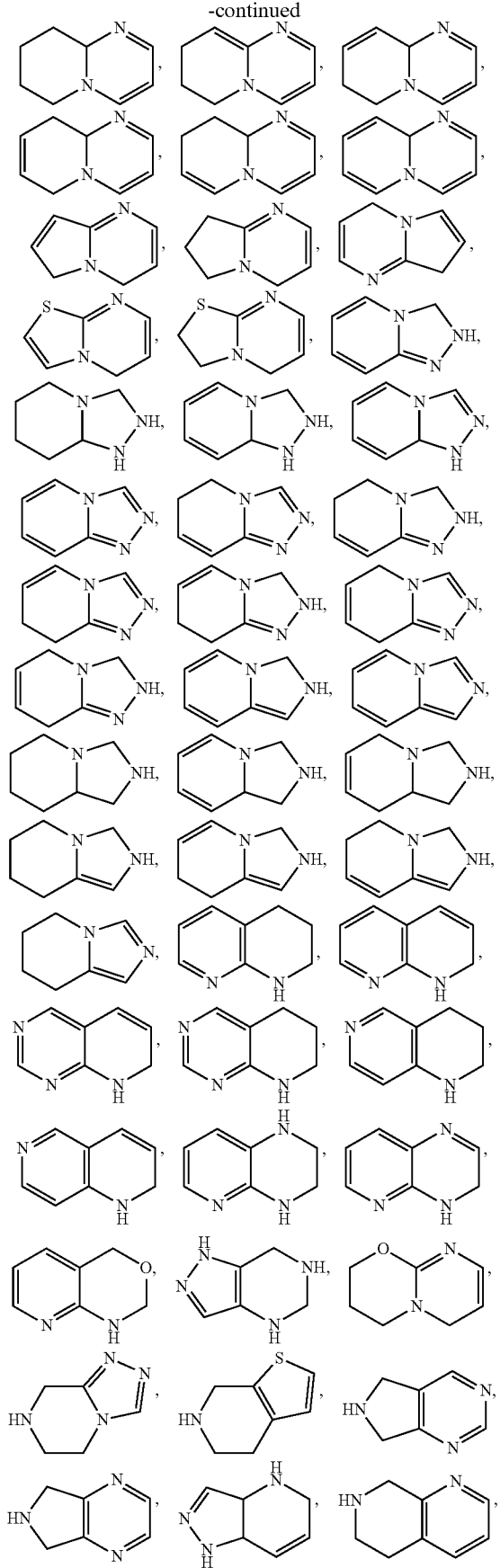

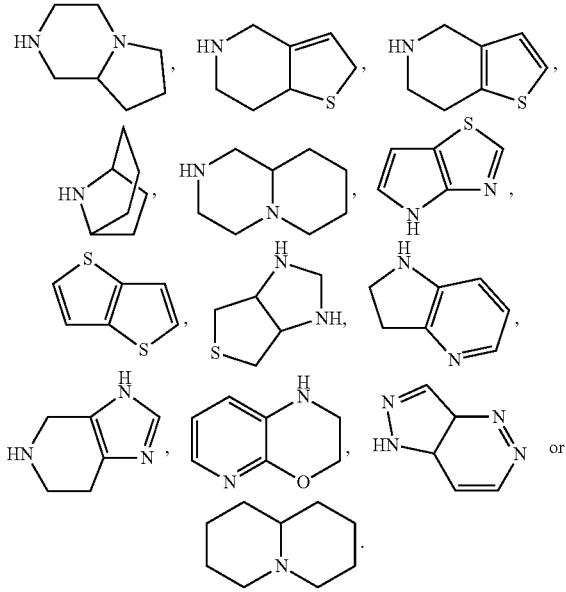

5. The heterocyclic compound, stereoisomer or pharmaceutically acceptable salt thereof according to claim 1, wherein, $R_1$ is hydrogen or 1 to 4 substituents each independently selected from the group consisting of halogen, hydroxy, mercapto, oxo(=O), thioxo(=S), C1~C4 alkoxy, halogenated C1~C4 alkoxy, C1~C4 alkylthio, C1~C4 alkyl, halogenated C1~C4 alkyl, nitro, amino, C1~C4 alkyl-substituted amino, cyano, carboxyl, aldehyde group, amino C1~C4 alkyl, hydroxyl C1~C4 alkyl, cyano C1~C4 alkyl, C1~C4 alkanoyl, halogenated C1~C4 alkanoyl, sulfonic group(—SO$_2$OH), aminosulfonyl(—SO$_2$NH$_2$), carbamoyl(—CONH$_2$), C1~C4 alkyl-substituted carbamoyl, carboxyl C1~C4 alkyl, C1~C4 alkylsulfonyl, halogenated C1~C4 alkylsulfonyl, C1~C4 alkyl-substituted amino C1~C4 alkyl, carbamoyl C1~C4 alkyl, and C1~C4 alkyl-substituted carbamoyl C1~C4 alkyl;

$R_2$ does not exist, or is 1 to 3 substituents each independently selected from the group consisting of halogen, hydroxy, mercapto, C1~C4alkoxy, halogenated C1~C4alkoxy, C1~C4alkylthio, C1~C4 alkyl, halogenated C1~C4 alkyl, nitro, amino, C1~C4 alkyl-substituted amino, cyano, carboxyl, aldehyde group, hydroxyl C1~C4 alkyl, cyano C1~C4 alkyl, C1~C4 alkanoyl, halogenated C1~C4 alkanoyl, sulfonic group (—SO$_2$OH), aminosulfonyl(—SO$_2$NH$_2$), carbamoyl (—CONH$_2$), C1~C4 alkyl-substituted carbamoyl, carboxy C1~C4 alkyl, C1~C4 alkylsulfonyl, halogenated C1~C4 alkylsulfonyl, amino C1~C4 alkyl, C1~C4 alkyl-substituted amino C1~C4 alkyl, carbamoyl C1~C4 alkyl, and C1~C4 alkyl-substituted carbamoyl C1~C4 alkyl;

$R_3$ is hydrogen or 1 to 4 substituents each independently selected from the group consisting of hydroxyl and C1~C4 alkyl;

L does not exist or is C1~C4 alkylene; and ring G is connected to L through a carbon atom on ring G; and ring G is optionally substituted with one or more substituents which are identical or different, the substituent on the ring G is selected from the group consisting of halogen, C1~C4 alkyl, halogenated C1~C4 alkyl, C1~C4 alkoxy, halogenated C1~C4 alkoxy, nitro, cyano, hydroxy, mercapto, amino, C1~C4 alkyl-substituted amino, azido, C1~C4 alkanoyl, halogenated C1~C4 alkanoyl, C2~C4 alkenyl, C2~C4 alkynyl, carboxyl C1~C4 alkyl, cyano C1~C4 alkyl, C2~C4 alkenyloxy, C2~C4 alkynyloxy, carbamoyl(—CONH$_2$), C1~C4 alkyl-substituted carbamoyl, carboxyl, hydroxyl C1~C4 alkyl, oxo(=O), thioxo(=S), aminosulfonyl(—SO$_2$NH$_2$), C1~C4 alkylthio, C1~C4 alkylsulfonyl, halogenated C1~C4 alkylsulfonyl, sulfonic group(—SO$_2$OH), aldehyde group, amino C1~C4 alkyl, C1~C4 alkyl substituted amino C1~C4 alkyl, carbamoyl C1~C4 alkyl, C1~C4 alkyl-substituted carbamoyl C1~C4 alkyl, C3~C7 cyclohydrocarbyl, C3~C7 cyclohydrocarbyl C1~C4 alkyl, C3~C7 cyclohydrocarbyl formamido, furanyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C7 cyclohydrocarbyl C1~C4 alkoxy, furanyl C1~C4 alkyl, furanyl C1~C4 alkoxy, thienyl C1~C4 alkyl, thienyl C1~C4 alkoxy, pyrrolyl C1~C4 alkyl, pyrrolyl C1~C4 alkoxy, pyrrolidinyl C1~C4 alkyl, pyrrolidinyl C1~C4 alkoxy, pyrazolyl C1~C4 alkyl, pyrazolyl C1~C4 alkoxy, triazolyl C1~C4 alkyl, triazolyl C1~C4 alkoxy, thiazolyl C1~C4 alkyl, thiazolyl C1~C4 alkoxy, isothiazolyl C1~C4 alkyl, isothiazolyl C1~C4 alkoxy, oxazolyl C1~C4 alkyl, oxazolyl C1~C4 alkoxy, isoxazolyl C1~C4 alkyl, isoxazolyl C1~C4 alkoxy, pyrazinyl C1~C4 alkyl, pyrazinyl C1~C4 alkoxy, pyridazinyl C1~C4 alkyl, pyridazinyl C1~C4 alkoxy, pyridyl C1~C4 alkyl, pyridyl C1~C4 alkoxy, pyrimidinyl C1~C4 alkyl, pyrimidinyl C1~C4 alkoxy, phenyl, phenoxy, phenylsulfonyl, phenyl C1~C4 alkyl, phenyl C1~C4 alkoxy, phenyl C1~C4 alkanoyl, and phenyl C1~C4 alkanoyloxy; said C3~C7 cyclohydrocarbyl, C3~C7 cyclohydrocarbyl C1~C4 alkyl, furanyl, thienyl, pyrrolyl, pyrrolidinyl, pyrazolyl, pyrazolidinyl, triazolyl, triazolidinyl, thiazolyl, thiazolidinyl, isothiazolyl, isothiazolidinyl, oxazolyl, oxazolidinyl, isoxazolyl, isoxazolidinyl, pyranyl, pyrazinyl, piperazinyl, pyridazinyl, pyridyl, piperidinyl, pyrimidinyl, imidazolyl, C3~C7 cyclohydrocarbyl C1~C4 alkoxy, furanyl C1~C4 alkyl, furanyl C1~C4 alkoxy, thienyl C1~C4 alkyl, thienyl C1~C4 alkoxy, pyrrolyl C1~C4 alkyl, pyrrolyl C1~C4 alkoxy, pyrrolidinyl C1~C4 alkyl, pyrrolidinyl C1~C4 alkoxy, pyrazolyl C1~C4 alkyl, pyrazolyl C1~C4 alkoxy, triazolyl C1~C4 alkyl, triazolyl C1~C4 alkoxy, thiazolyl C1~C4 alkyl, thiazolyl C1~C4 alkoxy, isothiazolyl C1~C4 alkyl, isothiazolyl C1~C4 alkoxy, oxazolyl C1~C4 alkyl, oxazolyl C1~C4 alkoxy, isoxazolyl C1~C4 alkyl, isoxazolyl C1~C4 alkoxy, pyrazinyl C1~C4 alkyl, pyrazinyl C1~C4 alkoxy, pyridazinyl C1~C4 alkyl, pyridazinyl C1~C4 alkoxy, pyridyl C1~C4 alkyl, pyridyl C1~C4 alkoxy, pyrimidinyl C1~C4 alkyl, pyrimidinyl C1~C4 alkoxy, phenyl, phenoxy, phenylsulfonyl, phenyl C1~C4 alkyl, phenyl C1~C4 alkoxy, phenyl C1~C4 alkanoyl and phenyl C1~C4 alkanoyloxy are optionally substituted with one or more substituents selected from the group consisting of halogen, C1~C4 alkyl, halogenated C1~C4 alkyl, C1~C4 alkoxy, C1~C4 alkoxycarbonyl, halogenated C1~C4 alkoxy, nitro, cyano, hydroxy, amino, C1~C4 alkanoyl, halogenated C1~C4 alkanoyl, carbamoyl, and carboxyl.

6. The heterocyclic compound, stereoisomer or pharmaceutically acceptable salt thereof according to claim 5, wherein,
   $R_1$ is hydrogen or 1 to 4 substituents each independently selected from the group consisting of fluorine, chlorine, bromine, hydroxy, mercapto, oxo(=O), thioxo(=S), methoxy, ethoxy, trifluoromethoxy, —SCH$_3$, —SCH$_2$CH$_3$, methyl, ethyl, propyl, isopropyl, t-butyl, trifluoromethyl, bromomethyl, chloromethyl, nitro, amino, N-methylamino, N-ethylamino, N,N-dimethylamino, N,N-diethylamino, cyano, carboxyl, aldehyde group, —CH$_2$NH$_2$, —CH$_2$CH$_2$NH$_2$, —CH$_2$OH, —CH$_2$CH$_2$OH, —CH$_2$CN, —CH$_2$CH$_2$CN, formyl, acetyl, propionyl, trifluoroacetyl, sulfonic group(—SO$_2$OH), aminosulfonyl (—SO$_2$NH$_2$), carbamoyl, N-methylcarbamoyl, N,N-dimethylcarbamoyl, N-ethylcarbamoyl, N,N-diethylcarbamoyl, —CH$_2$CO$_2$H, —CH$_2$CH$_2$CO$_2$H, —SO$_2$CH$_3$, —SO$_2$CF$_3$, —CH$_2$NHMe, —CH$_2$NMe$_2$, —CH$_2$CONH$_2$, —CH$_2$CONHMe and —CH$_2$CONMe$_2$;
   $R_2$ does not exist, or is 1 to 3 substituents each independently selected from the group consisting of fluorine, chlorine, bromine, hydroxy, mercapto, methoxy, ethoxy, trifluoromethoxy, —SCH$_3$, —SCH$_2$CH$_3$, methyl, ethyl, propyl, isopropyl, t-butyl, trifluoromethyl, bromomethyl, chloromethyl, nitro, amino, N-methylamino, N-ethylamino, N,N-dimethylamino, N,N-diethylamino, cyano, carboxyl, aldehyde group, —CH$_2$OH, —CH$_2$CH$_2$OH, —CH$_2$CN, —CH$_2$CH$_2$CN, formyl, acetyl, propionyl, trifluoroacetyl, sulfonic group(—SO$_2$OH), aminosulfonyl(—SO$_2$NH$_2$), carbamoyl, N-methylc arbamoyl, N,N-dimethylcarbamoyl, N-ethylcarbamoyl, N,N-diethylcarbamoyl, —CH$_2$CO$_2$H, —CH$_2$CH$_2$CO$_2$H, —SO$_2$CH$_3$, —SO$_2$CF$_3$, —CH$_2$NH$_2$, —CH$_2$CH$_2$NH$_2$, —CH$_2$NHMe, —CH$_2$NMe$_2$, —CH$_2$CONH$_2$, —CH$_2$CONHMe and —CH$_2$CONMe$_2$;
   $R_3$ is hydrogen or 1-4 substituents each independently selected from the group consisting of hydroxy, methyl and ethyl; and
   the substituent on the ring G is selected from the group consisting of fluorine, chlorine, bromine, methyl, ethyl, propyl, isopropyl, t-butyl, trifluoromethyl, methoxy, ethoxy, trifluoromethoxy, nitro, cyano, hydroxy, mercapto, amino, N-methylamino, N-ethylamino, N,N-dimethylamino, N,N-diethylamino, azido, formyl, acetyl, propionyl, trifluoroacetyl, —CH$_2$CO$_2$H, —CH$_2$CH$_2$CO$_2$H, —CH$_2$CN, —CH$_2$CH$_2$CN, carbamoyl, N-methylcarbamoyl, N,N-dimethylcarbamoyl, N-ethylcarbamoyl, N,N-diethylcarbamoyl, carboxyl, —CH$_2$OH, —CH$_2$CH$_2$OH, oxo(=O), thio(=S), aminosulfonyl(—SO$_2$NH$_2$), —SCH$_3$, —SCH$_2$CH$_3$, —SO$_2$CH$_3$, —SO$_2$CF$_3$, sulfonic group(—SO$_2$OH), aldehyde group, —CH$_2$NH$_2$, —CH$_2$CH$_2$NH$_2$, —CH$_2$NHMe, —CH$_2$NMe$_2$, —CH$_2$NHEt, —CH$_2$NEt$_2$, —CH$_2$CH$_2$NHMe, —CH$_2$CH$_2$NHEt, —CH$_2$CH$_2$NMe$_2$, —CH$_2$CH$_2$NEt$_2$, —CH$_2$CONH$_2$, —CH$_2$CONHMe, —CH$_2$CONMe$_2$, —CH$_2$CONHEt, —CH$_2$CONEt$_2$, —CH$_2$CH$_2$CONH$_2$, —CH$_2$CH$_2$CONHMe, —CH$_2$CH$_2$CONMe$_2$, —CH$_2$CH$_2$CONHEt, —CH$_2$CH$_2$CONEt$_2$, phenyl, phenoxy, phenylsulfonyl, —CH$_2$Ph, —CH$_2$CH$_2$Ph, —OCH$_2$Ph, —OCH$_2$CH$_2$Ph, —COPh, —COCH$_2$Ph and —CH$_2$Ph(OMe)$_2$.

7. The heterocyclic compound, stereoisomer or pharmaceutically acceptable salt thereof according to claim 1, wherein

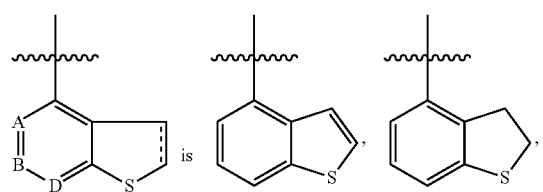
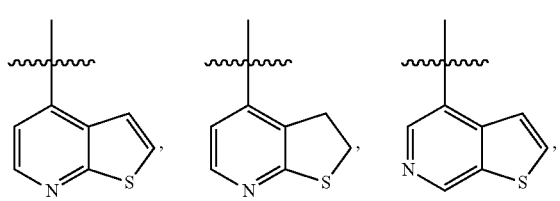
or
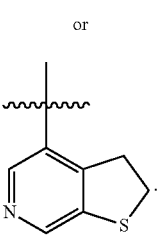
8. The heterocyclic compound, stereoisomer or pharmaceutically acceptable salt thereof according to claim 7, wherein,
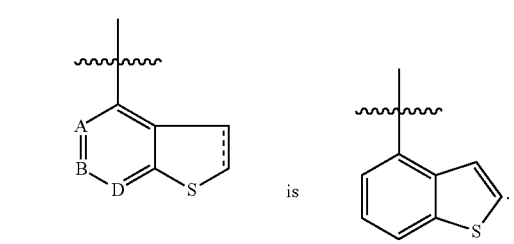
9. The heterocyclic compound, stereoisomer or pharmaceutically acceptable salt thereof according to claim 1, wherein the compound of the formula(I) is selected from the group consisting of:
(I-a)
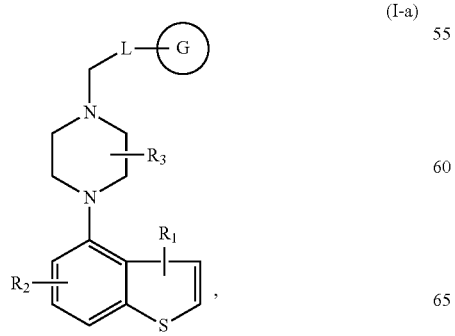
(I-b)
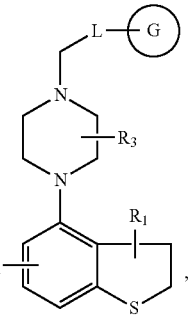
(I-c)
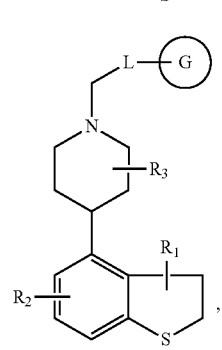
(I-d)
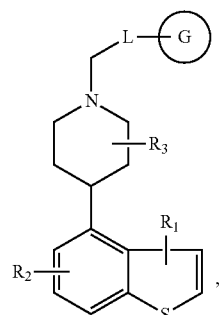
(I-e)
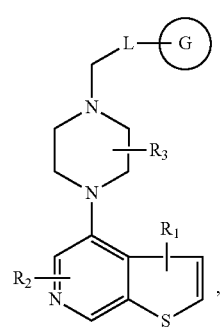
(I-f)
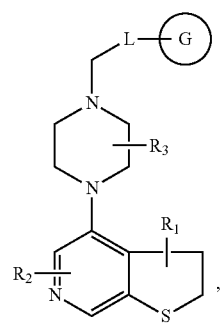

-continued
(I-g)
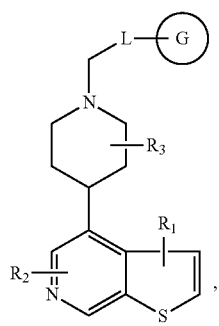
(I-h)
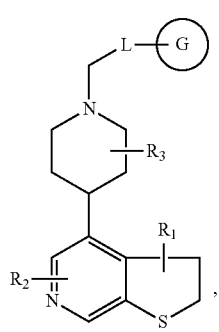
(I-i)
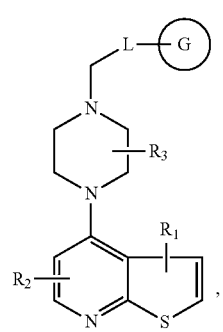
(I-j)
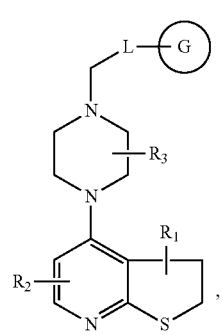
(I-k)
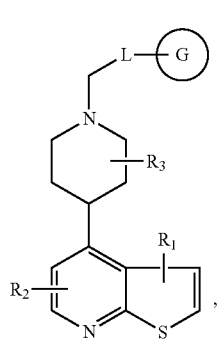
-continued
(I-l)
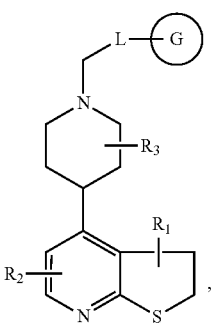
(I-n)
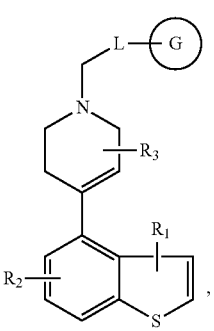
(I-o)
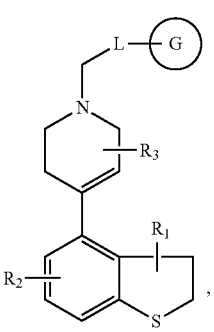
(I-p)
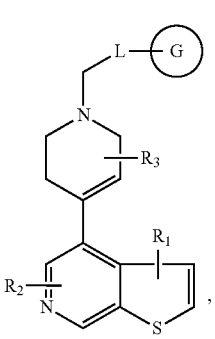
(I-q)

-continued

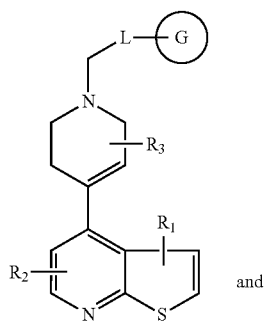
(I-r)

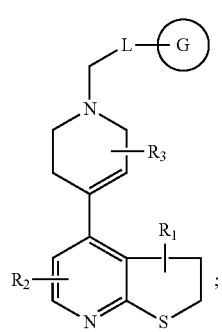
(I-s)

wherein, $R_1$, $R_2$, $R_3$, L and ring G are defined the same as those in the corresponding claim.

10. The heterocyclic compound, stereoisomer or pharmaceutically acceptable salt thereof according to claim 1, wherein the compound of general formula (I) is selected from the group consisting of:

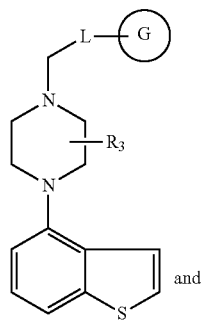
(I-t)

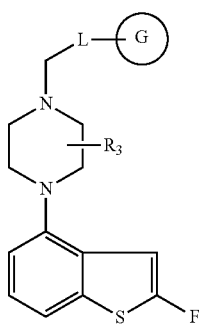
(I-u)

wherein, R3, L and ring G are defined the same as those in the corresponding claim.

11. The heterocyclic compound, stereoisomer or pharmaceutically acceptable salt thereof according to claim 1, wherein the compound of the formula (I) is selected from the group consisting of:

6-chloro-5-(2-(4-(2,3-dihydrobenzo[b]thiophen-4-yl)piperazin-1-yl)ethyl)indolin-2-one;
3-(2-(4-(2,3-dihydrobenzo[b]thiophen-4-yl)piperazin-1-yl)ethyl)-9-hydroxy-2-methyl-6,7,8,9-tetrahydropyrido[1,2-a]pyrimidin-4-one;
3-(2-(4-(benzo[b]thiophen-4-yl)piperazin-1-yl)ethyl)-2-methyl-6,7,8,9-tetrahydropyrido[1,2-a]pyrimidin-4-one;
3-(2-(4-(benzo[b]thiophen-4-yl)piperazin-1-yl)ethyl)-9-hydroxy-2-methyl-6,7,8,9-tetrahydropyrido[1,2-a]pyrimidin-4-one;
(+)-3-(2-(4-(benzo[b]thiophen-4-yl)piperazin-1-yl)ethyl)-9-hydroxy-2-methyl-6,7,8,9-tetrahydropyrido[1,2-a]pyrimidin-4-one;
(−)-3-(2-(4-(benzo[b]thiophen-4-yl)piperazin-1-yl)ethyl)-9-hydroxy-2-methyl-6,7,8,9-tetrahydropyrido[1,2-a]pyrimidin-4-one;
3-(2-(4-(benzo[b]thiophen-4-yl)piperazin-1-yl)ethyl)-2-methyl-7,8-dihydro-6H-pyrido[1,2-a]pyrimidine-4,9-dione;
3-(2-(4-(benzo[b]thiophen-4-yl)piperazin-1-yl)ethyl)-9-hydroxy-2,9-dimethyl-6,7,8,9-tetrahydropyrido[1,2-a]pyrimidin-4-one;
3-(2-(4-(benzo[b]thiophen-4-yl)piperazin-1-yl)ethyl)-9-fluoro-2-methyl-6,7,8,9-tetrahydropyrido[1,2-a]pyrimidin-4-one;
5-(2-(4-(benzo[b]thiophen-4-yl)piperazin-1-yl)ethyl)indolin-2-one;
7-(2-(4-(benzo[b]thiophen-4-yl)piperazin-1-yl)ethyl)quinolin-2(1H)-one;
7-(5-(4-(benzo[b]thiophen-4-yl)piperazin-1-yl)pentyl)-3,4-dihydroquinolin-2(1H)-one;
7-(5-(4-(benzo[b]thiophen-4-yl)piperazin-1-yl)pentyl)quinolin-2(1H)-one;
7-(5-(4-(2-chlorobenzo[b]thiophen-4-yl)piperazin-1-yl)pentyl)quinolin-2(1H)-one;
7-(5-(4-(2-fluorobenzo[b]thiophen-4-yl)piperazin-1-yl)pentyl)quinolin-2(1H)-one;
7-(5-(4-(benzo[b]thiophen-4-yl)-5,6-dihydropyridin-1(2H)-yl)pentyl)quinolin-2(1H)-one;
5-(2-(4-(benzo[b]thiophen-4-yl)piperazin-1-yl)ethyl)-6-chloroindolin-2-one;
3-(2-(4-(benzo[b]thiophen-4-yl)piperazin-1-yl)ethyl)-2-methyl-6,7-dihydropyrido[1,2-a]pyrimidin-4-one;
3-(2-(4-(benzo[b]thiophen-4-yl)piperazin-1-yl)ethyl)-9-(benzyloxy)-2-methyl-4H-pyrido[1,2-a]pyrimidin-4-one;
3-(2-(4-(benzo[b]thiophen-4-yl)piperazin-1-yl)ethyl)-9-hydroxy-2-methyl-4H-pyrido[1,2-a]pyrimidin-4-one;
7-(2-(4-(benzo[b]thiophen-4-yl)piperazin-1-yl)ethyl)-3,4-dihydroquinolin-2(1H)-one;
7-(4-(4-(benzo[b]thiophen-4-yl)piperazin-1-yl)butyl)-3,4-dihydroquinolin-2(1H)-one;
7-(2-(4-(benzo[b]thiophen-4-yl)piperazin-1-yl)ethyl)-6-chloro-3,4-dihydroquinolin-2(1H)-one;
6-(5-(4-(benzo[b]thiophen-4-yl)piperazin-1-yl)pentyl)-2-methylquinazolin-4(3H)-one;
7-(2-(4-(2,3-dihydrobenzo[b]thiophen-4-yl)piperazin-1-yl)ethyl)quinolin-2(1H)-one;
5-(2-(4-(benzo[b]thiophen-4-yl)piperazin-1-yl)ethyl)-4-methylthiazole;
5-(2-(4-(benzo[b]thiophen-4-yl)piperazin-1-yl)ethyl)-1H-benzo[d]imidazol-2(3H)-one;

3-(2-(4-(benzo[b]thiophen-4-yl)piperazin-1-yl)ethyl)-9,9-difluoro-2-methyl-6,7,8,9-tetrahydropyrido[1,2-a]pyrimidin-4-one;
6-(2-(4-(benzo[b]thiophen-4-yl)piperazin-1-yl)ethyl)benzo[d]thiazol-2(3H)-one;
6-(2-(4-(benzo[b]thiophen-4-yl)piperazin-1-yl)ethyl)-2H-benzo[b][1,4]oxazin-3(4H)-one;
6-(2-(4-(benzo[b]thiophen-4-yl)piperazin-1-yl)ethyl)-2H-benzo[b][1,4]thiazin-3(4H)-one;
7-(4-(4-(benzo[b]thiophen-4-yl)piperazin-1-yl)butyl)quinolin-2(1H)-one;
6-(5-(4-(benzo[b]thiophen-4-yl)piperazin-1-yl)pentyl)quinazolin-4(3H)-one;
2-(2-(4-(benzo[b]thiophen-4-yl)piperazin-1-yl)ethyl)quinazolin-4(3H)-one;
3-(2-(4-(benzo[b]thiophen-4-yl)piperidin-1-yl)ethyl)-9-hydroxy-2-methyl-6,7,8,9-tetrahydropyrido[1,2-a]pyrimidin-4-one;
5-(2-(4-(benzo[b]thiophen-4-yl)piperidin-1-yl)ethyl)-6-chloroindolin-2-one;
4-(2-(4-(benzo[b]thiophen-4-yl)piperazin-1-yl)ethyl)indolin-2-one;
6-(2-(4-(benzo[b]thiophen-4-yl)piperazin-1-yl)ethyl)indolin-2-one;
7-(2-(4-(benzo[b]thiophen-4-yl)piperazin-1-yl)ethyl)-6-chloroquinolin-2(1H)-one;
9-hydroxy-2-methyl-3-(2-(4-(thieno[2,3-c]pyrid-4-yepiperazin-1-yl)ethyl)-6,7,8,9-tetrahydropyrido[1,2-a]pyrimidin-4-one;
6-chloro-5-(2-(4-(thieno[2,3-c]pyridin-4-yl)piperazin-1-yl)ethyl)indolin-2-one;
7-(2-(4-(thieno[2,3-c]pyrid-4-yl)piperazin-1-yl)ethyl)quinolin-2(1H)-one;
7-(3-(4-(benzo[b]thiophen-4-yl)piperazin-1-yl)propyl)quinolin-2(1H)-one;
7-(3-(4-(benzo[b]thiophen-4-yl)piperazin-1-yl)propyl)-3,4-dihydroquinolin-2(1H)-one;
3-(2-(4-(benzo[b]thiophen-4-yl)piperazin-1-yl)ethyl)-1H-indole;
6-(2-(4-(benzo[b]thiophen-4-yl)piperazin-1-yl)ethyl)-3,4-dihydroquinolin-2(1H)-one;
5-(3-(4-(benzo[b]thiophen-4-yl)piperazin-1-yl)propyl)indolin-2-one;
7-(2-(4-(benzo[b]thiophen-4-yl)piperazin-1-yl)ethyl)-4,5-dihydro-1H-benzo[b]azepin-2(3H)-one;
3-(2-(4-(benzo[b]thiophen-4-yl)piperazin-1-yl)ethyl)-2-methyl-4H-pyrido[1,2-a]pyrimidin-4-one;
6-(2-(4-(benzo[b]thiophen-4-yl)piperazin-1-yl)ethyl)-3-methyl-3,4-dihydroquinazolin-2(1H)-one;
3-(2-(4-(benzo[b]thiophen-4-yl)piperazin-1-yl)ethyl)-9-chloro-2-methyl-6,7,8,9-tetrahydropyrido[1,2-a]pyrimidin-4-one;
5-(2-(4-(benzo[b]thiophen-4-yl)piperazin-1-yl)ethyl)indoline-2-thione;
7-(2-(4-(benzo[b]thiophen-4-yl)piperazin-1-yl)ethyl)quinoline-2(1H)-thione;
2-(2-(4-(benzo[b]thiophen-4-yl)piperazin-1-yl)ethyl)-5,6-diethylpyrimidin-4(3H)-one;
2-(2-(4-(benzo[b]thiophen-4-yl)piperazin-1-yl)ethyl)pyrimidin-4(3H)-one;
7-(2-(4-(2-fluorobenzo[b]thiophen-4-yl)piperazin-1-yl)ethyl)quinolin-2(1H)-one;
2-((4-(benzo[b]thiophen-4-yl)piperazin-1-yl)methyl)-1H-benzo[d]imidazole;
6-(2-(4-(benzo[b]thiophen-4-yl)piperazin-1-yl)ethyl)benzo[d]thiazole;
7-(2-(4-(2-fluorobenzo[b]thiophen-4-yl)piperazin-1-yl)ethyl)benzo[d]thiazol-2-amine;
N-(7-(2-(4-(2-fluorobenzo[b]thiophen-4-yl)piperazin-1-yl)ethyl)benzo[d]thiazol-2-yl)acetamide;
5-(2-(4-(2-fluorobenzo[b]thiophen-4-yl)piperazin-1-yl)ethyl)benzo[d]thiazol-2-amine;
N-(5-(2-(4-(2-fluorobenzo[b]thiophen-4-yl)piperazin-1-yl)ethyl)benzo[d]thiazol-2-yl)acetamide;
7-(2-(4-(2-fluorobenzo[b]thiophen-4-yl)piperazin-1-yl)ethyl)-3,4-dihydroquinolin-2(1H)-one;
6-(2-(4-(2-fluorobenzo[b]thiophen-4-yl)piperazin-1-yl)ethyl)-3,4-dihydroquinolin-2(1H)-one;
6-(2-(4-(benzo[b]thiophen-4-yl)piperazin-1-yl)ethyl)-7-fluoro-2H-benzo[b][1,4]oxazin-3(4H)-one;
7(2-(4-(3-methylbenzo[b]thiophen-4-yl)piperazin-1-yl)ethyl)-3,4-dihydroquinolin-2(1H)-one;
6-(2-(4-(benzo[b]thiophen-4-yl)piperazin-1-yl)ethyl)benzo[d]oxazol-2(3H)-one;
4-((4-(benzo[b]thiophen-4-yl)piperazin-1-yl)methyl)quinolin-2(1H)-one;
3-(4-(4-(benzo[b]thiophen-4-yl)piperazin-1-yl)butyl)-1H-indole-5-carbonitrile;
7-(5-(4-(6-fluorobenzo[b]thiophen-4-yl)piperazin-1-yl)pentyl)quinolin-2(1H)-one;
6-(4-(4-(benzo[b]thiophen-4-yl)piperazin-1-yl)butyl)-8-fluoro-2H-benzo[b][1,4]oxazin-3(4H)-one;
1-(benzo[b]thiophen-4-yl)-4-((2,3-dihydrobenzo[b][1,4]dioxin-2-yl)methyl)piperazine;
6-(4-(4-(2-fluorobenzo[b]thiophen-4-yl)piperazin-1-yl)butyl)-3,4-dihydroquinolin-2(1H)-one;
2-(2-(4-(benzo[b]thiophen-4-yl)piperazin-1-yl)ethyl)-1H-benzo[d]imidazole;
N-(6-(2-(4-(2-fluorobenzo[b]thiophen-4-yl)piperazin-1-yl)ethyl)benzo[d]thiazol-2-yl)acetamide;
5-(2-(4-(2-fluorobenzo[b]thiophen-4-yl)piperazin-1-yl)ethyl)-1H-benzo[d]imidazol-2(3H)-one;
6-(2-(4-(6-fluorobenzo[b]thiophen-4-yl)piperazin-1-yl)ethyl)-2H-benzo[b][1,4]oxazin-3(4H)-one;
5-(2-(4-(2-fluorobenzo[b]thiophen-4-yl)piperazin-1-yl)ethyl)indolin-2-one;
6-(2-(4-(benzo[b]thiophen-4-yl)piperazin-1-yl)ethyl)-2-methylquinazolin-4(3H)-one;
7-(2-(4-(benzo[b]thiophen-4-yl)piperazin-1-yl)ethyl)-1,1-dioxo-3,4-dihydro-2H-benzo[e][1,2]thiazine;
5-(2-(4-(benzo[b]thiophen-4-yl)piperidin-1-yl)ethyl)indolin-2-one;
7-(2-(4-(benzo[b]thiophen-4-yl)piperidin-1-yl)ethyl)-3,4-dihydroquinolin-2(1H)-one;
5-(2-(4-(6-fluorobenzo[b]thiophen-4-yl)piperazin-1-yl)ethyl)indolin-2-one;
7-(2-(4-(6-fluorobenzo[b]thiophen-4-yl)piperazin-1-yl)ethyl)-3,4-dihydroquinolin-2(1H)-one;
6-(2-(4-(benzo[b]thiophen-4-yl)piperazin-1-yl)ethyl)-1-methyl-1H-benzo[d]imidazol-2(3H)-one;
5-(2-(4-(benzo[b]thiophen-4-yl)piperazin-1-yl)ethyl)-1,3-dimethyl-1H-benzo[d]imidazol-2(3H)-one;
5-(2-(4-(benzo[b]thiophen-4-yl)piperazin-1-yl)ethyl)-1-methyl-1H-benzo[d]imidazol-2(3H)-one;
6-(2-(4-(2-methoxybenzo[b]thiophen-4-yl)piperazin-1-yl)ethyl)-3,4-dihydroquinolin-2(1H)-one;
3-(2-(4-(6-fluorobenzo[b]thiophen-4-yl)piperazin-1-yl)ethyl)-2-methyl-6,7,8,9-tetrahydro-4H-pyrido[1,2-a]pyrimidin-4-one;
7-(2-(4-(2-oxo-2,3-dihydrobenzo[b]thiophen-4-yl)piperazin-1-yl)ethyl)-3,4-dihydroquinolin-2(1H)-one;
6-(2-(4-(2-fluorobenzo[b]thiophen-4-yl)piperazin-1-yl)ethyl)-2H-benzo[b][1,4]oxazin-3(4H)-one;

5-(2-(4-(2-fluorobenzo[b]thiophen-4-yl)piperazin-1-yl)ethyl)-1,3-dimethyl-1H-benzo[d]imidazol-2(3H)-one;
6-fluoro-5-(2-(4-(2-fluorobenzo[b]thiophen-4-yl)piperazin-1-yl)ethyl)indolin-2-one;
5-(2-(4-(benzo[b]thiophen-4-yl)piperazin-1-yl)ethyl)-6-fluoroindolin-2-one;
7-(2-(4-(benzo[b]thiophen-4-yl)piperazin-1-yl)ethyl)-1-benzyl-3-methylquinazoline-2,4(1H,3H)-dione;
6-(2-(4-(benzo[b]thiophen-4-yl)piperidin-1-yl)ethyl)-2H-benzo[b][1,4]oxazin-3(4H)-one;
6-(2-(4-(benzo[b]thiophen-4-yl)piperidin-1-yl)ethyl)-3,4-dihydroquinolin-2(1H)-one;
3-(2-(4-(benzo[b]thiophen-4-yl)piperidin-1-yl)ethyl)-2-methyl-6,7,8,9-tetrahydro-4H-pyrido[1,2-a]pyrimidin-4-one;
6-(2-(4-(2-fluorobenzo[b]thiophen-4-yl)piperazin-1-yl)ethyl)quinolin-2(1H)-one;
5-(4-(4-(2-fluorobenzo[b]thiophen-4-yl)piperazin-1-yl)butyl)indolin-2-one;
7-(2-(4-(6-fluorobenzo[b]thiophen-4-yl)piperazin-1-yl)ethyl)quinolin-2(1H)-one;
3-(4-(4-(benzo[b]thiophen-4-yl)piperazin-1-yl)butyl)-6,7-dimethoxy-4H-chromen-4-one;
6-(4-(4-(benzo[b]thiophen-4-yl)piperidin-1-yl)butyl)-3,4-dihydroquinolin-2(1H)-one;
3-(2-(4-(benzo[b]thiophen-4-yl)piperazin-1-yl)ethyl)-5-methoxy-1H-indole;
3-(3-(4-(benzo[b]thiophen-4-yl)piperazin-1-yl)propyl)-5-methoxy-1H-indole;
3-(4-(4-(benzo[b]thiophen-4-yl)piperazin-1-yl)butyl)-5-methoxy-1H-indole;
3-(3-(4-(benzo[b]thiophen-4-yl)piperazin-1-yl)propyl)-1H-indole-5-carbonitrile;
3-(2-(4-(benzo[b]thiophen-4-yl)piperazin-1-yl)ethyl)-1H-indole-5-carbonitrile;
1-acetyl-3-(4-(4-(benzo[b]thiophen-4-yl)piperazin-1-yl)butyl)-1H-indole-5-carbonitrile;
6-(4-(4-(benzo[b]thiophen-4-yl)piperazin-1-yl)butyl)-3,4-dihydroquinolin-2(1H)-one;
5-(4-(4-(benzo[b]thiophen-4-yl)piperazin-1-yl)butyl)indolin-2-one;
6-chloro-5-(2-(4-(2-fluorobenzo[b]thiophen-4-yl)piperazin-1-yl)ethyl)indolin-2-one;
6-(2-(4-(benzo[b]thiophen-4-yl)piperazin-1-yl)ethyl)-4-methyl-2H-benzo[b][1,4]oxazin-3(4H)-one;
7-(2-(4-(benzo[b]thiophen-4-yl)piperazin-1-yl)ethyl)-1-methyl-3,4-dihydroquinolin-2(1H)-one;
5-(2-(4-(benzo[b]thiophen-4-yl)piperazin-1-yl)ethyl)benzo[d]thiazol-2-amine;
7-(2-(4-(benzo[b]thiophen-4-yl)piperazin-1-yl)ethyl)benzo[d]thiazol-2-amine;
N-(5-(2-(4-(benzo[b]thiophen-4-yl)piperazin-1-yl)ethyl)benzo[d]thiazol-2-yl)acetamide;
N-(7-(2-(4-(benzo[b]thiophen-4-yl)piperazin-1-yl)ethyl)benzo[d]thiazol-2-yl)acetamide;
4-(2-(4-(benzo[b]thiophen-4-yl)piperazin-1-yl)ethyl)benzo[d]thiazol-2-amine;
N-(4-(2-(4-(benzo[b]thiophen-4-yl)piperazin-1-yl)ethyl)benzo[d]thiazol-2-yl)acetamide;
7-(2-(4-(2-methylbenzo[b]thiophen-4-yl)piperazin-1-yl)ethyl)-3,4-dihydroquinolin-2(1H)-one;
3-((4-(benzo[b]thiophen-4-yl)piperazin-1-yl)methyl)-1-methyl-1H-indole;
1-(3-(2-(4-(benzo[b]thiophen-4-yl)piperazin-1-yl)ethyl)indolin-1-yl)ethanone;
3-(2-(4-(benzo[b]thiophen-4-yl)piperazin-1-yl)ethyl)-1-tosyl-1H-indole-5-carbonitrile;
3-(3-(4-(benzo[b]thiophen-4-yl)piperazin-1-yl)propyl)-1-tosyl-1H-indole-5-carbonitrile;
3-(4-(4-(benzo[b]thiophen-4-yl)piperazin-1-yl)butyl)-5-methoxy-1-tosyl-1H-indole;
3-(3-(4-(benzo[b]thiophen-4-yl)piperazin-1-yl)propyl)-5-methoxy-1-tosyl-1H-indole;
3-(2-(4-(benzo[b]thiophen-4-yl)piperazin-1-yl)ethyl)-5-methoxy-1-tosyl-1H-indole;
6-(2-(4-(2-oxo-2,3-dihydrobenzo[b]thiophen-4-yl)piperazin-1-yl)ethyl)-3,4-dihydroquinolin-2(1H)-one;
3-(2-(4-(2-fluorobenzo[b]thiophen-4-yl)piperazin-1-yl)ethyl)-9-hydroxy-2-methyl-6,7,8,9-tetrahydro-4H-pyrido[1,2-a]pyrimidin-4-one;
2-(2-(4-(benzo[b]thiophen-4-yl)piperazin-1-yl)ethyl)-2H-benzo[b][1,4]oxazin-3(4H)-one;
7-(2-(4-(benzo[b]thiophen-4-yl)piperazin-1-yl)ethyl)-3,4-dihydroquinoline-2(1H)-thione;
(3aR,4R,6aS)-4-(5-(4-(benzo[b]thiophen-4-yl)piperazin-1-yl)pentyl)tetrahydro-1H-thieno[3,4-d]imidazol-2(3H)-one;
pentyl(6-(2-(4-(benzo[b]thiophen-4-yl)piperazin-1-yl)ethyl)benzo[d]thiazol-2-yl)carbamate;
3-(2-(4-(benzo[b]thiophen-4-yl)piperazin-1-yl)ethyl)-2-methyl-4-oxo-6,7,8,9-tetrahydro-4H-pyrido[1,2-a]pyrimidin-9-yl benzoate;
6-(4-(4-(benzo[b]thiophen-4-yl)piperazin-1-yl)butyl)-2H-benzo[b][1,4]oxazin-3(4H)-one;
1-(benzo[b]thiophen-4-yl)-4-(4-(1-cyclohexyl-1H-tetrazol-5-yl)butyl)piperazine;
6-(2-(4-(benzo[b]thiophen-4-yl)piperazin-1-yl)ethyl)-8-fluoro-2H-benzo[b][1,4]oxazin-3(4H)-one;
N-(6-(2-(4-(benzo[b]thiophen-4-yl)piperazin-1-yl)ethyl)benzo[d]thiazol-2-yl)cyclopentylformamide;
N-(6-(2-(4-(benzo[b]thiophen-4-yl)piperazin-1-yl)ethyl)benzo[d]thiazol-2-yl)acetamide; and
6-(2-(4-(benzo[b]thiophen-4-yl)piperazin-1-yl)ethyl)benzo[d]thiazol-2-amine.

12. A pharmaceutical composition comprising a therapeutically effective amount of the heterocyclic compound, stereoisomer or pharmaceutically acceptable salt thereof according to claim 1, and one or more pharmaceutically acceptable carriers.

13. A method of preparing a pharmaceutical composition comprising mixing the heterocyclic compound, stereoisomer or pharmaceutically acceptable salt thereof according to claim 1 with one or more pharmaceutically acceptable carriers.

14. A method of preparing the heterocyclic compound, stereoisomer or pharmaceutically acceptable salt thereof according to claim 1, the method comprising:
reacting a compound of formula(II) or a salt thereof with a compound of formula(III) or a salt thereof as shown in Reaction Formula 1:

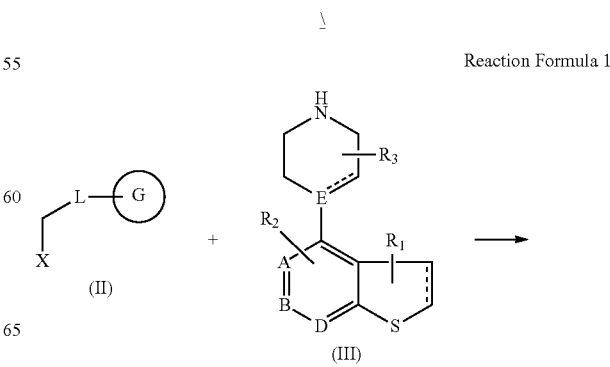

Reaction Formula 1

-continued

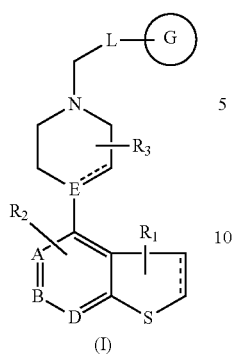

(I)

wherein, ring G, L, A, B, D, E, R$_1$, R$_2$, and R$_3$ are defined the same as those in the corresponding claim;
X represents a leaving group which is halogen, C1-C6 alkylsulfonyloxy, phenylsulfonyloxy, or naphthylsulfonyloxy, said C1-C6 alkylsulfonyloxy, phenylsulfonyloxy and naphthylsulfonyloxy are optionally substituted with one or more substituents selected from the group consisting of halogen, C1-C6 alkyl, C1-C6 alkoxy, nitro, hydroxy, amino, and C1-C6 alkanoyl group.

15. A method of preparing the heterocyclic compound, stereoisomer or pharmaceutically acceptable salt thereof according to claim 1, the method comprising:
reacting a compound of formula(IV) or a salt thereof with a compound of formula(V) or a salt thereof as shown in Reaction Formula 2:

Reaction Formula 2

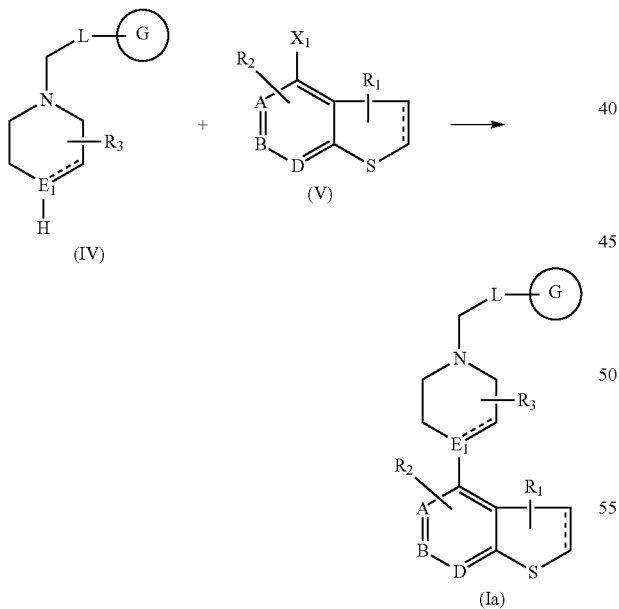

(Ia)

wherein, ring G L, A, B, D, R$_1$, R$_2$ and R$_3$ are defined the same as those in the corresponding claim, E$_1$ represents a nitrogen atom; and
X$_1$ represents halogen or trifluoromethylsulfonyloxy.

16. A method of preparing the heterocyclic compound, stereoisomer or pharmaceutically acceptable salt thereof according to claim 1, the method comprising:

reacting a compound of formula(VI) or a salt thereof with a compound of formula(III) or a salt thereof through amidation to obtain the compound of formula(VII) or a salt thereof, and
treating the compound of formula(VII) or a salt thereof with a reducing agent to give a compound of formula (I). as shown in Reaction Formula 3:

Reactin Formula 3

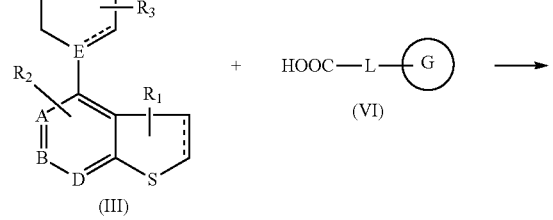

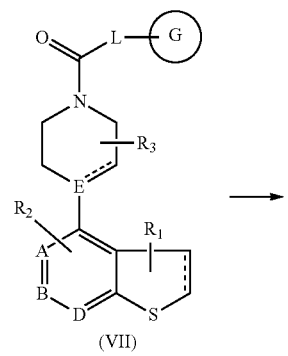

(VII)

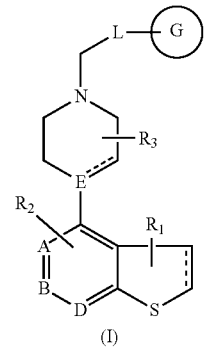

(I)

wherein, ring G, L, A, B, D, E, R$_1$, R$_2$ and R$_3$ are defined the same as those in the corresponding claim.

17. A method of preparing the heterocyclic compound, stereoisomer or pharmaceutically acceptable salt thereof according to claim 1, the method comprising:
reacting a compound of Formula(VIII) or a salt thereof with a compound of formula(III) or a salt thereof through a reductive amination to obtain the compound of Formula(I), as shown in Reaction Formula 4:

Reaction Formula 4
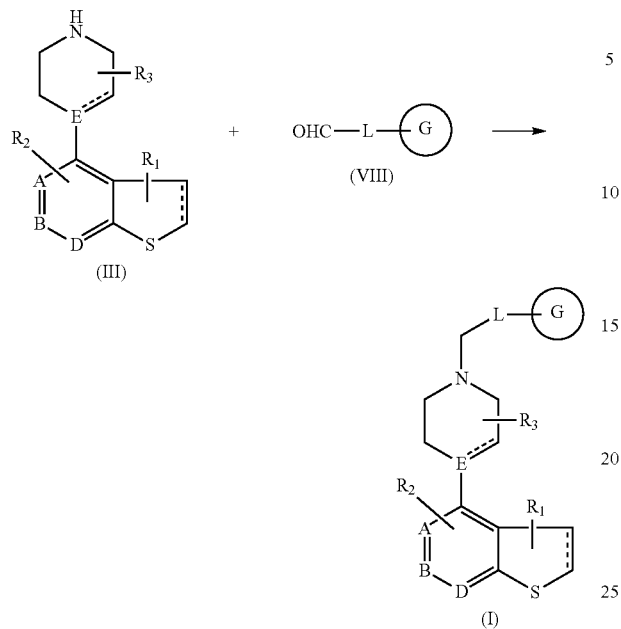
wherein, ring G, L, A, B, D, E, $R_1$, $R_2$ and $R_3$ are defined the same as those in the corresponding claim.
* * * * *